(12) United States Patent
Schadt et al.

(10) Patent No.: US 9,939,555 B2
(45) Date of Patent: Apr. 10, 2018

(54) CINNAMIC ACID DERIVATIVE, POLYMER THEREOF, AND LIQUID CRYSTAL ALIGNMENT LAYER COMPRISING CURED PRODUCT THEREOF

(75) Inventors: Martin Schadt, Seltisberg (CH); Sayaka Nose, Kitaadachi-gun (JP); Masayuki Iwakubo, Kitaadachi-gun (JP); Masanao Hayashi, Kitaadachi-gun (JP); Yutaka Nagashima, Kitaadachi-gun (JP); Isa Nishiyama, Kitaadachi-gun (JP); Haruyoshi Takatsu, Kitaadachi-gun (JP)

(73) Assignee: DIC CORPORATION, Tokyo (JP)

( * ) Notice: Subject to any disclaimer, the term of this patent is extended or adjusted under 35 U.S.C. 154(b) by 268 days.

(21) Appl. No.: 14/123,435

(22) PCT Filed: May 31, 2012

(86) PCT No.: PCT/JP2012/064081
§ 371 (c)(1),
(2), (4) Date: Dec. 2, 2013

(87) PCT Pub. No.: WO2012/165550
PCT Pub. Date: Dec. 6, 2012

(65) Prior Publication Data
US 2014/0121345 A1 May 1, 2014

(30) Foreign Application Priority Data

May 31, 2011 (JP) ................. 2011-121818
May 31, 2011 (JP) ................. 2011-121851
Jun. 30, 2011 (JP) ................. 2011-145095

(51) Int. Cl.
*G02B 1/04* (2006.01)
*C07D 257/08* (2006.01)
*C07D 207/452* (2006.01)
*C08F 20/40* (2006.01)
*C08F 22/40* (2006.01)
*C07C 69/732* (2006.01)
*C07C 69/92* (2006.01)
*C09K 19/56* (2006.01)
*G02F 1/1337* (2006.01)
*C09K 19/04* (2006.01)

(52) U.S. Cl.
CPC .............. *G02B 1/04* (2013.01); *C07C 69/732* (2013.01); *C07C 69/92* (2013.01); *C07D 207/452* (2013.01); *C07D 257/08* (2013.01); *C08F 20/40* (2013.01); *C08F 22/40* (2013.01); *C09K 19/56* (2013.01); *G02F 1/133788* (2013.01); *C07C 2101/02* (2013.01); *C07C 2101/04* (2013.01); *C07C 2101/08* (2013.01); *C07C 2101/14* (2013.01); *C09K 2019/0448* (2013.01); *G02F 1/133711* (2013.01)

(58) Field of Classification Search
None
See application file for complete search history.

(56) References Cited

U.S. PATENT DOCUMENTS

| | | | |
|---|---|---|---|
| 5,539,074 A | 7/1996 | Herr et al. | |
| 5,838,407 A | 11/1998 | Chigrinov et al. | |
| 6,107,427 A | 8/2000 | Herr et al. | |
| 6,335,409 B1 | 1/2002 | Herr et al. | |
| 6,548,127 B1 | 4/2003 | Benecke et al. | |
| 6,597,422 B1 | 7/2003 | Funfschilling et al. | |
| 2003/0043336 A1 | 3/2003 | Sasaki et al. | |
| 2003/0232927 A1* | 12/2003 | Gibbons | C08G 63/44 525/242 |
| 2003/0232930 A1* | 12/2003 | Gibbons | C08F 283/045 525/418 |
| 2005/0266177 A1* | 12/2005 | Sawatari | C09K 19/0225 428/1.2 |
| 2005/0288426 A1 | 12/2005 | Studer et al. | |
| 2006/0022167 A1 | 2/2006 | Lub et al. | |
| 2006/0051524 A1* | 3/2006 | Gibbons | C08G 73/101 428/1.2 |
| 2006/0197068 A1 | 9/2006 | Schadt et al. | |
| 2007/0154652 A1* | 7/2007 | Sawatari | G02F 1/133788 428/1.1 |

(Continued)

FOREIGN PATENT DOCUMENTS

| | | |
|---|---|---|
| EP | 0600064 A1 | 6/1994 |
| EP | 2727947 A1 | 5/2014 |

(Continued)

OTHER PUBLICATIONS

International Search Report dated Jul. 31, 2012, issued in corresponding application No. PCT/JP2012/064081.

(Continued)

*Primary Examiner* — Vu A Nguyen
(74) *Attorney, Agent, or Firm* — Westerman, Hattori, Daniels & Adrian, LLP

(57) ABSTRACT

Provided is a liquid crystal alignment layer of which a constituent member is a compound represented by the general formula (I).

$$L-Sp-(A)_r-\underset{\underset{O}{\overset{\|}{\underset{Y}{\mid}}}}{\overset{X}{\overset{\mid}{C}}}=\overset{}{C}-Z \qquad (I)$$

26 Claims, No Drawings

(56) References Cited

U.S. PATENT DOCUMENTS

| | | |
|---|---|---|
| 2009/0087590 A1 | 4/2009 | Aiki et al. |
| 2010/0048849 A1 | 2/2010 | Eckert et al. |
| 2010/0103358 A1 | 4/2010 | Gibbons et al. |
| 2010/0305230 A1 | 12/2010 | Li et al. |
| 2013/0116396 A1 | 5/2013 | Nose et al. |
| 2013/0281564 A1 | 10/2013 | Seiberle |
| 2014/0121345 A1 | 5/2014 | Schadt et al. |
| 2014/0154428 A1 | 6/2014 | Schadt et al. |
| 2014/0221574 A1 | 8/2014 | Schadt et al. |

FOREIGN PATENT DOCUMENTS

| | | | |
|---|---|---|---|
| JP | H02129149 A | 5/1990 | |
| JP | 5-232473 A | 9/1993 | |
| JP | 6-287453 A | 10/1994 | |
| JP | H06509889 A | 11/1994 | |
| JP | 9-118717 A | 5/1997 | |
| JP | 2002501111 A | 1/2002 | |
| JP | 2002090750 A | 3/2002 | |
| JP | 2002-517605 A | 6/2002 | |
| JP | 2002532755 A | 10/2002 | |
| JP | 2003-149647 A | 5/2003 | |
| JP | 2005208353 A | 8/2005 | |
| JP | 2005258430 A | 9/2005 | |
| JP | 2005528486 A | 9/2005 | |
| JP | 2005-531629 A | 10/2005 | |
| JP | 2005309362 A | 11/2005 | |
| JP | 2006511686 A | 4/2006 | |
| JP | 2006512422 A | 4/2006 | |
| JP | 2007086673 A | 4/2007 | |
| JP | 2007297606 A | 11/2007 | |
| JP | 2009086243 A | 4/2009 | |
| JP | 2009008596 A | 5/2009 | |
| JP | 2009215189 A | 9/2009 | |
| JP | 2009229524 A | 10/2009 | |
| JP | 2010528069 A | 8/2010 | |
| JP | 2010222280 A | 10/2010 | |
| JP | 20120275244 A | 12/2010 | |
| JP | 2011-20981 A * | 2/2011 | ............ C07C 89/54 |
| JP | 2011-020981 A | 2/2011 | |
| JP | 2011-68590 A | 4/2011 | |
| JP | 2011-84477 A | 4/2011 | |
| JP | 2011093812 A | 5/2011 | |
| JP | 4900518 B2 | 3/2012 | |
| JP | 4957976 B2 | 6/2012 | |
| JP | 4957977 B1 | 6/2012 | |
| JP | 5333685 B2 | 11/2013 | |
| JP | 2014501831 A | 1/2014 | |
| JP | 5549781 B2 | 7/2014 | |
| JP | 5679050 B2 | 3/2015 | |
| JP | 5794252 B2 | 10/2015 | |
| WO | 9400797 A1 | 1/1994 | |
| WO | 2012014915 A1 | 2/2012 | |

OTHER PUBLICATIONS

Lub, J. et al., "Photoisomerizable derivatives of phenylethanediol and cinnamic acid: useful compunds for single-layer R, G, and B cholesteric color filters", Molecular Crystals and Liquid Crystals, (2006), 457, p. 161-180, cited in International Search Report.

Bobrovskii, A. Yu. et al., "Photochromic liquid-crystalline copolymers bearing cinnamic acid-based chiral side groups", Vysokomolekulyarnye Soedineniya, Seriya A i Seriya B, (1999), 41(2), pp. 197-208, cited in International Search Report.

Chen, S.H. et al., "New thermotropic chiral nematic copolymers using (1S, 2S, 3S, 5R)-(+)-and (1R, 2R, 3R, 5S)-(-)-isopinocampheol as building blocks", Macromolecules, (1990), 23(24), pp. 5055-5058, cited in International Search Report.

Extended European Search Report dated Jan. 7, 2015, issued in corresponding European Patent Application No. 12792317.5 (10 pages).

Polymer Preprints, 1998, vol. 39(2), pp. 336-337.

Comptes Rendus des Seances de l'Academie des Sciences, 1976, 283(5), pp. 219-221.

Journal of Applied Polymer Science, 2010, vol. 116(6), pp. 3569-3580.

Macromolecules, 2008, vol. 41(13), pp. 4642-4650.

Barros, Ana I.R.N.A. et al., Database Reaxys [Online]; Database accession No. XRN 10346955; "Synthesis of n'-allyl-2-styrylchromones by a Baker Venkataraman transformation", Heterocyclic Communications, vol. 12, No. 2, 2006, pp. 141-150.

Fukunaga, Kenji et al., "Liquid Crystal Control. A Remarkable Enhancement of Both Efficiency and Diastereoselectivity of Intramolecular Thermal Cycloadditions in Smectic Solvents", Tetrahedron Letters, vol. 40, No. 33 Aug. 13, 1999, pp. 6041-6044.

* cited by examiner

CINNAMIC ACID DERIVATIVE, POLYMER THEREOF, AND LIQUID CRYSTAL ALIGNMENT LAYER COMPRISING CURED PRODUCT THEREOF

TECHNICAL FIELD

The present invention relates to a compound, a polymer, a liquid crystal alignment layer, a liquid crystal display element, and an optical anisotropic body. More specifically, the present invention relates to a liquid crystal display element, a liquid crystal alignment layer in the liquid crystal display element, a compound and a polymer for producing the liquid crystal alignment layer, and an optical anisotropic body useful for an optical anisotropy film used in optical compensation of a liquid crystal display element, or the like.

BACKGROUND ART

An alignment layer for aligning a liquid crystal is important for keeping the order of alignment of the liquid crystals and realizing optical characteristics based on refractive index anisotropy of liquid crystal molecules, and is an essential compositional member that constitutes a liquid crystal display element. Alignment of the liquid crystals significantly affects display characteristics of liquid crystal display elements, and thus various methods for aligning the liquid crystal have been investigated. The liquid crystal display elements can be broadly classified into two types, that is, a vertical alignment type and a horizontal alignment type.

A liquid crystal display element (sometimes referred to as a VA mode liquid crystal display element) using a liquid crystal layer of a vertical alignment type has been widely used in displays for their excellent display characteristics such as high contrast. However, since it cannot be said that the liquid crystal display element using a liquid crystal layer of a vertical alignment type necessarily has sufficient viewing angle characteristics, various methods have been investigated to improve the viewing angle characteristics. As a method for improving the viewing angle characteristics, a multi-domain vertical alignment mode (MVA mode) has become prevalent, in which a plurality of liquid crystal domains having different alignment directions is formed in one pixel (an alignment division structure is incorporated therein). In the MVA mode, it is necessary to control the tilt alignment of the liquid crystal molecules in order to form the alignment division structure, and as such a method, a method in which a slit (opening) or a rib (projection structure) is provided in electrodes, is used. However, with the use of the slit or the rib, the slit or the rib is linear unlike a case where a pretilt direction is defined by an alignment film used in a TN mode used in the related art, and thus, the ability to control the alignment for the liquid crystal molecules becomes uneven within a pixel, whereby a problem of generation of a distribution in the response speeds arises.

In addition, there is another problem that a region provided with a slit or a rib exhibits decreased optical transmittance, resulting in a decrease in display luminance.

As another method for controlling the tilt alignment, there is disclosed a polymer alignment support (PSA; Polymer Sustained Alignment) technology in which photo- or thermo-polymerizable monomers are incorporated into a liquid crystal, the monomers being polymerized while tilting the liquid crystal molecules by voltage application so that the tilt direction of the liquid crystal molecules is memorized (see PTL 1). This method can overcome the problem in the distribution of the response speeds or a decrease in the optical transmittance in the slit-and-rib method. However, this method faces a problem such as changes in characteristics caused by the addition of monomers in the liquid crystal material, difficulty in controlling the process, and adverse effects of the residual monomers.

In order to avoid these problems, it is preferable even for the VA mode liquid crystal display element to form an alignment division structure by controlling the tilt alignment with an alignment film. As a method of providing an ability to control the tilt alignment on the vertical alignment film, there is a rubbing method, in which an alignment film made of a polyimide or the like is applied onto a substrate, and then the alignment film is rubbed with rubbing cloth to control the alignment direction and the pretilt angle. However, it is difficult to form a precise alignment division structure by the rubbing method, and thus problems of static electricity caused by friction and generation of impurities arise.

Meanwhile, as one of liquid crystal display elements using a liquid crystal layer of the horizontal alignment type, there is an IPS mode liquid crystal display element. The IPS mode liquid crystal display element has little dependency on viewing angles, for example in contrast and color tone, and is widely used in displays due to its excellent display characteristics. In the IPS mode, in order to reduce viewing angle dependency in the black display and the color reproducibility, it is required to have a low pretilt angle of one degree or less on the electrode surface. Even when achieving the horizontal alignment, a rubbing method as a general alignment method is used. However, when a horizontal alignment treatment is carried out by a rubbing treatment of a polyimide alignment film, the pretilt angle provided to the liquid crystal molecules exceeds one degree, and thus, a problem that the display characteristics are deteriorated arises.

From these problems, in any alignment mode of the vertical alignment type and the horizontal alignment type, it is important to control the alignment direction and the pretilt angle using the alignment film so as to improve the display characteristics. As a method for controlling the tilt alignment with an alignment film, a photo-alignment method is known, in addition to the methods using rubbing treatment (see PTL 2). In the photo-alignment method, a precise alignment division structure can be formed easily by changing the illumination pattern of light, and generation of static electricity or impurities is difficult, as compared with the rubbing treatment since a non-contact treatment on the alignment film can be carried out, and thus, it is expected to solve the above-described problems and to improve the display characteristics.

As the materials which can be a photo-alignment layer for the liquid crystal display element, a compound having a photochemically isomerizable site, such as an azobenzene derivative (see PTL 3), a compound having a photochemically crosslinkable site, such as a cinnamic acid derivative, a coumarin derivative, and a chalcone derivative (see PTLs 4, 5, and 6), a compound causing an anisotropic photodegradation, such as a polyimide derivative, and the like are known.

However, the photo-alignment method using these compounds has a problem such as a low voltage holding ratio (VHR), as compared with a case using an ordinary alignment film. Therefore, various characteristics such as reliability, which allows realization of performance for controlling the tilt alignment of the liquid crystals and use in active matrix driving, are required, and photo-alignment layers for liquid crystals, which satisfy the requirements, have been required. Incidentally, the voltage holding ratio (VHR) means how much voltage applied to each pixel in a liquid crystal display element is held for a predetermined period of time (for example, one frame in the liquid crystal display element, 16.7 msec).

As described above, there has been a demand for a liquid crystal alignment layer having a superior ability to control the alignment of the liquid crystals and the pretilt angles and further, a high voltage holding ratio (VHR).

CITATION LIST

Patent Literature

[PTL 1] Japanese Unexamined Patent Application, First Publication No. 2003-149647
[PTL 2] Japanese Patent No. 2682771
[PTL 3] Japanese Unexamined Patent Application, First Publication No. H05-232473
[PTL 4] Japanese Unexamined Patent Application, First Publication No. H06-287453
[PTL 5] Japanese Unexamined Patent Application, First Publication No. H09-118717
[PTL 6] Japanese Unexamined Patent Application Publication (Translation of PCT Application) No. 2002-517605

SUMMARY OF INVENTION

Technical Problem

The present invention has an object to provide a liquid crystal alignment layer which is efficiently provided with an alignment property at a low dose of irradiation of polarized light, and has a superior ability to control the alignment of liquid crystals and the pretilt angles, a high voltage holding ratio (VHR), and coatability; a polymer used for the liquid crystal alignment layer; a compound constituting the polymer; a liquid crystal display element using the liquid crystal alignment layer; and an optical anisotropic body using the polymer.

Solution to Problem

The present inventors have made extensive studies on various materials in order to solve the problems, and as a result, they have found that a liquid crystal alignment layer which is efficiently provided with an alignment property at a low dose of irradiation of polarized light during the production, is excellent in the control of the alignment of the liquid crystals and the pretilt angles, coatability, and the like, and has a high voltage holding ratio (VHR); a polymer used for the liquid crystal alignment layer; a compound constituting the polymer; a liquid crystal display element using the liquid crystal alignment layer; and an optical anisotropic body using the polymer, are obtained by applying a polymer obtained from a specific cinnamic acid derivative onto a substrate, and curing it, thereby leading to the completion of the present invention.

Specifically, the present invention provides the following (1) to (77).

(1) A compound represented by the general formula (I):

[Chem. 1]

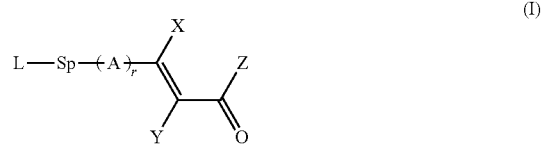

(I)

(wherein L represents a polymerizable group and Sp represents a spacer unit,

A represents a group selected from the group consisting of:

(a) a trans-1,4-cyclohexylene group (one methylene group or two or more non-adjacent methylene groups present in this group may be substituted with —O—, —NH—, or —S—), (b) a 1,4-phenylene group (one or two or more —CH=='s present in this group may be substituted with —N=), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, r represents 0, 1, or 2, but in the case where r represents 2, a plurality of A's, may be the same as or different from each other, X and Y each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one $CH_2$ group or two or more non-adjacent $CH_2$ groups may be substituted with —O—, —CO—O—, —O—CO— and/or —CH=CH—, and Z is represented by the general formula (IIa) or (IIb):

[Chem. 2]

(IIa)

(IIb)

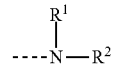

(wherein the broken line represents a bond to a carbon atom, to which Z is bonded, and $R^1$ and $R^2$ each independently represent a hydrogen atom or a linear or branched alkyl group having 1 to 30 carbon atoms, one —$CH_2$— group or two or more non-adjacent —$CH_2$— groups in $R^1$ and $R^2$ may be substituted with —O—, —CO—, —CO—O—, —O—CO—, —CO—NH—, —NH—CO—, —$NCH_3$—, —CH=CH—, —CF=CF—, and/or —C≡C—, one or two or more —$CH_2$— groups in $R^1$ and $R^2$ may be each independently substituted with a cycloalkyl group having a ring member number of 3 to 8, and a hydrogen atom in $R^1$ and $R^2$ may be substituted with an alkyl group having 1 to 20 carbon atoms, a cyano group, or a halogen atom)).

(2) The compound as described in (1), in which in the general formula (IIa) or (IIb), $R^1$ represents a linear or branched alkyl group having 1 to 30 carbon atoms (one —$CH_2$— group or two or more non-adjacent —$CH_2$— groups in the alkyl group are substituted with —O—, —CO—, —CO—O—, —O—CO—, —CO—NH—, —NH—CO—, or —$NCH_3$—, one or two or more —$CH_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), and $R^2$ represents a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom).

(3) The compound as described in (1) or (2), in which in the general formula (IIa) or (IIb), $R^1$ is represented by the general formula (IIc):

[Chem. 3]

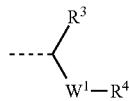

(IIc)

(wherein the broken line represents a bond to an oxygen atom or a nitrogen atom, $W^1$ represents a methylene group (a hydrogen atom in the methylene group may be unsubstituted or substituted with an alkyl group having 1 to 5 carbon atoms), —CO—O—, or —CO—NH—, $R^3$ represents a hydrogen atom or an alkyl group having 1 to 5 carbon atoms, and $R^4$ represents a linear or branched alkyl group having 1 to 20 carbon atoms (one —$CH_2$— group or two or more non-adjacent —$CH_2$— groups in the alkyl group are substituted with —O—, —CO—, —CO—O—, —O—CO—, —CO—NH—, —NH—CO—, or —$NCH_3$—, one or two or more —$CH_2$— groups in the alkyl group may be each independently substituted with a cycloalkyl group having a ring member number of 3 to 8, and a hydrogen atom in the alkyl group may be unsubstituted or substituted with a fluorine atom or a chlorine atom).

(4) The compound as described in (1), in which in the general formula (IIa) or (IIb), $R^1$ represents a linear or branched alkyl group having 1 to 30 carbon atoms (one —$CH_2$— group or two or more non-adjacent —$CH_2$— groups in the alkyl group are substituted with —CH=CH—, —CF=CF—, and/or —C≡C—, and one or two or more —$CH_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), and $R^2$ represents a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom).

(5) The compound as described in (1) or (4), in which in the general formula (IIa) or (IIb), $R^1$ is represented by the general formulae (IId) to (IIg):

[Chem. 4]

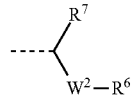

(IId)

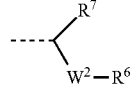

(IIe)

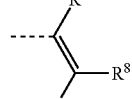

(IIf)

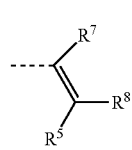

(IIg)

(wherein the broken line represents a bond to an oxygen atom or a nitrogen atom, $W^2$ represents a single bond, —$CH_2$—, —CO—O—, or —CO—NH—, $R^7$ represents a hydrogen atom or an alkyl group having 1 to 5 carbon atoms, $R^8$ represents a hydrogen atom, or a linear or branched alkyl group having 1 to 20 carbon atoms (one or two or more —$CH_2$— groups in the alkyl group may be each independently substituted with a cycloalkyl group having a ring member number of 3 to 8, and a hydrogen atom in the alkyl group may be unsubstituted or substituted with a fluorine atom or a chlorine atom), $R^5$ represents an alkyl group having 1 to 20 carbon atoms, in which a hydrogen atom in the alkyl group may be substituted with a fluorine atom, and $R^6$ represents an alkyl group having 1 to 20 carbon atoms (one —$CH_2$— group or two or more non-adjacent —$CH_2$— groups in the alkyl group are substituted with —CH=CH—, —CF=CF—, and/or —C≡C—, and one or two or more —$CH_2$— groups in the alkyl group may be each independently substituted with a cycloalkyl group having a ring member number of 3 to 8, and a hydrogen atom in the alkyl group may be substituted with a fluorine atom or a chlorine atom)).

(6) The compound as described in any one of (1) to (5), in which in the general formula (I), Sp is represented by the following general formula (IVa):

[Chem. 5]

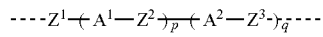

(IVa)

(wherein the left broken line represents a bond to L, and the right broken line represents a bond to A or a bond to a carbon atom, to which X is bonded, $Z^1$, $Z^2$ and $Z^3$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, but one or more of the non-adjacent $CH_2$ groups in these substituents may be independently substituted with —O—, —CO—, —CO—O—, —O—CO—, —$Si(CH_3)_2$—O—$Si(CH_3)_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^1$ and $A^2$ each independently represent a group selected from the group consisting of:

(a) a trans-1,4-cyclohexylene group (one methylene group or two or more non-adjacent methylene groups present in this group may be substituted with —O—, —NH—, or —S—), (b) a 1,4-phenylene group (one or two or more —CH='s present in this group may be substituted with —N=), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, and p and q each independently represent 0 or 1).

(7) The compound as described in (1), in which in the general formula (IIa) or (IIb), $R^1$ represents a hydrogen atom or a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), and $R^2$ represents a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom), and in the general formula (I), Sp is represented by the general formula (IVc):

[Chem. 6]

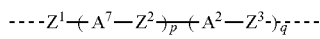

(IVc)

(wherein $Z^1$, $Z^2$, $Z^3$, and $A^2$ have the same definitions as in the general formula (IVa)), $A^7$ represents a group selected from the group consisting of:

a 1,4-phenylene group (three or more —CH='s present in this group are substituted with —N=), a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, and these may be each unsubstituted or have one or more hydrogen atoms substituted with a fluorine atom, a chlorine atom, a cyano group, a methyl group, or a methoxy group, and p represents 1 and q represents 1 or 2, but, in the case where q represents 2, a plurality of $A^2$ and $Z^3$ are present, and they may be the same as or different from each other).

(8) The compound as described in (1), in which in the general formula (IIa) or (IIb), $R^1$ represents a linear or branched alkyl group having 1 to 30 carbon atoms (one or two or more —$CH_2$— groups in the alkyl group are each independently substituted with a cycloalkyl group having a ring member number of 3 to 8, and a hydrogen atom in the alkyl group may be substituted with an alkyl group having 1 to 20 carbon atoms, a cyano group, or a halogen atom), and $R^2$ represents a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom), and in the general formula (I), Sp is represented by the general formula (IVb):

[Chem. 7]

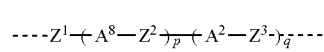

(IVb)

(wherein $Z^1$, $Z^2$, $Z^3$, $A^2$, p and q have the same definitions as in the general formula (IVa)), and $A^8$ represents:

a trans-1,4-cyclohexylene group (one methylene group or two or more non-adjacent methylene groups present in this group may be substituted with —O—, —NH—, or —S—), and a 1,4-phenylene group (one or two —CH='s present in this group may be substituted with —N=), and these may be each unsubstituted or have one or more hydrogen atoms substituted with a fluorine atom, a chlorine atom, a cyano group, a methyl group, or a methoxy group).

(9) The compound as described in any one of (1) to (8), in which in the general formula (I), L represents any substituent selected from the group consisting of the general formulae (III-1) to (III-17):

[Chem. 8]

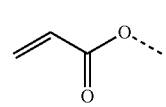

(III-1)

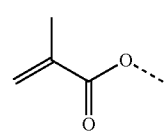

(III-2)

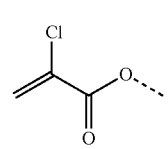

(III-3)

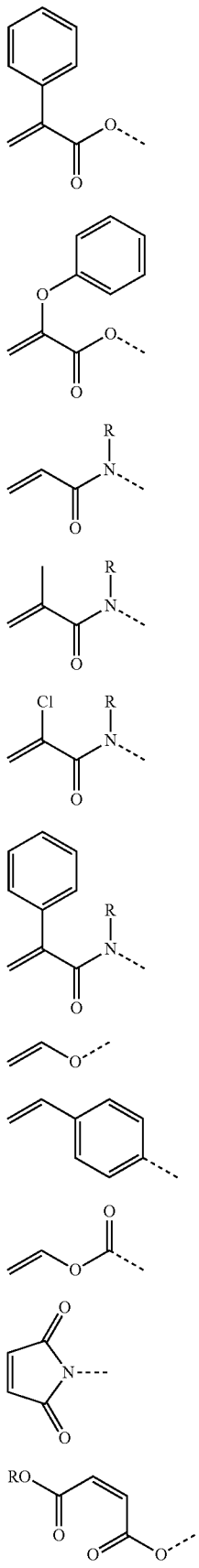

(wherein the broken line represents a bond to Sp and R's independently represent hydrogen or an alkyl group having 1 to 5 carbon atoms).

(10) The compound as described in any one of (1) to (9), in which in the general formula (I), X and Y each represent a hydrogen atom.

(11) The compound as described in any one of (6) to (8), in which in the general formulae (IVa), (IVb), and (IVc), $A^2$ represents any group of a trans-1,4-cyclohexylene group, a 2,6-naphthylene group, a pyridine-2,5-diyl group, a pyrimidine-2,5-diyl group, or a 1,4-phenylene group, one or more hydrogen atoms in any group of these groups may be substituted with a fluorine atom, a chlorine atom, a methyl group, or a methoxy group, $Z^3$ represents any one of a single bond, —(CH$_2$)$_u$— (wherein u represents 1 to 20), —OCH$_2$—, —CH$_2$O—, —COO—, —OCO—, —CH═CH—, or —C≡C—, one or more of the non-adjacent CH$_2$ groups in any one of these groups may be independently substituted with —O—, —CO—, —CO—O—, —O—CO—, —CH═CH—, or —C≡C—, and q represents 1.

(12) The compound as described in any one of (1) to (11), in which in the general formula (I), L is represented by the general formula (III-1), (III-2), (III-6), (III-7), or (III-13).

(13) The compound as described in any one of (1) to (12), in which in the general formula (I), A represents a 1,4-phenylene group having one or more hydrogen atoms which may be substituted with a fluorine atom, a chlorine atom, a methyl group, or a methoxy group.

(14) The compound as described in any one of (6) to (13), in which in the general formulae (IVa), (IVb), and (IVc), $A^2$ represents a 1,4-phenylene group having one or more hydrogen atoms which may be substituted with a fluorine atom, a chlorine atom, a methyl group, or a methoxy group.

(15) The compound as described in any one of (1) to (14), in which in the general formula (I), L is represented by the general formula (III-1) or (III-2).

(16) The compound as described in any one of (7), (9) to (15), in which in the general formula (IVc), $A^7$ represents a 2,6-naphthylene group and one or more hydrogen atoms in the 2,6-naphthylene group may be substituted with a fluorine atom, a chlorine atom, a methyl group, or a methoxy group.

(17) A polymer constituted with a cured product of a composition containing a compound as described in any one of (1) to (16), in which the cured product has a structural unit represented by the general formula (PI):

[Chem. 9]

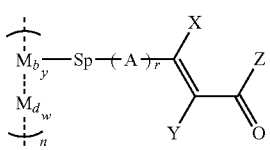
(PI)

(wherein Sp, A, X, Y, Z and r have the same definitions as in the general formula (I), $M_b$ and $M_d$ each represent a monomer unit of the polymer, y and w each represent a molar fraction of the copolymer, each satisfying $0<y\leq1$ and $0\leq w<1$, n represents 4 to 100,000, the order in which $M_b$ and $M_d$ are arranged may be the same as or different from that shown in the formula, and the monomer units of $M_b$ and $M_d$ may be each independently constituted with one or two or more different units).

(18) The polymer as described in (17), in which in the general formula (PI), $M_b$ represents any one or more selected from the group consisting of the general formulae (QIII-A-1) to (QIII-A-17):

[Chem. 10]

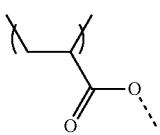
(QIII-A-1)

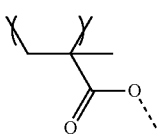
(QIII-A-2)

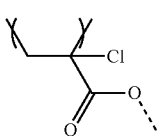
(QIII-A-3)

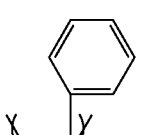
(QIII-A-4)

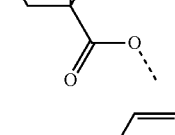
(QIII-A-5)

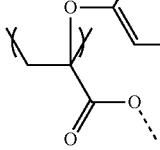
(QIII-A-6)

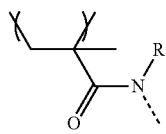
(QIII-A-7)

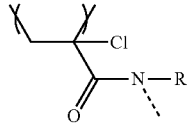
(QIII-A-8)

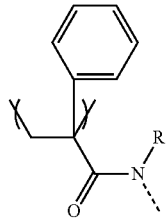
(QIII-A-9)

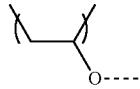
(QIII-A-10)

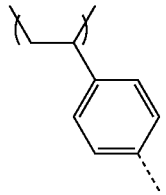
(QIII-A-11)

(QIII-A-12)

(QIII-A-13)

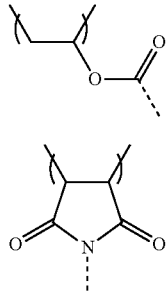
(QIII-A-14)

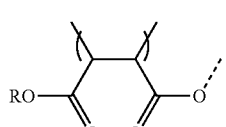
(QIII-A-15)

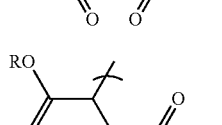
(QIII-A-16)

(QIII-A-17)

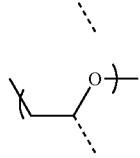

(wherein the broken line represents a bond to Sp, R's independently represent hydrogen or an alkyl group having 1 to 5 carbon atoms, and any hydrogen atom in each of the structures may be substituted with a fluorine atom, a chlorine atom, a methyl group, or a methoxy group).

(19) The polymer as described in (17) or (18), in which in the general formula (PI), $M_d$ represents any one or more selected from the group consisting of the general formulae (QIII-1) to (QIII-17):

[Chem. 11]

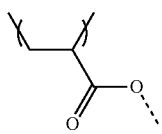 (QIII-A-1)

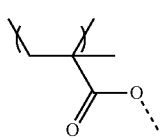 (QIII-A-2)

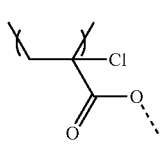 (QIII-A-3)

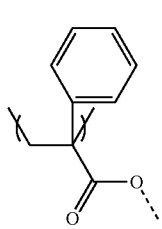 (QIII-A-4)

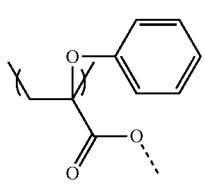 (QIII-A-5)

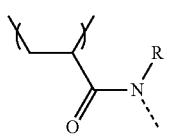 (QIII-A-6)

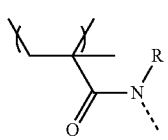 (QIII-A-7)

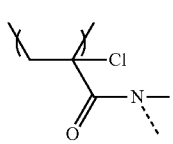 (QIII-A-8)

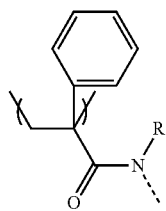 (QIII-A-9)

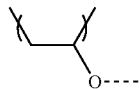 (QIII-A-10)

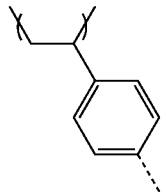 (QIII-A-11)

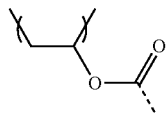 (QIII-A-12)

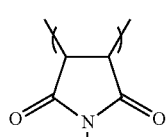 (QIII-A-13)

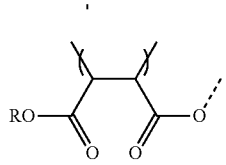 (QIII-A-14)

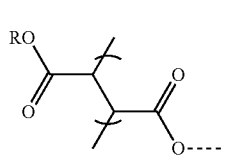 (QIII-A-15)

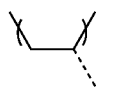 (QIII-A-16)

(QIII-A-17)

(wherein the broken line represents a bond to a hydrogen atom or a monovalent organic group, R's independently represent hydrogen or an alkyl group having 1 to 5 carbon atoms, and any hydrogen atom in each of the structures may be substituted with a fluorine atom, a chlorine atom, a methyl group, or a methoxy group).

(20) The polymer as described in any one of (17) to (19), in which in the general formulae (QIII-1) to (QIII-17), the monovalent organic group is represented by the general formula (QIV):

[Chem. 12]

$$—S_a—V_a \quad (QIV)$$

(wherein the broken line represents a bond to $M_d$, $S_a$ represents a structure represented by the general formula (IVa), and $V_a$ is represented by the following general formula (VI):

[Chem. 13]

$$--(-A^3—Z^4)_{r1}(-A^4—Z^5)_{s1}(-A^5—Z^6)_{t1}(-A^6—Z^7)_{u1}-R^{12} \quad (VI)$$

(wherein the broken line represents a bond to $S_a$;

$Z^4$, $Z^5$, $Z^6$ and $Z^7$ each independently represent a single bond, —(CH$_2$)$_u$— (wherein u represents 1 to 20), —OCH$_2$—, —CH$_2$O—, —COO—, —OCO—, —CH═CH—, —CF═CF—, —CF$_2$O—, —OCF$_2$—, —CF$_2$CF$_2$— or —C≡C—, but one or more of the non-adjacent CH$_2$ groups in these substituents may be independently substituted with —O—, —CO—, —CO—O—, —O—CO—, —Si(CH$_3$)$_2$—O—Si(CH$_3$)$_2$—, —NR—, —NR—CO—, —CO—NR—, —NR—CO—O—, —O—CO—NR—, —NR—CO—NR—, —CH═CH—, —C≡C—, or —O—CO—O— (wherein R's independently represent hydrogen or an alkyl group having 1 to 5 carbon atoms), $A^3$, $A^4$, $A^5$ and $A^6$ each independently represent a group selected from the group consisting of:

(a) a trans-1,4-cyclohexylene group (one methylene group or two or more non-adjacent methylene groups present in this group may be substituted with —O—, —NH—, or —S—), (b) a 1,4-phenylene group (one or two or more —CH═'s present in this group may be substituted with —N═), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be unsubstituted or may have one or more hydrogen atoms substituted with a fluorine atom, a chlorine atom, a cyano group, a methyl group, or a methoxy group, r1, s1, t1, and u1 each independently represent 0 or 1, and $R^{12}$ represents hydrogen, fluorine, chlorine, a cyano group, or an alkyl group having 1 to 20 carbon atoms, a hydrogen atom in the alkyl group may be substituted with a fluorine atom, and one CH$_2$ group or two or more non-adjacent CH$_2$ groups may be substituted with —O—, —CO—O—, —O—CO— and/or —CH═CH—)).

(21) A liquid crystal alignment layer for a vertical alignment mode liquid crystal display element, using the polymer as described in any one of (17) to (20).

(22) A vertical alignment mode liquid crystal display element using the liquid crystal alignment layer as described in (21).

(23) A liquid crystal alignment layer for a horizontal alignment mode liquid crystal display element, using the polymer as described in any one of (17) to (20).

(24) A horizontal alignment mode liquid crystal display element using the liquid crystal alignment layer as described in (23).

(25) An optical anisotropic body constituted with a polymer of a polymerizable liquid crystal composition, in which polymerizable liquid crystal molecules in the polymerizable liquid crystal composition are aligned using the polymer as described in any one of (17) to (20).

(26) A compound represented by the general formula (I):

[Chem. 14]

$$L—Sp—(A)_r—C(X)(Y)—C(═O)—Z \quad (I)$$

(wherein L represents a polymerizable group and Sp represents a spacer unit,

A's each independently represent a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, these may be unsubstituted or may have one or more hydrogen atoms substituted with a fluorine atom, a chlorine atom, a methyl group, or a methoxy group, X and Y each independently represent a hydrogen atom, a fluorine atom, a chlorine atom, a cyano group, or an alkyl group having 1 to 20 carbon atoms, a hydrogen atom in the alkyl group may be substituted with a fluorine atom, and one CH$_2$ group or two or more non-adjacent CH$_2$ groups in the alkyl group may be substituted with —O—, —CO—O—, —O—CO— and/or —CH═CH—, and Z is represented by the general formula (IIa) or (IIb):

[Chem. 15]

$$----O—R^1 \quad (IIa)$$

$$----N(R^1)—R^2 \quad (IIb)$$

(wherein the broken line represents a bond to a carbon atom, to which Z is bonded, $R^1$ represents a hydrogen atom or a linear or branched alkyl group having 1 to 30 carbon atoms (one or two or more —CH$_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), and $R^2$ represents a linear or branched alkyl group having 1 to 30 carbon atoms (one or two or more —CH$_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom)), and r represents 1 or 2).

(27) The compound as described in (26), in which in the general formula (I), L represents any substituent selected from the group consisting of the general formulae (III-1) to (III-17):

[Chem. 16]

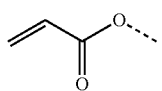 (III-1)

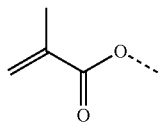 (III-2)

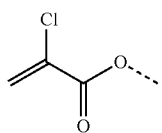 (III-3)

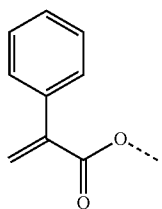 (III-4)

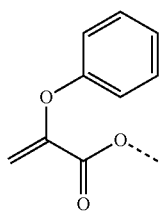 (III-5)

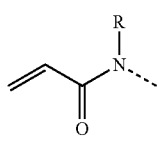 (III-6)

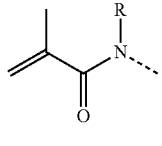 (III-7)

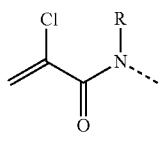 (III-8)

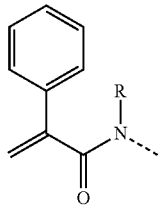 (III-9)

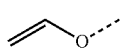 (III-10)

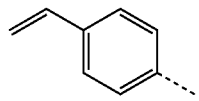 (III-11)

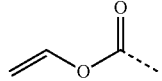 (III-12)

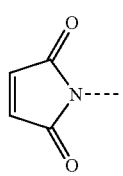 (III-13)

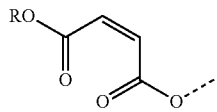 (III-14)

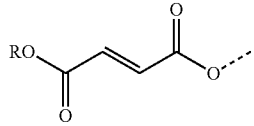 (III-15)

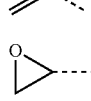 (III-16)

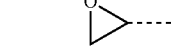 (III-17)

(wherein the broken line represents a bond to Sp and R's independently represent hydrogen or an alkyl group having 1 to 5 carbon atoms).

(28) The compound as described in (26) or (27), in which in the general formula (I), Sp is represented by the following general formula (IVc):

[Chem. 17]

$$----Z^1-\!\!\!+\!\!A^7-Z^2\!\!+\!\!_p\!\!+\!\!A^2-Z^3\!\!+\!\!_q----$$  (IVc)

(wherein the left broken line represents a bond to L and the right broken line represents a bond to A, $Z^1$, $Z^2$ and $Z^3$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, and one or more of the non-adjacent $CH_2$ groups in these groups may be independently substituted with —O—, —CO—, —CO—O—, —O—CO—, —Si$(CH_3)_2$—O—Si$(CH_3)_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^7$ represents any group of a 1,4-naphthylene group, a 2,6-naphthylene group, a 2,5-thiophenylene group, a 1,2,4,5-tetrazine-3,6-diyl group, or a 2,5-furanylene group, and one or more hydrogen atoms in any group of these groups may be substituted with a fluorine atom, a chlorine atom, a methyl group, or a methoxy group, and A² represents any group of a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-3,6-diyl group, a 2,5-thiophenylene group, a 2,5-furanylene group, or a 1,4-phenylene group, one or more hydrogen atoms in any group of these groups may be substituted with a fluorine atom, a chlorine atom, a methyl group, or a methoxy group, p represents 1, and q represents 1 or 2).

(29) The compound as described in any one of (26) to (28), in which in the general formula (I), X and Y each represent a hydrogen atom.

(30) The compound as described in (28) or (29), in which in the general formula (IVc), A² represents any group of a trans-1,4-cyclohexylene group, a 2,6-naphthylene group, a pyridine-2,5-diyl group, a pyrimidine-2,5-diyl group, or a 1,4-phenylene group, one or more hydrogen atoms in any group of these groups may be substituted with a fluorine atom, a chlorine atom, a methyl group, or a methoxy group, Z³ represents a single bond or any group of —(CH₂)ᵤ— (wherein u represents 1 to 20), —OCH₂—, —CH₂O—, —COO—, —OCO—, —CH=CH—, or —C≡C—, one or more of the non-adjacent CH₂ groups in any group of these groups may be independently substituted with —O—, —CO—, —CO—O—, —O—CO—, —CH=CH—, or —C≡C—, and q represents 1.

(31) The compound as described in any one of (27) to (30), in which in the general formula (I), L is represented by the general formula (III-1), (III-2), (III-6), (III-7), or (III-13).

(32) The compound as described in any one of (28) to (31), in which in the general formula (IVc), A¹ represents a 2,6-naphthylene group and one or more hydrogen atoms in the 2,6-naphthylene group may be substituted with a fluorine atom, a chlorine atom, a methyl group, or a methoxy group.

(33) The compound as described in any one of (26) to (32), in which in the general formula (I), A represents a 1,4-phenylene group having one or more hydrogen atoms which may be substituted with a fluorine atom, a chlorine atom, a methyl group, or a methoxy group.

(34) The compound as described in any one of (28) to (33), in which in the general formula (IVc), A² represents a 1,4-phenylene group having one or more hydrogen atoms which may be substituted with a fluorine atom, a chlorine atom, a methyl group, or a methoxy group.

(35) The compound as described in any one of (27) to (34), in which in the general formula (I), L is represented by the general formula (III-1) or (III-2).

(36) A polymer constituted with a cured product of a composition containing the compound as described in any one of (26) to (35), wherein the cured product has a structural unit represented by the general formula (PI):

[Chem. 18]

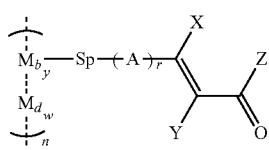

(PI)

(wherein Sp, A, X, Y, r, and Z have the same definitions as in the general formula (I), $M_b$ and $M_d$ each represent a monomer unit of the polymer, y and w each represent a molar fraction of the copolymer, each satisfying $0<y\leq1$ and $0\leq w<1$, n represents 4 to 100,000, the order in which $M_b$ and $M_d$ are arranged may be the same as or different from that shown in the formula, and the monomer units of $M_b$ and $M_d$ may be each independently constituted with one or two or more different units).

(37) The polymer as described in (36), in which in the general formula (PI), $M_b$ represents any one or more selected from the group consisting of the general formulae (QIII-A-1) to (QIII-A-17):

[Chem. 19]

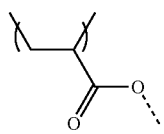

(QIII-A-1)

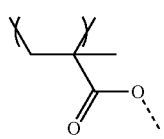

(QIII-A-2)

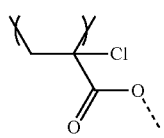

(QIII-A-3)

(QIII-A-4)

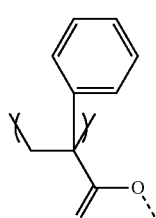

(QIII-A-5)

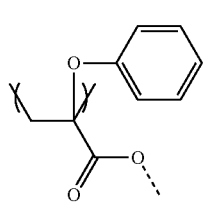

(QIII-A-6)

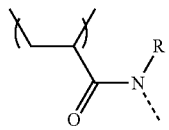

(QIII-A-7)

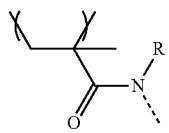

(QIII-A-8)

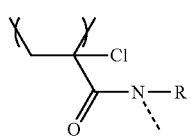

-continued (QIII-A-9) 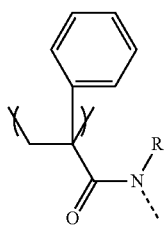

(QIII-A-10) 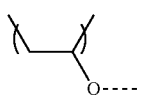

(QIII-A-11) 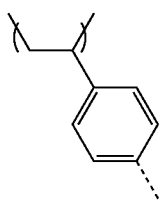

(QIII-A-12) 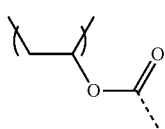

(QIII-A-13) 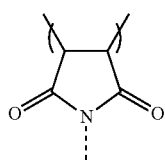

(QIII-A-14) 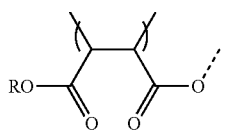

(QIII-A-15) 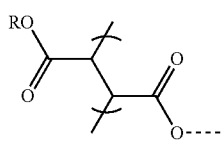

(QIII-A-16) 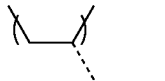

(QIII-A-17) 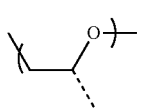

(wherein the broken line represents a bond to Sp, R's independently represent a hydrogen atom or an alkyl group having 1 to 5 carbon atoms, and any hydrogen atom in each of the structures may be substituted with a fluorine atom, a chlorine atom, a methyl group, or a methoxy group).

(38) The polymer as described in (36) or (37), in which in the general formula (PI), $M_d$ represents any one or more selected from the group consisting of the general formulae (QIII-1) to (QIII-17):

[Chem. 20]

(QIII-1) 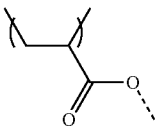

(QIII-2) 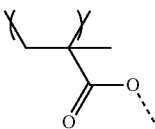

(QIII-3) 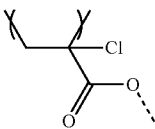

(QIII-4) 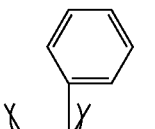

(QIII-5) 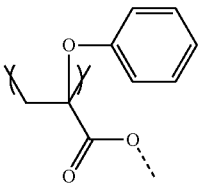

(QIII-6) 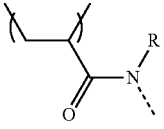

(QIII-7) 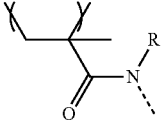

(QIII-8) 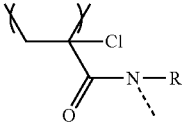

(QIII-9) 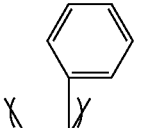

(QIII-10) 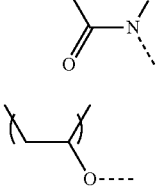

-continued (QIII-11) 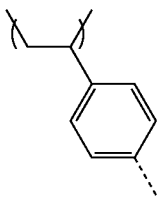

(QIII-12) 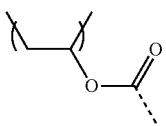

(QIII-13) 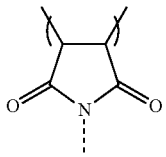

(QIII-14) 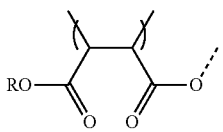

(QIII-15) 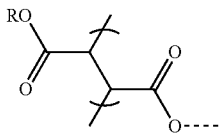

(QIII-16) 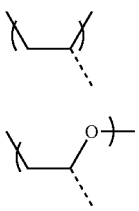

(QIII-17)

(wherein the broken line represents a bond to a hydrogen atom or a monovalent organic group, and R's independently represent hydrogen or an alkyl group having 1 to 5 carbon atoms, and any hydrogen atom in each of the structures may be substituted with a fluorine atom, a chlorine atom, a methyl group, or a methoxy group).

In the general formulae (QIII-1) to (QIII-17) of (38), the monovalent organic group is preferably represented by the general formula (QIV):

[Chem. 21]

$$-S_a-V_a \quad (QIV)$$

(wherein the broken line represents a bond to $M_d$, $S_a$ represents a structure represented by the general formula (IVc), and $V_a$ is represented by the following general formula (VI):

[Chem. 22]

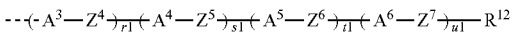

(VI)

(wherein the broken line represents a bond to $S_a$; $Z^4$, $Z^5$, $Z^6$ and $Z^7$ each independently represent a single bond, $-(CH_2)_u-$ (wherein u represents 1 to 20), $-OCH_2-$, $-CH_2O-$, $-COO-$, $-OCO-$, $-CH=CH-$, $-CF=CF-$, $-CF_2O-$, $-OCF_2-$, $-CF_2CF_2-$, or $-C\equiv C-$, but one or more of the non-adjacent $CH_2$ groups in these substituents may be independently substituted with $-O-$, $-CO-$, $-CO-O-$, $-O-CO-$, $-Si(CH_3)_2-O-Si(CH_3)_2-$, $-NR-$, $-NR-CO-$, $-CO-NR-$, $-NR-CO-O-$, $-O-CO-NR-$, $-NR-CO-NR-$, $-CH=CH-$, $-C\equiv C-$, or $-O-CO-O-$ (wherein R's independently represent hydrogen or an alkyl group having 1 to 5 carbon atoms), $A^3$, $A^4$, $A^5$ and $A^6$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, r1, s1, t1, and u1 each independently represent 0 or 1, and $R^{12}$ represents hydrogen, fluorine, chlorine, a cyano group, or an alkyl group having 1 to 20 carbon atoms, a hydrogen atom in the alkyl group may be substituted with a fluorine atom, and one $CH_2$ group or two or more non-adjacent $CH_2$ groups may be substituted with $-O-$, $-CO-O-$, $-O-CO-$, and/or $-CH=CH-$)).

(39) A liquid crystal alignment layer for a vertical alignment mode liquid crystal display element, using the polymer as described in any one of (36) to (38).

(40) A vertical alignment mode liquid crystal display element using the liquid crystal alignment layer as described in (39).

(41) A liquid crystal alignment layer for a horizontal alignment mode liquid crystal display element, using the polymer as described in any one of (36) to (38).

(42) A horizontal alignment mode liquid crystal display element using the liquid crystal alignment layer as described in (41).

(43) A liquid crystal alignment layer for an optical anisotropic body, using the polymer as described in any one of (36) to (38).

(44) An optical anisotropic body constituted with a polymer of a polymerizable liquid crystal composition, in which polymerizable liquid crystal molecules in the polymerizable liquid crystal composition are aligned using the liquid crystal alignment layer as described in (43).

(45) A compound represented by the general formula (I):

[Chem. 23]

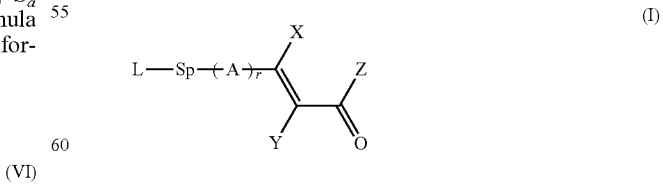

(wherein L represents a polymerizable group and Sp represents a spacer unit,

A's each independently represent a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or may have one or more hydrogen atoms substituted with a fluorine atom, a chlorine atom, a methyl group, or a methoxy group, X and Y each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one $CH_2$ group or two or more non-adjacent $CH_2$ groups may be substituted with —O—, —CO—O—, —O—CO—, and/or —CH=CH—, and Z is represented by the general formula (IIa) or (IIb):

[Chem. 24]

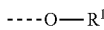
(IIa)

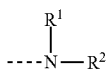
(IIb)

(wherein the broken line represents a bond to a carbon atom, to which Z is bonded, $R^1$ represents a linear or branched alkyl group having 1 to 30 carbon atoms (one —$CH_2$— group or two or more non-adjacent —$CH_2$— groups in the alkyl group are substituted with —CH=CH—, —CF=CF—, and/or —C≡C—, one or two or more —$CH_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), and $R^2$ represents a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom)).

In the general formula (IIa) or (IIb) of (45), $R^1$ is preferably represented by the general formulae (IId) to (IIg):

[Chem. 25]

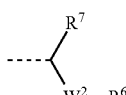
(IId)

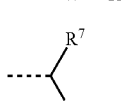
(IIe)

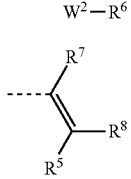
(IIf)

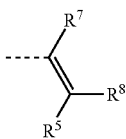
(IIg)

(wherein the broken line represents a bond to an oxygen atom or a nitrogen atom, $W^2$ represents a single bond, —$CH_2$—, —CO—O—, or —CO—NH—, $R^7$ represents a hydrogen atom or an alkyl group having 1 to 5 carbon atoms, $R^8$ represents a hydrogen atom, or a linear or branched alkyl group having 1 to 20 carbon atoms (one or two or more —$CH_2$— groups in the alkyl group may be each independently substituted with a cycloalkyl group having a ring member number of 3 to 8, and a hydrogen atom in the alkyl group may be unsubstituted or substituted with a fluorine atom or a chlorine atom), $R^5$ represents an alkyl group having 1 to 20 carbon atoms, in which a hydrogen atom in the alkyl group may be substituted with a fluorine atom, $R^6$ represents an alkyl group having 1 to 20 carbon atoms (one —$CH_2$— group or two or more non-adjacent —$CH_2$— groups in the alkyl group are substituted with —CH=CH—, —CF=CF—, and/or —C≡C—, one or two or more —$CH_2$— groups in the alkyl group may be each independently substituted with a cycloalkyl group having a ring member number of 3 to 8, and a hydrogen atom in the alkyl group may be substituted with a fluorine atom or a chlorine atom), and r represents 0, 1, or 2).

(47) The compound as described in (45), in which in the general formula (I), L represents any substituent selected from the group consisting of the general formulae (III-1) to (III-17):

[Chem. 26]

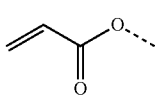
(III-1)

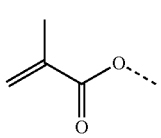
(III-2)

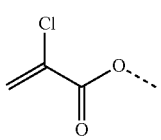
(III-3)

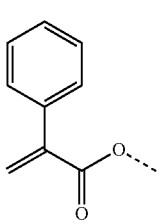
(III-4)

-continued (III-5) 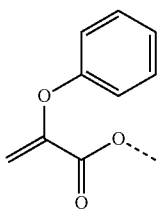

(III-6) 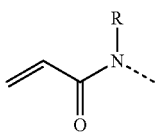

(III-7) 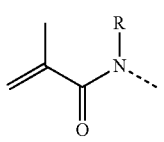

(III-8) 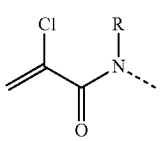

(III-9) 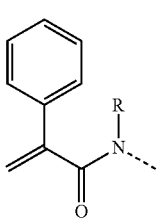

(III-10) 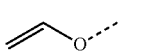

(III-11) 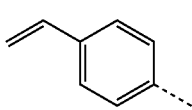

(III-12) 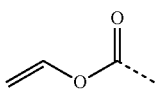

(III-13) 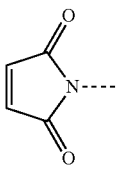

(III-14) 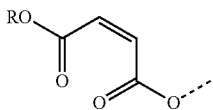

(III-15) 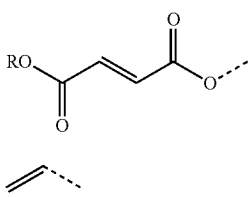

(III-16) 

(III-17) 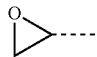

(wherein the broken line represents a bond to Sp and R's independently represent hydrogen or an alkyl group having 1 to 5 carbon atoms).

(47) The compound as described in (45) or (46), in which in the general formula (I), Sp is represented by the following general formula (IVa):

[Chem. 27]

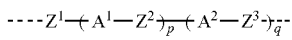  (IVa)

(wherein the left broken line represents a bond to L, the right broken line represents a bond to A or a bond to a carbon atom, to which X is bonded, $Z^1$, $Z^2$ and $Z^3$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, but one or more of the non-adjacent $CH_2$ groups in these substituents may be independently substituted with —O—, —CO—, —CO—O—, —O—CO—, —$Si(CH_3)_2$—O—$Si(CH_3)_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^1$ and $A^2$ each independently represent any group of a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and one or more hydrogen atoms in any group of these groups may be substituted with a fluorine atom, a chlorine atom, a methyl group, or a methoxy group, and p and q each independently represent 0 or 1).

(48) The compound as described in any one of (45) to (47), in which in the general formula (I), X and Y each represent a hydrogen atom.

(49) The compound as described in any one of (45) to (48), in which in the general formula (IVa), $A^2$ represents any group of a trans-1,4-cyclohexylene group, a 2,6-naphthylene group, a pyridine-2,5-diyl group, a pyrimidine-2,5-diyl group, or a 1,4-phenylene group, one or more hydrogen atoms in any group of these groups may be substituted with a fluorine atom, a chlorine atom, a methyl group, or a methoxy group, $Z^3$ represents any one of a single bond, —$(CH_2)_u$— (wherein u represents 1 to 20), —$OCH_2$—, —$CH_2O$—, —COO—, —OCO—, —CH=CH—, or —C≡C—, one or more of the non-adjacent $CH_2$ groups in any one of these groups may be independently substituted with —O—, —CO—, —CO—O—, —O—CO—, —CH=CH—, or —C≡C—, and q represents 1.

(50) The compound as described in any one of (45) to (49), in which in the general formula (I), L is represented by the general formula (III-1), (III-2), (III-6), (III-7), or (III-13).

(51) The compound as described in any one of (45) to (50), in which in the general formula (I), A represents a 1,4-phenylene group having one or more hydrogen atoms which may be substituted with a fluorine atom, a chlorine atom, a methyl group, or a methoxy group.

(52) The compound as described in any one of (45) to (51), in which in the general formula (IVa), $A^2$ represents a 1,4-phenylene group having one or more hydrogen atoms which may be substituted with a fluorine atom, a chlorine atom, a methyl group, or a methoxy group.

(53) The compound as described in any one of (45) to (52), in which in the general formula (I), L is represented by the general formula (III-1) or (III-2).

(54) A polymer constituted with a cured product of a composition containing a compound as described in any one of (45) to (53), wherein the cured product has a structural unit represented by the general formula (PI):

[Chem. 28]

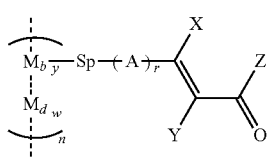
(PI)

(wherein Sp, A, X, Y, r and Z have the same definitions as in the general formula (I), $M_b$ and $M_d$ each represent a monomer unit of the polymer, y and w each represent a molar fraction of the copolymer, each satisfying $0<y\leq1$ and $0\leq w<1$, n represents 4 to 100,000, the order in which $M_b$ and $M_d$ are arranged may be the same as or different from that shown in the formula, and the monomer units of $M_b$ and $M_d$ may be each independently constituted with one or two or more different units).

(55) The polymer as described in (54), in which in the general formula (V), $M_b$ represents any one or more selected from the group consisting of the general formulae (QIII-A-1) to (QIII-A-17):

[Chem. 29]

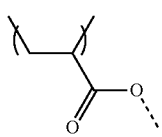
(QIII-A-1)

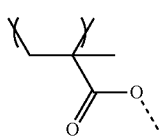
(QIII-A-2)

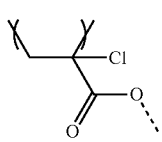
(QIII-A-3)

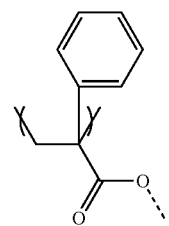
(QIII-A-4)

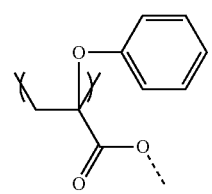
(QIII-A-5)

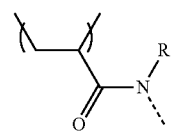
(QIII-A-6)

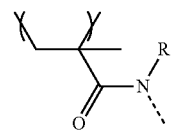
(QIII-A-7)

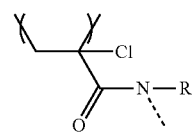
(QIII-A-8)

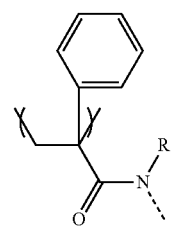
(QIII-A-9)

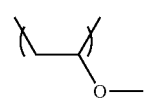
(QIII-A-10)

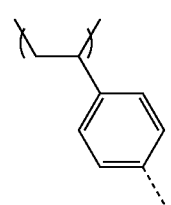
(QIII-A-11)

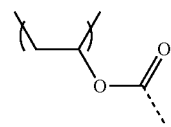
(QIII-A-12)

-continued (QIII-A-13)
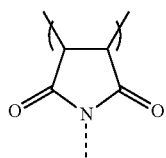

(QIII-A-14)
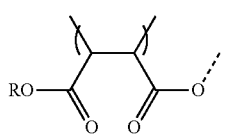

(QIII-A-15)
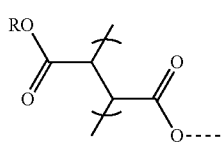

(QIII-A-16)

(QIII-A-17)
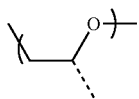

(wherein the broken line represents a bond to Sp, R's independently represent hydrogen or an alkyl group having 1 to 5 carbon atoms, and any hydrogen atom in each of the structures may be substituted with a fluorine atom, a chlorine atom, a methyl group, or a methoxy group).

(56) The polymer as described in (54) or (55), in which in the general formula (V), $M_d$ represents any one or more selected from the group consisting of the general formulae (QIII-1) to (QIII-17):

[Chem. 30]

(QIII-1)
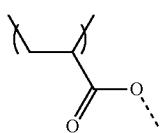

(QIII-2)
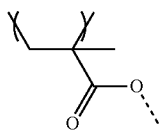

(QIII-3)
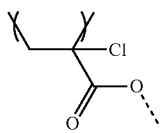

-continued (QIII-4)
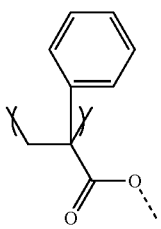

(QIII-5)
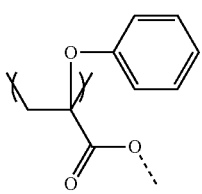

(QIII-6)
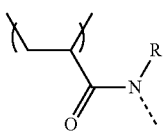

(QIII-7)
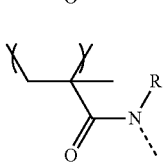

(QIII-8)
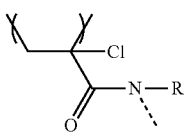

(QIII-9)
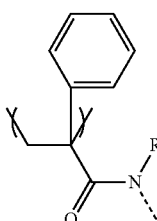

(QIII-10)
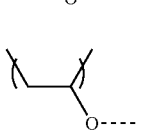

(QIII-11)

(QIII-12)

-continued

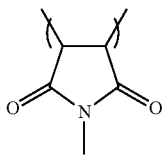
(QIII-13)

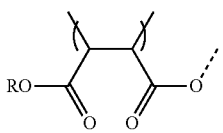
(QIII-14)

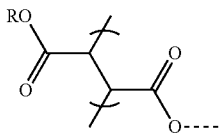
(QIII-15)

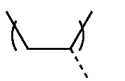
(QIII-16)

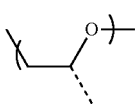
(QIII-17)

(wherein the broken line represents a bond to a hydrogen atom or a monovalent organic group, R's independently represent hydrogen or an alkyl group having 1 to 5 carbon atoms, and any hydrogen atom in each of the structures may be substituted with a fluorine atom, a chlorine atom, a methyl group, or a methoxy group).

In the general formulae (QIII-1) to (QIII-17) of (56), the monovalent organic group is preferably represented by the general formula (QIV):

[Chem. 31]

$$-S_a-V_a \qquad (QIV)$$

(wherein the broken line represents a bond to $M_d$, $S_a$ represents a structure represented by the general formula (IVa), and $V_a$ is represented by the following general formula (VI):

[Chem. 32]

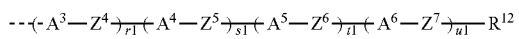
(VI)

(wherein the broken line represents a bond to $S_a$;

$Z^4$, $Z^5$, $Z^6$ and $Z^7$ each independently represent a single bond, —(CH$_2$)$_u$— (wherein u represents 1 to 20), —OCH$_2$—, —CH$_2$O—, —COO—, —OCO—, —CH=CH—, —CF=CF—, —CF$_2$O—, —OCF$_2$—, —CF$_2$CF$_2$—, or —C≡C—, but one or more of the non-adjacent CH$_2$ groups in these substituents may be independently substituted with —O—, —CO—, —CO—O—, —O—CO—, —Si(CH$_3$)$_2$—O—Si(CH$_3$)$_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^3$, $A^4$, $A^5$ and $A^6$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, r1, s1, t1, and u1 each independently represent 0 or 1, and $R^{12}$ represents hydrogen, fluorine, chlorine, a cyano group, or an alkyl group having 1 to 20 carbon atoms, a hydrogen atom in the alkyl group may be substituted with a fluorine atom, and one CH$_2$ group or two or more non-adjacent CH$_2$ groups may be substituted with —O—, —CO—O—, —O—CO—, and/or —CH=CH—)).

(57) A liquid crystal alignment layer for a vertical alignment mode liquid crystal display element, using the polymer as described in any one of (54) to (56).

(58) A vertical alignment mode liquid crystal display element using the liquid crystal alignment layer as described in (57).

(59) A liquid crystal alignment layer for a horizontal alignment mode liquid crystal display element, using the polymer as described in any one of (54) to (56).

(60) A horizontal alignment mode liquid crystal display element using the liquid crystal alignment layer as described in (59).

(61) An optical anisotropic body constituted with a polymer of a polymerizable liquid crystal composition, in which polymerizable liquid crystal molecules in the polymerizable liquid crystal composition are aligned using the polymer as described in any one of (54) to (56).

(62) A compound represented by the general formula (I):

[Chem. 33]

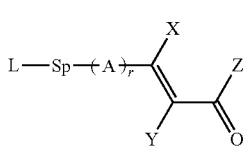
(I)

(wherein L represents a polymerizable group, Sp represents a spacer unit, A's each independently represent a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, X and Y each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one CH$_2$ group or two or more non-adjacent CH$_2$ groups may be substituted with —O—, —CO—O—, —O—CO—, and/or —CH=CH—, and Z is represented by the general formula (IIa) or (IIb):

[Chem. 34]

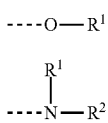

(IIa)

(IIb)

(wherein the broken line represents a bond to a carbon atom, to which Z is bonded, $R^1$ represents a linear or branched alkyl group having 1 to 30 carbon atoms (one —$CH_2$— group or two or more non-adjacent —$CH_2$— groups in the alkyl group are substituted with —O—, —CO—, —CO—O—, —O—CO—, —CO—NH—, —NH—CO—, —$NCH_3$—, and one or two or more —$CH_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), and $R^2$ represents a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom)), and r represents 0, 1, or 2).

In the general formula (IIa) or (IIb) of (62), $R^1$ is preferably represented by the general formula (IIc):

[Chem. 35]

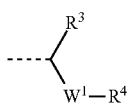

(IIc)

(wherein the broken line represents a bond to an oxygen atom or a nitrogen atom, $W^1$ represents a methylene group (a hydrogen atom of the methylene group may be unsubstituted or substituted with an alkyl group having 1 to 5 carbon atoms), —CO—O—, or —CO—NH—, $R^3$ represents a hydrogen atom or an alkyl group having 1 to 5 carbon atoms, and $R^4$ represents a linear or branched alkyl group having 1 to 20 carbon atoms (one —$CH_2$— group or two or more non-adjacent —$CH_2$— groups in the alkyl group are substituted with —O—, —CO—, —CO—O—, —O—CO—, —CO—NH—, —NH—CO—, —$NCH_3$—, one or two or more —$CH_2$— groups in the alkyl group may be each independently substituted with a cycloalkyl group having a ring member number of 3 to 8, and a hydrogen atom in the alkyl group may be unsubstituted or substituted with a fluorine atom or a chlorine atom)).

(63) The compound as described in (62), in which in the general formula (I), L represents any substituent selected from the group consisting of the general formulae (III-1) to (III-17):

[Chem. 36]

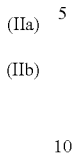

(III-1)

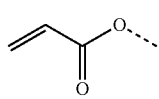

(III-2)

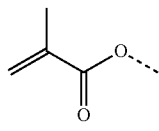

(III-3)

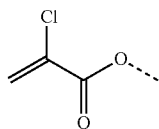

(III-4)

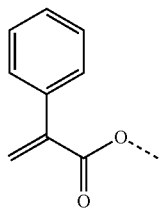

(III-5)

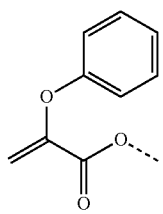

(III-6)

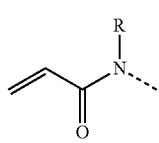

(III-7)

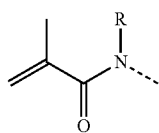

(III-8)

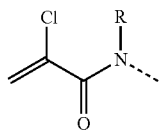

(III-9)

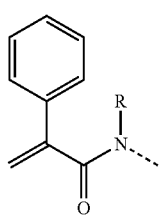

(III-10)

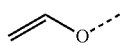

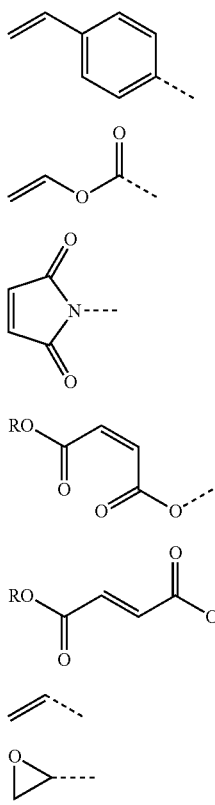

(wherein the broken line represents a bond to Sp and R's independently represent hydrogen or an alkyl group having 1 to 5 carbon atoms).

(64) The compound as described in (62) or (63), in which in the general formula (I), Sp is represented by the following general formula (IVa):

[Chem. 37]

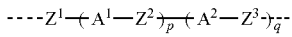

(IVa)

(wherein the left broken line represents a bond to L, the right broken line represents a bond to A, $Z^1$, $Z^2$ and $Z^3$ each independently represent a single bond, —(CH$_2$)$_u$— (wherein u represents 1 to 20), —OCH$_2$—, —CH$_2$O—, —COO—, —OCO—, —CH=CH—, —CF=CF—, —CF$_2$O—, —OCF$_2$—, —CF$_2$CF$_2$—, or —C≡C—, but one or more of the non-adjacent CH$_2$ groups in these substituents may be independently substituted with —O—, —CO—, —CO—O—, —O—CO—, —Si(CH$_3$)$_2$—O—Si(CH$_3$)$_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^1$ and $A^2$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, and p and q each independently represent 0 or 1).

(65) The compound as described in any one of (62) to (64), in which in the general formula (I), X and Y each represent a hydrogen atom.

(66) The compound as described in any one of (62) to (65), in which in the general formula (IVa), $A^2$ represents a trans-1,4-cyclohexylene group, a 2,6-naphthylene group, a pyridine-2,5-diyl group, a pyrimidine-2,5-diyl group, a 1,4-phenylene group (these may be unsubstituted or have one or more hydrogen atoms which may be substituted with a fluorine atom, a chlorine atom, a methyl group, or a methoxy group), $Z^3$ represents a single bond, —(CH$_2$)$_u$— (wherein u represents 1 to 20), —OCH$_2$—, —CH$_2$O—, —COO—, —OCO—, —CH=CH—, or —C≡C— (one or more of the non-adjacent CH$_2$ groups in these substituents may be independently substituted with —O—, —CO—, —CO—O—, —O—CO—, —CH=CH—, or —C≡C—), and q represents 1.

(67) The compound as described in any one of (62) to (66), in which in the general formula (I), L is represented by the general formula (III-1), (III-2), (III-6), (III-7), or (III-13).

(68) The compound as described in any one of (62) to (67), in which in the general formula (I), A represents a 1,4-phenylene group (these may be unsubstituted or have one or more hydrogen atoms which may be substituted with a fluorine atom, a chlorine atom, a methyl group, or a methoxy group).

(69) The compound as described in any one of (62) to (68), in which in the general formula (IVa), $A^2$ represents a 1,4-phenylene group (these may be unsubstituted or have one or more hydrogen atoms which may be substituted with a fluorine atom, a chlorine atom, a methyl group, or a methoxy group).

(70) The compound as described in any one of (62) to (69), in which in the general formula (I), L is represented by the general formula (III-1) or (III-2).

(71) A polymer constituted with a cured product of a composition containing a compound as described in any one of (62) to (70), wherein the cured product has a structural unit represented by the general formula (PI):

[Chem. 38]

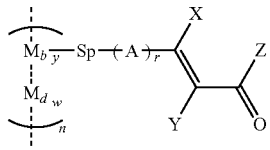

(PI)

(wherein Sp, A, X, Y, Z and r have the same definitions as in the general formula (I), $M_b$ and $M_d$ each represent a monomer unit of the polymer, y and w each represent a molar fraction of the copolymer, each satisfying 0<y≤1 and, 0≤w<1, n represents 4 to 100,000, the order in which $M_b$ and $M_d$ are arranged may be the same as or different from that shown in the formula, and the monomer units of $M_d$ may be constituted with one or two or more different units).

(72) The polymer as described in (71), in which in the general formula (PI), $M_b$ represents any substituent selected from the group consisting of the general formulae (QIII-A-1) to (QIII-A-17):

[Chem. 39]

(QIII-A-1) 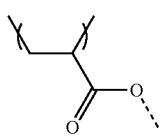

(QIII-A-2) 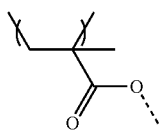

(QIII-A-3) 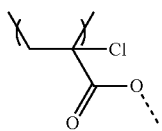

(QIII-A-4) 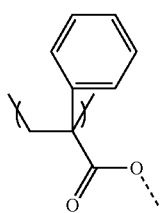

(QIII-A-5) 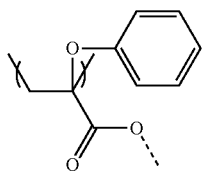

(QIII-A-6) 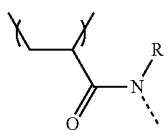

(QIII-A-7) 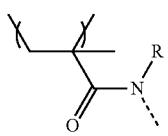

(QIII-A-8) 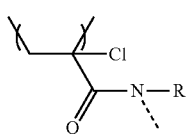

(QIII-A-9) 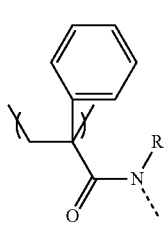

(QIII-A-10) 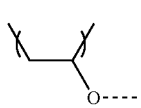

(QIII-A-11) 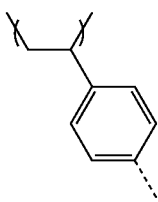

(QIII-A-12) 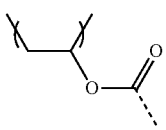

(QIII-A-13) 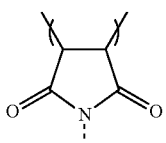

(QIII-A-14) 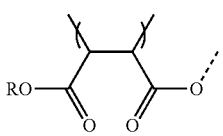

(QIII-A-15) 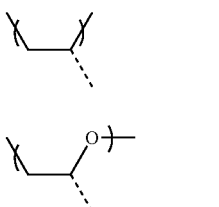

(QIII-A-16) 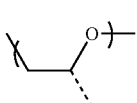

(QIII-A-17) 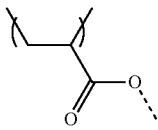

(wherein the broken line represents a bond to Sp and R's independently represent hydrogen or an alkyl group having 1 to 5 carbon atoms).

In the general formula (PI) of (71), $M_d$ preferably represents any substituent selected from the group consisting of the general formulae (QIII-1) to (QIII-17):

[Chem. 40]

(QIII-1) 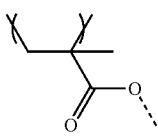

(QIII-2)

(QIII-3) 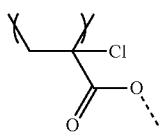

(QIII-4) 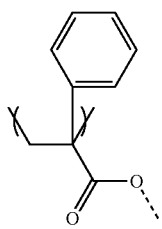

(QIII-5) 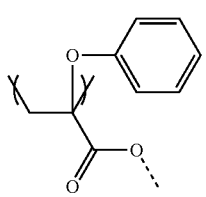

(QIII-6) 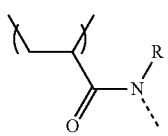

(QIII-7) 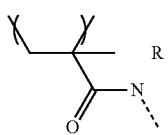

(QIII-8) 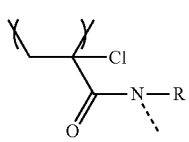

(QIII-9) 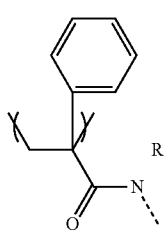

(QIII-10) 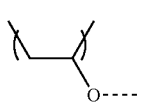

(QIII-11) 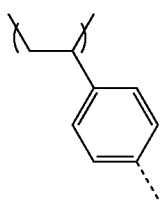

(QIII-12) 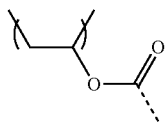

(QIII-13) 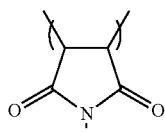

(QIII-14) 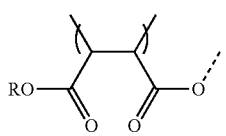

(QIII-15) 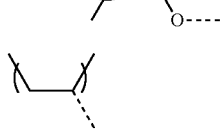

(QIII-16) 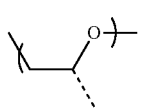

(QIII-17)

(wherein the broken line represents a bond to a hydrogen atom or a monovalent organic group, and R's independently represent hydrogen or an alkyl group having 1 to 5 carbon atoms).

Preferably, in the general formulae (QIII-1) to (QIII-17), the monovalent organic group is represented by the general formula (QIV):

[Chem. 41]

$$-S_a-V_a \quad \text{(QIV)}$$

(wherein the broken line represents a bond to $M_d$, $S_a$ represents a structure represented by the general formula (IVa), and $V_a$ represents the following general formula (V):

[Chem. 42]

$$---(A^3-Z^4)_{\overline{r1}}(A^4-Z^5)_{\overline{s1}}(A^5-Z^6)_{\overline{t1}}(A^6-Z^7)_{\overline{u1}}R^{12} \quad \text{(V)}$$

(wherein the broken line represents a bond to $S_a$;
$Z^4$, $Z^5$, $Z^6$ and $Z^7$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, but one or more of the non-adjacent $CH_2$ groups in these substituents may be independently substituted with —O—, —CO—, —CO—O—, —O—CO—, —Si(CH$_3$)$_2$—O—Si(CH$_3$)$_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^3$, $A^4$, $A^5$ and $A^6$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, r1, s1, t1, and u1 each independently represent 0 or 1, and $R^{12}$ represents hydrogen, fluorine, chlorine, a cyano group, or an alkyl group having 1 to 20 carbon atoms, a hydrogen atom in the alkyl group may be substituted with a fluorine atom, and one $CH_2$ group or two or more non-adjacent $CH_2$ groups may be substituted with —O—, —CO—O—, —O—CO—, and/or —CH═CH—).

(73) A liquid crystal alignment layer for a vertical alignment mode liquid crystal display element, using the polymer as described in (71) or (72).

(74) A vertical alignment mode liquid crystal display element using the liquid crystal alignment layer as described in (73).

(75) A liquid crystal alignment layer for a horizontal alignment mode liquid crystal display element, using the polymer as described in (71) or (72).

(76) A horizontal alignment mode liquid crystal display element using the liquid crystal alignment layer as described in (75).

(77) An optical anisotropic body constituted with a polymer of a polymerizable liquid crystal composition, in which polymerizable liquid crystal molecules in the polymerizable liquid crystal composition are aligned using the polymer as described in (71) or (72).

Advantageous Effects of Invention

By using the compound (cinnamic acid derivative) of the present invention and a polymer thereof, a liquid crystal alignment layer which has a superior ability to control the alignment of the liquid crystals and the pretilt angles, and a high voltage holding ratio (VHR) can be produced, which is efficiently provided with an alignment property at a low dose of irradiation of polarized light. Since the liquid crystal alignment layer of the present invention has a high voltage holding ratio (VHR) and is excellent in the control of the alignment of the liquid crystals and the pretilt angles, and coatability, it can be used to efficiently produce a liquid crystal display element and a liquid crystal display element, each exhibiting excellent display properties and reliability. Further, the optical anisotropic body of the present invention is useful for the production of an optical anisotropy film that can be used in optical compensation or the like.

DESCRIPTION OF EMBODIMENTS

Hereinafter, preferable examples of the present invention will be described, but the present invention is not limited thereto in any case. Within a range not departing from the spirit of the present invention, addition, deletion, replacement, and other modifications in the constitution may be made.

First Embodiment

The first embodiment of the present invention will be described.

(Cinnamic Acid Derivative)

The cinnamic acid derivative of the present invention is specifically preferably a structure represented by the general formula (I).

[Chem. 43]

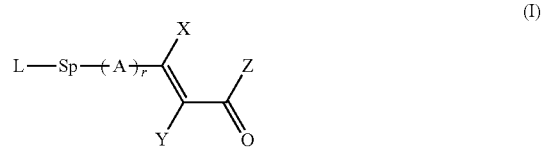
(I)

In the general formula (I), L represents a polymerizable group, Sp represents a spacer unit, A's each independently represent a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, X and Y each independently represent a hydrogen atom, a fluorine atom, a chlorine atom, a cyano group, or an alkyl group having 1 to 20 carbon atoms, a hydrogen atom in the alkyl group may be substituted with a fluorine atom, and one $CH_2$ group or two or more non-adjacent $CH_2$ groups in the alkyl group may be substituted with —O—, —CO—O—, —O—CO— and/or —CH═CH—, Z is represented by the general formula (IIa) or (IIb), and r represents 1 or 2.

[Chem. 44]

(IIa)
(IIb)

In the general formulae (IIa) and (IIb), the broken line represents a bond to a carbon atom, to which Z is bonded, $R^1$ represents a hydrogen atom or a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), and $R^2$ represents a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom).

The alkyl group having 1 to 30 carbon atoms, represented by $R^1$, is preferably a linear or branched alkyl group or a cycloalkyl group having a ring member number of 3 to 8, which may have the alkyl group interposed therein as a linking group.

The alkyl group having 1 to 30 carbon atoms, represented by $R^2$, is preferably a linear or branched alkyl group or a cycloalkyl group having a ring member number of 3 to 8, which may have the alkyl group interposed therein as a linking group.

In the present specification and claims, "two or more non-adjacent CH$_2$ groups" means "two or more CH$_2$ groups that are not adjacent to each other".

In the general formula (I), (IIa), or (IIb), in order to improve the liquid crystal alignment properties of the liquid crystal alignment layer of the present invention, A is preferably a pyridine-2,5-diyl group, a pyrimidine-2,5-diyl group, a 1,2,4,5-tetrazine-2,5-diyl group, or a 1,4-phenylene group.

Furthermore, in order to improve the solubility of the polymer of the present invention, A is preferably a 1,4-naphthylene group, a 2,6-naphthylene group, a 2,5-thiophenylene group, or a 2,5-furanylene group.

Moreover, in order to reduce the light irradiation dose required for aligning the liquid crystal in the liquid crystal alignment layer of the present invention, A is preferably a pyridine-2,5-diyl group, a pyrimidine-2,5-diyl group, a 2,5-thiophenylene group, or a 1,4-phenylene group.

In addition, in the liquid crystal alignment layer of the present invention, in order to realize photo-alignment at a longer wavelength, A is preferably a pyrimidine-2,5-diyl group, a 2,5-thiophenylene group, a 2,6-naphthylene group, or a 2,5-furanylene group, and X and Y are each preferably a fluorine atom, a chlorine atom, or a cyano group.

Incidentally, in order to improve the voltage holding ratio in the liquid crystal alignment layer of the present invention, X and Y are each preferably a hydrogen atom, and R$^2$ is preferably a linear or cyclic alkyl group having 1 to 12 carbon atoms.

In addition, in order to reduce the residual charges in the liquid crystal alignment layer of the present invention, R$^2$ is preferably a linear or cyclic alkyl group having 1 to 6 carbon atoms.

In the compound represented by the general formula (I) of the present invention, X and Y are each preferably a hydrogen atom. The voltage holding ratio in the liquid crystal alignment layer of the present invention using the polymer obtained by using the compound can be improved.

In the compound represented by the general formula (I) of the present invention, A is preferably a 1,4-phenylene group having one or more hydrogen atoms which may be substituted with a fluorine atom, a chlorine atom, a methyl group, or a methoxy group.

By using the compound, a display element using a liquid crystal alignment layer which has good coatability, a superior ability to control the alignment of the liquid crystals and the pretilt angles, and a high voltage holding ratio (VHR), and the composition is obtained.

In addition, when one or more hydrogen atoms of the 1,4-phenylene group are substituted with methoxy groups, an alignment layer having a superior ability to control the alignment of the liquid crystals and the pretilt angles is formed, which is thus preferable.

Since the compounds represented by the general formula (I) have polymerizable substituents therein, the compounds can be polymerized with each other. The polymerizable substituent is preferably specifically any substituent selected from the group consisting of the substituents of the general formula (I), in which L is represented by any one of the general formulae (III-1) to (III-17), and among these, the general formula (III-1), (III-2), (III-6), (III-7), or (III-13) is preferable, and the general formula (III-1) or (III-2) is more preferable.

[Chem. 45]

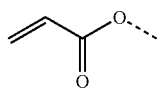 (III-1)

[Chem. 45]

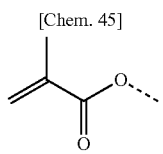 (III-2)

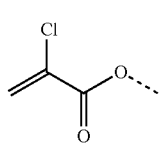 (III-3)

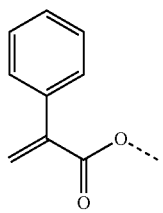 (III-4)

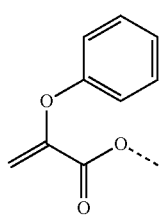 (III-5)

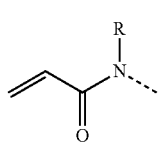 (III-6)

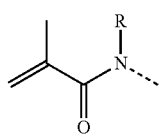 (III-7)

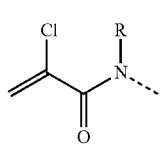 (III-8)

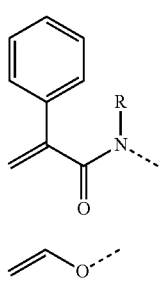 (III-9)

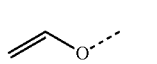 (III-10)

-continued

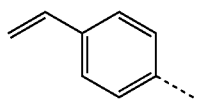 (III-11)

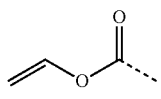 (III-12)

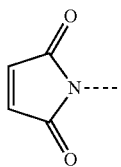 (III-13)

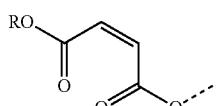 (III-14)

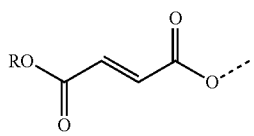 (III-15)

 (III-16)

 (III-17)

(wherein the broken line represents a bond to Sp and R's independently represent hydrogen atom or an alkyl group having 1 to 5 carbon atoms).

In order to improve the solubility of the polymer of the present invention, the general formula (III-1), (III-2), (III-3), (III-6), (III-7), (III-8), (III-10), (III-12), (III-14), (III-16), or (III-17) is preferable, and among these, the general formula (III-1), (III-2), (III-10), (III-12), or (III-17) is particularly preferable.

Incidentally, in order to improve the polymerization speed of the compound of the present invention, the general formula (III-3), (III-8), (III-10), (III-12), (III-13), (III-14), (III-15), (III-16), or (III-17) is preferable, and among these, the general formula (III-3), (III-8), (III-10), (III-12), or (III-17) is more preferable.

Furthermore, in order to attain a narrow distribution of molecular weights of the polymer of the present invention, the general formula (III-2), (III-10), (III-11), or (III-12) is preferable.

Moreover, in order to improve the alignment stability in the liquid crystal alignment layer of the present invention, the general formula (III-2), (III-4), (III-5), (III-7), (III-9), (III-13), (III-14), or (III-15) is preferable.

In addition, in order to improve the adhesion of the polymer of the present invention to a substrate, the general formula (III-1), (III-6), (III-7), (III-8), (III-9), (III-10), (III-12), (III-13), or (III-17) is preferable, and among these, the general formula (III-6), (III-7), (III-8), or (III-13) is particularly preferable.

For the molecular weight distribution of the polymer of the present invention, Mw/Mn is preferably from 1.2 to 6.0, and more preferably from 1.4 to 4.0.

The compound represented by the general formula (I) of the present invention is preferably a compound in which L is represented by the general formula (III-1), (III-2), (III-6), (III-7), or (III-13). By using the compound, the above-described effects can be obtained.

The compound represented by the general formula (I) of the present invention is preferably a compound in which L is represented by the general formula (III-1) or (III-2).

By using the compound, a display element using a liquid crystal alignment layer having a superior ability to control the alignment of the liquid crystals and the pretilt angles and having effects such as a high voltage holding ratio (VHR) and the composition can be obtained.

In the general formula (I), Sp is preferably a structure represented by the following general formula (IVc):

[Chem. 46]

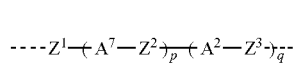 (IVc)

(wherein the left broken line represents a bond to L and the right broken line represents a bond to A, $Z^1$, $Z^2$ and $Z^3$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, but one or more of the non-adjacent $CH_2$ groups in these groups may be independently substituted with —O—, —CO—, —CO—O—, —O—CO—, —Si(CH$_3$)$_2$—O—Si(CH$_3$)$_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^7$ represents any group of a 1,4-naphthylene group, a 2,6-naphthylene group, a 2,5-thiophenylene group, a 1,2,4,5-tetrazine-3,6-diyl group, or a 2,5-furanylene group, and one or more hydrogen atoms in any group of these groups may be substituted with a fluorine atom, a chlorine atom, a methyl group, or a methoxy group, $A^2$ represents any group of a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and one or more hydrogen atoms in any group of these groups may be substituted with a fluorine atom, a chlorine atom, a methyl group, or a methoxy group, and p represents 1, and q represents 1 or 2).

In the general formula (IVc), $Z^1$, $Z^2$ and $Z^3$ are each independently preferably a single bond, —$(CH_2)_u$— (wherein u represents 1 to 20, one or more of the non-adjacent $CH_2$ groups may be independently substituted with —O—, —CO—, —CO—O—, —O—CO—, —NR—, —NR—CO—, —CO—NR—, —NR—CO—NR—, —CH=CH—, —C≡C—, or —O—CO—O—, and R represents hydrogen, a methyl group, or an ethyl group), —$OCH_2$—, —$CH_2O$—, —COO—, —OCO—, —CH=CH—, —$CF_2O$—, —$OCF_2$—, or —C≡C—.

In the general formula (IVc), $Z^1$, $Z^2$ and $Z^3$ are each independently more preferably a single bond, —$(CH_2)_u$— (wherein u represents 1 to 20, and one or more of the non-adjacent $CH_2$ groups may be independently substituted with —O—, —CO—O—, —O—CO—, —CH═CH—, or —C≡C—), —OCH$_2$—, —CH$_2$O—, —COO—, —OCO—, —CH═CH—, or —C≡C—.

In the general formula (IVc), Z$^1$, Z$^2$ and Z$^3$ are each independently particularly preferably a single bond, —(CH$_2$)$_u$— (wherein u represents 1 to 20, and one or more of the non-adjacent CH$_2$ groups may be independently substituted with —O—, —CO—O—, —O—CO—, —CH═CH—, or —C≡C—), —OCH$_2$—, —CH$_2$O—, —COO—, —OCO—, —CH═CH—, or —C≡C—.

Here, "one or more of the non-adjacent CH$_2$ groups" means "one or more CH$_2$ groups that are not adjacent to each other".

In the general formula (IVc), q is preferably 1.
In the general formula (IVc), p is preferably 1.
In the general formula (IVc), A$^7$ is preferably a 1,4-naphthylene group, a 2,5-thiophenylene group, a 1,2,4,5-tetrazine-3,6-diyl group, or a 2,6-naphthylene group. A hydrogen atom of these groups may be unsubstituted or one or more hydrogen atoms of these groups may be substituted with a fluorine atom, a chlorine atom, a methyl group, or a methoxy group.

In the general formula (IVc), A$^2$ is preferably any group of a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, or a 1,4-phenylene group. A hydrogen atom of these groups may be unsubstituted or one or more hydrogen atoms of these groups may be substituted with a fluorine atom, a chlorine atom, a methyl group, or a methoxy group.

In the general formula (IVc), A$^7$ is more preferably a 1,4-naphthylene group or a 2,6-naphthylene group. A hydrogen atom of these groups may be unsubstituted or one or more hydrogen atoms of these groups may be substituted with a fluorine atom, a chlorine atom, a methyl group, or a methoxy group.

In the general formula (IVc), A$^2$ is still more preferably any group of a trans-1,4-cyclohexylene group, a 2,6-naphthylene group, a pyridine-2,5-diyl group, a pyrimidine-2,5-diyl group, or a 1,4-phenylene group. A hydrogen atom of these groups may be unsubstituted or one or more hydrogen atoms of these groups may be substituted with a fluorine atom, a chlorine atom, a methyl group, or a methoxy group.

In the general formula (IVc), A$^7$ is particularly preferably a 2,6-naphthylene group. A hydrogen atom of these groups may be unsubstituted or one or more hydrogen atoms of these groups may be substituted with a fluorine atom, a methyl group, or a methoxy group.

In the general formula (IVc), A$^2$ is each independently particularly preferably any group of a trans-1,4-cyclohexylene group, a 2,6-naphthylene group, or a 1,4-phenylene group. A hydrogen atom of these groups may be unsubstituted or one or more hydrogen atoms of these groups may be substituted with a fluorine atom, a methyl group, or a methoxy group.

Because it is possible to provide an alignment property efficiently at a low dose of irradiation of polarized light during the production of the liquid crystal alignment layer of the present invention, in the general formula (IVc), A$^7$ is preferably a 1,4-naphthylene group, a 2,5-thiophenylene group, a 1,2,4,5-tetrazine-3,6-diyl group, or a 2,6-naphthylene group, more preferably a 1,4-naphthylene group or a 2,6-naphthylene group, and still more preferably a 2,6-naphthylene group.

Because it is possible to provide an alignment property efficiently at a low dose of irradiation of polarized light during the production of the liquid crystal alignment layer of the present invention, in the general formula (IVc), A$^2$ is preferably a 1,4-naphthylene group, a 2,6-naphthylene group, or a 1,4-phenylene group, more preferably a 2,6-naphthylene group or a 1,4-phenylene group, and still more preferably a 1,4-phenylene group. If a hydrogen atom of the 1,4-phenylene group is unsubstituted or one or more hydrogen atoms are substituted with a fluorine atom, a methyl group, or a methoxy group, an alignment property may be sometimes provided at a lower dose of irradiation of polarized light, which is thus preferable.

In order to improve the liquid crystal alignment property in the liquid crystal alignment layer of the present invention, in the general formula (IVc), Z$^1$, Z$^2$ and Z$^3$ are each independently preferably a single bond, —(CH$_2$)$_u$— (wherein u represents 1 to 8 and one or two of the non-adjacent CH$_2$ groups may be independently substituted with —O—, —CO—O—, —O—CO—, —Si(CH$_3$)$_2$—O—Si(CH$_3$)$_2$—, —CH═CH—, or —C≡C—), —COO—, —OCO—, —CH═CH—, —CF═CF—, or —C≡C—, A$^7$ is preferably a 1,4-naphthylene group or a 2,6-naphthylene group, and A$^2$ is preferably a trans-1,4-cyclohexylene group, a trans-1,3-dioxane-2,5-diyl group, a pyridine-2,5-diyl group, a pyrimidine-2,5-diyl group, a 1,2,4,5-tetrazine-2,5-diyl group, a 2,5-thiophenylene group, or a 1,4-phenylene group.

Furthermore, in order to improve the thermal stability of the alignment in the liquid crystal alignment layer of the present invention, in the general formula (IVc), Z$^1$, Z$^2$ and Z$^3$ are each independently preferably —NR—CO—, —CO—NR—, —NR—CO—O—, —O—CO—NR—, —NR—CO—NR—, or —O—CO—O—, A$^7$ is preferably a 1,4-naphthylene group or a 2,6-naphthylene group, and A$^2$ is preferably a trans-1,4-cyclohexylene group, a trans-1,3-dioxane-2,5-diyl group, a pyridine-2,5-diyl group, a pyrimidine-2,5-diyl group, a 2,5-thiophenylene group, or a 1,4-phenylene group.

Furthermore, in order to improve the solubility of the polymer of the present invention, Z$^1$, Z$^2$ and Z$^3$ are each independently preferably —OCH$_2$—, —CH$_2$O—, —CF$_2$O—, —OCF$_2$—, —CF$_2$CF$_2$—, —NR—, or —CO—, A$^7$ is preferably a 1,4-naphthylene group or a 2,6-naphthylene group, and A$^2$ is preferably a trans-1,4-cyclohexylene group, a 1,4-naphthylene group, a 2,6-naphthylene group, or a 2,5-furanylene group.

Sp represented by the general formula (IVc) is preferably, for example, one represented by the following chemical formulae (Sp-a-1) to (Sp-ad-9). Among these chemical formulae, the left broken line represents a bond to L and the right broken line represents a bond to A.

Among these, those represented by the chemical formulae (Sp-a-6) to (Sp-a-16), the chemical formulae (Sp-b-3) to (Sp-b-10), the chemical formulae (Sp-c-3) to (Sp-c-10), the chemical formulae (Sp-d-3) to (Sp-d-12), the chemical formulae (Sp-k-4) to (Sp-k-7), the chemical formulae (Sp-l-13) to (Sp-l-17), the chemical formulae (Sp-o-3) to (Sp-o-14), the chemical formulae (Sp-p-2) to (Sp-p-13), the chemical formulae (Sp-s-1) to (Sp-s-8), the chemical formulae (Sp-t-1) to (Sp-t-8), the chemical formulae (Sp-y-1) to (Sp-y-9), the chemical formulae (Sp-aa-1) to (Sp-aa-9), the chemical formulae (Sp-ae-1) to (Sp-ae-9), the chemical formulae (Sp-af-1) to (Sp-af-8), the chemical formulae (Sp-ag-1) to (Sp-ag-9), and the chemical formulae (Sp-ah-1) to (Sp-ah-8) are more preferable.

[Chem. 47]
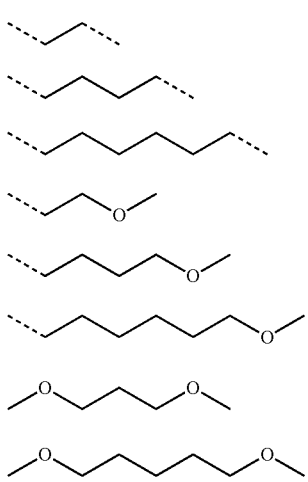 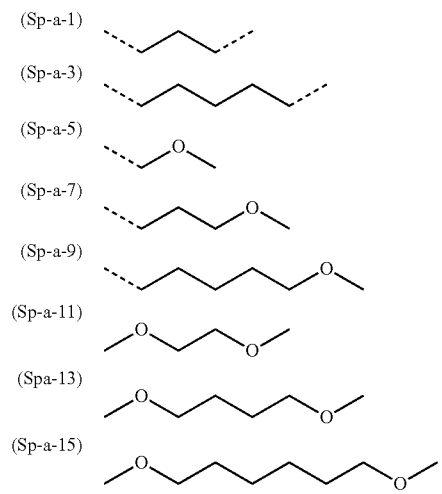
[Chem. 48]
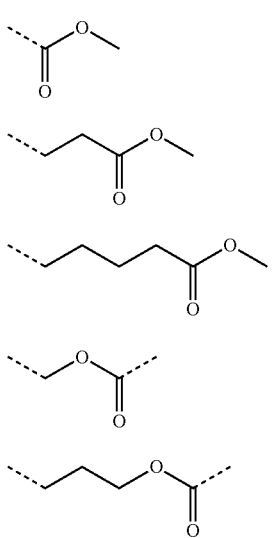 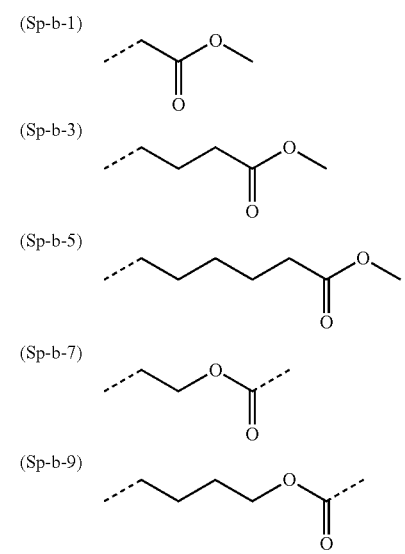
[Chem. 49]
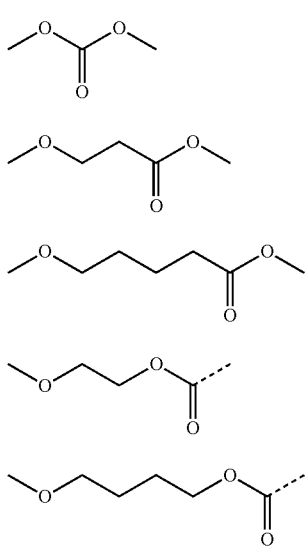 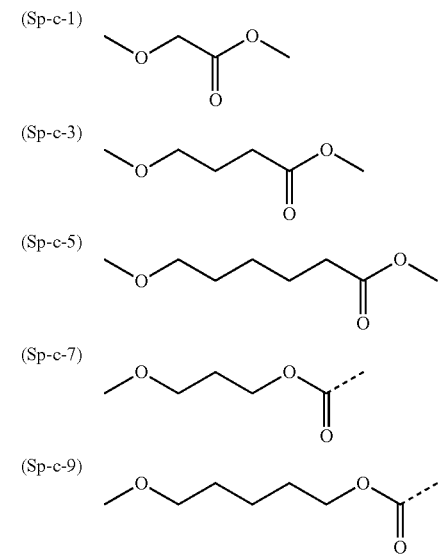

[Chem. 50]
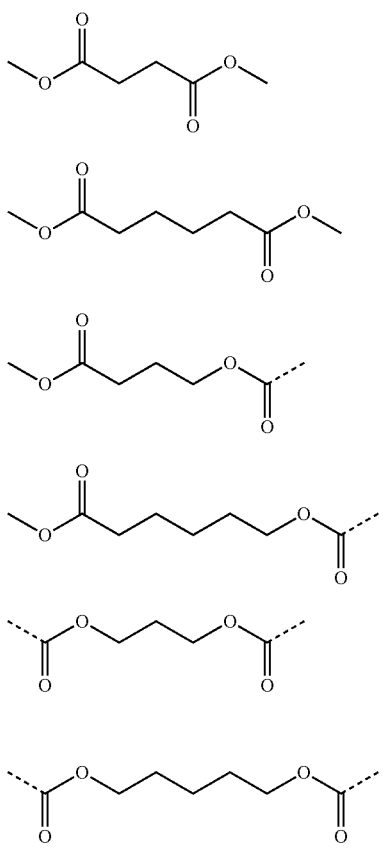
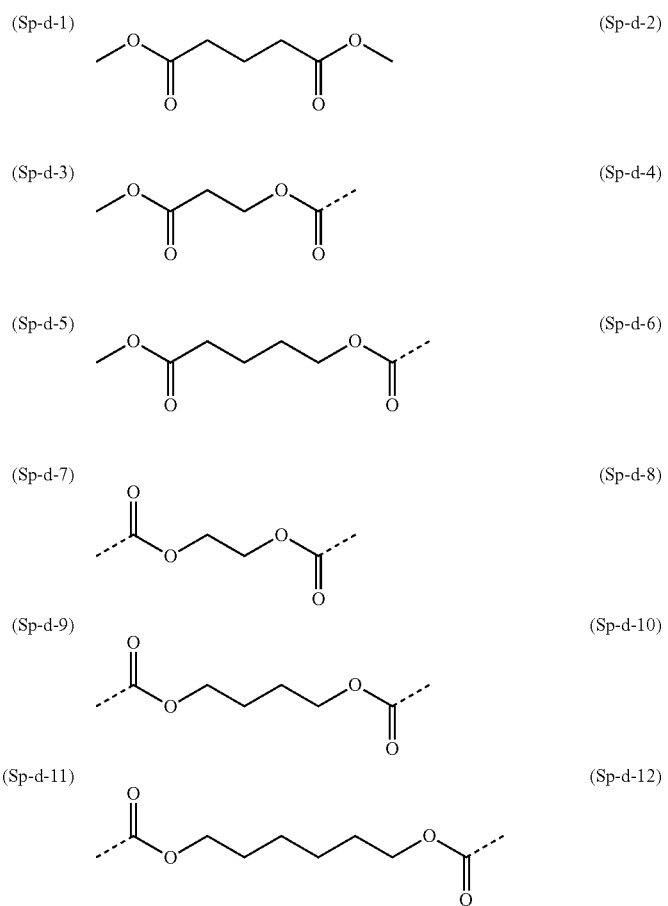
(Sp-d-1) (Sp-d-2) (Sp-d-3) (Sp-d-4) (Sp-d-5) (Sp-d-6) (Sp-d-7) (Sp-d-8) (Sp-d-9) (Sp-d-10) (Sp-d-11) (Sp-d-12)
[Chem. 51]
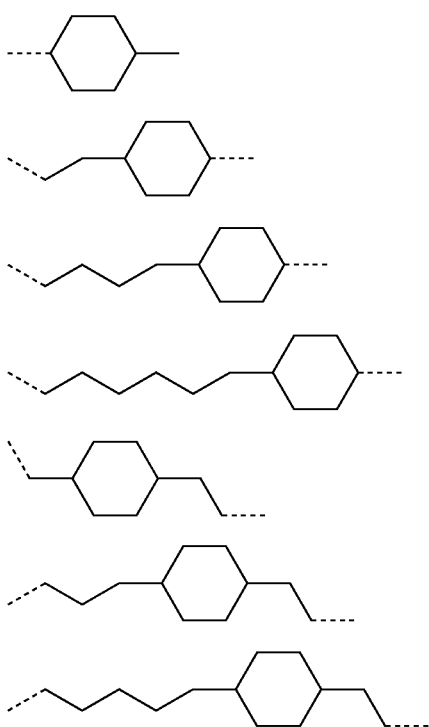
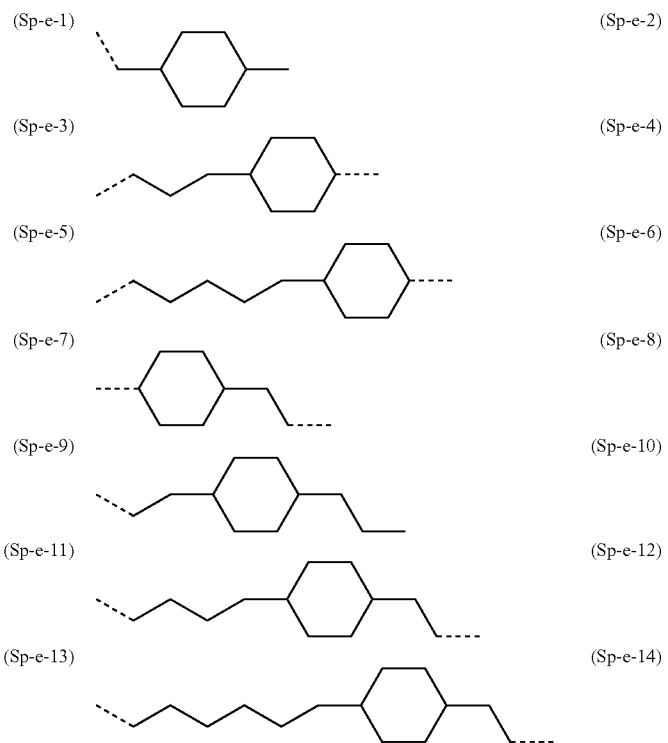
(Sp-e-1) (Sp-e-2) (Sp-e-3) (Sp-e-4) (Sp-e-5) (Sp-e-6) (Sp-e-7) (Sp-e-8) (Sp-e-9) (Sp-e-10) (Sp-e-11) (Sp-e-12) (Sp-e-13) (Sp-e-14)

[Chem. 52]
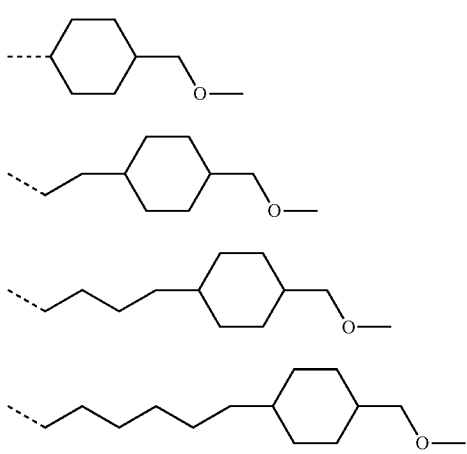
(Sp-f-1) (Sp-f-2) (Sp-f-3) (Sp-f-4) (Sp-f-5) (Sp-f-6) (Sp-f-7)
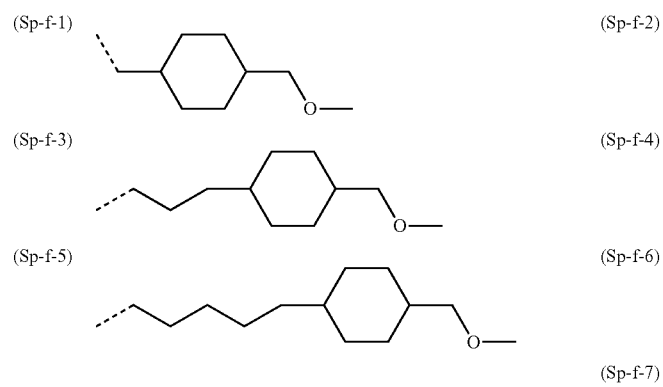
[Chem. 53]
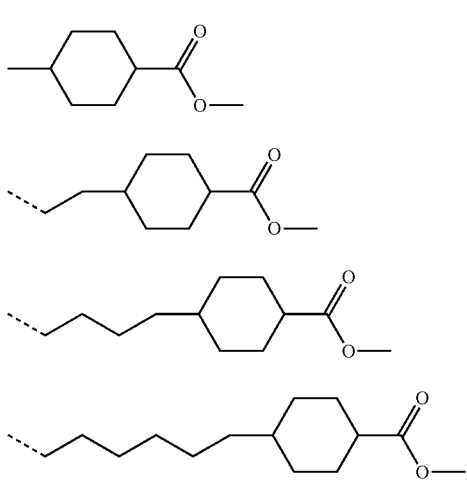
(Sp-g-1) (Sp-g-2) (Sp-g-3) (Sp-g-4) (Sp-g-5) (Sp-g-6) (Sp-g-7)
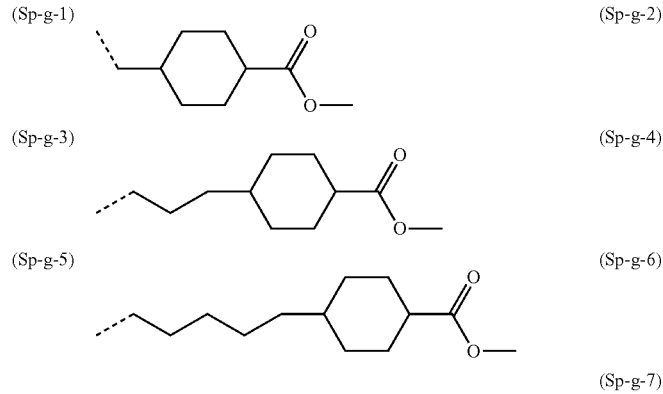
[Chem. 54]
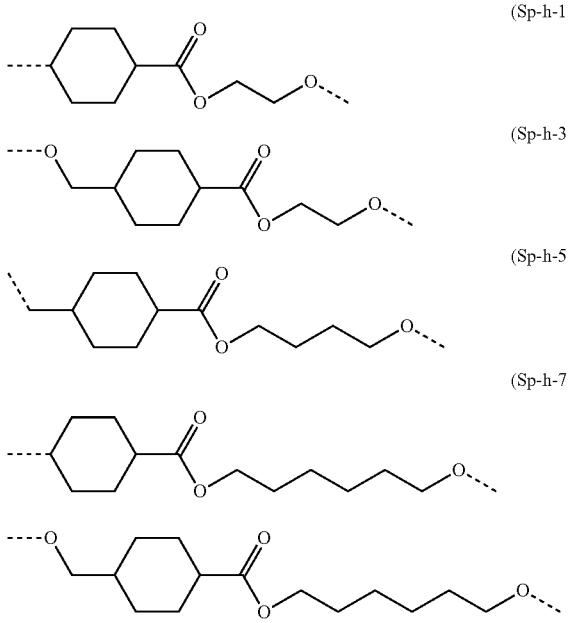
(Sp-h-1) (Sp-h-2) (Sp-h-3) (Sp-h-4) (Sp-h-5) (Sp-h-6) (Sp-h-7) (Sp-h-8) (Sp-h-9)
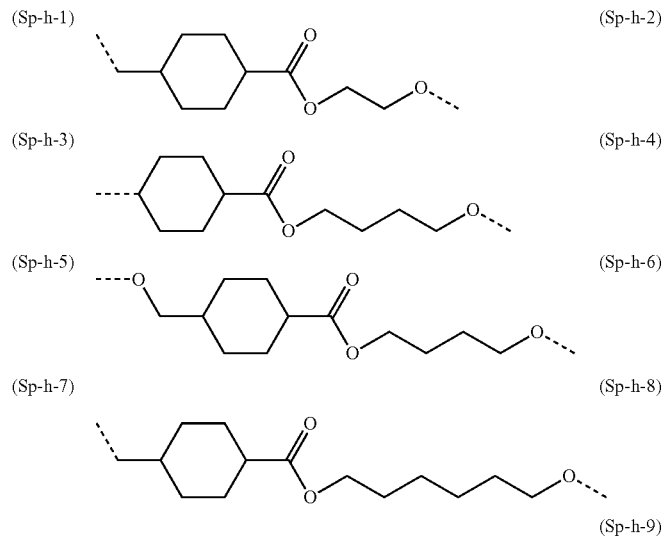

-continued
[Chem. 55]
(Sp-i-1) 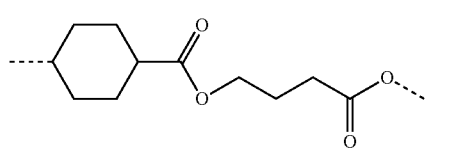
(Sp-i-2) 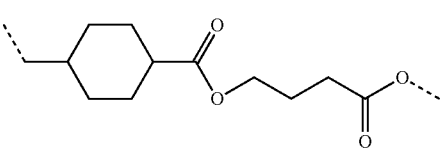
(Sp-i-3) 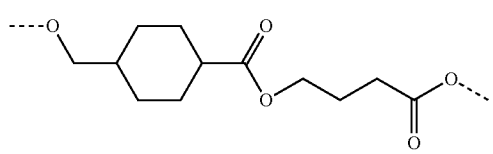
(Sp-i-4) 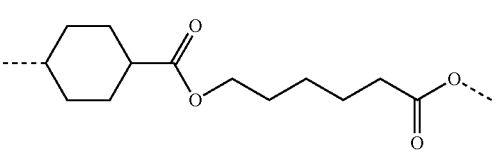
(Sp-i-5) 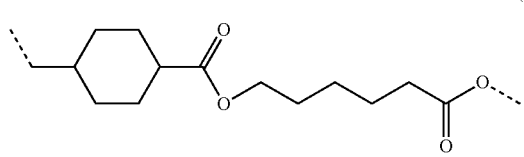
(Sp-i-6) 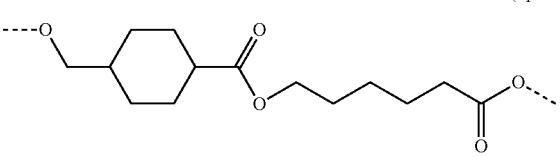
[Chem. 56]
(Sp-j-1) 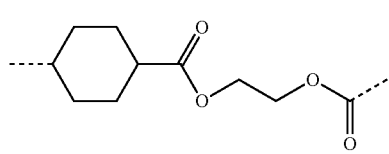
(Sp-j-2) 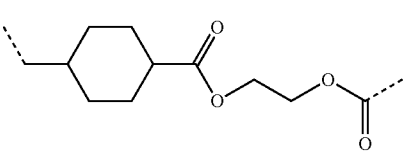
(Sp-j-3) 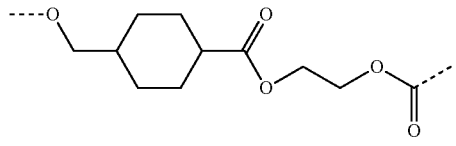
(Sp-j-4) 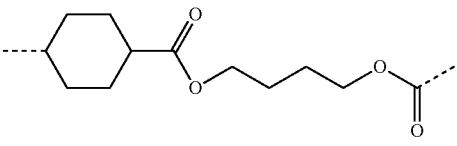
(Sp-j-5) 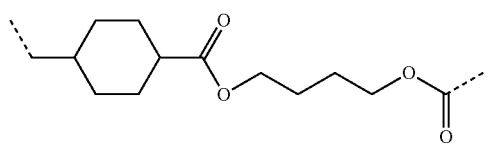
(Sp-j-6) 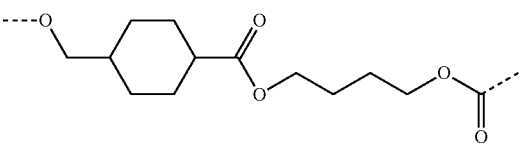
(Sp-j-7) 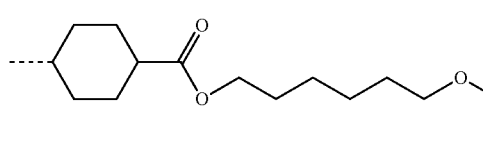
(Sp-j-8) 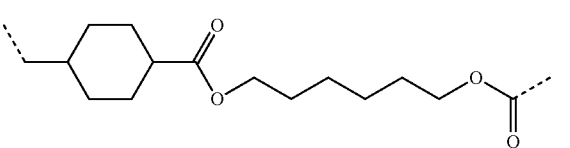
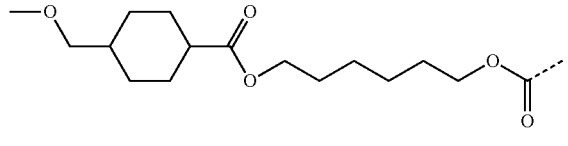
(Sp-j-9) 
[Chem. 57]
(Sp-k-1) 
(Sp-k-2) 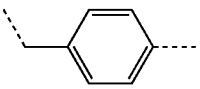
(Sp-k-3) 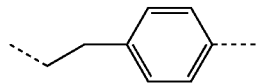
(Sp-k-4) 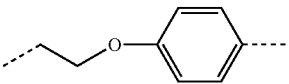

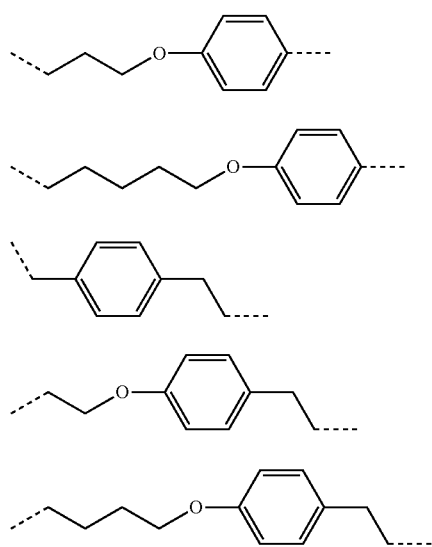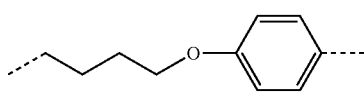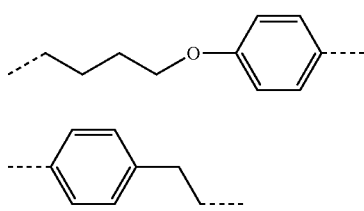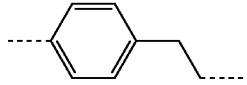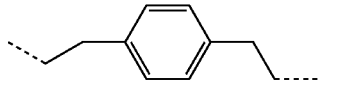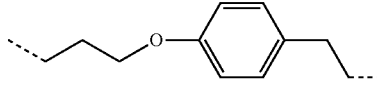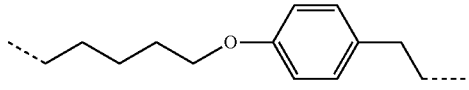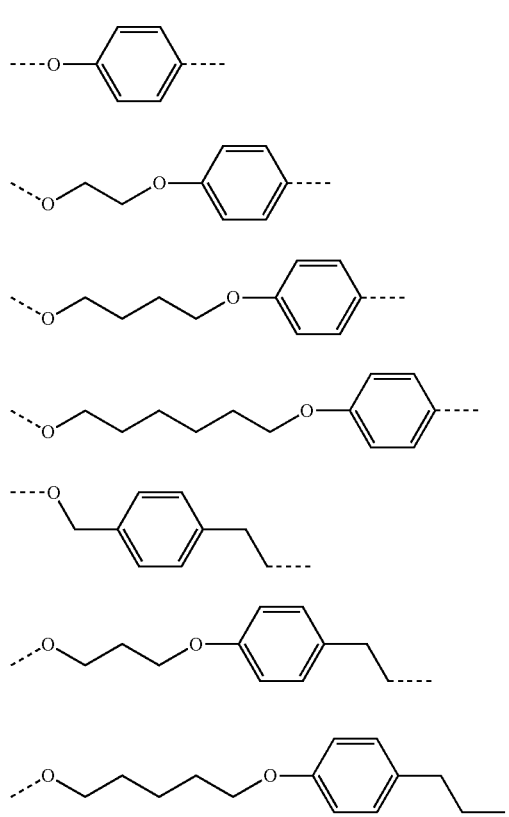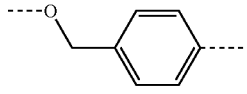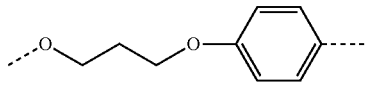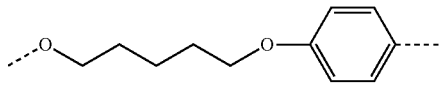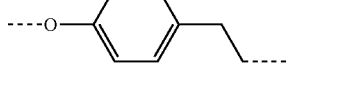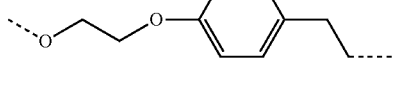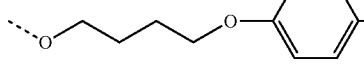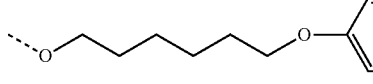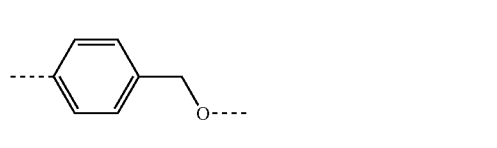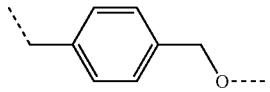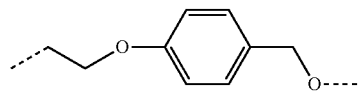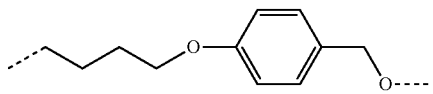

-continued
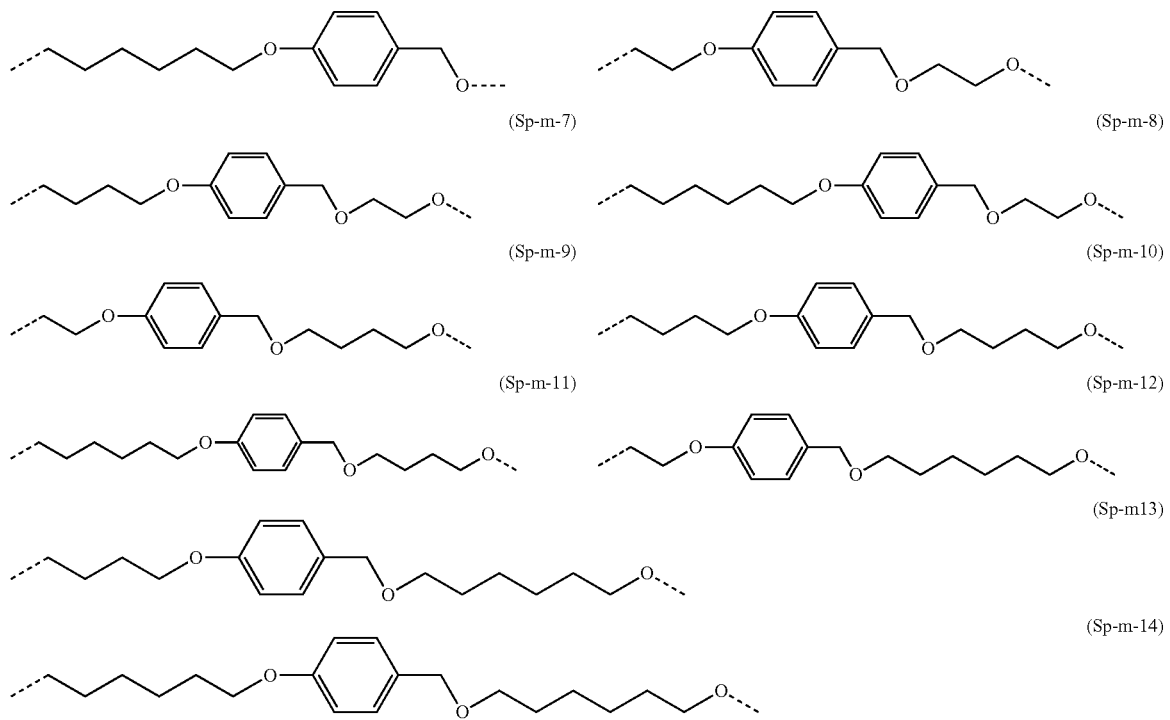
[Chem. 60]
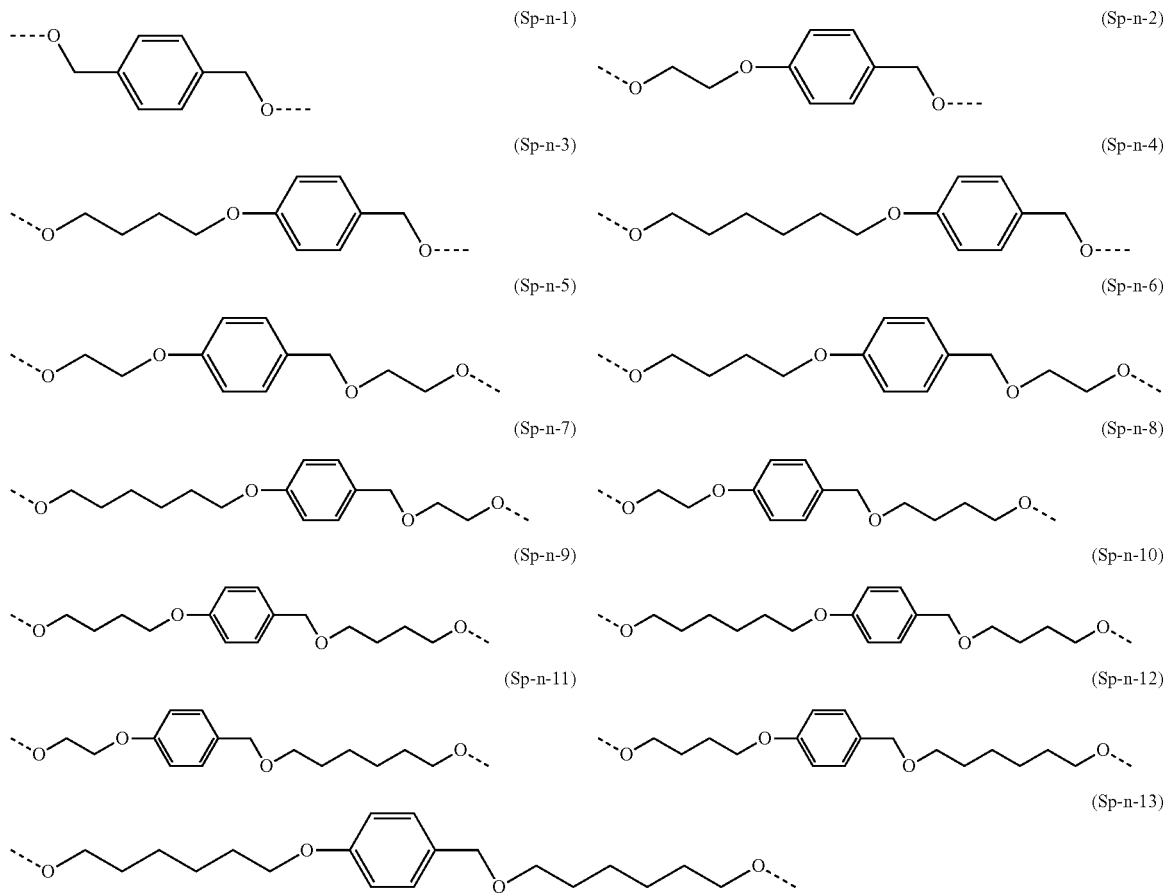

[Chem. 61]
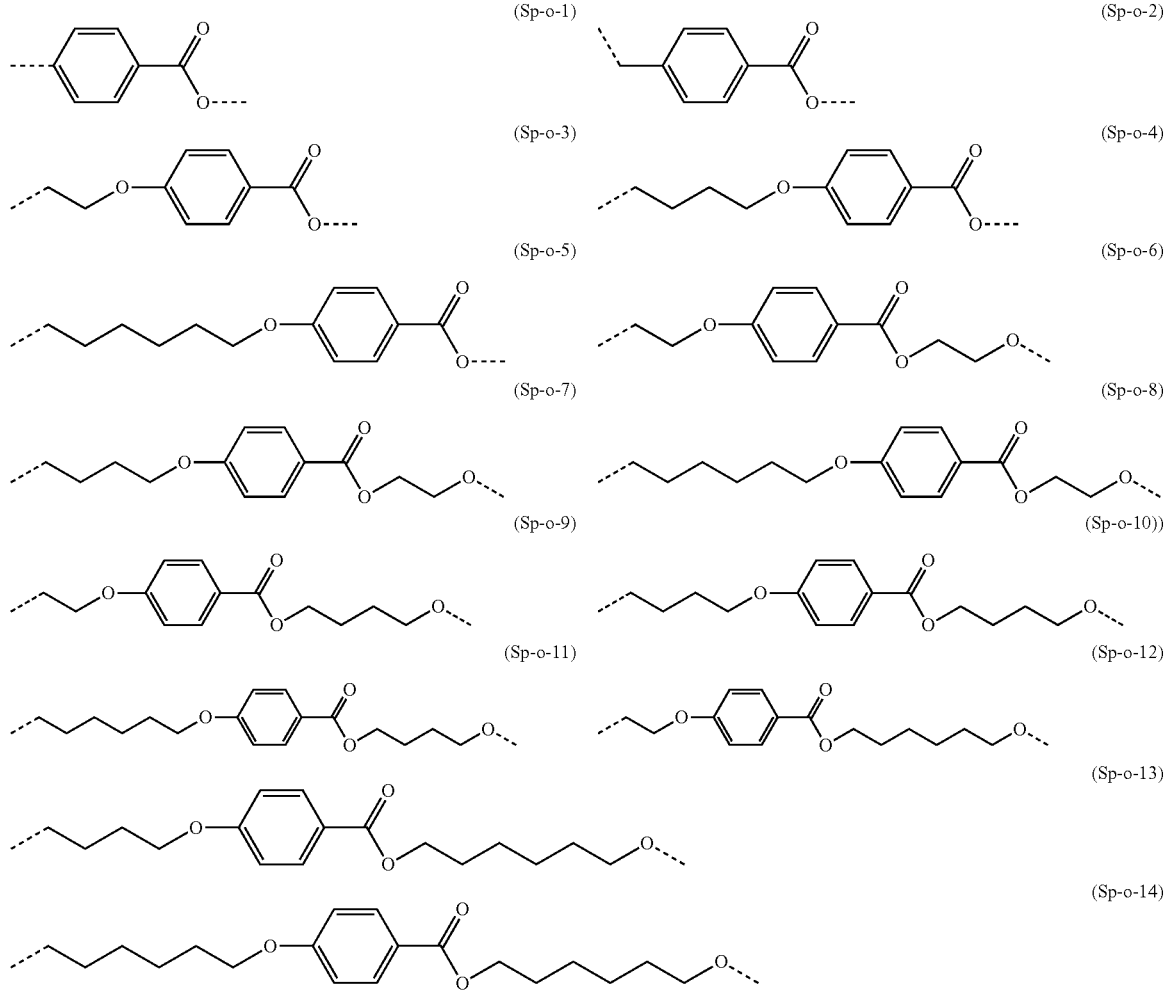
[Chem. 62]
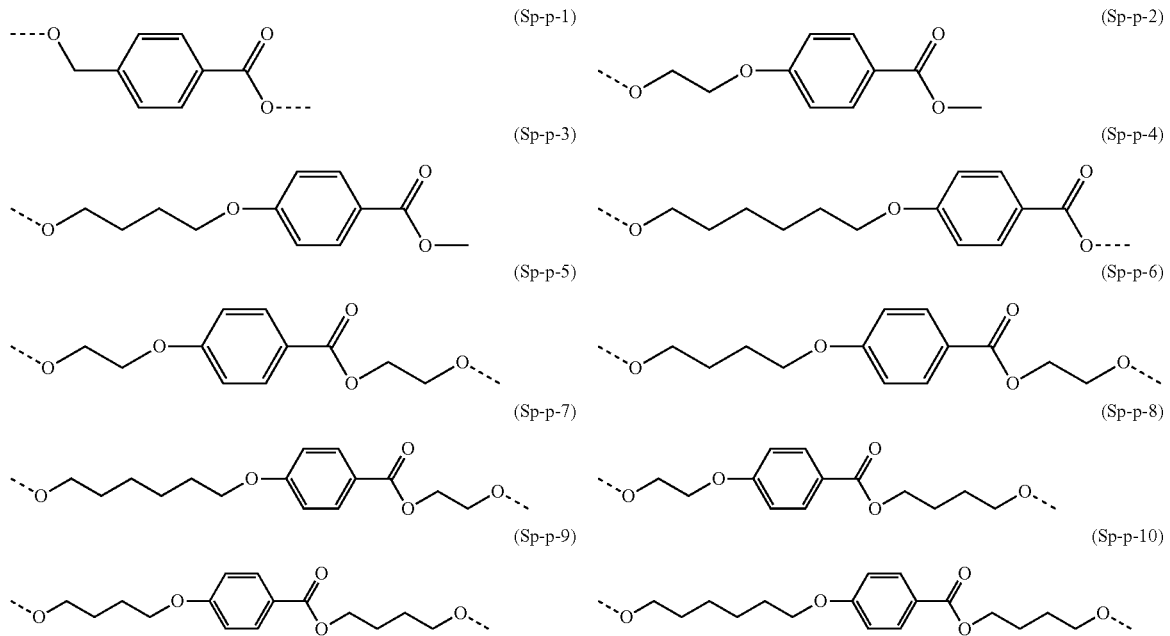

(Sp-p-11) 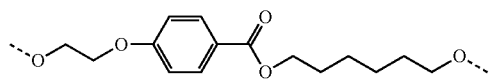
(Sp-p-12) 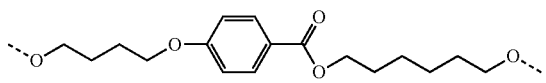
(Sp-p-13) 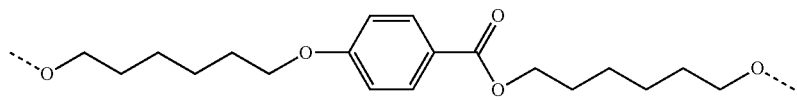
[Chem. 63]
(Sp-q-1) 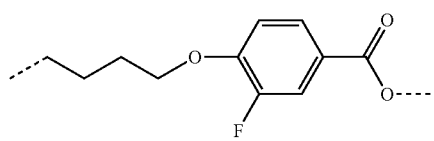  (Sp-q-2) 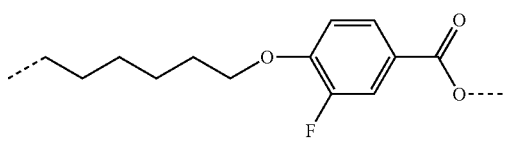
(Sp-q-3) (Sp-q-4)
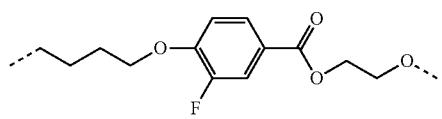
(Sp-q-5) (Sp-q-6)
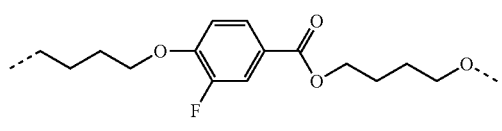
(Sp-q-7) (Sp-q-8)
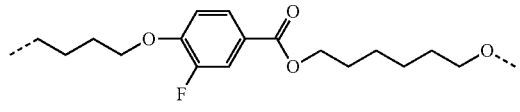
[Chem. 64]
(Sp-r-1) (Sp-r-2)
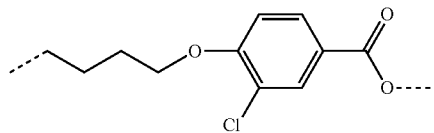
(Sp-r-3) (Sp-r-4)
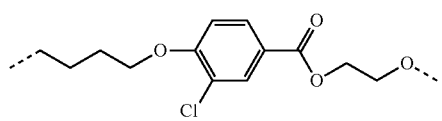
(Sp-r-5) (Sp-r-6)
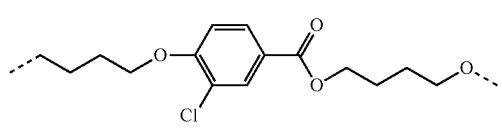
(Sp-r-7) 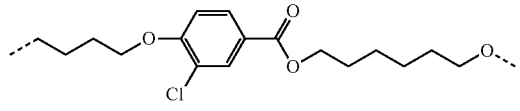  (Sp-r-8) 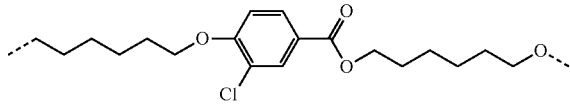

[Chem. 65]
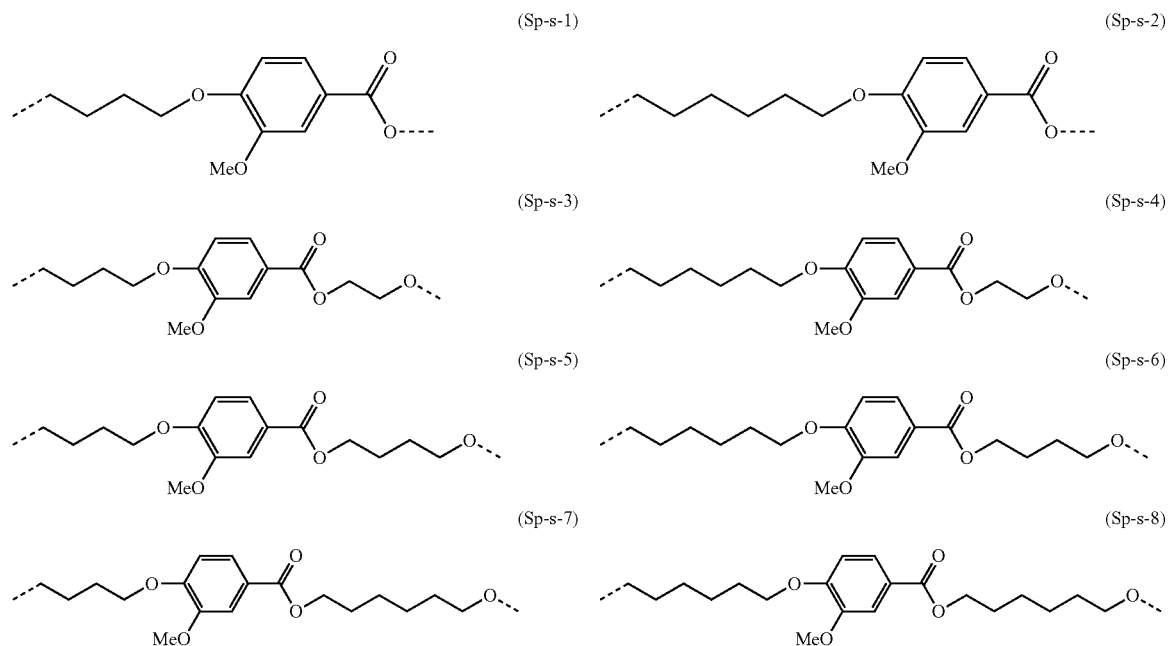
[Chem. 66]
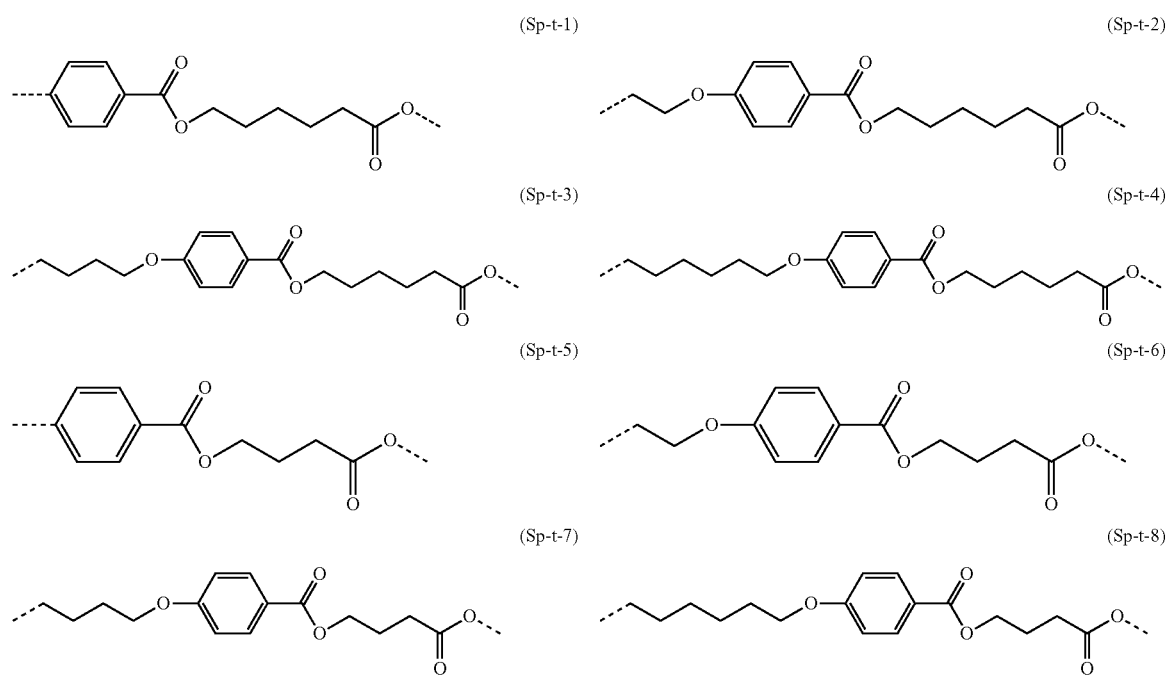
[Chem. 67]
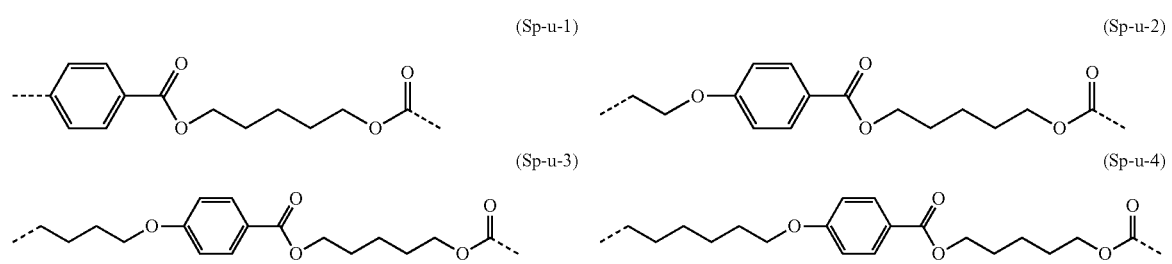

(Sp-u-5)
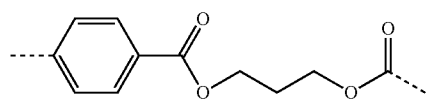
(Sp-u-6)
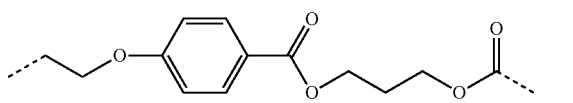
(Sp-u-7)
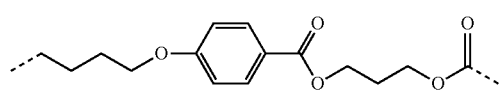
(Sp-u-8)
[Chem. 68]
(Sp-v-1)
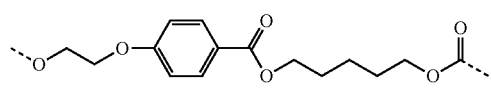
(Sp-v-2)
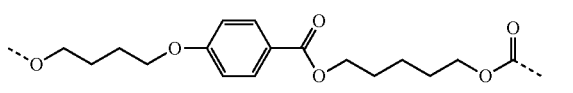
(Sp-v-3)
(Sp-v-4)
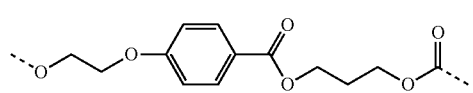
(Sp-v-5)
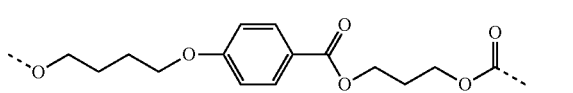
(Sp-v-6)
[Chem. 69]
(Sp-w-1)
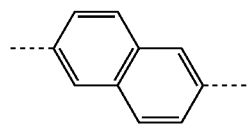
(Sp-w-2)
(Sp-w-3)
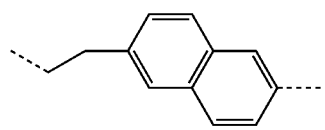
(Sp-w-4)
(Sp-w-5)
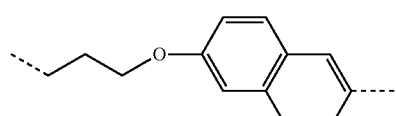
(Sp-w-6)
(Sp-w-7)
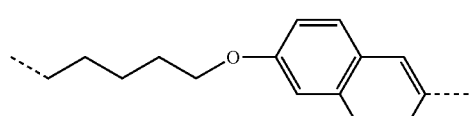
(Sp-w-8)
[Chem. 70]
(Sp-x-1)
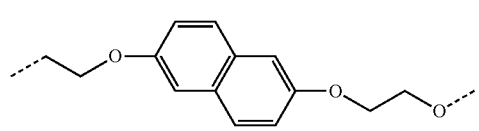
(Sp-x-2)
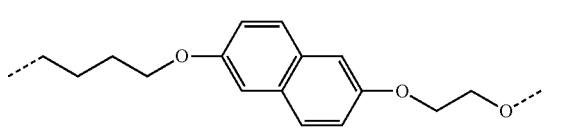

-continued
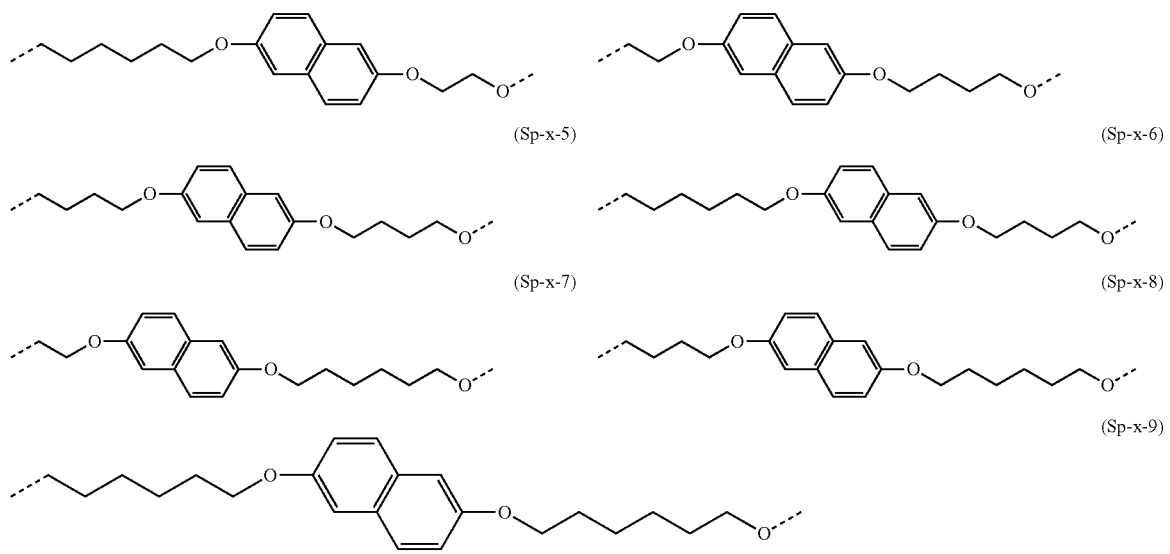
[Chem. 71]
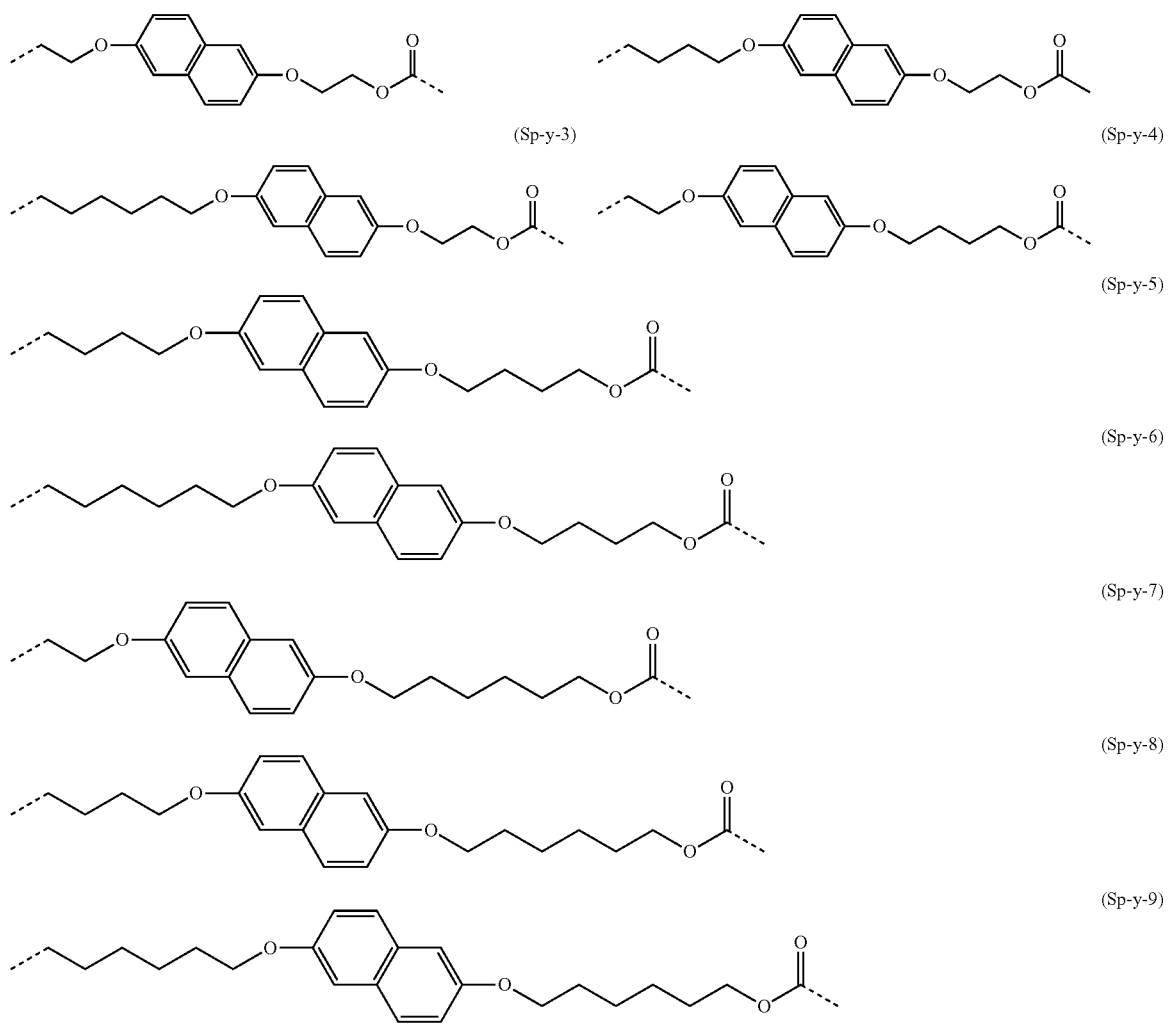

-continued
[Chem. 72]
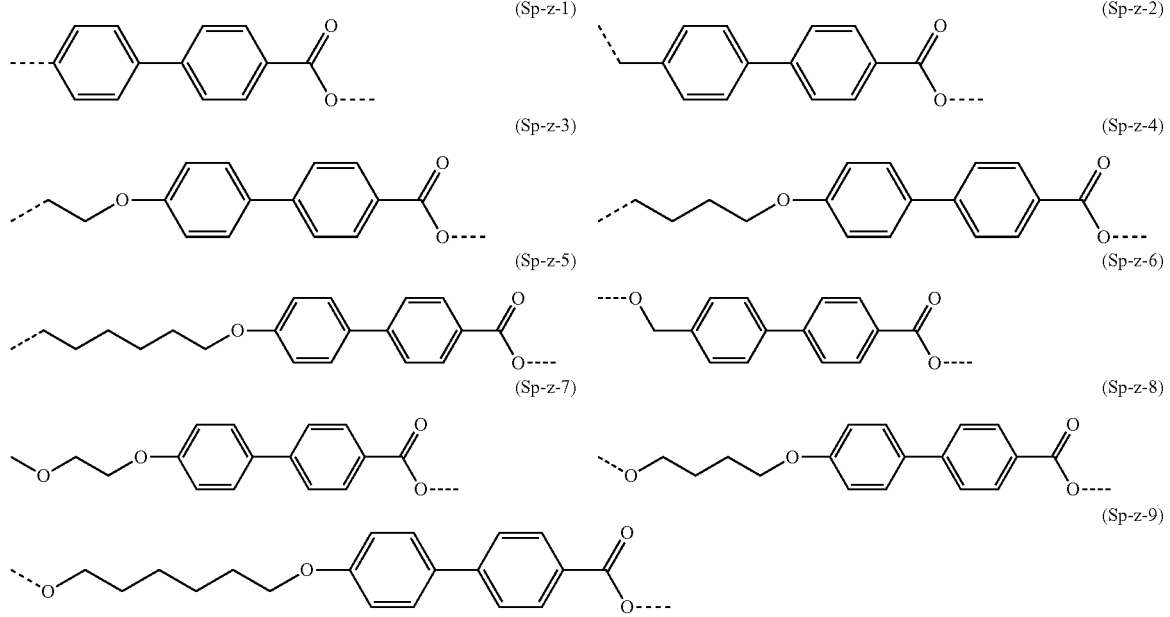
[Chem. 73]
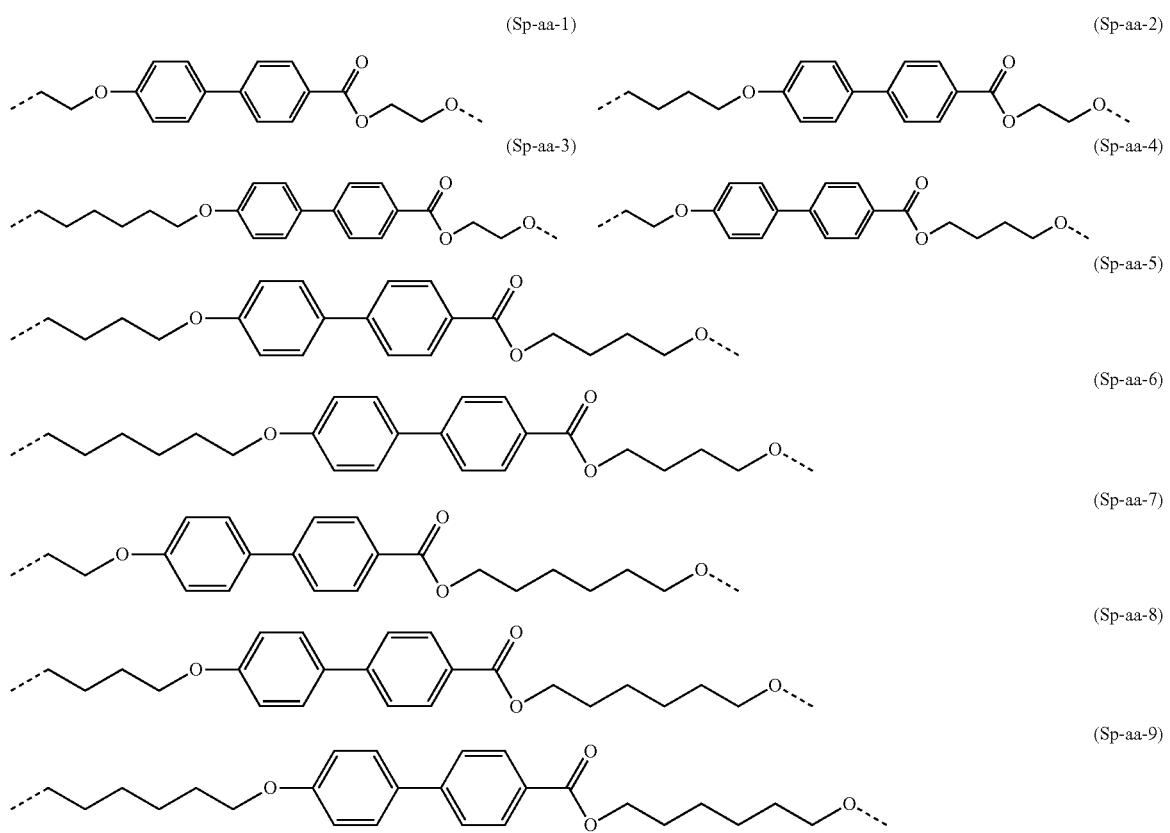
[Chem. 74]
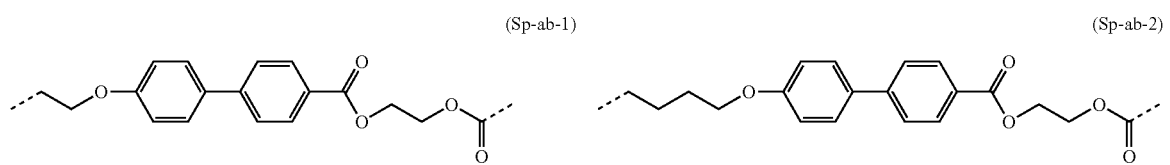

-continued
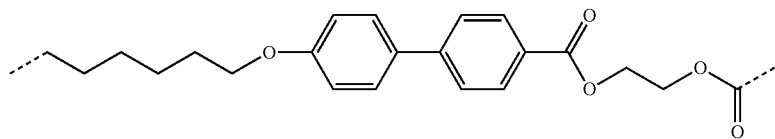
(Sp-ab-3)
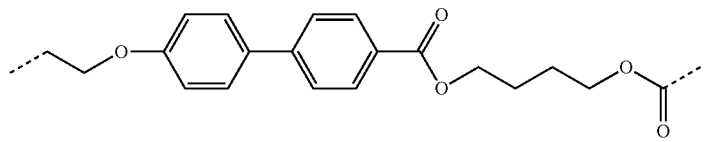
(Sp-ab-4)
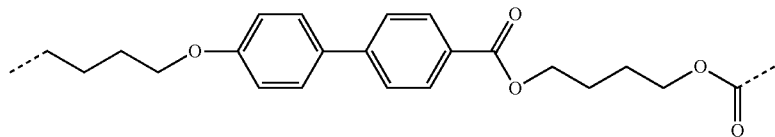
(Sp-ab-5)
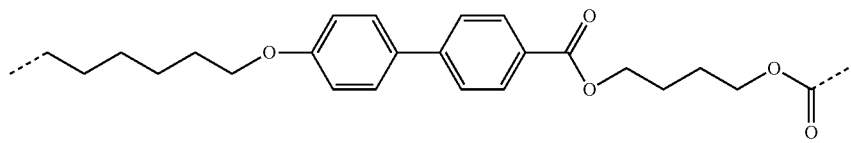
(sp-ab-6)
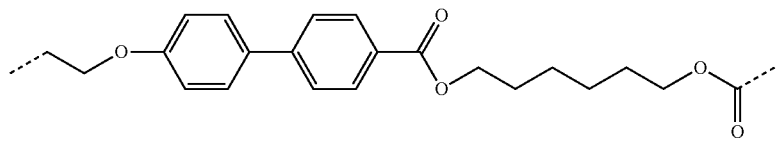
(Sp-ab-7)
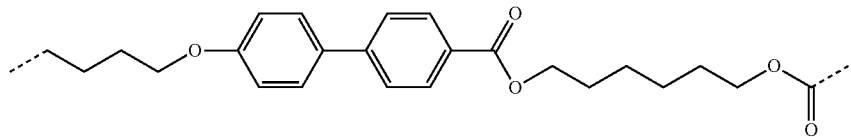
(Sp-ab-8)
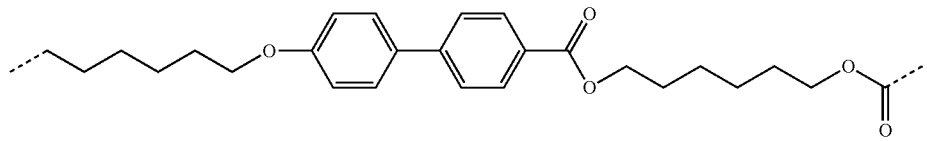
(Sp-ab-9)
[Chem. 75]
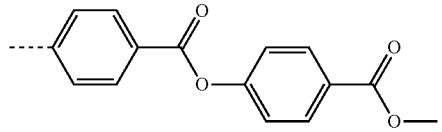
(Sp-ac-1)
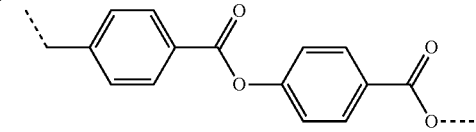
(Sp-ac-2)
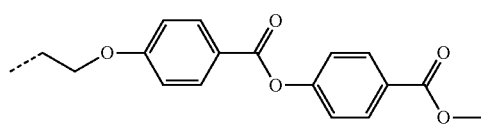
(Sp-ac-3)
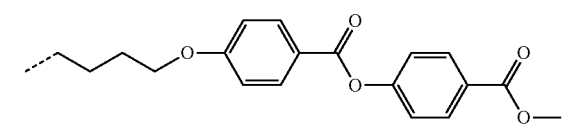
(Sp-ac-4)
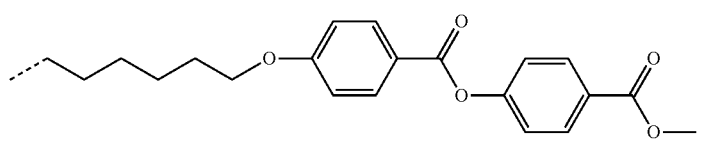
(Sp-ac-5)

-continued
(Sp-ad-1) 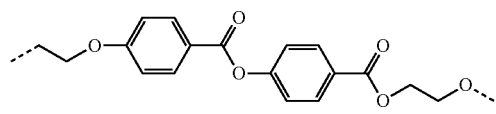
(Sp-ad-2) 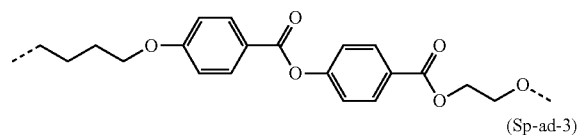
(Sp-ad-3) 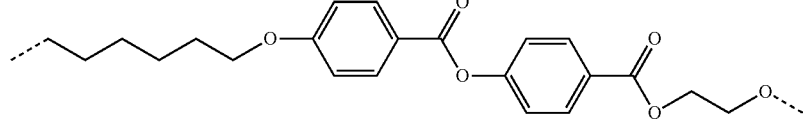
(Sp-ad-4) 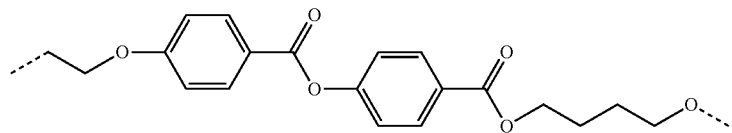
(Sp-ad-5) 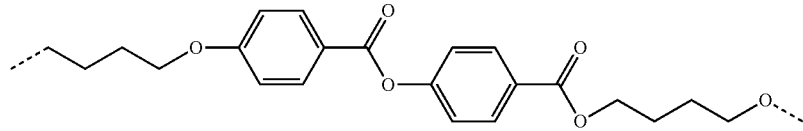
(Sp-ad-6) 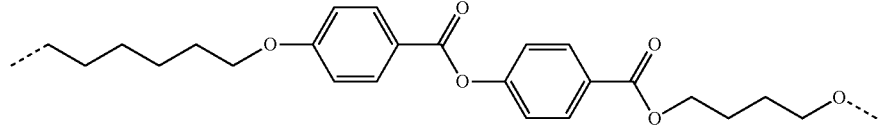
(Sp-ad-7) 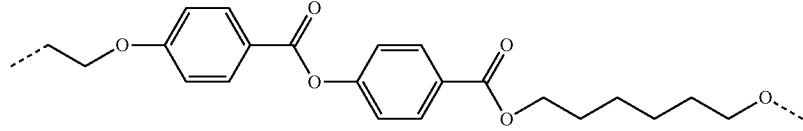
(Sp-ad-8) 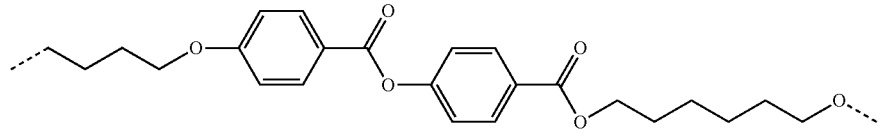
(Sp-ad-9) 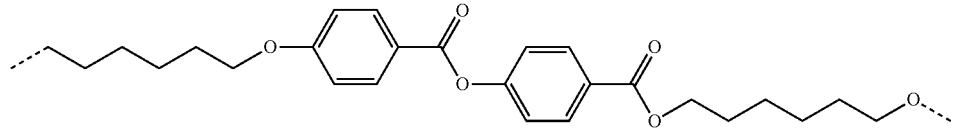
(Sp-ae-1) 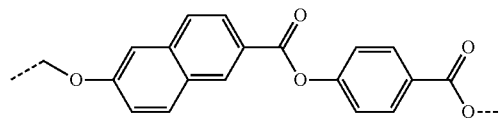
(Sp-ae-2) 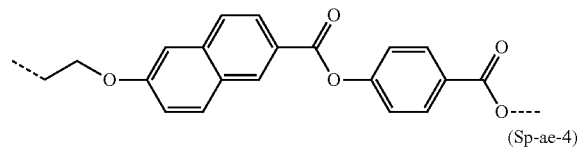
(Sp-ae-3) 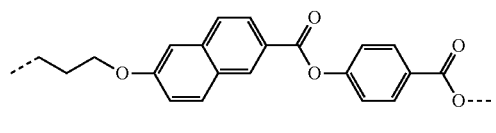
(Sp-ae-4) 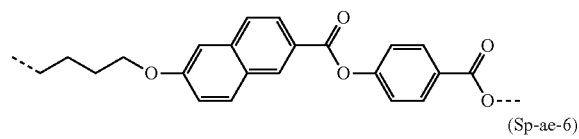
(Sp-ae-5) 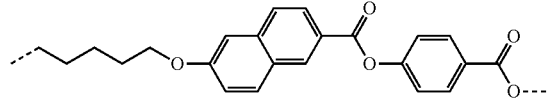
(Sp-ae-6) 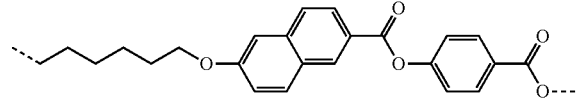

-continued
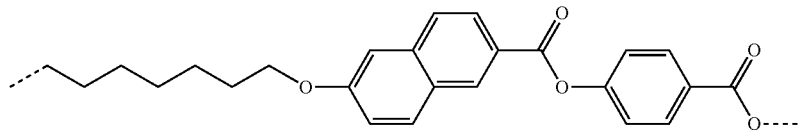
(Sp-ae-7)
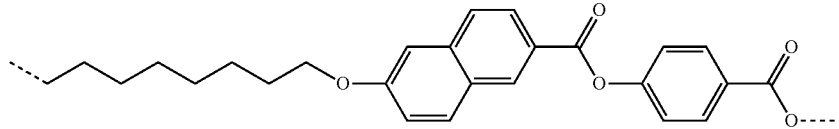
(Sp-ae-8)
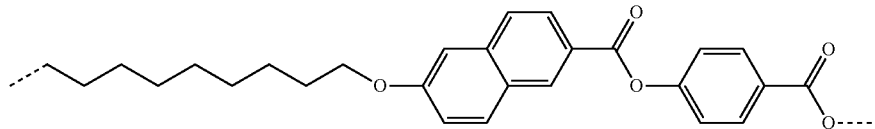
(Sp-ae-9)
[Chem. 78]
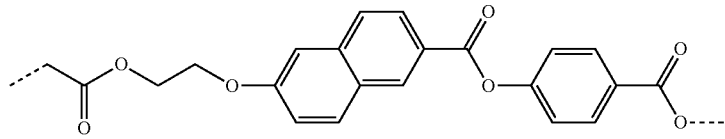
(Sp-af-1)
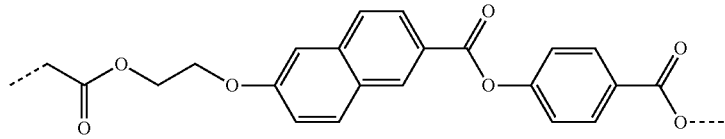
(Sp-af-2)
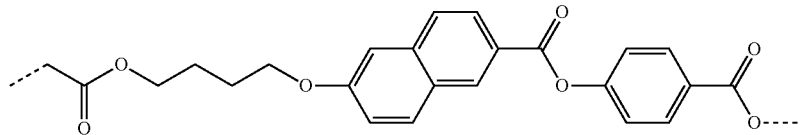
(Sp-af-3)
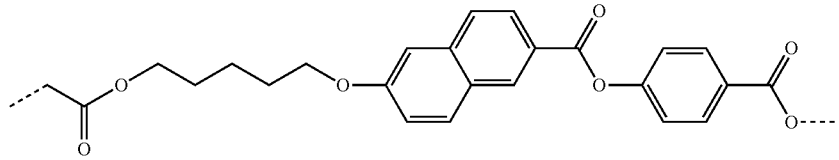
(Sp-af-4)
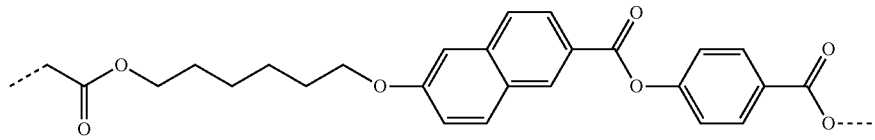
(Sp-af-5)
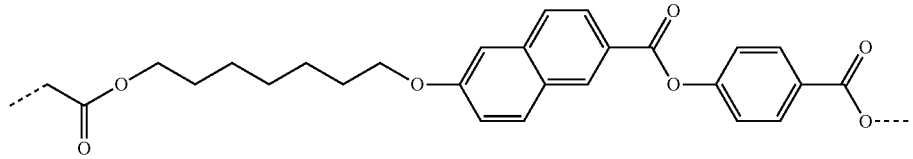
(Sp-af-6)
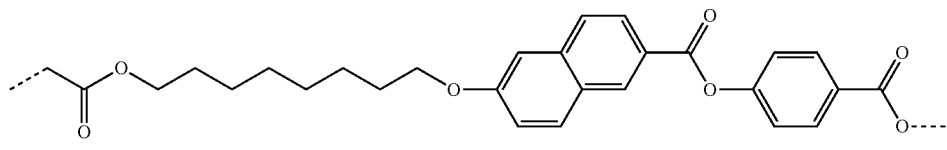
(Sp-af-7)

-continued
(Sp-af-8)
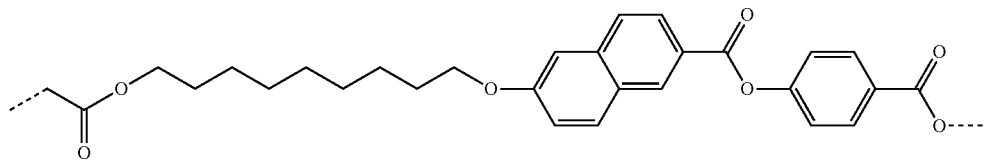
[Chem. 79]
(Sp-ag-1)
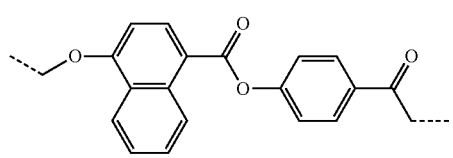
(Sp-ag-2)
(Sp-ag-3)
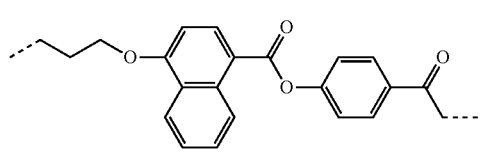
(Sp-ag-4)
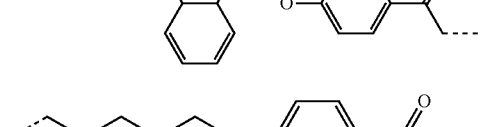
(Sp-ag-5)
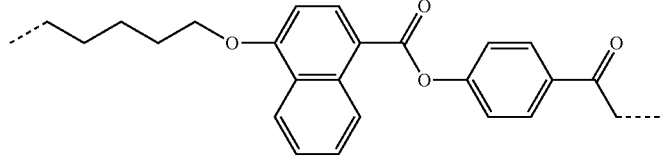
(Sp-ag-6)
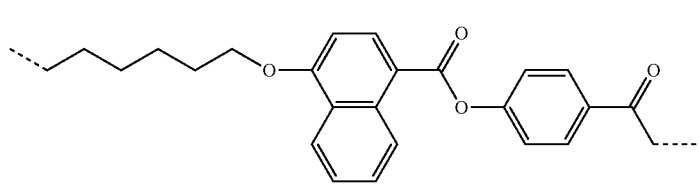
(Sp-ag-7)
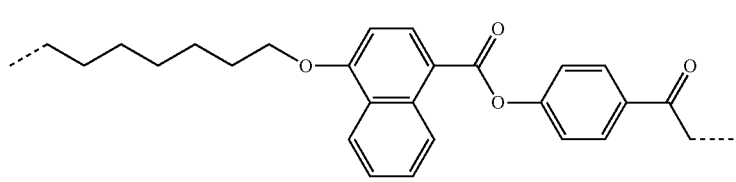
(Sp-ag-8)
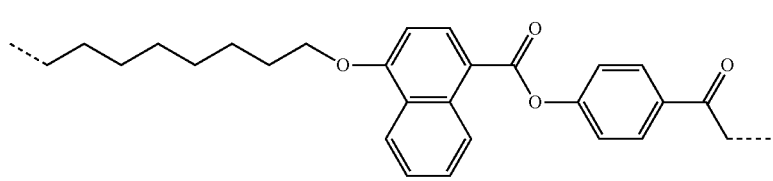
(Sp-ag-9)
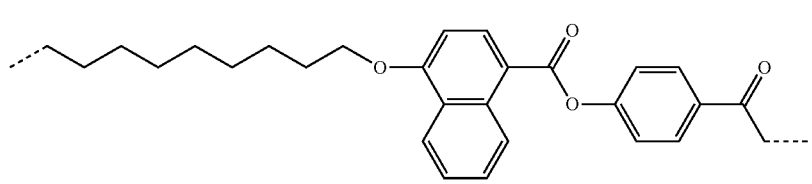
[Chem. 80]
(Sp-ah-1)
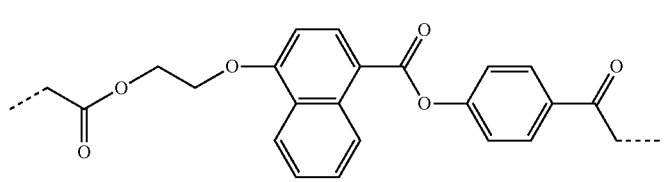

-continued

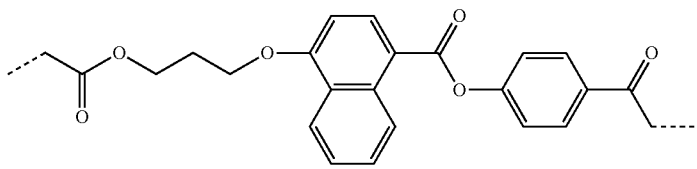
(Sp-ah-2)

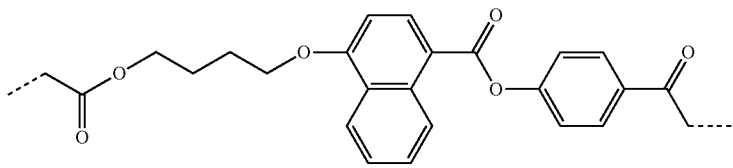
(Sp-ah-3)

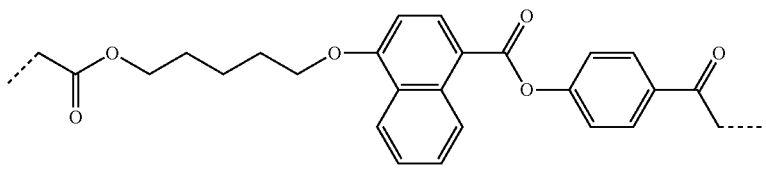
(Sp-ah-4)

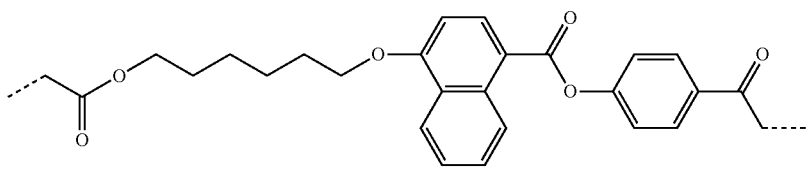
(Sp-ah-5)

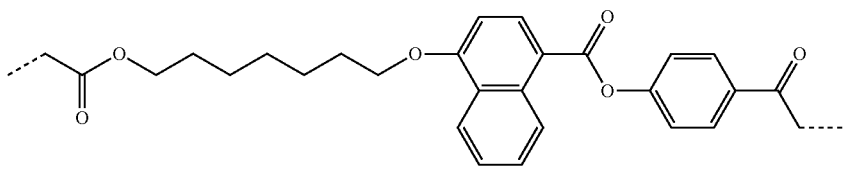
(Sp-ah-6)

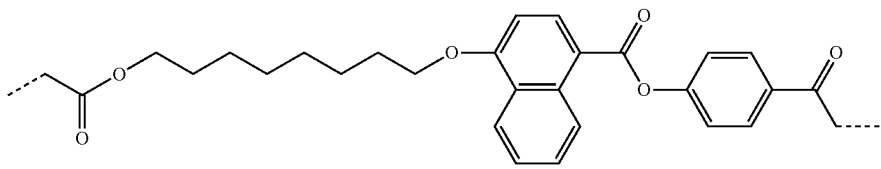
(Sp-ah-7)

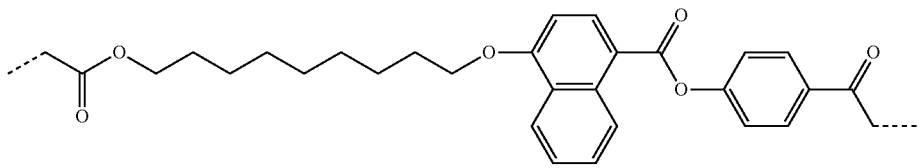
(Sp-ah-8)

A preferable compound of the present invention is a compound, in which Sp is represented by the general formula (IVc), in the general formula (IVc), $A^7$ represents a 1,4-naphthylene group or a 2,6-naphthylene group, one or more hydrogen atoms in any group of these groups may be substituted with a fluorine atom, a chlorine atom, a methyl group, or a methoxy group, $Z^2$ represents a single bond or any group of —$(CH_2)_u$— (wherein u represents 1 to 20), —$OCH_2$—, —$CH_2O$—, —COO—, —OCO—, —CH=CH—, or —C≡C—, one or more of the non-adjacent $CH_2$ groups in any group of these groups may be independently substituted with —O—, —CO—, —COO—, —O—CO—, —CH=CH—, or —C≡C—, and p represents 1.

By using the compound, an alignment property can be efficiently provided at a low dose of irradiation of polarized light during the production of the liquid crystal alignment layer, and thus, a display element using a liquid crystal alignment layer which has a superior ability to control the alignment of the liquid crystals and the pretilt angles, and a high voltage holding ratio (VHR), and the composition can be obtained.

A more preferable compound of the present invention is a compound, in which Sp is represented by the general formula (IVc), and in the general formula (IVc), $A^7$ represents a 1,4-naphthylene group or a 2,6-naphthylene group, having one or more hydrogen atoms which may be substituted with a fluorine atom, a chlorine atom, a methyl group, or a methoxy group.

By using the compound, an alignment property can be efficiently provided at a low dose of irradiation of polarized light during the production of the liquid crystal alignment layer, and thus, a display element using a liquid crystal alignment layer which has a superior ability to control the alignment of the liquid crystals and the pretilt angles, and a high voltage holding ratio (VHR), and the composition can be obtained.

A preferable compound of the present invention is a compound, in which Sp is represented by the general formula (IVc), in the general formula (IVc), $A^2$ represents any group of a trans-1,4-cyclohexylene group, a 2,6-naphthylene group, a pyridine-2,5-diyl group, a pyrimidine-2,5-diyl group, or a 1,4-phenylene group, one or more hydrogen atoms in any group of these groups may be substituted with a fluorine atom, a chlorine atom, a methyl group, or a methoxy group, $Z^3$ represents a single bond or any group of —$(CH_2)_u$— (wherein u represents 1 to 20), —$OCH_2$—, —$CH_2O$—, —COO—, —OCO—, —CH=CH—, or —C≡C—, one or more of the non-adjacent $CH_2$ groups in any group of these groups may be independently substituted with —O—, —CO—, —CO—O—, —O—CO—, —CH=CH—, or —C≡C—, and q represents 1.

By using the compound, a display element using a liquid crystal alignment layer which has a superior ability to control the alignment of the liquid crystals and the pretilt angles, and a high voltage holding ratio (VHR), and the composition can be obtained.

A more preferable compound of the present invention is a compound, in which Sp is represented by the general formula (IVc), and in the general formula (IVc), $A^2$ represents 1,4-phenylene group having one or more hydrogen atoms which may be substituted with a fluorine atom, a chlorine atom, a methyl group, or a methoxy group.

By using the compound, a display element using a liquid crystal alignment layer which has a superior ability to control the alignment of the liquid crystals and the pretilt angles, and a high voltage holding ratio (VHR), and the composition can be obtained.

(Polymer)

The liquid crystal alignment layer of the present invention is obtained by forming a polymer for a liquid crystal alignment layer on the surface of a base material used for aligning the liquid crystal, and irradiating it with light to conduct crosslinking and/or isomerization. The liquid crystal alignment layer of the present invention is produced using a cured product of the cinnamic acid derivative or a composition containing the cinnamic acid derivative. The cured product is preferably a polymer having a structural unit represented by the following general formula (PI). These specific aspects are preferably those described as follows.

[Chem. 81]

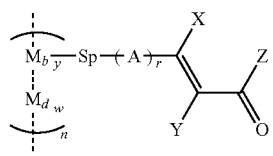

(PI)

(wherein Sp, A, X, Y, r and Z have the same definitions as in the general formula (I), $M_b$ and $M_d$ each represent a monomer unit of the polymer, y and w each represent a molar fraction of the copolymer, each satisfying $0<y\leq 1$ and $0\leq w<1$, n represents 4 to 100,000, the order in which $M_b$ and $M_d$ are arranged may be the same as or different from that shown in the formula, and the monomer units of $M_b$ and $M_d$ may be each constituted with one or two or more different units).

In the present specification and claims, the "monomer unit $(M_b)$" and the "monomer unit $(M_d)$" are sometimes abbreviated as "$M_b$" and "$M_d$", respectively.

In the general formula (PI), a hydrogen atom of $M_b$ is substituted with Sp and Sp is bonded to $M_b$.

$M_b$ and $M_d$ may be the same as or different from each other except that Sp is bonded to $M_b$, and a known monomer unit can be used while not being particularly limited. Further, the sequencing order and randomness of the monomer units ($M_b$ and $M_d$) in the polymer are not particularly limited.

In addition, as $M_b$ and $M_d$, as one kind of the monomer units, each independently, or in combination of two or more kinds of the monomer units can be used. In this case, they are preferably used to a degree which does not interfere with the effects exerted by the polymer as a liquid crystal alignment film.

In the general formula (PI), $M_b$ is preferably any one or more selected from the group consisting of the following general formulae (QIII-A-1) to (QIII-A-17).

[Chem. 82]

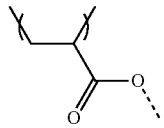

(QIII-A-1)

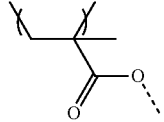

(QIII-A-2)

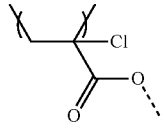

(QIII-A-3)

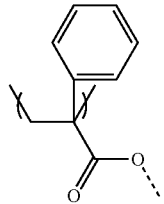

(QIII-A-4)

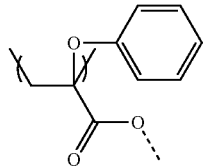

(QIII-A-5)

(QIII-A-6) 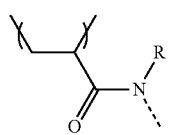

(QIII-A-7) 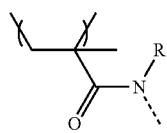

(QIII-A-8) 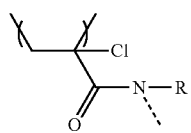

(QIII-A-9) 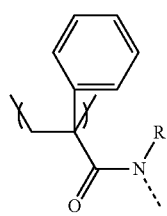

(QIII-A-10) 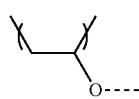

(QIII-A-11) 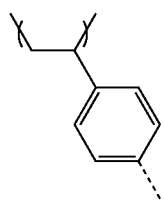

(QIII-A-12) 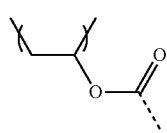

(QIII-A-13) 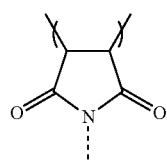

(QIII-A-14) 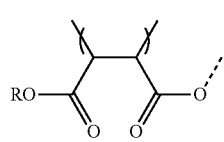

(QIII-A-15) 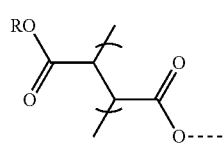

(QIII-A-16) 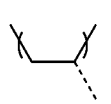

(QIII-A-17) 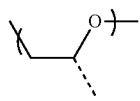

(wherein the broken line represents a bond to Sp, R's independently represent hydrogen or an alkyl group having 1 to 5 carbon atoms, and any hydrogen atom in each of the structures may be substituted with a fluorine atom, a chlorine atom, a methyl group, or a methoxy group).

In the general formula (PI), $M_d$ is preferably any one or more selected from the group consisting of the following general formulae (QIII-1) to (QIII-17).

[Chem. 83]

(QIII-1)

(QIII-2)

(QIII-3)

(QIII-4) 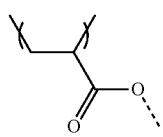

(QIII-5) 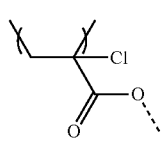

(QIII-6)

(QIII-7) 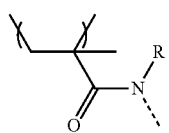

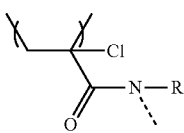
(QIII-8)

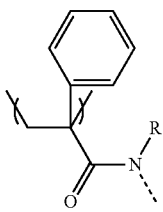
(QIII-9)

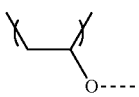
(QIII-10)

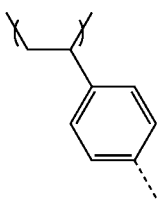
(QIII-11)

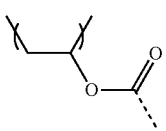
(QIII-12)

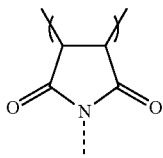
(QIII-13)

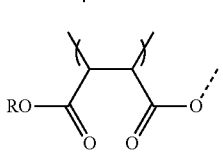
(QIII-14)

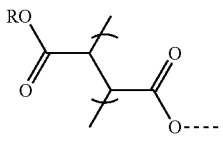
(QIII-15)

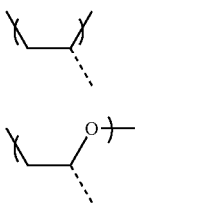
(QIII-16)

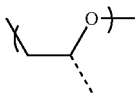
(QIII-17)

(wherein the broken line represents a bond to a hydrogen atom or a monovalent organic group, R's independently represent hydrogen or an alkyl group having 1 to 5 carbon atoms, and any hydrogen atom in each of the structures may be substituted with a fluorine atom, a chlorine atom, a methyl group, or a methoxy group).

Examples of the monovalent organic group include hydrogen, an alkyl group having 1 to 20 carbon atoms (any hydrogen atom in the alkyl group may be substituted with a fluorine atom, a chlorine atom, a methyl group, or a methoxy group, and one $CH_2$ group or two or more non-adjacent $CH_2$ groups in the alkyl group may be substituted with —O—, —CO—O—, —O—CO—, and/or —CH=CH—).

Incidentally, examples of the monovalent organic group include a trans-1,4-cyclohexylene group, a trans-1,3-dioxan-2,5-yl group, a 1,4-naphthylene group, a 2,6-naphthylene group, a 2,5-pyridyl group, a 2,5-pyrimidyl group, a 1,2,4,5-tetrazine-2,5-diyl group, a 2,5-thiophenylene group, a 2,5-furanylene group, or a 1,4-phenylene group (any hydrogen atom in each of the structures may be substituted with a fluorine atom, a chlorine atom, a methyl group, or a methoxy group).

Moreover, particularly in order to obtain an alignment layer for vertical alignment, examples of the monovalent organic group include the general formula (QIV):

[Chem. 84]

$$-S_a-V_a \qquad (QIV)$$

(wherein the broken line represents a bond to a monomer unit ($M_d$), $S_a$ represents a spacer unit, and $V_a$ represents a moiety that stabilizes the vertical alignment).

$S_a$ may be a single bond or use a spacer unit represented by the general formula (IVc) as described above.

$V_a$ is preferably a structure represented by the following general formula (VI).

[Chem. 85]

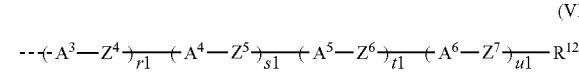

In the general formula (VI), the broken line represents a bond to $S_a$, $Z^4$, $Z^5$, $Z^6$ and $Z^7$ each independently represent a single bond, —$(CH_2)_u$— (wherein u represents 1 to 20), —OCH$_2$—, —CH$_2$O—, —COO—, —OCO—, —CH=CH—, —CF=CF—, —CF$_2$O—, —OCF$_2$—, —CF$_2$CF$_2$—, or —C≡C—, but one or more of the non-adjacent $CH_2$ groups in these substituents may be independently substituted with —O—, —CO—, —CO—O—, —O—CO—, —Si(CH$_3$)$_2$—O—Si(CH$_3$)$_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^3$, $A^4$, $A^5$ and $A^6$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, r1, s1, t1, and u1 each independently represent 0 or 1, and $R^{12}$ represents hydrogen, fluorine, chlorine, a cyano group, or an alkyl group having 1 to 20 carbon atoms, a hydrogen atom in the alkyl group may be substituted with a fluorine atom, and one $CH_2$ group or two or more non-adjacent CH$_2$ groups in the alkyl group may be substituted with —O—, —CO—O—, —O—CO—, and/or —CH═CH—.

$Z^4$, $Z^5$, $Z^6$ and $Z^7$ are each independently preferably a single bond, —(CH$_2$)$_u$— (wherein u represents 1 to 12, one or more of the non-adjacent CH$_2$ groups may be independently substituted with —O—, —CO—, —CO—O—, —O—CO—, —NR—CO—, —CO—NR—, —NR—CO—NR—, —CH═CH—, —C≡C—, or —O—CO—O—, and R's independently represent hydrogen, a methyl group, or an ethyl group), —OCH$_2$—, —CH$_2$O—, —COO—, —OCO—, —CH═CH—, —CF$_2$O—, —OCF$_2$—, or —C≡C—.

$A^3$, $A^4$, $A^5$ and $A^6$ each independently preferably represent a trans-1,4-cyclohexylene group, a 2,6-naphthylene group, a pyridine-2,5-diyl group, a pyrimidine-2,5-diyl group, or a 1,4-phenylene group. Preferably, these groups are unsubstituted or have one or more hydrogen atoms substituted with a fluorine atom, a chlorine atom, a methyl group, or a methoxy group.

For r1, s1, t1, and u1, r1+s1+t1+u1 is preferably from 0 to 3, $R^{12}$ is preferably a structure represented by hydrogen, fluorine, chlorine, a cyano group, or an alkyl group having 1 to 18 carbon atoms (one CH$_2$ group or two or more non-adjacent CH$_2$ groups in the alkyl group may be substituted with —O—, —C—O—O—, —O—CO—, and/or —CH═CH—).

In order to improve the liquid crystal alignment property in the liquid crystal alignment layer of the present invention, $Z^4$, $Z^5$, $Z^6$ and $Z^7$ are each independently preferably a single bond, —(CH$_2$)$_u$— (wherein u represents 1 to 8, and one or two of the non-adjacent CH$_2$ groups may be independently substituted with —O—, —C—O—O—, —O—CO—, —Si(CH$_3$)$_2$—O—Si(CH$_3$)$_2$—, —CH═CH—, or —C≡C—), —COO—, —OCO—, —CH═CH—, —CF═CF—, or —C≡C—, and $A^3$, $A^4$, $A^5$ and $A^6$ are each independently preferably a trans-1,4-cyclohexylene group, a trans-1,3-dioxane-2,5-diyl group, a pyridine-2,5-diyl group, a pyrimidine-2,5-diyl group, a 1,2,4,5-tetrazine-2,5-diyl group, a 2,5-thiophenylene group, or a 1,4-phenylene group.

Moreover, in order to improve the thermal stability of alignment in the liquid crystal alignment layer of the present invention, $Z^4$, $Z^5$, $Z^6$ and $Z^7$ are each independently preferably —NR—CO—, —CO—NR—, —NR—CO—O—, —O—CO—NR—, —NR—CO—NR—, or —O—CO—O—, and $A^3$, $A^4$, $A^5$ and $A^6$ are each independently preferably a 1,4-naphthylene group, a 2,6-naphthylene group, a pyridine-2,5-diyl group, a pyrimidine-2,5-diyl group, a 2,5-thiophenylene group, a 2,5-furanylene group, or a 1,4-phenylene group.

Furthermore, in order to improve the solubility of the polymer of the present invention, $Z^4$, $Z^5$, $Z^6$ and $Z^7$ are each independently preferably —OCH$_2$—, —CH$_2$O—, —CF$_2$O—, —OCF$_2$—, —CF$_2$CF$_2$—, —NR—, or —CO—, and $A^3$, $A^4$, $A^5$ and $A^6$ are each independently preferably a trans-1,4-cyclohexylene group, a 1,4-naphthylene group, a 2,6-naphthylene group, or a 2,5-furanylene group.

Furthermore, in order to provide a pretilt angle of 80 degrees or more to the liquid crystal alignment layer of the present invention, $Z^4$, $Z^5$, $Z^6$ and $Z^7$ are each independently preferably a single bond, —OCH$_2$—, —CH$_2$O—, —COO—, —OCO—, and —C≡C—, $A^3$, $A^4$, $A^5$ and $A^6$ are each independently preferably a trans-1,4-cyclohexylene group, a trans-1,3-dioxane-2,5-diyl group, and a 1,4-phenylene group, and $R^{12}$ is preferably an alkyl group having 1 to 20 carbon atoms, an alkoxy group, fluorine, a trifluoromethyl group, and a trifluoromethoxy group.

In the case of providing a pretilt angle of 80 degrees or more for the liquid crystal alignment layer of the present invention, as Va represented by the general formula (VI), for example, compounds represented by the following chemical formulae (VI-a-1) to (VI-q-10) are particularly preferable. Among these chemical formulae, the broken line represents a bond to $S_a$.

Among these, the chemical formulae (VI-a-1) to (VI-a-15), the chemical formulae (VI-b-11) to (VI-b-15), the chemical formulae (VI-c-1) to (VI-c-11), the chemical formulae (VI-d-10) to (VI-d-15), the chemical formulae (VI-f-1) to (VI-f-10), the chemical formulae (VI-g-1) to (VI-g-10), the chemical formulae (VI-h-1) to (VI-h-10), the chemical formulae (VI-j-1) to (VI-j-9), the chemical formulae (VI-l-1) to (VI-l-11), or the chemical formulae (VI-m-1) to (VI-m-11) are more preferable.

[Chem. 86]

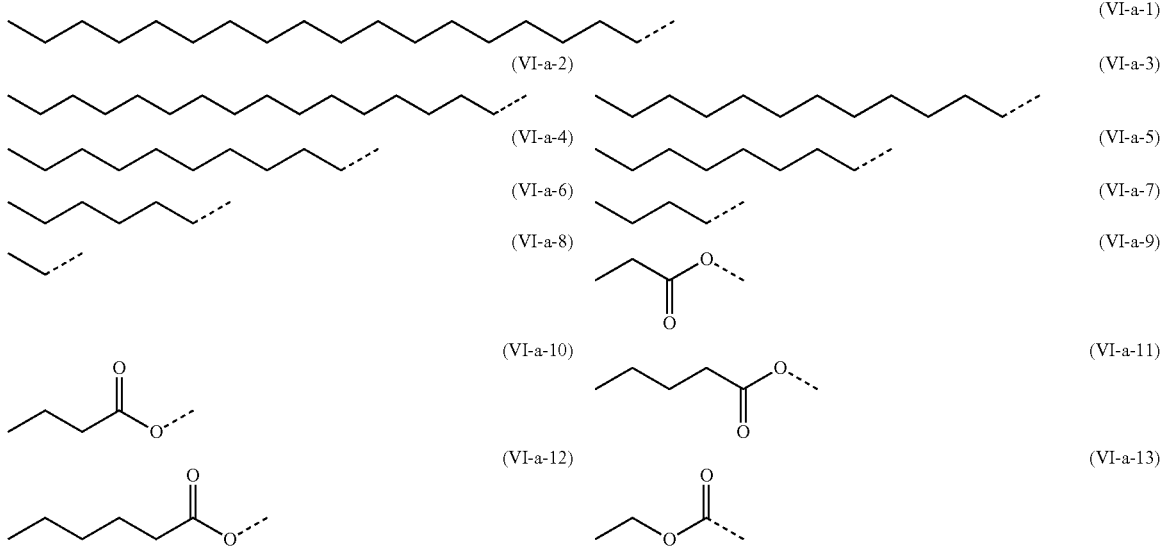

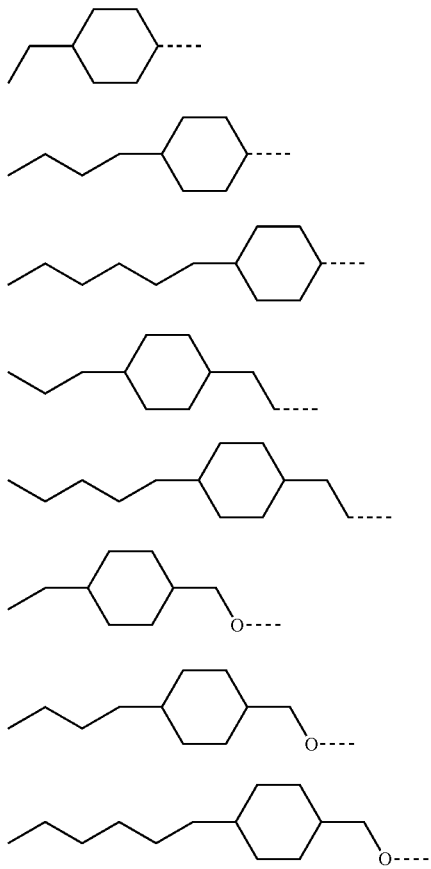
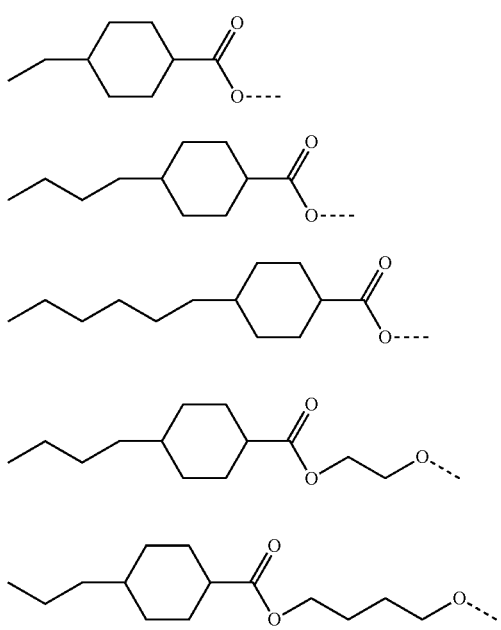
-continued
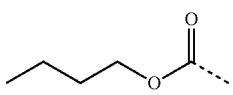

-continued
(VI-c-11)
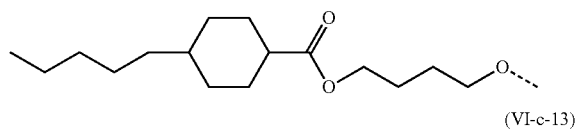
(VI-c-12)
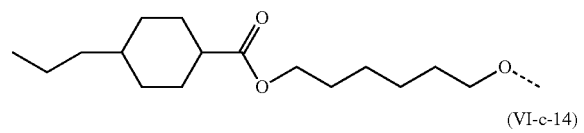
(VI-c-13)
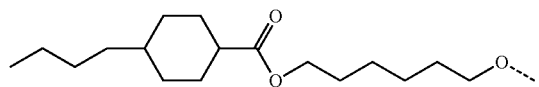
(VI-c-14)
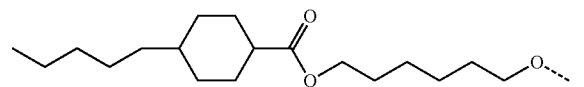
[Chem. 89]
(VI-d-1)
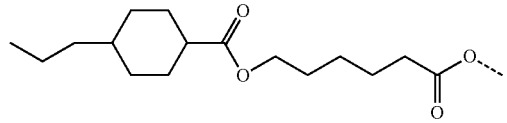
(VI-d-2)
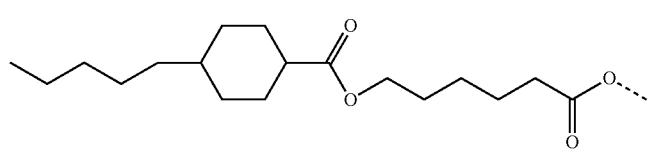
(VI-d-3)
(VI-d-4)
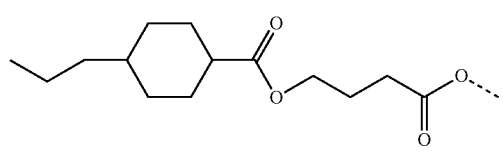
(VI-d-5)
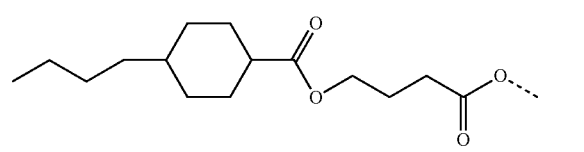
(VI-d-6)
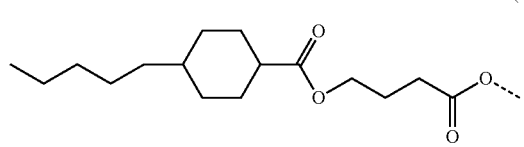
(VI-d-7)
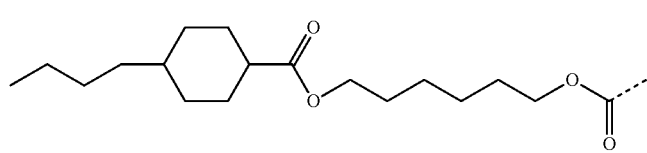
(VI-d-8)
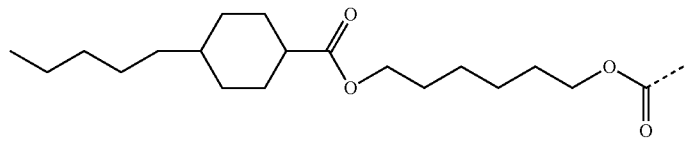
(VI-d-9)
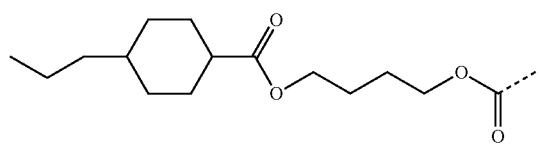
(VI-d-10)
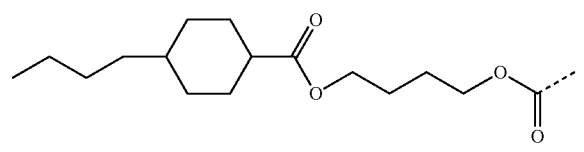
(VI-d-11)
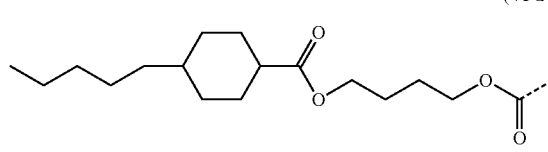
(VI-d-12)
(VI-d-13)
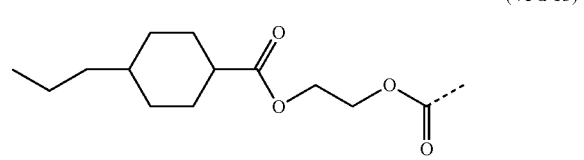

-continued
(VI-d-14) 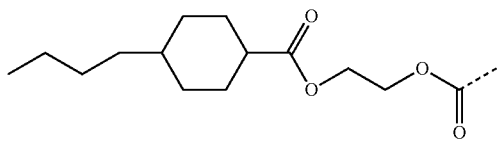
(VI-d-15) 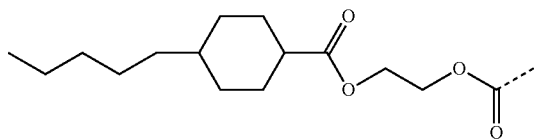
[Chem. 90]
(VI-e-1) 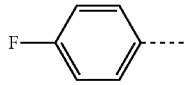
(VI-e-2) 
(VI-e-3) 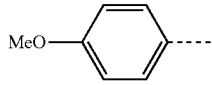
(VI-e-4) 
(VI-e-5) 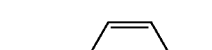
(VI-e-6) 
(VI-e-7) 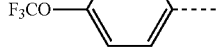
(VI-e-8) 
(VI-e-9) 
[Chem. 91]
(VI-f-1) 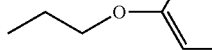
(VI-f-2) 
(VI-f-3) 
(VI-f-4) 
(VI-f-5) 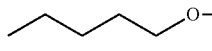
(VI-f-6) 
(VI-f-7) 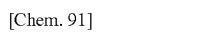
(VI-f-8) 
(VI-f-9) 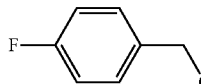
(VI-f-10) 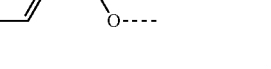
[Chem. 92]
(VI-g-1) 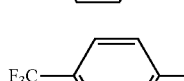
(VI-g-2) 
(VI-g-3) 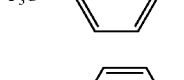
(VI-g-4) 
(VI-g-5) 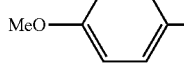
(VI-g-6) 

-continued
(VI-g-7)
(VI-g-8)
(VI-g-9)
(VI-g-10)
[Chem. 93]
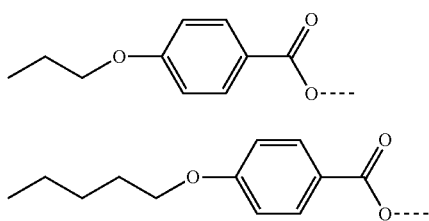
(VI-h-1) (VI-h-2)
(VI-h-3) (VI-h-4)
(VI-h-5) (VI-h-6)
(VI-h-7) (VI-h-8)
(VI-h-9) (VI-h-10)
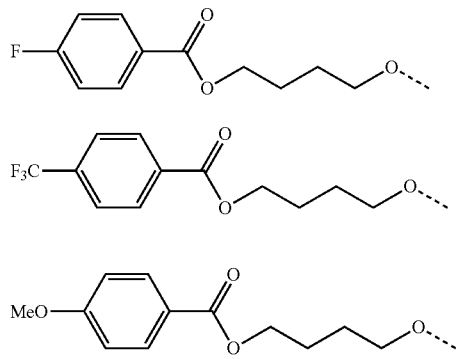
[Chem. 94]
(VI-i-1) (VI-i-2)
(VI-i-3) (VI-i-4)
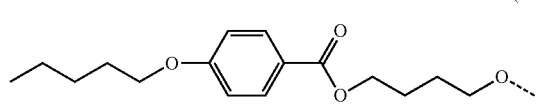
(VI-i-5) (VI-i-6)
(VI-i-7) (VI-i-8)
(VI-i-9)
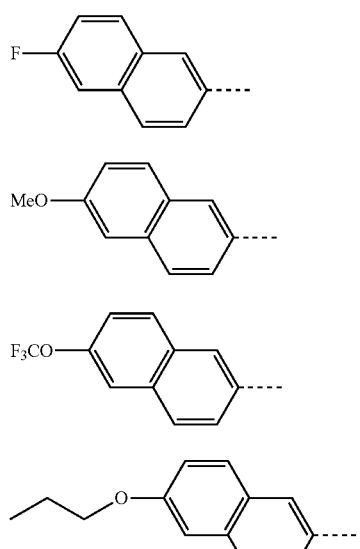

-continued
[Chem. 95]
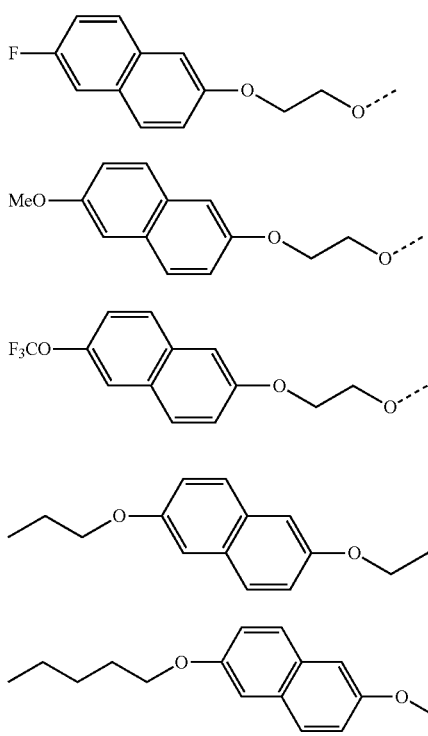
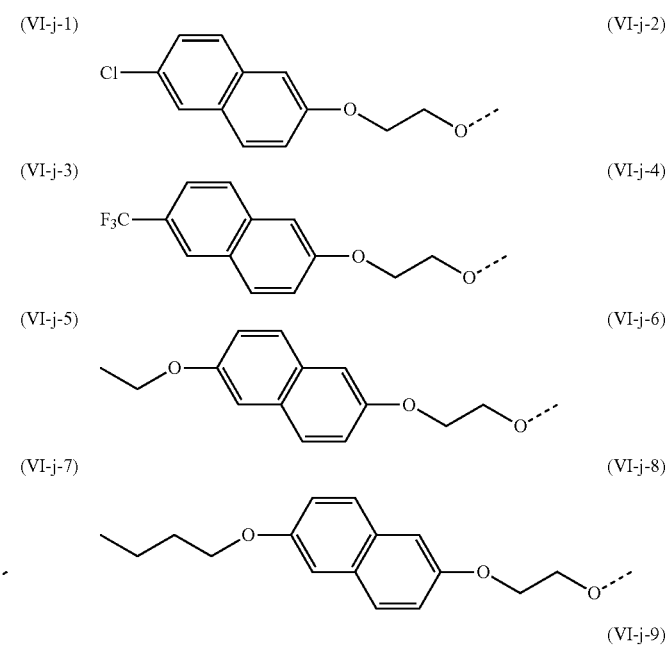
[Chem. 96]
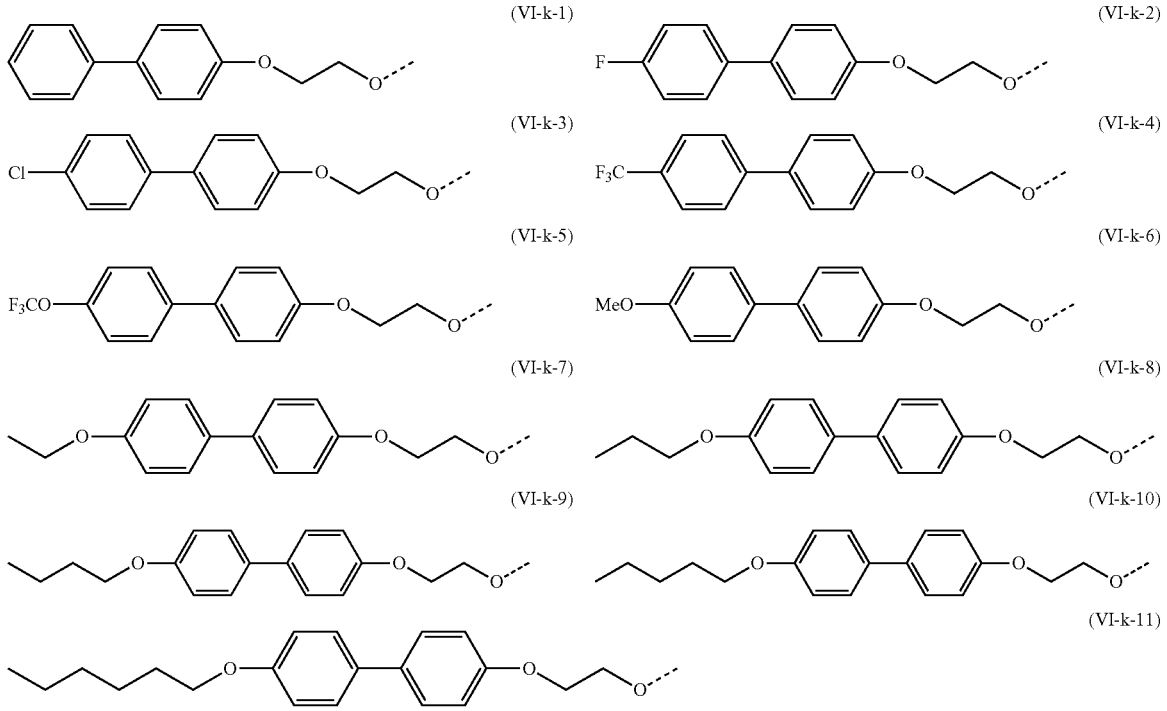
[Chem. 97]

-continued
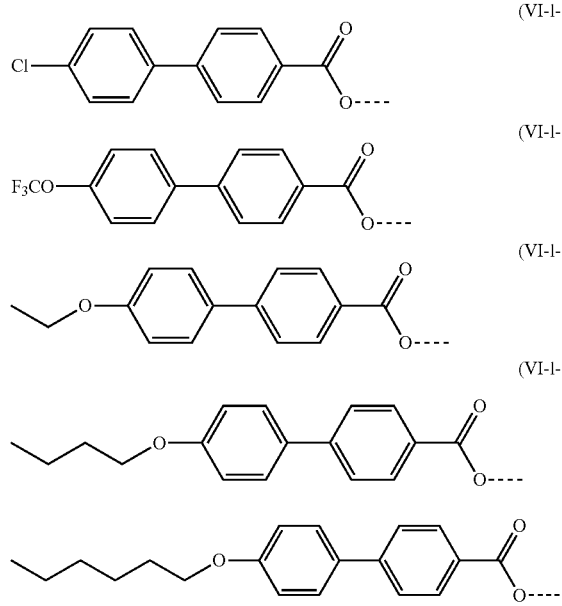
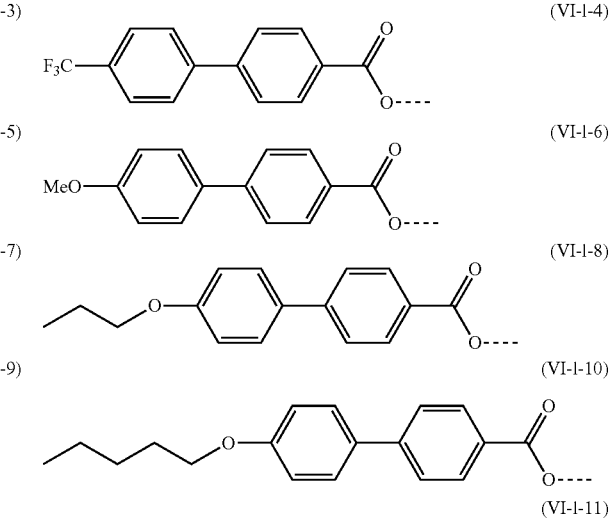
[Chem. 98]
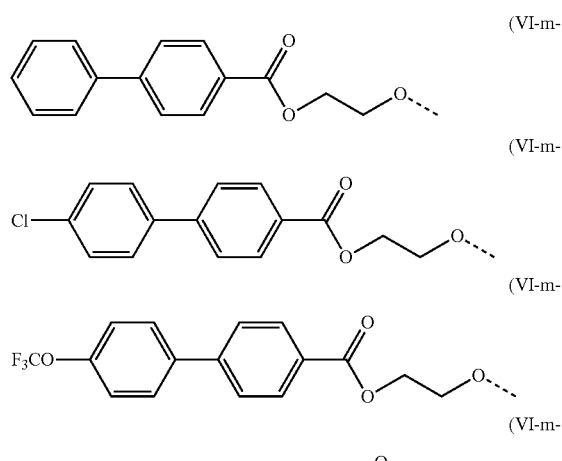
[Chem. 99]
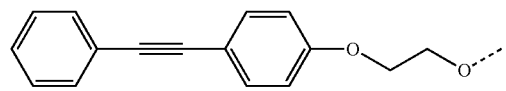
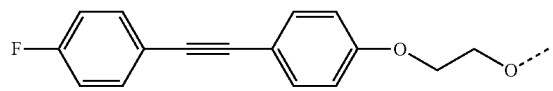

-continued
(VI-n-3) (VI-n-4)
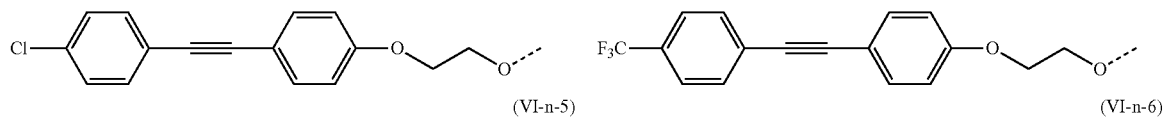
(VI-n-5) (VI-n-6)
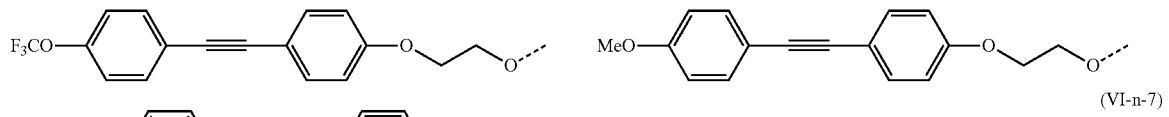
(VI-n-7)
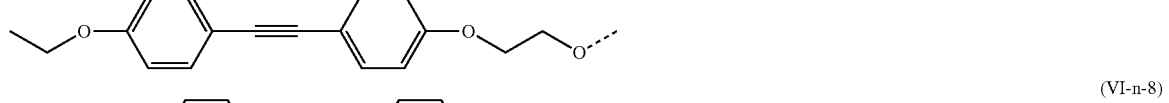
(VI-n-8)
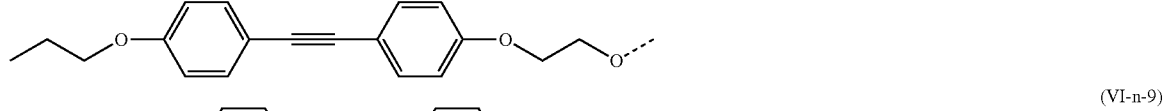
(VI-n-9)
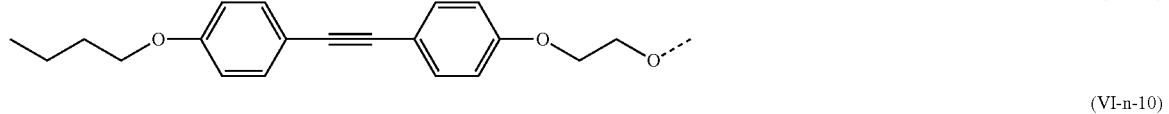
(VI-n-10)
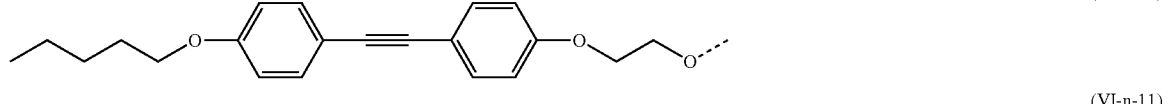
(VI-n-11)
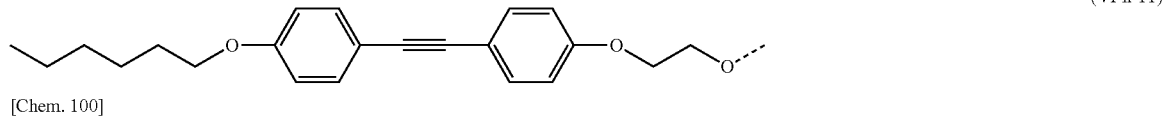
[Chem. 100]
(VI-o-1) (VI-o-2)
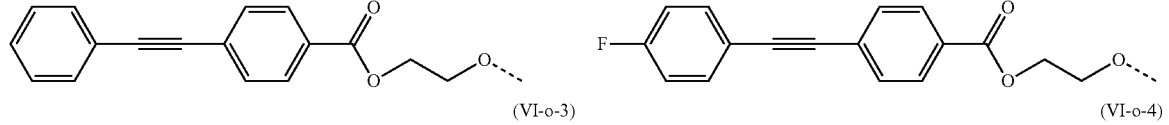
(VI-o-3) (VI-o-4)
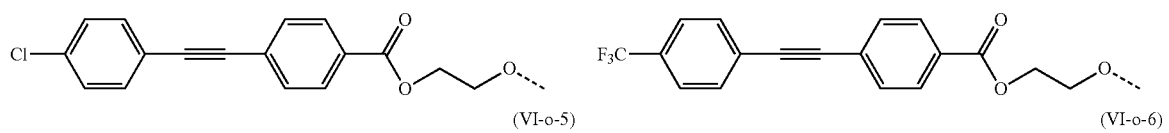
(VI-o-5) (VI-o-6)
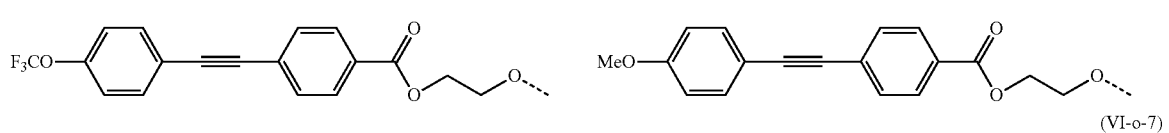
(VI-o-7)
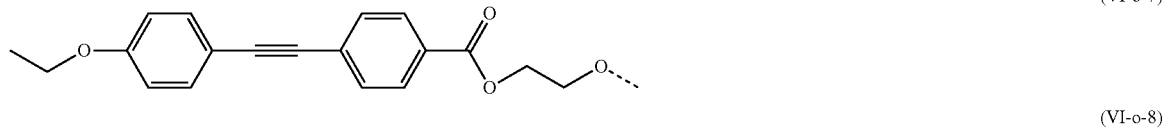
(VI-o-8)
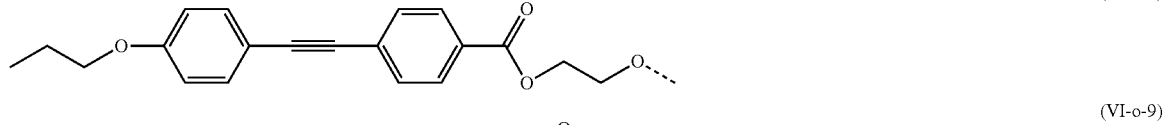
(VI-o-9)
(VI-o-10)
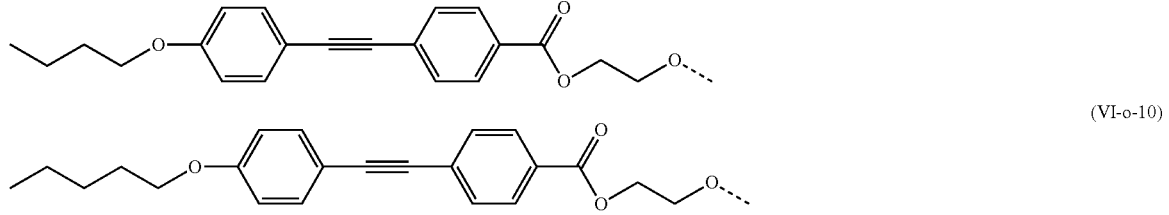

-continued
(VI-o-11)
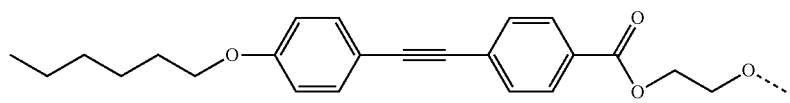
[Chem. 101]
(VI-p-1)
(VI-p-2) (VI-p-3)
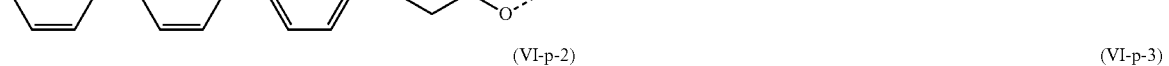
(VI-p-4) (VI-p-5)
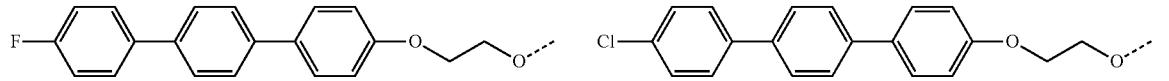
(VI-p-6)
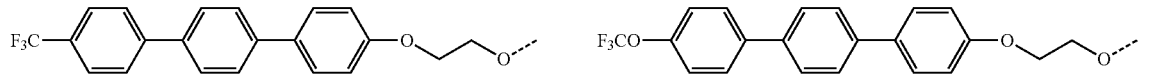
(VI-p-7)
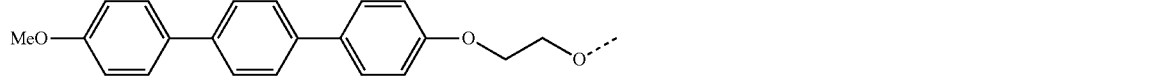
(VI-p-8)
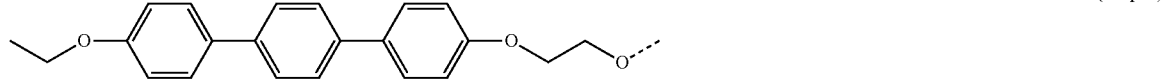
(VI-p-9)
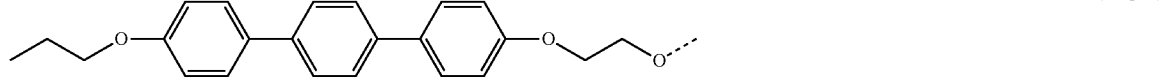
(VI-p-10)
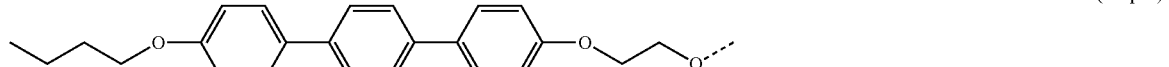
(VI-p-11)
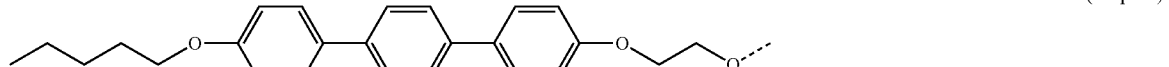
[Chem. 102]
(VI-q-1) (VI-q-2)
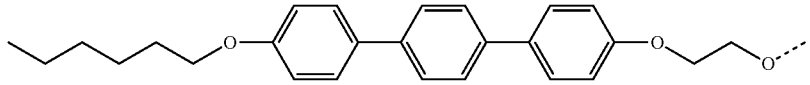
(VI-q-3) (VI-q-4)
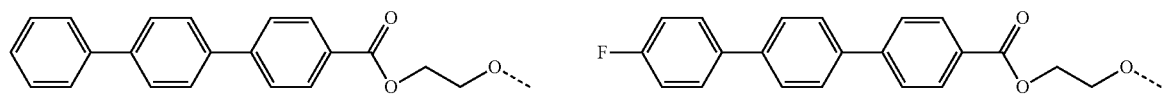
(VI-q-5)
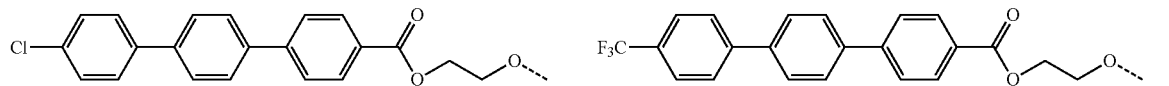
(VI-q-6)
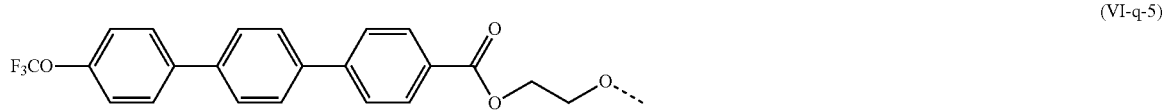

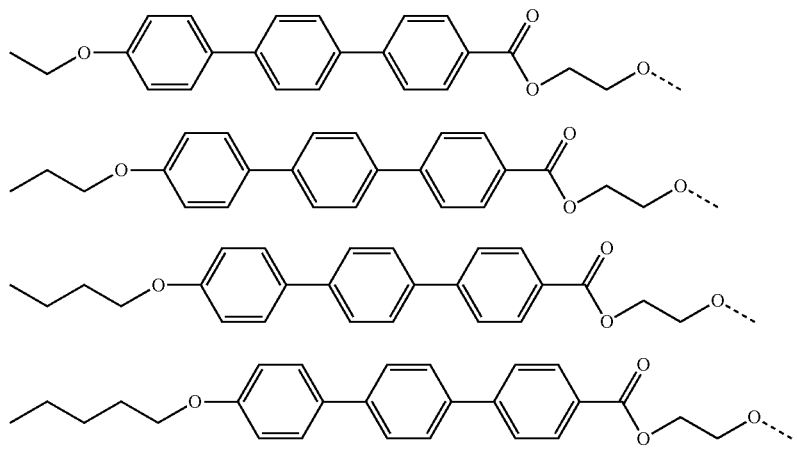

(VI-q-7)
(VI-q-8)
(VI-q-9)
(VI-q-10)

In the polymer represented by the general formula (PI) of the present invention, as $M_b$ or $M_d$, for example, acrylate, methacrylate, acrylamide, methacrylamide, maleic acid derivatives, siloxanes, epoxides, an acryloyloxy group, a methacryloyloxy group, a 2-chloroacryloyloxy group, a 2-phenylacryloyloxy group, a 2-phenyloxyacryloyloxy group, an acrylamide group, a methacrylamide group, a 2-chloromethacrylamide group, a 2-phenylacrylamide group, a vinyloxy group, a styryl group, a vinyloxycarbonyl group, a maleimide group, maleic esters, fumaric esters, siloxanes, a vinyl group, or an epoxy group may be used.

Preparation of Polymer for Alignment Layer

The cinnamic acid derivative in the present invention may be used alone as a material for the polymer, or the cinnamic acid derivative may be used in a composition formed by mixing other monomers with the cinnamic acid derivative. In the composition, it is possible to prepare the polymer at an arbitrary mixing ratio of the cinnamic acid derivative and the other monomers. For example, the ratio of the other monomers relative to 100 moles of the cinnamic acid derivative is preferably from 0.1 to 30 moles. Further, the other monomers are preferably liquid crystalline compounds.

It is preferable that the material and the composition include a solvent and/or a polymerization initiator.

The polymer of the present invention can be prepared by polymerizing the cinnamic acid derivative or the composition in the present invention.

During the polymerization, a polymerization initiator may be optionally used, depending on the polymerization mode of the polymerizable functional group. Examples of the polymerization initiator include those as described in known publications such as "Synthesis and Reaction of Polymers, edited by The Society of Polymer Science, Japan and published by Kyoritsu Shuppan Co., Ltd.".

Examples of the thermal polymerization initiator in the radical polymerization include azo compounds such as azobisisobutyronitrile and peroxides such as benzoyl peroxide.

Examples of a photopolymerization initiator include aromatic ketone compounds such as benzophenone, Michler's ketone, xanthone, and thioxanthone, quinone compounds such as 2-ethylanthraquinone, acetophenone compounds such as acetophenone, trichloroacetophenone, 2-hydroxy-2-methylpropiophenone, 1-hydroxycyclohexyl phenyl ketone, benzoin ether, 2,2-diethoxyacetophenone, and 2,2-dimethoxy-2-phenylacetophenone, diketone compounds such as benzyl and methylbenzoyl formate, acyloxime ester compounds such as 1-phenyl-1,2-propanedione-2-(o-benzoyl) oxime, acylphosphine oxide compounds such as 2,4,6-trimethylbenzoyldiphenylphosphine oxide, sulfur compounds such as tetramethylthiuram and dithiocarbamate, organic peroxides such as benzoyl peroxide, and azo compounds such as azobisisobutyronitrile.

Further, examples of the thermal polymerization initiator used in cationic polymerization include aromatic sulfonium salt compounds.

In addition, examples of the photopolymerization initiator include organic sulfonium salt compounds, iodonium salt compounds, and phosphonium compounds.

The amount of the polymerization initiator added is preferably from 0.1 to 10% by mass, more preferably from 0.1 to 6% by mass, and still more preferably from 0.1 to 3% by mass in the composition. Further, a desired polymer can be synthesized by an addition reaction to a polymer main chain, as in the case of a polysiloxane compound.

The polymer in the present invention is obtained by first subjecting the materials or the composition to a polymerization reaction in a reactor made of glass, stainless steel, or the like, and then purifying the resulting polymer. Preferable examples of the solvent which may be included in the materials or the composition include benzene, toluene, xylene, ethylbenzene, pentane, hexane, heptane, octane, cyclohexane, cycloheptane, methanol, ethanol, 1-propanol, 2-propanol, ethylene glycol, ethylene glycol monomethyl ether, ethylene glycol dimethyl ether, 2-butanone, acetone, tetrahydrofuran, γ-butyrolactone, N-methyl-pyrrolidone, dimethyl sulfoxide, and dimethylformamide. The organic solvents may be used alone or in combination of two or more kinds thereof.

The polymer according to the present invention can also be obtained by dissolving the cinnamic acid derivative or the composition in a solvent, applying the solution onto a substrate to remove the solvent by drying, and conducting a polymerization reaction by heating or light irradiation.

Method for Forming Liquid Crystal Alignment Layer

The ability to control the alignment of liquid crystal molecules and the stability of the alignment of the liquid crystal molecules against heat and light can be developed by irradiating the polymer in the present invention with light. The liquid crystal alignment layer obtained by conducting light irradiation may be referred to as a photo-alignment film.

An example of a method for producing the liquid crystal alignment layer (photo-alignment film) of the present invention is a method of dissolving the polymer in a solvent, applying the solution onto a substrate, and then irradiating the coating film with light to exhibit the ability to control the alignment to give a photo-alignment film.

The solvent used for dissolving the polymer is preferably a solvent that dissolves but does not react with the polymer of the present invention and other components optionally used. Examples of the solvent include 1,1,2-trichloroethane, N-methylpyrrolidone, butoxyethanol, γ-butyrolactone, ethylene glycol, polyethylene glycol monomethyl ether, propylene glycol, 2-pyrrolidone, N,N-dimethylformamide, phenoxyethanol, tetrahydrofuran, dimethylsulfoxide, methyl isobutyl ketone, and cyclohexanone. The organic solvents may be used alone or in combination of two or more kinds thereof.

Another method for producing the liquid crystal alignment layer (photo-alignment film) of the present invention is a method of dissolving the cinnamic acid derivative or the composition of the present invention in a solvent, applying the solution onto a substrate, heating the coating film or irradiating the coating film with light to prepare a polymer, and further irradiating the polymer with light to exhibit the ability to control the alignment, thereby giving a photo-alignment film.

As a solvent used for dissolving the cinnamic acid derivative or the composition, the same solvent as the solvent used for dissolving the polymer may be used.

In the method for producing the liquid crystal alignment layer (photo-alignment film) of the present invention, preparation of the polymer and exhibition of an ability to control the alignment may be simultaneously conducted by light irradiation. Further, preparation of the polymer and exhibition of an ability to control the alignment may be separately conducted by a method of combining heating and light irradiation or by a method of using two or more light beams having different wavelengths.

In any of the methods of producing the liquid crystal alignment layer (photo-alignment film) of the present invention, an alignment film may be preliminarily formed on a substrate and then a photo-alignment film using the cinnamic acid derivative, the composition, or the polymer of the present invention may be produced on the substrate so that the substrate may be provided with an ability to control the alignment direction and the alignment angle.

Examples of the material for the substrate include glass, silicon, polyethylene terephthalate, polybutylene terephthalate, polyether sulfone, polycarbonate, and triacetyl cellulose. An electrode layer (conductive layer) such Cr, Al, an ITO film composed of $In_2O_2$—$SnO_2$, and a NESA film composed of $SnO_2$ may be provided to this substrate. For the patterning of these electrode layers, a photoetching method may be applied. Further, the electrode layers may also be patterned by, for example, a method using a mask, in forming the electrode layers. In addition, a color filter layer or the like may also be formed on the substrate.

Examples of the method of applying a solution of the cinnamic acid derivative, the composition, or the polymer of the present invention onto a substrate include spin coating, die coating, gravure coating, flexographic printing, and ink jet printing.

The concentration of the solid content in the solution used in the application is preferably 0.5 to 10% by weight, and is more preferably selected from this range by considering a method of applying the solution on the substrate, viscosity, volatility, or the like.

Further, the applied surface is preferably heated after the application so as to remove the solvent. The drying conditions are preferably 50 to 300° C., and more preferably 80 to 200° C. for preferably 2 to 200 minutes, and more preferably 2 to 100 minutes.

In the case where the cinnamic acid derivative or the composition of the present invention is used, a polymer may be prepared on the substrate by conducting thermal polymerization by the heating treatment, and in this case, a polymerization initiator is preferably added to the material and the composition. Alternatively, a polymer may be prepared by photopolymerization through irradiating the composition with unpolarized light after removal of the solvent in the heating treatment, or alternatively, thermal polymerization and photopolymerization may be combined.

In the case of preparing the polymer by thermal polymerization on the substrate, the heating temperature may be any temperature sufficient for allowing the polymerization to proceed. Typically, the heating temperature is about 50 to 250° C., and more preferably about 70 to 200° C. Further, the polymerization initiator may or may not be added to the composition.

In preparing the polymer by photopolymerization on the substrate, unpolarized ultraviolet light is preferably used for light irradiation. Moreover, a polymerization initiator is preferably incorporated into the composition. The irradiation energy is preferably 10 mJ/cm$^2$ to 8000 mJ/cm$^2$, and more preferably 40 mJ/cm$^2$ to 5000 mJ/cm$^2$. The luminous intensity is preferably 2 to 1000 mW/cm$^2$, and more preferably 4 to 500 mW/cm$^2$. The radiation wavelength preferably has a peak in a range of 250 to 450 nm.

Next, a photocrosslinking reaction is conducted on a coating film composed of the polymer formed by the method, by applying linear polarized light in the coated surface normal direction and applying unpolarized or linear polarized light in a tilt direction and curing is conducted to exhibit an ability to control the alignment. Further, these irradiation methods may be combined. In order to form a desired pretilt angle, irradiation with linear polarized light in a tilt direction is preferable. The tilt direction refers to inclination with respect to a direction parallel to the substrate surface and this angle of inclination is referred to as a pretilt angle. In the case where the film is used as the alignment film for vertical alignment, the pretilt angle is typically preferably 70 to 89.8°. Further, in the case where the film is used as an alignment film for horizontal alignment, typically, the pretilt angle is preferably 1 to 7°, and in an IPS mode, the pretilt angle is preferably 0 to 1°.

As the light used for irradiation when subjecting a coating film composed of the polymer to curing (photocrosslinking reaction), thereby forming the film into a liquid crystal alignment layer (photo-alignment film), for example, ultraviolet rays or visible rays containing light having a wavelength of 150 nm to 800 nm may be used, and among these, ultraviolet rays having a wavelength of 270 nm to 450 nm are particularly preferable. In the case where the cinnamic acid derivative constituting the polymer has a naphthylene group, the naphthylene group sufficiently absorbs ultraviolet rays at 270 to 450 nm, and as a result, the efficiency for providing the alignment property by light irradiation can be further increased.

Examples of the light source include a xenon lamp, a high-pressure mercury lamp, an ultrahigh-pressure mercury lamp, and a metal halide lamp. Linear polarized light is obtained by using a polarizing filter and a polarizing prism for light from these light sources. Further, the ultraviolet light and visible light obtained from such light sources may have a wavelength range for irradiation restricted by using an interference filter or a color filter.

In addition, the irradiation energy is preferably 15 mJ/cm$^2$ to 500 mJ/cm$^2$, and more preferably 20 mJ/cm$^2$ to 300 mJ/cm$^2$. The luminous intensity is more preferably 2 to 500 mW/cm$^2$, and still more preferably 5 to 300 mW/cm$^2$.

The thickness of the liquid crystal alignment layer (photo-alignment film) to be formed is preferably about 10 to 250 nm, and more preferably about 10 to 100 nm.

Method for Producing Liquid Crystal Display Element

A liquid crystal cell including a pair of substrates and a liquid crystal composition sandwiched between the substrates, and a liquid crystal display element using the same can be produced by using the liquid crystal alignment layer (photo-alignment film) formed by the method as described above, for example, by the following manner.

By preparing two substrates on which the liquid crystal alignment layer in the present invention is formed and arranging liquid crystal between the two substrates, a liquid crystal cell can be produced. Further, the liquid crystal alignment layer may be formed on only one of the two substrates.

Examples of a method for producing the liquid crystal cell include the following methods.

First, two substrates are arranged so that the respective liquid crystal alignment layers face each other, and the peripheral portions of the two substrates are bonded with a sealing agent while maintaining a particular space (cell gap) between the two substrates. Liquid crystal is poured into a cell gap defined by the substrate surfaces and the sealing agent to fill the cell gap, and the inlet hole is sealed to produce a liquid crystal cell.

The liquid crystal cell may also be produced by a technique called a One Drop Fill (ODF) process. The process can be conducted, for example, by the following procedure. For example, an ultraviolet light-curable sealing agent is applied to a predetermined position on a substrate on which the liquid crystal alignment layer is formed, a liquid crystal is dropped onto the liquid crystal alignment layer, and another substrate is then bonded so that the liquid crystal alignment layers face each other. Then, the entire surfaces of the substrates are irradiated with UV light to cure the sealing agent, thereby producing a liquid crystal cell.

Regardless of the method with which the liquid crystal cell is produced, the liquid crystal used is preferably heated to a temperature at which the liquid crystal transitions to an isotropic phase and slowly cooled to room temperature so as to eliminate the alignment induced by the flow during pouring.

For example, an epoxy resin may be used as the sealing agent.

In order to keep the cell gap constant, beads of silica gel, alumina, acrylic resin, or the like may be used as a spacer prior to bonding the two substrates. These spacers may be spread over the coating film of the liquid crystal alignment layer, or added to a sealing agent and then two substrates may be bonded.

For example, nematic-type liquid crystals may be used as the liquid crystal.

For a vertical alignment-type liquid crystal cell, a liquid crystal having a negative dielectric anisotropy is preferable, and for example, dicyanobenzene-based liquid crystals, pyridazine-based liquid crystals, Schiff-base-based liquid crystals, azoxy-based liquid crystals, naphthalene-based liquid crystals, biphenyl-based liquid crystals, and phenylcyclohexane-based liquid crystals are used.

In the case of the horizontal alignment type liquid crystal cell, a liquid crystal having a positive dielectric anisotropy is preferable, and for example, cyanobenzene-based liquid crystals, difluorobenzene-based liquid crystals, trifluorobenzene-based liquid crystals, trifluoromethylbenzene-based liquid crystals, trifluoromethoxybenzene-based liquid crystals, pyrimidine-based liquid crystals, naphthalene-based liquid crystals, biphenyl-based liquid crystals, and phenyl cyclohexane-based liquid crystals are used.

A liquid crystal display element can be obtained by bonding a polarizing plate to an outer surface of the liquid crystal cell thus produced. Examples of the polarizing plate include a polarizing plate formed of an "H film" in which iodine has been absorbed while stretching and aligning a polyvinyl alcohol, and a polarizing plate having an H film sandwiched between cellulose acetate protective films.

The liquid crystal display element of the present invention thus produced is excellent in various performance such as display characteristics and reliability. Further, the alignment mode of the liquid crystal display element can be produced in any one of a horizontal alignment mode and a vertical alignment mode.

Method for Producing Optical Anisotropic Body

An optical anisotropic body may also be produced by applying a polymerizable liquid crystal composition onto the photo-alignment film and polymerizing it while aligning the polymerizable liquid crystal molecules in the polymerizable liquid crystal composition. Furthermore, the optical anisotropic body means a material having differences in optical properties such as light speed, the refractive index, and absorption, depending on the moving direction of the light, when light moves into the material.

The polymerizable liquid crystal composition is a liquid crystal composition containing a polymerizable liquid crystal which exhibits liquid crystal properties either alone or in a composition with another liquid crystal compound. Examples thereof include a compound having a polymerizable group. Examples of such compounds include rod-shaped polymerizable liquid crystal compounds having a rigid site, referred to as a mesogen in which a plurality of structures such as a 1,4-phenylene group and a 1,4-cyclohexylene group are connected, and a polymerizable functional group such as a (meth)acryloyloxy group, a vinyloxy group, and an epoxy group, as described in the Handbook of Liquid Crystals (edited by D. Demus, J. W. Goodby, G. W. Gray, H. W. Spiess, V. Vill, published by Wiley-VCH publishers, 1998), Kikan Kagaku Sosetsu No. 22, Liquid Crystal Chemistry (edited by Chemical Society of Japan, 1994), or Japanese Unexamined Patent Application, First Publication Nos. H07-294735, H08-3111, H08-29618, H11-80090, H11-148079, 2000-178233, 2002-308831, and 2002-145830; rod-shaped polymerizable liquid crystal compounds having a maleimide group as described in Japanese Unexamined Patent Application, First Publication Nos. 2004-2373 and 2004-99446; rod-shaped polymerizable liquid crystal compounds having an allyl ether group as described in Japanese Unexamined Patent Application, First Publication No. 2004-149522; and for example, discotic polymerizable compounds as described in the Handbook of Liquid Crystals, (edited by D. Demus, J. W. Goodby, G. W. Gray, H. W. Spiess, V. Vill, published by Wiley-VCH, 1998), Kikan Kagaku Sosetsu No. 22, Liquid Crystal Chemistry (edited by Chemical Society of Japan, 1994) or Japanese Unexamined Patent Application, First Publication No. H07-146409. Among these, the rod-shaped liquid crystal compounds having a polymerizable group are preferable since a film having a low liquid crystal temperature range which is in the vicinity of room temperature is easily fabricated.

Second Embodiment

Next, a second embodiment of the present invention will be described while focusing on the difference from the first embodiment, and the description of the same contents will be omitted.

In the general formula (I), L represents a polymerizable group and Sp represents a spacer unit, A's each independently represent a 1,4-naphthylene group, a 2,6-naphthylene group, a pyridine-2,5-diyl group, a pyrimidine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, X and Y each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one $CH_2$ group or two or more non-adjacent $CH_2$ groups may be substituted with —O—, —CO—O—, —O—CO—, and/or —CH=CH—, Z is represented by the general formula (IId), (IIe), (IIf) or (IIg), and r represents 1 or 2.

[Chem. 103]

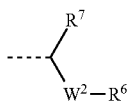
(IId)

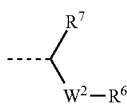
(IIe)

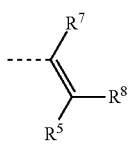
(IIf)

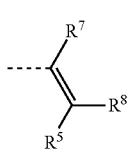
(IIg)

In the general formulae (IId), (IIe), (IIf), and (IIg), the broken line represents a bond to an oxygen atom or a nitrogen atom, $W^2$ represents a single bond, —$CH_2$—, —CO—O—, or —CO—NH—, $R^7$ represents a hydrogen atom or an alkyl group having 1 to 5 carbon atoms, $R^8$ represents a hydrogen atom, or a linear or branched alkyl group having 1 to 20 carbon atoms (one or two or more —$CH_2$— groups in the alkyl group may be each independently substituted with a cycloalkyl group having a ring member number of 3 to 8, and a hydrogen atom in the alkyl group may be unsubstituted or substituted with a fluorine atom or a chlorine atom), $R^5$ represents an alkyl group having 1 to 20 carbon atoms, in which a hydrogen atom in the alkyl group may be substituted with a fluorine atom, and $R^6$ represents an alkyl group having 1 to 20 carbon atoms (one —$CH_2$— group or two or more non-adjacent —$CH_2$— groups in the alkyl group are substituted with —CH=CH—, —CF=CF—, and/or —C≡C—, and one or two or more —$CH_2$— groups in the alkyl group may be each independently substituted with a cycloalkyl group having a ring member number of 3 to 8, and a hydrogen atom in the alkyl group may be substituted with a fluorine atom or a chlorine atom).

The alkyl group having 1 to 20 carbon atoms, represented by $R^8$, is preferably a linear or branched alkyl group or a cycloalkyl group having a ring member number of 3 to 8.

In the general formula (I), (IId), (IIe), (IIf), or (IIg), in order to improve the liquid crystal alignment property of the liquid crystal alignment layer of the present invention, A is preferably a pyridine-2,5-diyl group, a pyrimidine-2,5-diyl group, a 1,2,4,5-tetrazine-2,5-diyl group, or a 1,4-phenylene group.

Furthermore, in order to improve the solubility of the polymer of the present invention, A is preferably a 1,4-naphthylene group, a 2,6-naphthylene group, a 2,5-thiophenylene group, or a 2,5-furanylene group.

Moreover, in order to reduce the light irradiation dose required for aligning the liquid crystal in the liquid crystal alignment layer of the present invention, A is preferably a pyridine-2,5-diyl group, a pyrimidine-2,5-diyl group, a 2,5-thiophenylene group, or a 1,4-phenylene group.

In addition, in the liquid crystal alignment layer of the present invention, in order to realize photo-alignment at a longer wavelength, A is preferably a pyrimidine-2,5-diyl group, a 2,5-thiophenylene group, a 2,6-naphthylene group, or a 2,5-furanylene group, and X and Y are preferably a fluorine atom, a chlorine atom, or a cyano group.

Furthermore, in order to improve the voltage holding ratio in the liquid crystal alignment layer of the present invention, X and Y are each preferably a hydrogen atom, $W^2$ is preferably a single bond or —$CH_2$—, $R^6$ is preferably an alkyl group having 1 to 12 carbon atoms, and one $CH_2$ group is preferably substituted with —CH=CH— or —C≡C—.

In addition, in order to reduce the residual charges in the liquid crystal alignment layer of the present invention, $W^2$ is preferably —CO—O— or —CO—NH—, $R^6$ is preferably an alkyl group having 1 to 6 carbon atoms, and one $CH_2$ group is preferably substituted with —CH=CH— or —C≡C—.

[Chem. 104]

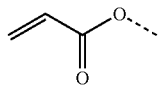
(III-1)

-continued (III-2) 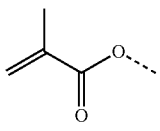

(III-3) 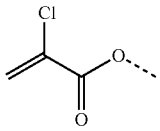

(III-4) 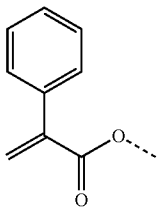

(III-5) 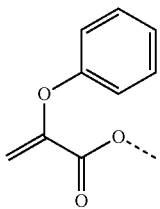

(III-6) 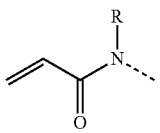

(III-7) 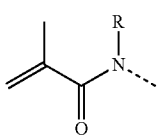

(III-8) 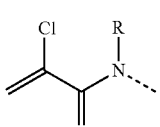

(III-9) 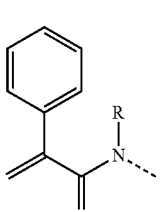

(III-10) 

(III-11) 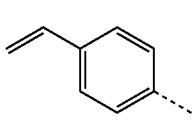

(III-12) 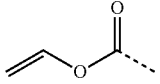

-continued (III-13) 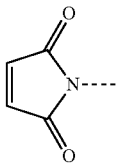

(III-14) 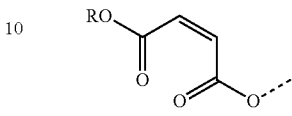

(III-15) 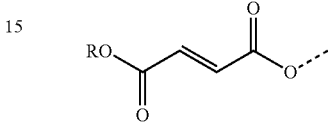

(III-16) 

(III-17) 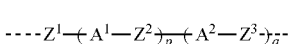

(wherein the broken line represents a bond to Sp and R's independently represent hydrogen or an alkyl group having 1 to 5 carbon atoms).

The compound represented by the general formula (I) of the present invention is preferably the compound in which L is represented by the general formula (III-1) or (III-2).

By using the compound, a display element using a liquid crystal alignment layer having the effects such as having good coatability, a superior ability to control the alignment of the liquid crystals and the pretilt angles, and a high voltage holding ratio (VHR), and the composition is obtained.

[Chem. 105]

$$\text{----}Z^1\text{---}(\text{A}^1\text{---}Z^2)_p\text{---}(\text{A}^2\text{---}Z^3)_q\text{---} \quad (\text{IVa})$$

(wherein the left broken line represents a bond to L, the right broken line represents a bond to A or a bond to a carbon atom, to which X is bonded, $Z^1$, $Z^2$ and $Z^3$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, but one or more of the non-adjacent $CH_2$ groups in these substituents may be independently substituted with —O—, —CO—, —CO—O—, —O—CO—, —Si(CH_3)_2—O—Si(CH_3)_2—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^1$ and $A^2$ each independently represent any group of a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and one or more hydrogen atoms in any group of these groups may be substituted with a fluorine atom, a chlorine atom, a methyl group, or a methoxy group, and p and q each independently represent 0 or 1).

In the general formula (IVa), q is preferably 1.

In the general formula (IVa), p is preferably 0.

In the general formula (IVa), $A^1$ and $A^2$ are each independently preferably any group of a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, or a 1,4-phenylene group. A hydrogen atom of these groups may be unsubstituted or one or more hydrogen atoms of these groups may be substituted with a fluorine atom, a chlorine atom, a methyl group, or a methoxy group.

In the general formula (IVa), $A^1$ and $A^2$ are each independently more preferably any group of a trans-1,4-cyclohexylene group, a 2,6-naphthylene group, a pyridine-2,5-diyl group, a pyrimidine-2,5-diyl group, or a 1,4-phenylene group. A hydrogen atom of these groups may be unsubstituted or one or more hydrogen atoms of these groups may be substituted with a fluorine atom, a chlorine atom, a methyl group, or a methoxy group.

In the general formula (IVa), $A^1$ and $A^2$ are each independently particularly preferably any group of a trans-1,4-cyclohexylene group, a 2,6-naphthylene group, or a 1,4-phenylene group. A hydrogen atom of these groups may be unsubstituted or one or more hydrogen atoms of these groups may be substituted with a fluorine atom, a methyl group, or a methoxy group.

In the general formula (IVa), $A^2$ is most preferably a 1,4-phenylene group. A hydrogen atom of the 1,4-phenylene group may be unsubstituted or one or more hydrogen atoms of the 1,4-phenylene group may be substituted with a fluorine atom, a methyl group, or a methoxy group.

Sp represented by the general formula (IVa) is preferably, for example, one represented by the following chemical formulae (Sp-a-1) to (Sp-ad-9). Among these chemical formulae, the left broken line represents a bond to L and the right broken line represents a bond to A or a bond to a carbon atom, to which X is bonded.

Among these, those represented by the chemical formulae (Sp-a-6) to (Sp-a-16), the chemical formulae (Sp-b-3) to (Sp-b-10), the chemical formulae (Sp-c-3) to (Sp-c-10), the chemical formulae (Sp-d-3) to (Sp-d-12), the chemical formulae (Sp-k-4) to (Sp-k-7), the chemical formulae (Sp-l-13) to (Sp-l-17), the chemical formulae (Sp-o-3) to (Sp-o-14), the chemical formulae (Sp-p-2) to (Sp-p-13), the chemical formulae (Sp-s-1) to (Sp-s-8), the chemical formulae (Sp-t-1) to (Sp-t-8), the chemical formulae (Sp-y-1) to (Sp-y-9), and the chemical formulae (Sp-aa-1) to (Sp-aa-9) are more preferable.

A preferable compound of the present invention is a compound, in which Sp is represented by the general formula (IVa), in the general formula (IVa), $A^2$ represents any group of a trans-1,4-cyclohexylene group, a 2,6-naphthylene group, a pyridine-2,5-diyl group, a pyrimidine-2,5-diyl group, or a 1,4-phenylene group, one or more hydrogen atoms in any group of these groups may be substituted with a fluorine atom, a chlorine atom, a methyl group, or a methoxy group, $Z^3$ represents any group of a single bond, —$(CH_2)_u$— (wherein u represents 1 to 20), —$OCH_2$—, —$CH_2O$—, —COO—, —OCO—, —CH=CH—, or —C≡C—, one or more of the non-adjacent $CH_2$ groups in any group of these groups may be independently substituted with —O—, —CO—, —CO—O—, —O—CO—, —CH=CH—, or —C≡C—, and q represents 1.

By using the compound, a display element using a liquid crystal alignment layer which has good coatability, a superior ability to control the alignment of the liquid crystals and the pretilt angles, and a high voltage holding ratio (VHR), and the composition can be obtained.

A more preferable compound of the present invention is a compound, in which Sp is represented by the general formula (IVa), and in the general formula (IVa), $A^2$ represents a 1,4-phenylene group having one or more hydrogen atoms which may be substituted with a fluorine atom, a chlorine atom, a methyl group, or a methoxy group.

By using the compound, a display element using a liquid crystal alignment layer which has good coatability, a superior ability to control the alignment of the liquid crystals and the pretilt angles, and a high voltage holding ratio (VHR), and the composition can be obtained.

In the general formula (PI), $M_d$ is preferably any one or more selected from the group consisting of the following general formulae (QIII-1) to (QIII-17):

(QIII-1)

(QIII-2)

(QIII-3)

(QIII-4)

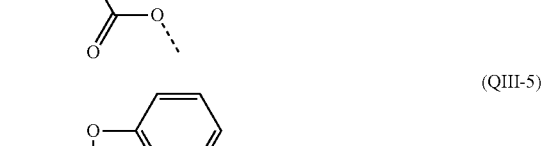
(QIII-5)

(QIII-6)

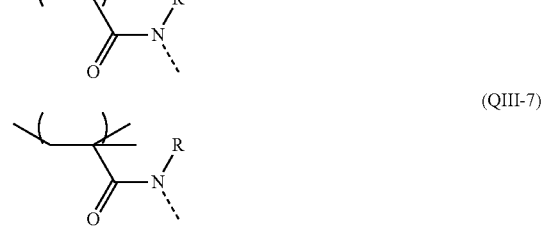
(QIII-7)

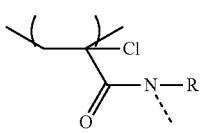 (QIII-8)

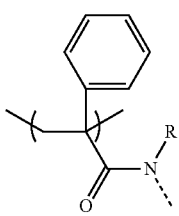 (QIII-9)

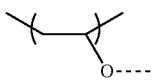 (QIII-10)

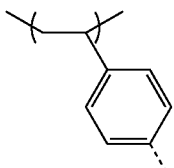 (QIII-11)

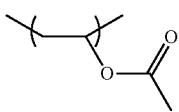 (QIII-12)

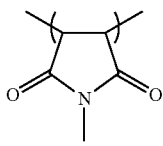 (QIII-13)

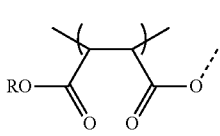 (QIII-14)

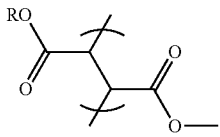 (QIII-15)

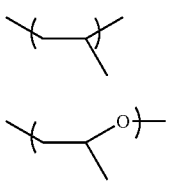 (QIII-16)

(QIII-17)

(wherein the broken line represents a bond to a hydrogen atom H or a monovalent organic group, R's independently represent hydrogen or an alkyl group having 1 to 5 carbon atoms, and any hydrogen atom in each of the structures may be substituted with a fluorine atom, a chlorine atom, a methyl group, or a methoxy group).

As $S_a$, a spacer unit represented by the general formula (IVa) as described above may be used.

$V_a$ is preferably a structure represented by the following general formula (VI).

[Chem. 107]

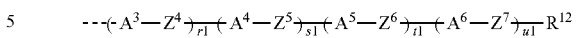 (VI)

In order to improve the liquid crystal alignment property in the liquid crystal alignment layer of the present invention, $Z^4$, $Z^5$, $Z^6$ and $Z^7$ are each independently preferably a single bond, —$(CH_2)_u$— (wherein u represents 1 to 8, and one or two of the non-adjacent $CH_2$ groups independently represent —O—, —CO—O—, —O—CO—, —Si$(CH_3)_2$—O—Si$(CH_3)_2$—, —CH=CH—, or —C≡C—), —COO—, —OCO—, —CH=CH—, —CF=CF—, or —C≡C—, and $A^3$, $A^4$, $A^5$ and $A^6$ are each independently preferably a trans-1,4-cyclohexylene group, a trans-1,3-dioxane-2,5-diyl group, a pyridine-2,5-diyl group, a pyrimidine-2,5-diyl group, a 1,2,4,5-tetrazine-2,5-diyl group, a 2,5-thiophenylene group, or a 1,4-phenylene group.

As the light used for irradiation when subjecting a coating film composed of the polymer to curing, for example, ultraviolet rays or visible rays containing light having a wavelength of 150 nm to 800 nm may be used, and among these, ultraviolet rays having a wavelength of 270 nm to 450 nm are particularly preferable. Examples of the light source include a xenon lamp, a high-pressure mercury lamp, an ultrahigh-pressure mercury lamp, and a metal halide lamp. Linear polarized light is obtained by using a polarizing filter and a polarizing prism for light from these light sources. Further, the ultraviolet light and visible light obtained from such light sources may have a wavelength range for irradiation restricted by using an interference filter or a color filter. In addition, the irradiation energy is preferably 15 mJ/cm² to 500 mJ/cm², and more preferably 20 mJ/cm² to 300 mJ/cm². The luminous intensity is preferably 2 to 500 mW/cm², and more preferably 5 to 300 mW/cm².

The film thickness of the photo-alignment film to be formed is preferably about 10 to 250 nm and more preferably about 10 to 100 nm.

Method for Producing Liquid Crystal Display Element

A liquid crystal cell including a pair of substrates and a liquid crystal composition sandwiched between the substrates, and a liquid crystal display element including the same can be produced by using the alignment film (photo-alignment film) formed by the method as described above, for example, by the following manner.

By preparing two substrates on which the alignment film in the present invention is formed and arranging liquid crystal between the two substrates, a liquid crystal cell can be produced. Further, the alignment film may be formed on only one of the two substrates.

Examples of a method for producing the liquid crystal cell include the following methods.

First, two substrates are arranged so that the respective alignment films face each other, and the peripheral portions of the two substrates are bonded with a sealing agent while maintaining a particular space (cell gap) between the two substrates. Liquid crystal is poured into a cell gap defined by the substrate surfaces and the sealing agent to fill the cell gap, and the inlet hole is sealed to produce a liquid crystal cell.

The liquid crystal cell may also be produced by a technique called a One Drop Fill (ODF) process. The process can be conducted, for example, by the following procedure. For example, an ultraviolet light-curable sealing agent is applied to a predetermined position on a substrate on which the alignment film is formed, a liquid crystal is dropped onto the alignment film, and another substrate is then bonded so that the alignment films face each other. Then, the entire surfaces of the substrates are irradiated with UV light to cure the sealing agent, thereby producing a liquid crystal cell.

In any case where the liquid crystal cell is produced by any method, the liquid crystal used is preferably heated to a temperature at which the liquid crystal transitions to an isotropic phase and slowly cooled to room temperature so as to eliminate the alignment induced by the flow during pouring.

For example, an epoxy resin may be used as the sealing agent.

In order to keep the cell gap constant, beads of silica gel, alumina, acrylic resin, or the like may be used as a spacer prior to bonding the two substrates. These spacers may be spread over the coating film of the alignment film or added to a sealing agent and then two substrates may be bonded.

Third Embodiment

Next, a third embodiment of the present invention will be described while focusing on the difference from the first embodiment, and the description of the same contents will be omitted.

(Cinnamic Acid Derivative)

The cinnamic acid derivative of the present invention is specifically preferably a compound represented by the general formula (I):

[Chem. 108]

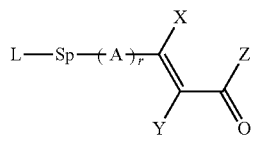

(I)

(wherein L represents a polymerizable group, Sp represents a spacer unit, A's each independently represent a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, these may be unsubstituted or may have one or more hydrogen atoms substituted with a fluorine atom, a chlorine atom, a methyl group, or a methoxy group, X and Y each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one $CH_2$ group or two or more non-adjacent $CH_2$ groups may be substituted with —O—, —CO—O—, —O—CO—, and/or —CH=CH—, Z is represented by the general formula (IIa) or (IIb):

[Chem. 109]

(IIa)

(IIb)

(wherein the broken line represents a bond to a carbon atom, to which Z is bonded, $R^1$ represents a linear or branched alkyl group having 1 to 30 carbon atoms (one —$CH_2$— group or two or more non-adjacent —$CH_2$— groups in the alkyl group are substituted with —O—, —CO—, —CO—O—, —O—CO—, —CO—NH—, —NH—CO—, —$NCH_3$—, one or two or more —$CH_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), $R^2$ represents a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom)), and r represents 0, 1, or 2).

In the general formula (IIa) or (IIb), $R^1$ is preferably a compound represented by the general formula (IIc):

[Chem. 110]

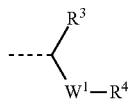

(IIc)

(wherein the broken line represents a bond to an oxygen atom or a nitrogen atom, $W^1$ represents a methylene group (a hydrogen atom of the methylene group may be unsubstituted or substituted with an alkyl group having 1 to 5 carbon atoms), —CO—O—, or —CO—NH—, $R^3$ represents a hydrogen atom or an alkyl group having 1 to 5 carbon atoms, and $R^4$ represents a linear or branched alkyl group having 1 to 20 carbon atoms (one —$CH_2$— group or two or more non-adjacent —$CH_2$— groups in the alkyl group may be substituted with —O—, —CO—, —CO—O—, —O—CO—, —CO—NH—, —NH—CO—, —$NCH_3$—, one or two or more —$CH_2$— groups in the alkyl group may be each independently substituted with a cycloalkyl group having a ring member number of 3 to 8, and a hydrogen atom in the alkyl group may be unsubstituted or substituted with a fluorine atom or a chlorine atom).

In the general formula (I), (IIa), or (IIb), in order to improve the liquid crystal alignment property, A is preferably a pyridine-2,5-diyl group, a pyrimidine-2,5-diyl group, a 1,2,4,5-tetrazine-2,5-diyl group, or a 1,4-phenylene group. Further, in order to improve the solubility of the polymer, A is preferably a 1,4-naphthylene group, a 2,6-naphthylene group, a 2,5-thiophenylene group, or a 2,5-furanylene group. Further, in order to reduce the dose of light irradiation required for aligning the liquid crystal, A is preferably a pyridine-2,5-diyl group, a pyrimidine-2,5-diyl group, a 2,5-thiophenylene group, or a 1,4-phenylene group. Further, in order to conduct photo-alignment at a longer wavelength, A is preferably a pyrimidine-2,5-diyl group, a 2,5-thiophenylene group, a 2,6-naphthylene group, or a 2,5-furanylene group, and X and Y are each preferably a fluorine atom, a chlorine atom, or a cyano group. Further, in order to improve the voltage holding ratio, X and Y are each preferably a hydrogen atom, $W^1$ is preferably —$CH_2$—, $R^4$ is preferably an alkyl group having 1 to 12 carbon atoms, and one $CH_2$ group is preferably substituted with O. Further, in order to reduce the residual voltage, $W^1$ is preferably —CO—O— or —CO—NH—, $R^4$ is preferably an alkyl group having 1 to 6 carbon atoms, and one $CH_2$ group is preferably substituted with O, —CO—O—, —O—CO—, or —N($CH_3$)—.

From the viewpoint that the compound represented by the general formula (I) has polymerizability, the compound has a polymerizable substituent, and therefore, the compounds can be polymerized with each other. As the polymerizable substituent, specifically, in the general formula (I), L is preferably any substituent selected from the group consisting of the general formulae (III-1) to (III-17), and among these, the general formula (III-1), (III-2), (III-6), (III-7), or (III-13) is preferable, and the general formula (III-1) or (III-2) is more preferable.

[Chem. 111]

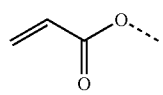
(III-1)

[Chem. 45]

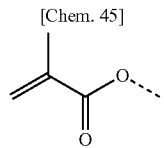
(III-2)

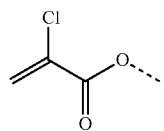
(III-3)

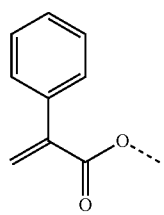
(III-4)

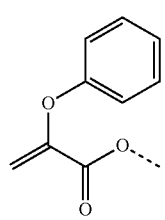
(III-5)

-continued

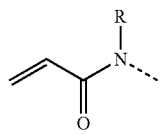
(III-6)

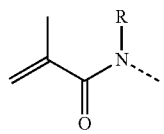
(III-7)

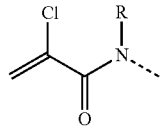
(III-8)

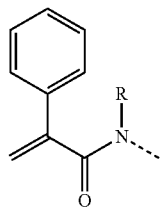
(III-9)

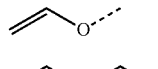
(III-10)

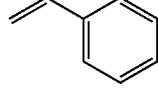
(III-11)

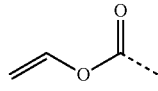
(III-12)

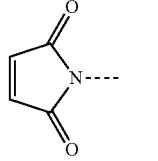
(III-13)

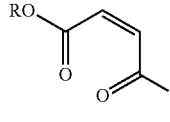
(III-14)

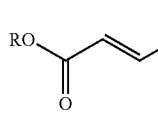
(III-15)

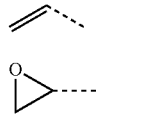
(III-16)

(III-17)

(wherein the broken line represents a bond to Sp and R's independently represent hydrogen or an alkyl group having 1 to 5 carbon atoms).

In order to improve the solubility of the polymer, the general formulae (III-1), (III-2), (III-3), (III-6), (III-7), (III-8), (III-10), (III-12), (III-14), (III-16), or (III-17) is preferable, and among these, the general formulae (III-1), (III-2), (III-10), (III-12), or (III-17) is particularly preferable. Further, in order to improve the polymerization speed, the general formulae (III-3), (III-8), (III-10), (III-12), (III-13), (III-14), (III-15), (III-16), or (III-17) is preferable, and among these, the general formulae (III-3), (III-8), (III-10), (III-12), or (III-17) is more preferable. Further, in order to narrow the molecular weight distribution of the polymer, the general formulae (III-2), (III-10), (III-11), or (III-12) is preferable. Further, in order to improve the stability of alignment, the general formulae (III-2), (III-4), (III-5), (III-7), (III-9), (III-13), (III-14), or (III-15) is preferable. Further, in order to improve the adhesion onto a substrate, the general formulae (III-1), (III-6), (III-7), (III-8), (III-9), (III-10), (III-12), (III-13), or (III-17) is preferable, and among these, the general formulae (III-6), (III-7), (III-8), or (III-13) is particularly preferable.

(Polymer)

The liquid crystal alignment layer is obtained by forming a layer of a polymer for a liquid crystal alignment layer on a surface of a base material used for aligning a liquid crystal, and then irradiating the layer with light to conduct crosslinking. The liquid crystal alignment layer is produced using a polymer of a composition containing the cinnamic acid derivative or the cinnamic acid derivative, but the specific aspects are preferably those as described below.

A structure is preferable which is constituted of a polymer of a composition containing the cinnamic acid derivative or the cinnamic acid derivative as described in the aspects of cinnamic acid derivatives, the polymer is represented by the general formula (PI):

[Chem. 112]

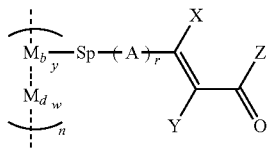

(PI)

(wherein Sp, A, X, Y, Z, and r have the same definitions as in the general formula (I), $M_b$ and $M_d$ each represent a monomer unit of the polymer, y and w each represent a molar fraction of the copolymer, each satisfying $0<y\leq 1$ and $0\leq w<1$, n represents 4 to 100,000, the order in which $M_b$ and $M_d$ are arranged may be the same as or different from that shown in the formula, and the monomer units of $M_d$ may be each independently constituted with one or two or more different units).

The liquid crystal alignment layer is obtained by forming a layer of the polymer on the surface of a base material used for aligning the liquid crystal, and then irradiating it with light to conduct crosslinking and/or isomerization, thereby curing it.

The monomer unit ($M_b$) may be the same as or different from the monomer unit ($M_d$), and a known monomer unit can be used without a particular limitation. Further, the sequencing order and randomness of the monomer units ($M_b$ and $M_d$) in the polymer are not particularly limited. Further, as the monomer units ($M_d$), one kind of the monomer units or combination of two or more kinds of the monomer units may be used. They are preferably used to a degree which does not interfere with the effects exerted by the polymer as a liquid crystal alignment film. As the monomer units ($M_d$), acrylate, methacrylate, acrylamide, methacrylamide, maleic acid derivatives, siloxanes, or epoxides is preferable, and examples thereof include an acryloyloxy group, a methacryloyloxy group, a 2-chloroacryloyloxy group, a 2-phenylacryloyloxy group, a 2-phenyloxyacryloyloxy group, an acrylamide group, a methacrylamide group, a 2-chloromethacrylamide group, a 2-phenylacrylamide group, a vinyloxy group, a styryl group, a vinyloxycarbonyl group, a maleimide group, maleic esters, fumaric esters, siloxanes, a vinyl group, and an epoxy group.

As the monomer unit ($M_b$), specifically, the formulae (QIII-A-1) to (QIII-A-17) may be used:

[Chem. 113]

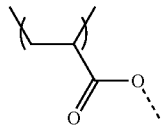
(QIII-A-1)

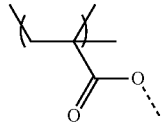
(QIII-A-2)

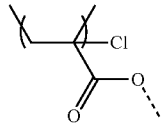
(QIII-A-3)

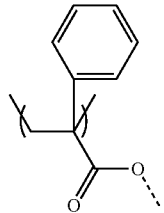
(QIII-A-4)

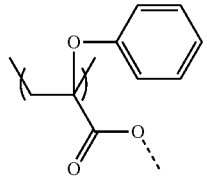
(QIII-A-5)

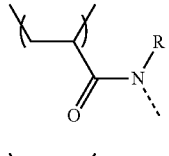
(QIII-A-6)

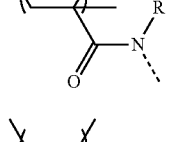
(QIII-A-7)

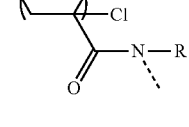
(QIII-A-8)

-continued
(QIII-A-9) 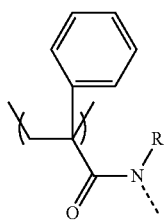
(QIII-A-10) 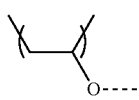
(QIII-A-11) 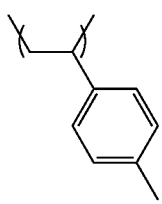
(QIII-A-12) 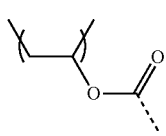
(QIII-A-13) 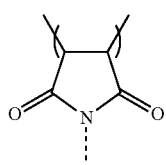
(QIII-A-14) 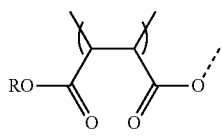
(QIII-A-15) 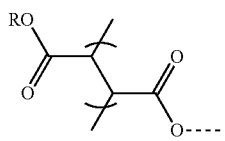
(QIII-A-16) 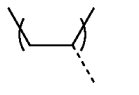
(QIII-A-17) 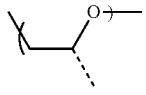
(wherein the broken line represents a bond to Sp and R's independently represent hydrogen or an alkyl group having 1 to 5 carbon atoms).
As the monomer unit ($M_d$), specifically, the formulae (QIII-1) to (QIII-17) may be used:
[Chem. 114]
(QIII-1) 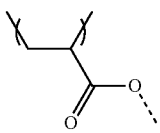
(QIII-2) 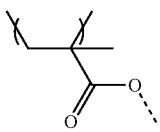
(QIII-3) 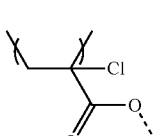
(QIII-4) 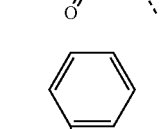
(QIII-5) 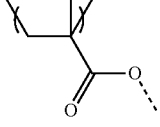
(QIII-6) 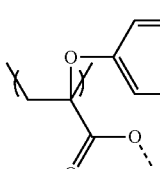
(QIII-7) 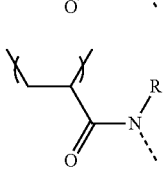
(QIII-8) 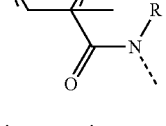
(QIII-9) 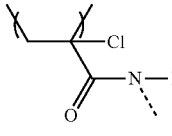
(QIII-10) 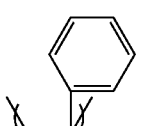

(QIII-11)

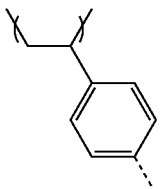

(QIII-12)

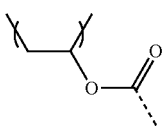

(QIII-13)

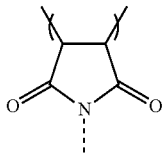

(QIII-14)

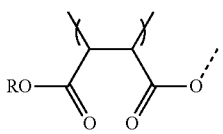

(QIII-15)

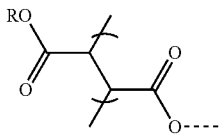

(QIII-16)

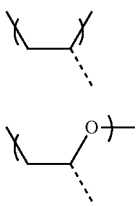

(QIII-17)

(wherein the broken line represents a bond to a monovalent organic group, R's independently represent hydrogen or an alkyl group having 1 to 5 carbon atoms, and any hydrogen atom in each of the structures may be substituted with a fluorine atom, a chlorine atom, a methyl group, or a methoxy group).

Examples of the monovalent organic group include hydrogen, an alkyl group having 1 to 12 carbon atoms (any hydrogen atom in the alkyl group may be substituted with a fluorine atom, a chlorine atom, a methyl group, or a methoxy group, and one $CH_2$ group or two or more non-adjacent $CH_2$ groups in the alkyl group may be substituted with —O—, —CO—O—, —O—CO—, and/or —CH=CH—). Other examples of the monovalent organic group include a trans-1,4-cyclohexylene group, a trans-1,3-dioxan-2,5-yl group, a 1,4-naphthylene group, a 2,6-naphthylene group, a 2,5-pyridyl group, a 2,5-pyrimidyl group, a 1,2,4,5-tetrazine-2,5-diyl group, a 2,5-thiophenylene group, a 2,5-furanylene group, and a 1,4-phenylene group (any hydrogen atom in each of the structures may be substituted with a fluorine atom, a chlorine atom, a methyl group, or a methoxy group).

Furthermore, particularly, in order to obtain an alignment layer for vertical alignment, examples of the monovalent organic group include the general formula (QIV):

[Chem. 115]

$$—S_a—V_a \quad (QIV)$$

(wherein the broken line represents a bond to a monomer unit ($M_a$), $S_a$ represents a spacer unit, and $V_a$ represents a moiety that stabilizes vertical alignment).

As Sa, a structure which is the same as Sp in the general formula (I) may be used.

$V_a$ is preferably a structure represented by the following general formula (V):

[Chem. 116]

$$\text{---}(A^3—Z^4)_{r1}(A^4—Z^5)_{s1}(A^5—Z^6)_{t1}(A^6—Z^7)_{u1}R^{12} \quad (V)$$

(wherein the broken line represents a bond to $S_a$;

$Z^4$, $Z^5$, $Z^6$ and $Z^7$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, but one or more of the non-adjacent $CH_2$ groups in these substituents may be independently substituted with —O—, —CO—, —CO—O—, —O—CO—, —Si(CH_3)_2—O—Si(CH_3)_2—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^3$, $A^4$, $A^5$ and $A^6$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, r1, s1, t1, and u1 each independently represent 0 or 1, and $R^{12}$ represents hydrogen, fluorine, chlorine, a cyano group, or an alkyl group having 1 to 20 carbon atoms, a hydrogen atom in the alkyl group may be substituted with a fluorine atom, and one $CH_2$ group or two or more non-adjacent $CH_2$ groups may be substituted with —O—, —CO—O—, —O—CO—, and/or —CH=CH—).

$Z^4$, $Z^5$, $Z^6$ and $Z^7$ are each independently preferably a single bond, —$(CH_2)_u$— (wherein u represents 1 to 12, one or more of the non-adjacent $CH_2$ groups independently represent —O—, —CO—, —CO—O—, —O—CO—, —NR—CO—, —CO—NR—, —NR—CO—NR—, —CH=CH—, —C≡C—, or —O—CO—O—, and R's independently represent hydrogen, a methyl group, or an ethyl group), —$OCH_2$—, —$CH_2O$—, —COO—, —OCO—, —CH=CH—, —$CF_2O$—, —$OCF_2$—, or —C≡C—, and $A^3$, $A^4$, $A^5$ and $A^6$ each independently represent a trans-1,4-cyclohexylene group, a 2,6-naphthylene group, a pyridine-2,5-diyl group, a pyrimidine-2,5-diyl group, or a 1,4-phenylene group, and these are preferably unsubstituted or have one or more hydrogen atoms substituted with a fluorine atom, a chlorine atom, a methyl group, or a methoxy group, for r1, s1, t1, and u1, r1+s1+t1+u1 is preferably from 0 to 3, and $R^{12}$ is preferably a structure represented by hydrogen, fluorine, chlorine, a cyano group, or an alkyl group having 1 to 18 carbon atoms (one $CH_2$ group or two or more non-adjacent $CH_2$ groups in the alkyl group may be substituted with —O—, —CO—O—, —O—CO—, and/or —CH=CH—).

In order to improve the liquid crystal alignment property in the liquid crystal alignment layer of the present invention, $Z^4$, $Z^5$, $Z^6$ and $Z^7$ are each independently preferably a single bond, —$(CH_2)_u$— (wherein u represents 1 to 8, and one or two of the non-adjacent $CH_2$ groups independently represent —O—, —CO—O—, —O—CO—, —Si$(CH_3)_2$—O—Si$(CH_3)_2$—, —CH=CH—, or —C≡C—), —COO—, —OCO—, —CH=CH—, —CF=CF—, or —C≡C—, and $A^3$, $A^4$, $A^5$ and $A^6$ are each independently preferably a trans-1,4-cyclohexylene group, a trans-1,3-dioxane-2,5-diyl group, a pyridine-2,5-diyl group, a pyrimidine-2,5-diyl group, a 1,2,4,5-tetrazine-2,5-diyl group, a 2,5-thiophenylene group, or a 1,4-phenylene group.

Furthermore, in order to improve the thermal stability of alignment in the liquid crystal alignment layer of the present invention, $Z^4$, $Z^5$, $Z^6$ and $Z^7$ are each independently preferably —NR—CO—, —CO—NR—, —NR—CO—O—, —O—CO—NR—, —NR—CO—NR—, or —O—CO—O—, and $A^3$, $A^4$, $A^5$ and $A^6$ are each independently preferably a 1,4-naphthylene group, a 2,6-naphthylene group, a pyridine-2,5-diyl group, a pyrimidine-2,5-diyl group, a 2,5-thiophenylene group, a 2,5-furanylene group, or a 1,4-phenylene group. Further, in order to improve the solubility of the polymer, $Z^4$, $Z^5$, $Z^6$ and $Z^7$ are each independently preferably —OCH$_2$—, —CH$_2$O—, —CF$_2$O—, —OCF$_2$—, —CF$_2$CF$_2$—, —NR—, or —CO—, and $A^3$, $A^4$, $A^5$ and $A^6$ are each independently preferably a trans-1,4-cyclohexylene group, a 1,4-naphthylene group, a 2,6-naphthylene group, or a 2,5-furanylene group.

Furthermore, in order to provide a pretilt angle of 80 degrees or more, $Z^4$, $Z^5$, $Z^6$ and $Z^7$ are each independently preferably a single bond, —OCH$_2$—, —CH$_2$O—, —COO—, —OCO—, and —C≡C—, $A^3$, $A^4$, $A^5$ and $A^6$ are each independently preferably a trans-1,4-cyclohexylene group, a trans-1,3-dioxane-2,5-diyl group, and a 1,4-phenylene group, and $R^2$ is preferably an alkyl group having 1 to 20 carbon atoms, an alkoxy group, fluorine, a trifluoromethyl group, and a trifluoromethoxy group.

Many compounds belong to the general formula (V), but in order to provide a pretilt angle of 80 degrees or more, specifically, the compounds represented by the following general formulae (V-a-1) to (V-q-10) are particularly preferable:

[Chem. 117]

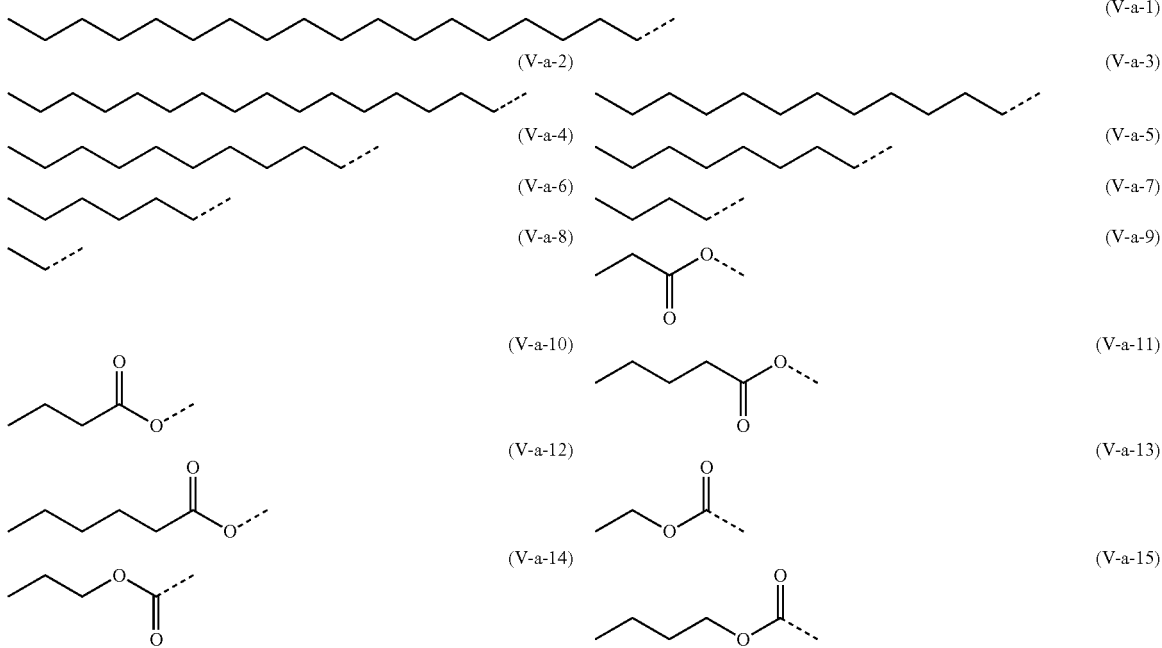

[Chem. 118]

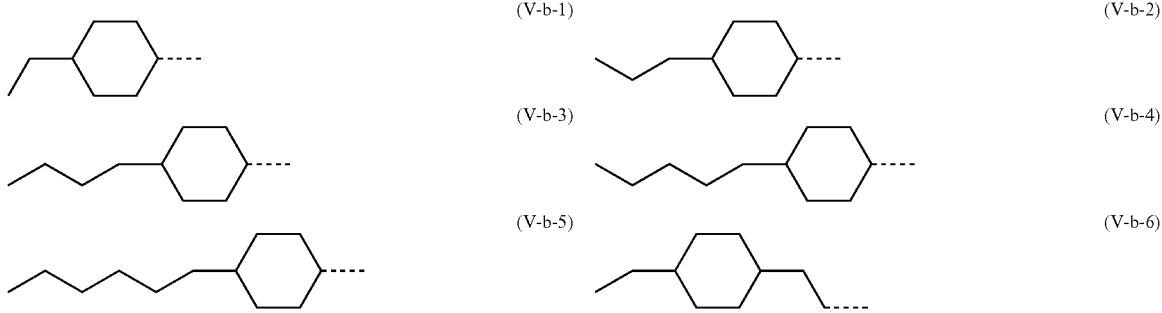

-continued
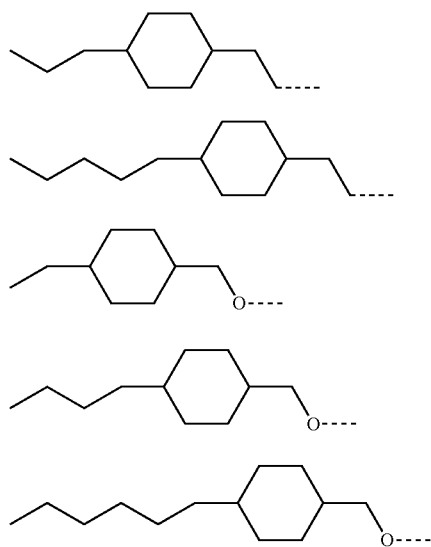
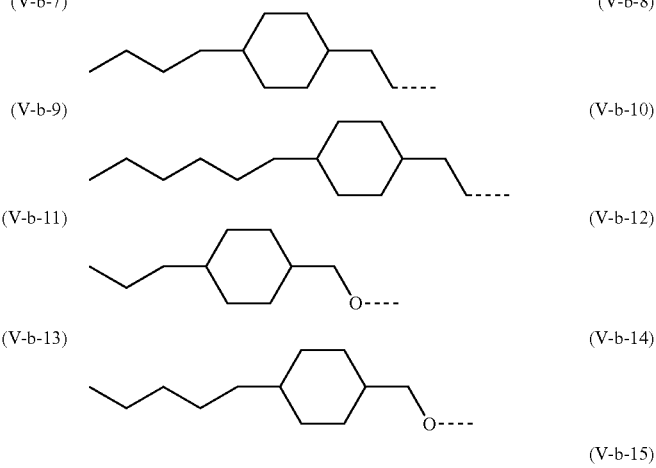
[Chem. 119]
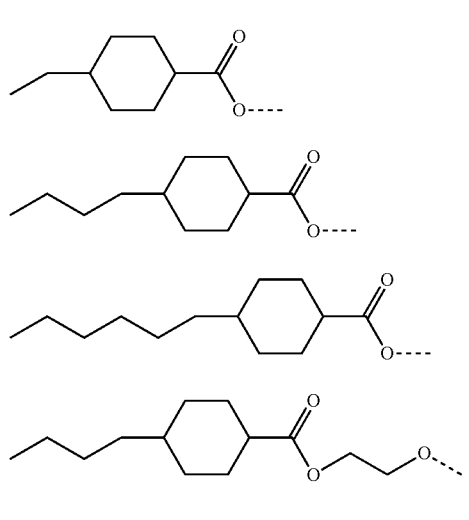
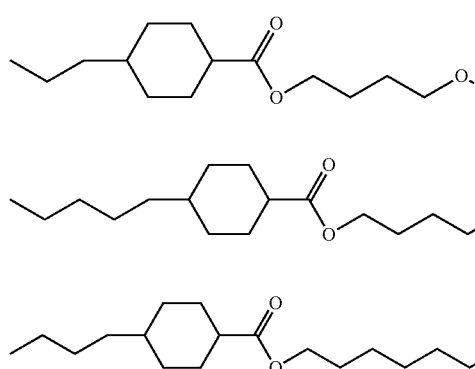
[Chem. 120]
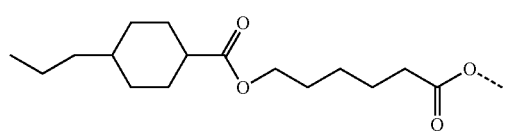
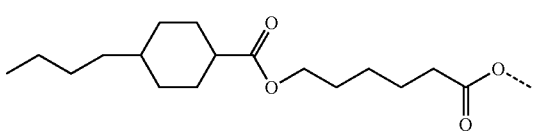

-continued
(V-d-3)
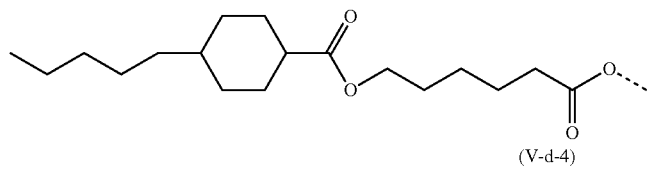
(V-d-4)  (V-d-5)
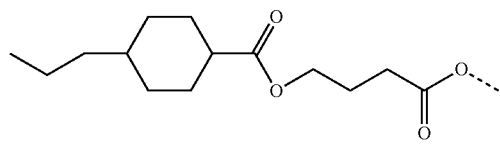
(V-d-6)  (V-d-7)
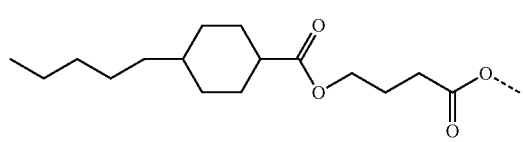
(V-d-8)
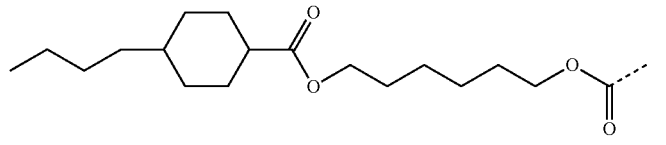
(V-d-9)
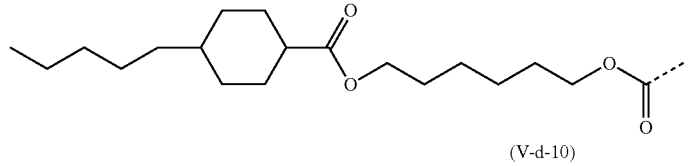
(V-d-10)  (V-d-11)
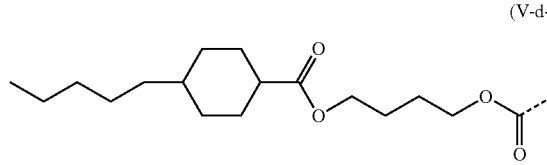
(V-d-12)  (V-d-13)
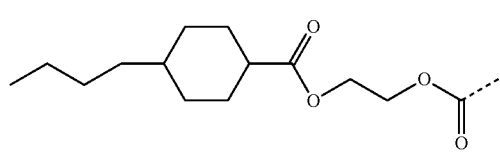
(V-d-14)  (V-d-15)
[Chem. 121]
(V-e-1)  (V-e-2)
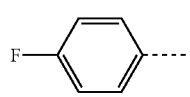   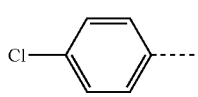
(V-e-3)  (V-e-4)
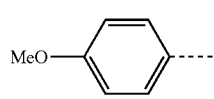  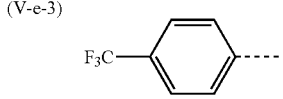
(V-e-5)  (V-e-6)
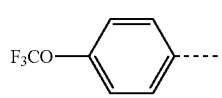  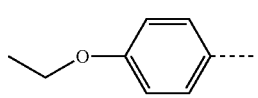

-continued
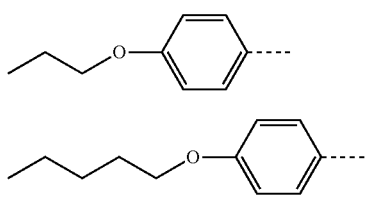
(V-e-7)
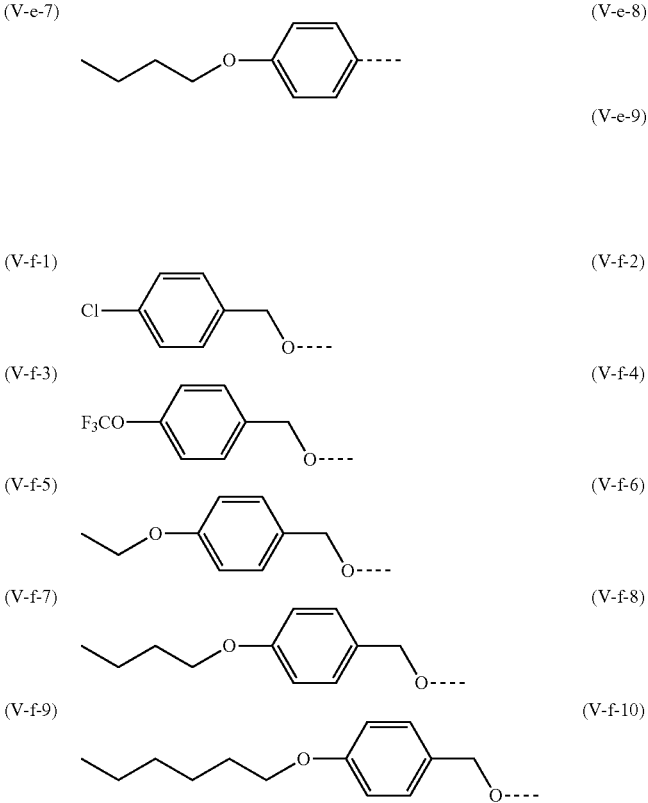
(V-e-8)
(V-e-9)
(V-f-1)
(V-f-2)
(V-f-3)
(V-f-4)
(V-f-5)
(V-f-6)
[Chem. 122]
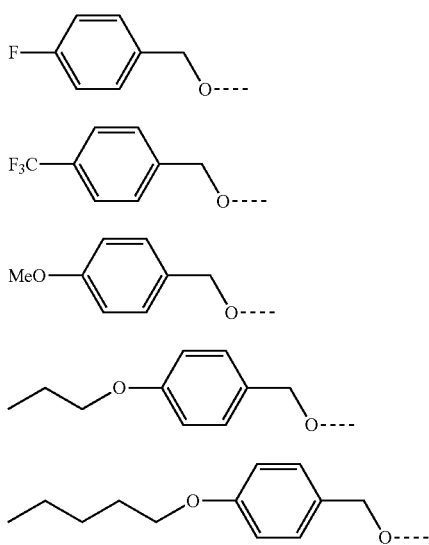
(V-f-1)
(V-f-3)
(V-f-5)
(V-f-7)
(V-f-9)
[Chem. 123]
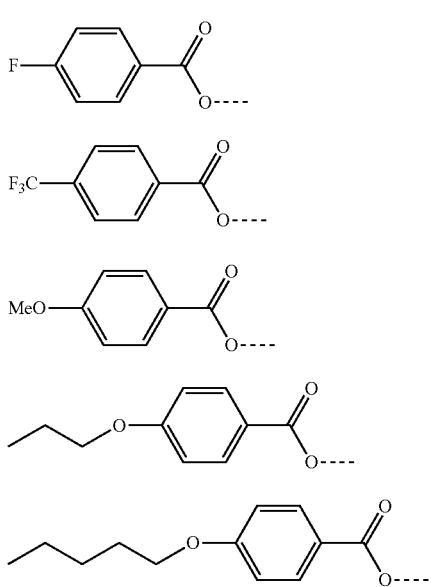
(V-g-1)
(V-g-3)
(V-g-5)
(V-g-7)
(V-g-9)
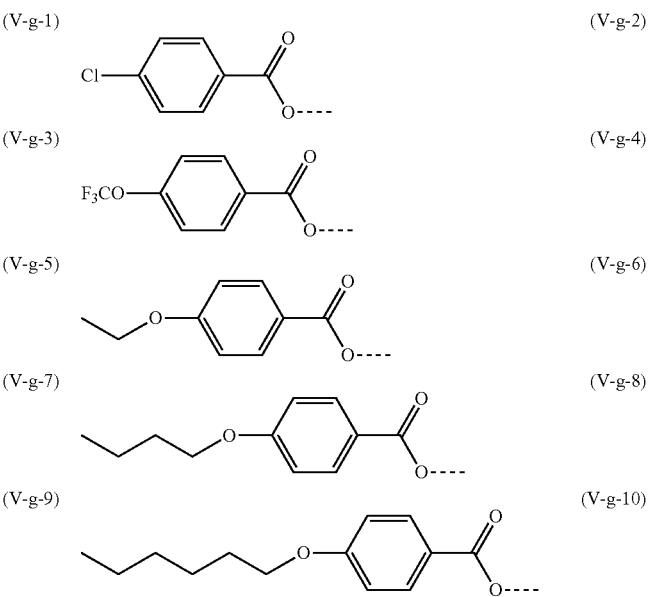
(V-f-7)
(V-f-8)
(V-f-9)
(V-f-10)
(V-g-1)
(V-g-2)
(V-g-3)
(V-g-4)
(V-g-5)
(V-g-6)
(V-g-7)
(V-g-8)
(V-g-9)
(V-g-10)
[Chem. 124]
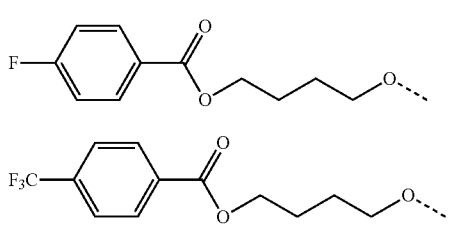
(V-h-1)
(V-h-3)
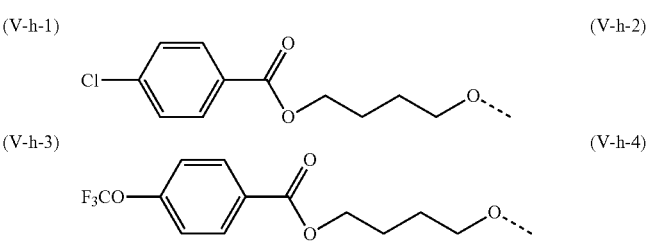
(V-h-2)
(V-h-4)

-continued
(V-h-5) 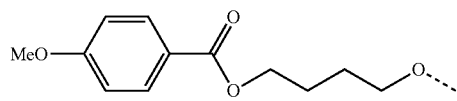 (V-h-6)
(V-h-7) 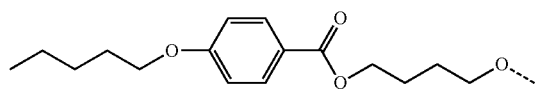 (V-h-8)
(V-h-9) (V-h-10)
[Chem. 125]
(V-i-1) 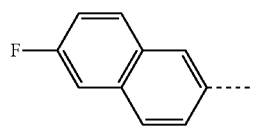 (V-i-2)
(V-i-3) 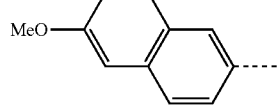 (V-i-4)
(V-i-5) 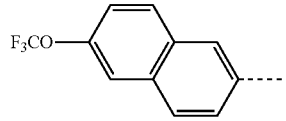 (V-i-6)
(V-i-7) 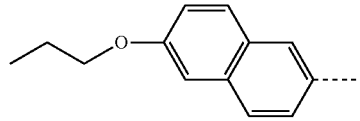 (V-i-8)
(V-i-9) 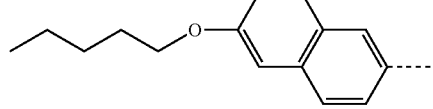
[Chem. 126]
(V-j-1) 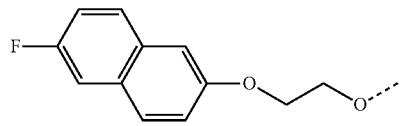 (V-j-2)
(V-j-3) 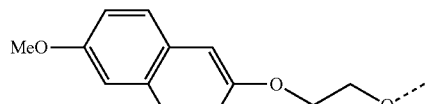 (V-j-4)
(V-j-5) 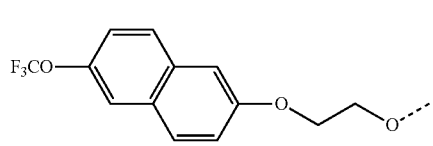 (V-j-6)

(V-j-7) 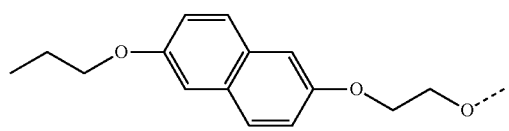
(V-j-8) 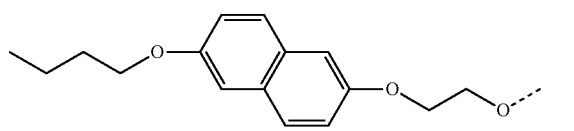
(V-j-9) 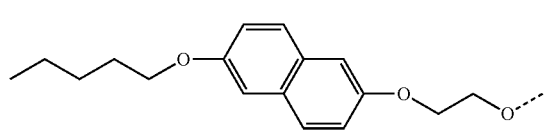
[Chem. 127]
(V-k-1) 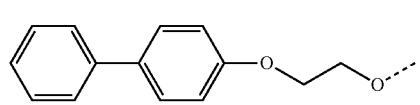
(V-k-2) 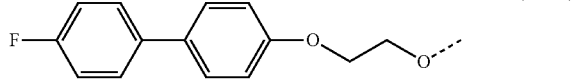
(V-k-3) 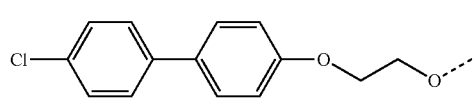
(V-k-4) 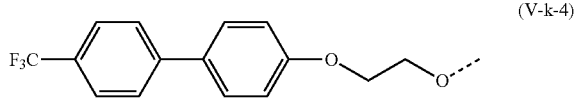
(V-k-5) 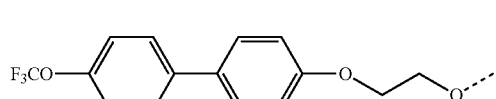
(V-k-6) 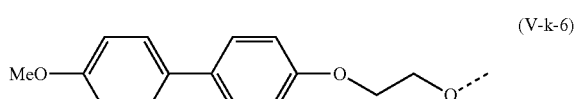
(V-k-7) 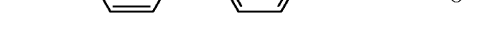
(V-k-8) 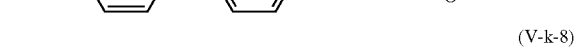
(V-k-9) 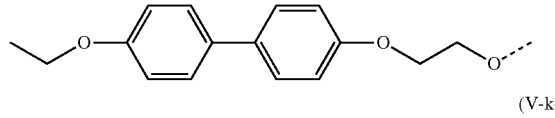
(V-k-10) 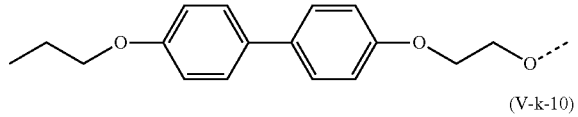
(V-k-11) 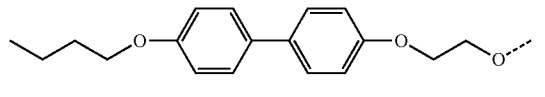
[Chem. 128]
(V-l-1) 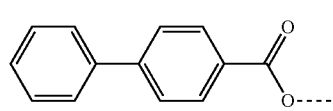
(V-l-2) 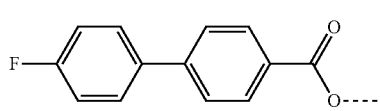
(V-l-3) 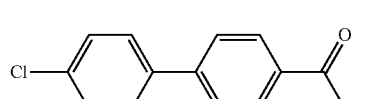
(V-l-4) 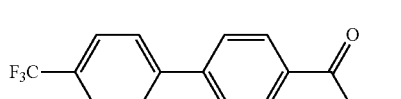
(V-l-5) 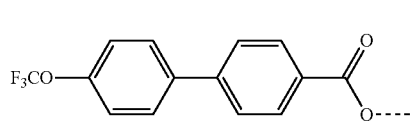
(V-l-6) 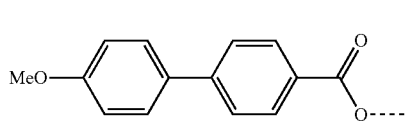
(V-l-7) 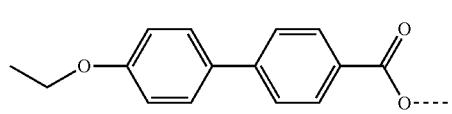
(V-l-8) 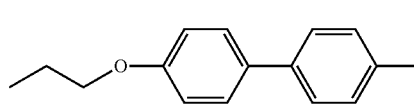
(V-l-9) 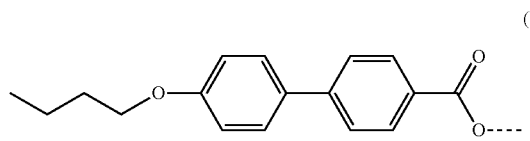
(V-l-10) 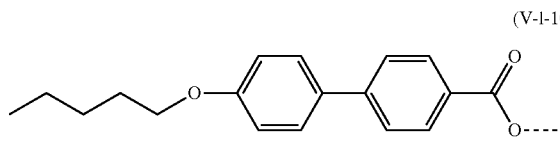
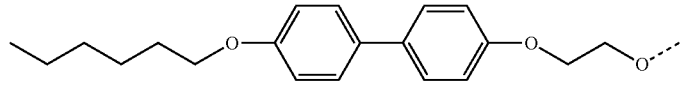

-continued
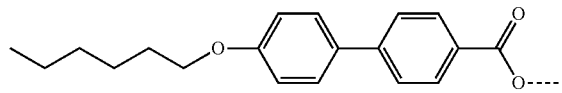
(V-l-11)
[Chem. 129]
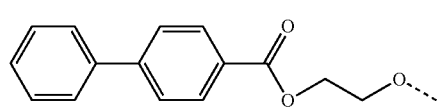 (V-m-1)
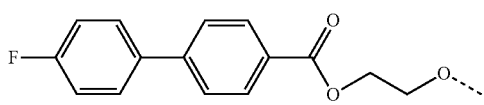 (V-m-2)
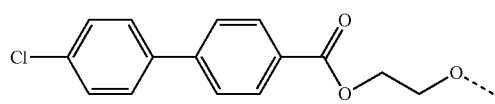 (V-m-3)
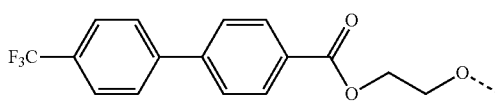 (V-m-4)
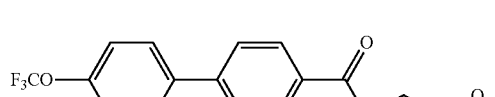 (V-m-5)
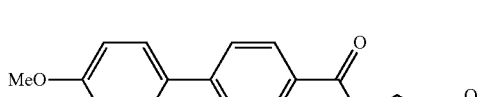 (V-m-6)
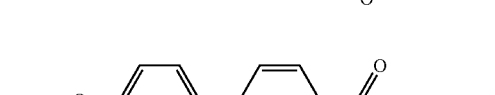 (V-m-7)
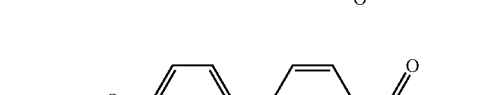 (V-m-8)
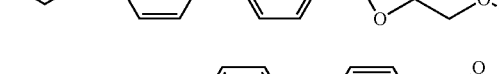 (V-m-9)
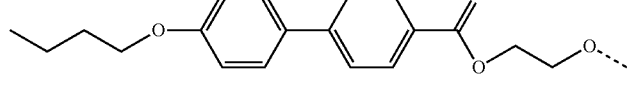 (V-m-10)
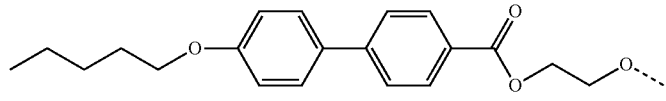 (V-m-11)
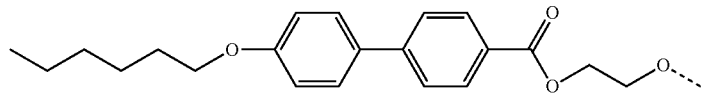
[Chem. 130]
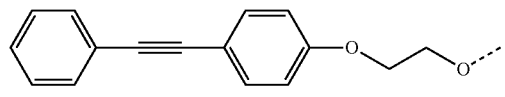 (V-n-1)
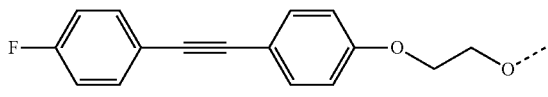 (V-n-2)
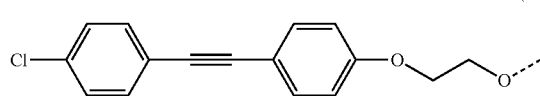 (V-n-3)
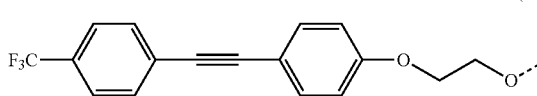 (V-n-4)
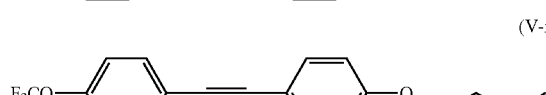 (V-n-5)
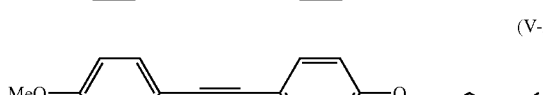 (V-n-6)
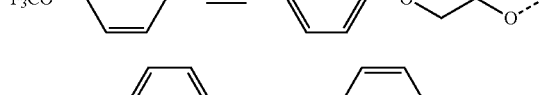 (V-n-7)
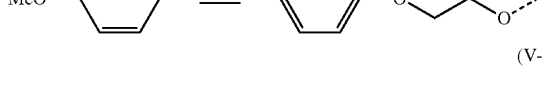 (V-n-8)
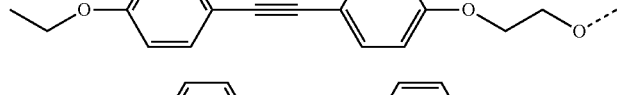
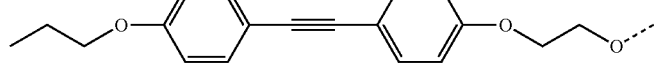

-continued
(V-n-9)
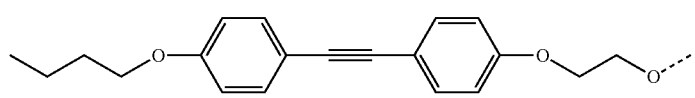
(V-n-10)
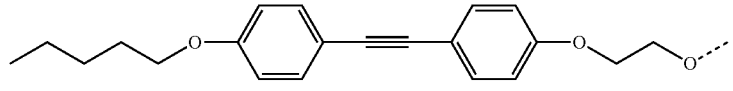
(V-n-11)
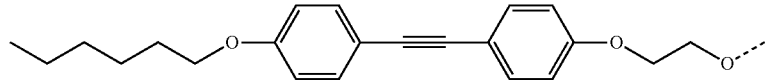
[Chem. 131]
(V-o-1)
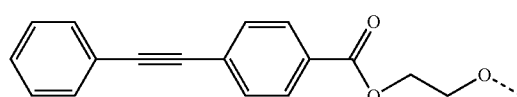
(V-o-2)
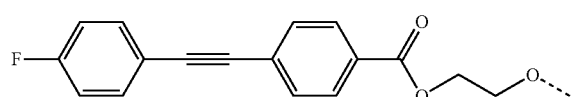
(V-o-3)
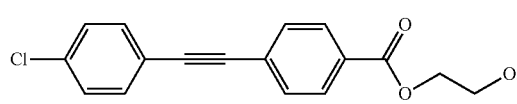
(V-o-4)
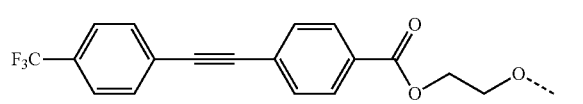
(V-o-5)
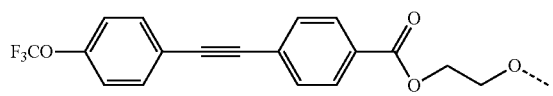
(V-o-6)
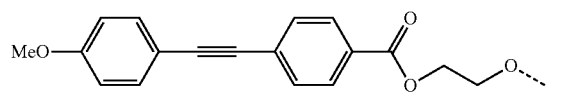
(V-o-7)
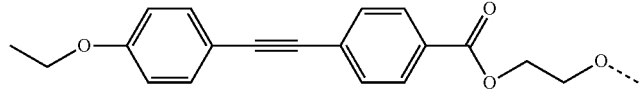
(V-o-8)
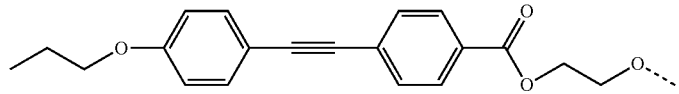
(V-o-9)
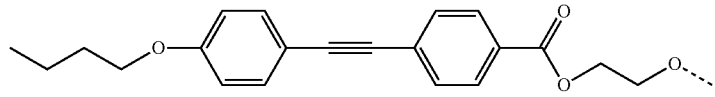
(V-o-10)
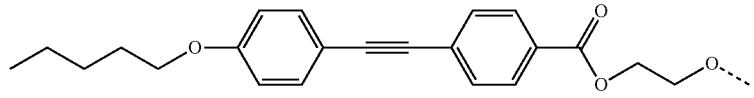
(V-o-11)
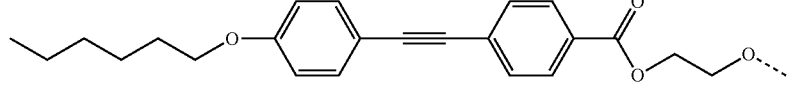
[Chem. 132]
(V-p-1)
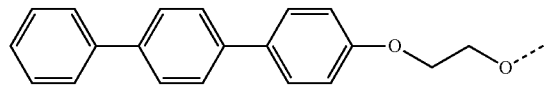
(V-p-2)
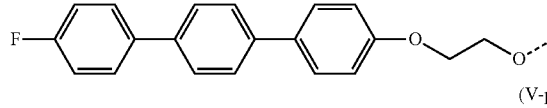
(V-p-3)
(V-p-4)
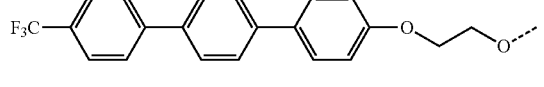
(V-p-5)
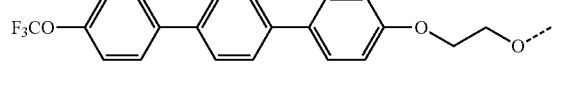

(V-p-6)
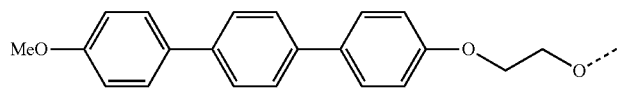
(V-p-7)
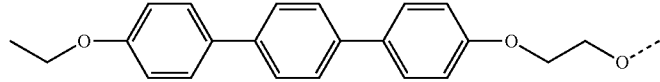
(V-p-8)
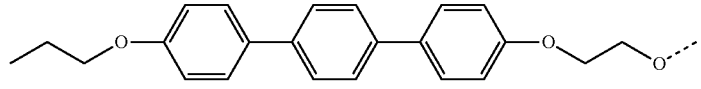
(V-p-9)
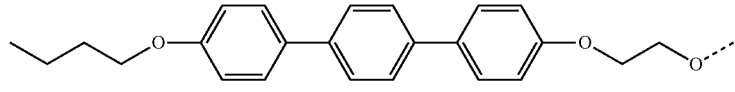
(V-p-10)
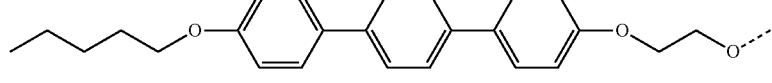
(V-p-11)
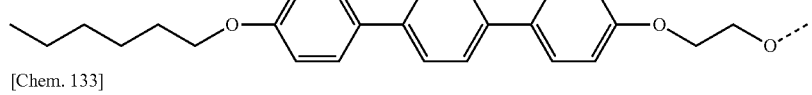
[Chem. 133]
(V-q-1)
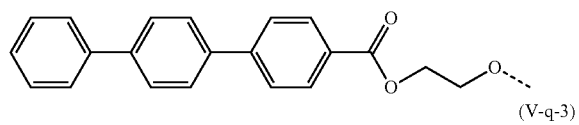
(V-q-2)
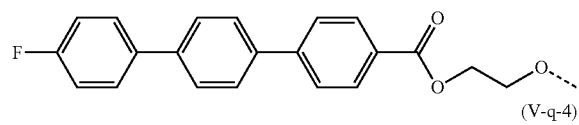
(V-q-3)
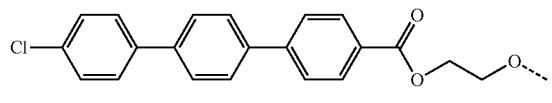
(V-q-4)
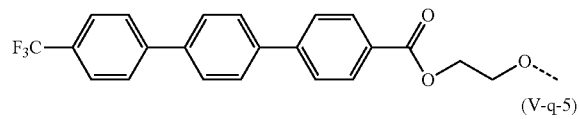
(V-q-5)
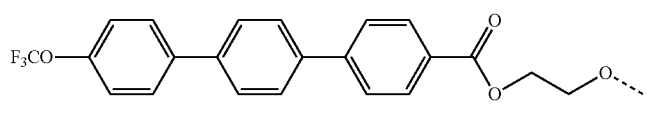
(V-q-6)
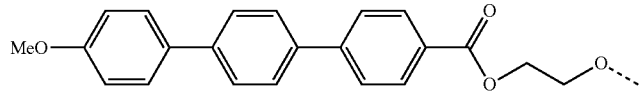
(V-q-7)
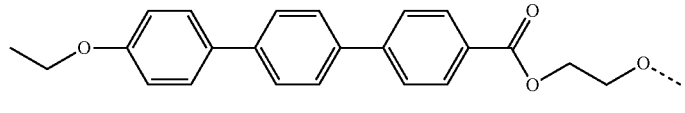
(V-q-8)
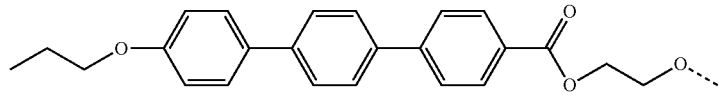
(V-q-9)
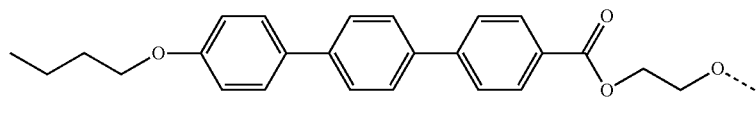
(V-q-10)
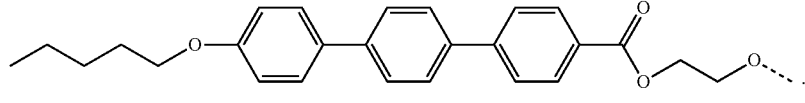
Among these, the general formulae (V-a-1) to (V-a-15), the general formulae (V-b-11) to (V-b-15), the general formulae (V-c-1) to (V-c-11), the general formulae (V-d-10) to (V-d-15), the general formulae (V-f-1) to (V-f-10), the general formulae (V-g-1) to (V-g-10), the general formulae (V-h-1) to (V-h-10), the general formulae (V-j-1) to (V-j-9), the general formulae (V-l-1) to (V-l-11), or the general formulae (V-m-1) to (V-m-11) are more preferable.

In the general formula (I), Sp is a structure represented by the following general formula (IVa):

[Chem. 134]

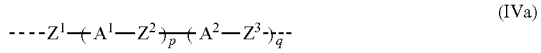

(IVa)

(wherein the left broken line represents a bond to L, the right broken line represents a bond to A, $Z^1$, $Z^2$ and $Z^3$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, but one or more of the non-adjacent $CH_2$ groups in these substituents may be independently substituted with —O—, —CO—, —CO—O—, —O—CO—, —Si(CH$_3$)$_2$—O—Si(CH$_3$)$_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), $A^1$ and $A^2$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 1,2,4,5-tetrazine-2,5-diyl group, a 2,5-thiophenylene group, a 2,5-furanylene group, or a 1,4-phenylene group, and these may be unsubstituted or have one or more hydrogen atoms substituted with a fluorine atom, a chlorine atom, a methyl group, or a methoxy group, and p and q each independently represent 0 or 1), $Z^1$, $Z^2$ and $Z^3$ are each independently preferably a single bond, —$(CH_2)_u$— (wherein u represents 1 to 20, and one or more of the non-adjacent $CH_2$ groups independently represent —O—, —CO—, —CO—O—, —O—CO—, —NR—, —NR—CO—, —CO—NR—, —NR—CO—NR—, —CH=CH—, —C≡C—, or —O—CO—O—, and R represents hydrogen, a methyl group, or an ethyl group), —$OCH_2$—, —$CH_2O$—, —COO—, —OCO—, —CH=CH—, —$CF_2O$—, —$OCF_2$—, or —C≡C—, $A^1$ and $A^2$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, or a 1,4-phenylene group, these are preferably unsubstituted or have one or more hydrogen atoms substituted with a fluorine atom, a chlorine atom, a methyl group, or a methoxy group, $Z^1$, $Z^2$ and $Z^3$ are each independently more preferably a single bond, —$(CH_2)_u$— (wherein u represents 1 to 20), —$OCH_2$—, —$CH_2O$—, —COO—, —OCO—, —CH=CH—, or —C≡C— (one or more of the non-adjacent $CH_2$ groups in these substituents may be independently substituted with —O—, —CO—, —CO—O—, —O—CO—, —CH=CH—, or —C≡C—), q is more preferably 1, $A^1$ and $A^2$ each independently represent a trans-1,4-cyclohexylene group, a 2,6-naphthylene group, a pyridine-2,5-diyl group, a pyrimidine-2,5-diyl group, or a 1,4-phenylene group, these are more preferably unsubstituted or have one or more hydrogen atoms substituted with a fluorine atom, a chlorine atom, a methyl group, or a methoxy group, $Z^1$, $Z^2$ and $Z^3$ are each independently particularly preferably a single bond, —$(CH_2)_u$— (wherein u represents 1 to 20, and one or more of the non-adjacent $CH_2$ groups independently represent —O—, —CO—O—, —O—CO—, —CH=CH—, or —C≡C—), —$OCH_2$—, —$CH_2O$—, —COO—, —OCO—, —CH=CH—, or —C≡C, $A^1$ and $A^2$ each independently represent a trans-1,4-cyclohexylene group, a 2,6-naphthylene group, or a 1,4-phenylene group, these are particularly preferably unsubstituted or have one or more hydrogen atoms substituted with a fluorine atom, a methyl group, or a methoxy group, $A^2$ represents a 1,4-phenylene group, and these are most preferably unsubstituted or have one or more hydrogen atoms substituted with a fluorine atom, a methyl group, or a methoxy group.

In the general formula (IVa), in order to improve the liquid crystal alignment property, $Z^1$, $Z^2$ and $Z^3$ are each independently preferably a single bond, —$(CH_2)_u$— (wherein u represents 1 to 8, and one or two of the non-adjacent $CH_2$ groups independently represent —O—, —CO—O—, —O—CO—, —Si(CH$_3$)$_2$—O—Si(CH$_3$)$_2$—, —CH=CH—, or —C≡C—), —COO—, —OCO—, —CH=CH—, —CF=CF—, or —C≡C—, and $A^1$ and $A^2$ are each independently preferably a trans-1,4-cyclohexylene group, a trans-1,3-dioxane-2,5-diyl group, a pyridine-2,5-diyl group, a pyrimidine-2,5-diyl group, a 2,5-thiophenylene group, or a 1,4-phenylene group. Further, in order to improve the thermal stability of alignment, $Z^1$, $Z^2$ and $Z^3$ are each independently preferably —NR—CO—, —CO—NR—, —NR—CO—O—, —O—CO—NR—, —NR—CO—NR—, or —O—CO—O—, and $A^1$ and $A^2$ are each independently preferably a 1,4-naphthylene group, a 2,6-naphthylene group, a pyridine-2,5-diyl group, a pyrimidine-2,5-diyl group, a 2,5-thiophenylene group, a 2,5-furanylene group, or a 1,4-phenylene group. Further, in order to improve the solubility of the polymer, $Z^1$, $Z^2$ and $Z^3$ are each independently preferably —$OCH_2$—, —$CH_2O$—, —$CF_2O$—, —$OCF_2$—, —$CF_2CF_2$—, —NR—, or —CO—, and $A^1$ and $A^2$ are each independently preferably a trans-1,4-cyclohexylene group, a 1,4-naphthylene group, a 2,6-naphthylene group, or a 2,5-furanylene group.

Many compounds belong to the general formula (IVa), but specifically, the compounds represented by the following general formulae (S-a-1) to (S-ad-9) are particularly preferable:

[Chem. 135]

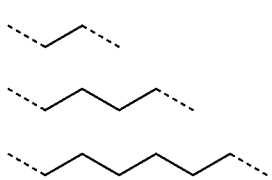

(S-a-1) (S-a-2)

(S-a-3) (S-a-4)

(S-a-5) (S-a-6)

-continued
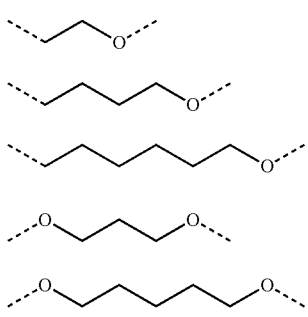
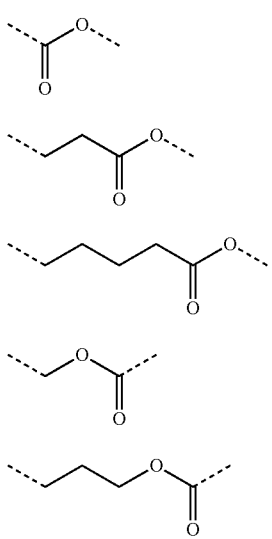
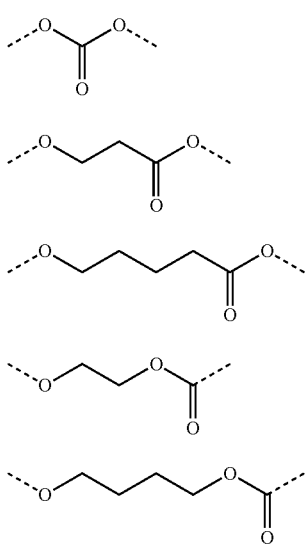
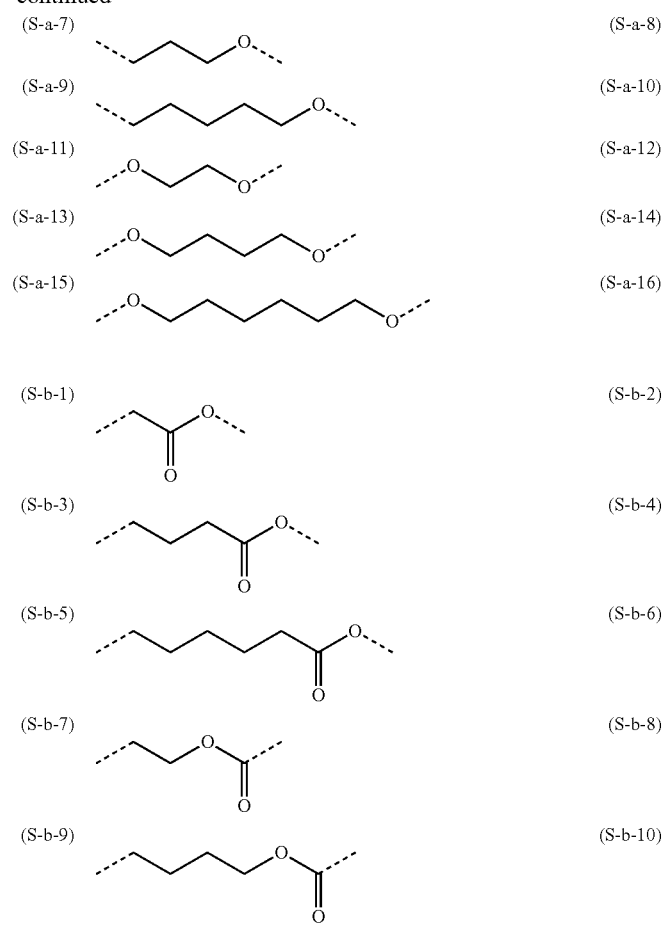
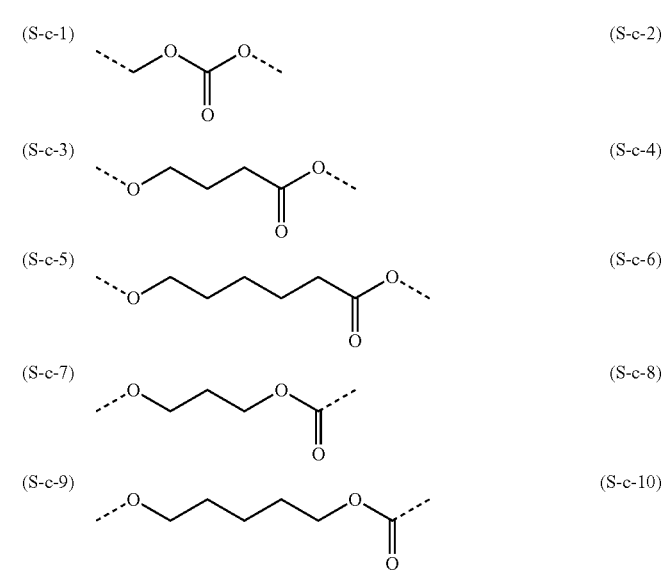
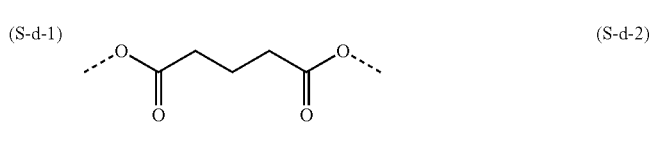

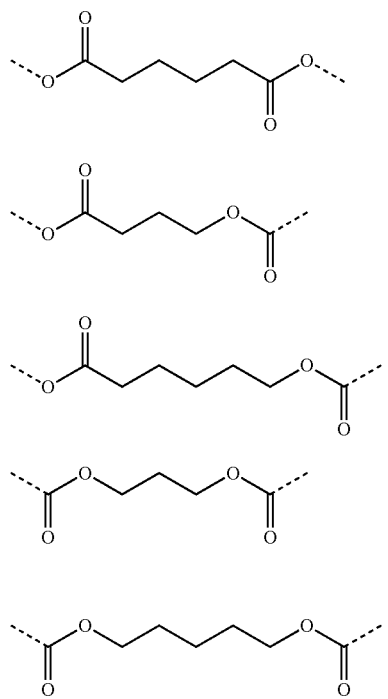
(S-d-3)
(S-d-5)
(S-d-7)
(S-d-9)
(S-d-11)
[Chem. 139]
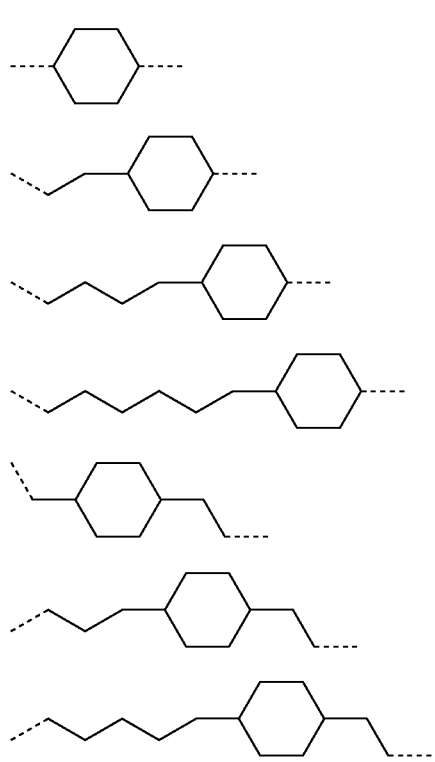
[Chem. 140]
-continued
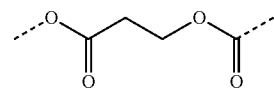 (S-d-4)
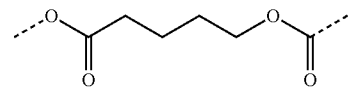 (S-d-6)
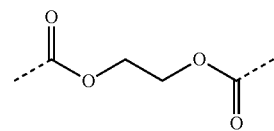 (S-d-8)
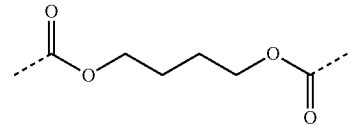 (S-d-10)
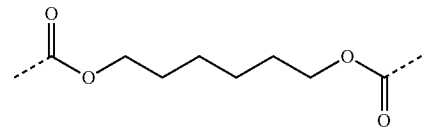 (S-d-12)
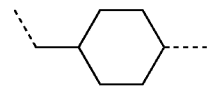 (S-e-2)
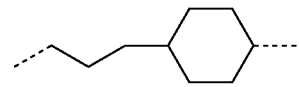 (S-e-4)
 (S-e-6)
 (S-e-8)
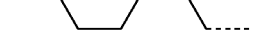 (S-e-10)
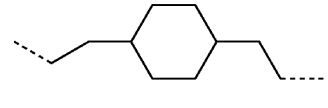 (S-e-12)
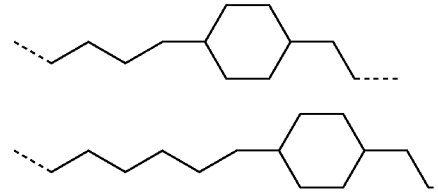 (S-e-14)
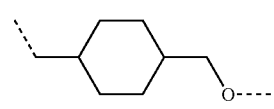 (S-f-2)

-continued
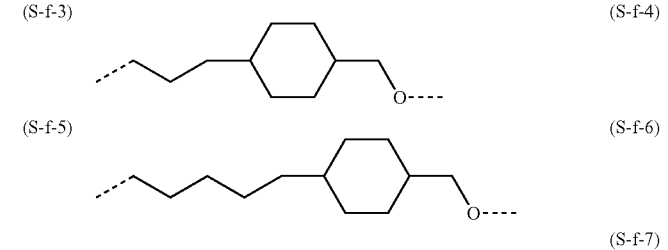
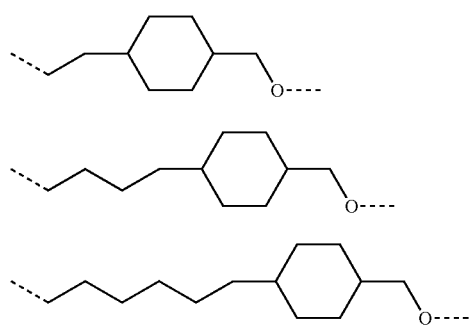
[Chem. 141]
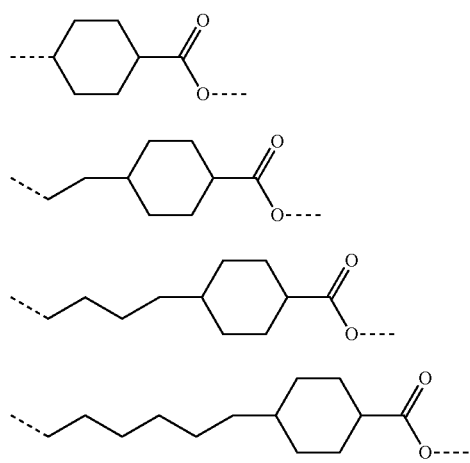
[Chem. 142]
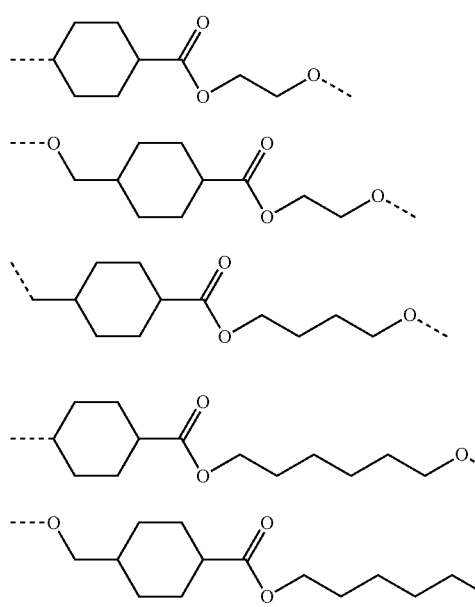
[Chem. 143]
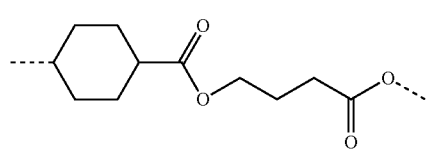

-continued
(S-i-3) 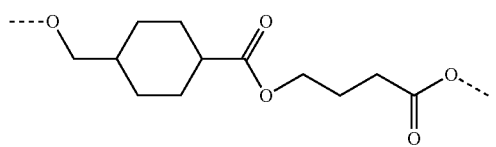
(S-i-4) 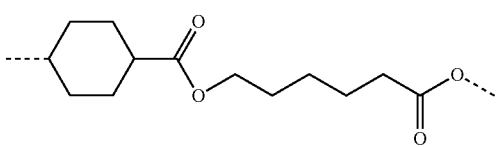
(S-i-5) 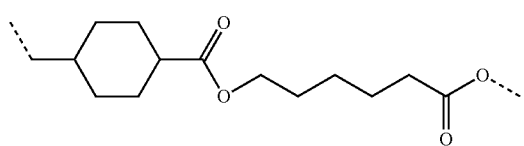
(S-i-6) 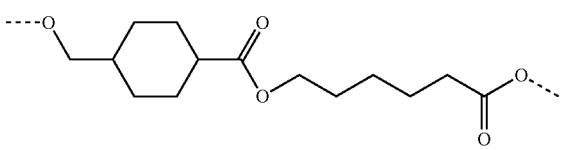
[Chem. 144]
(S-j-1) 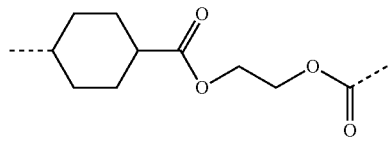
(S-j-2)
(S-j-3) 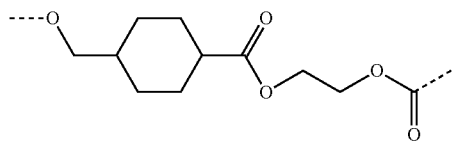
(S-j-4) 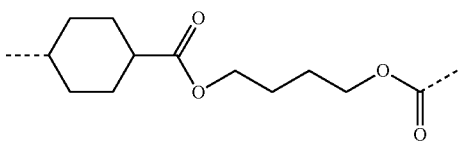
(S-j-5) 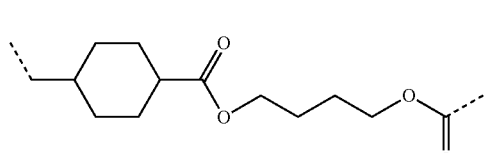
(S-j-6) 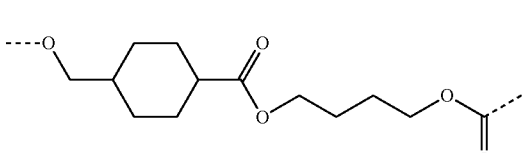
(S-j-7) 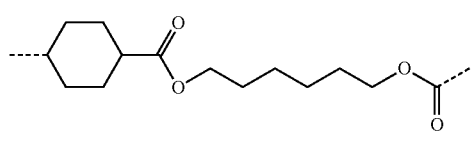
(S-j-8) 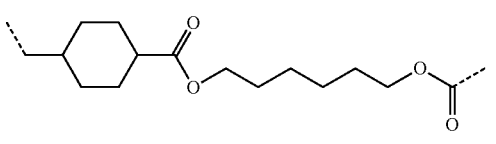
(S-j-9) 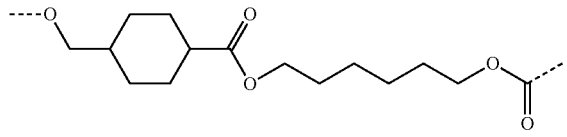
[Chem. 145]
(S-k-1) 
(S-k-2) 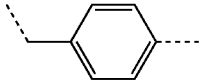
(S-k-3) 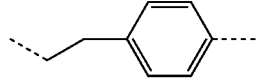
(S-k-4) 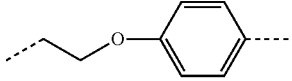
(S-k-5) 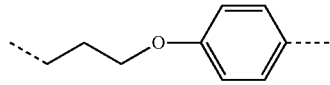
(S-k-6) 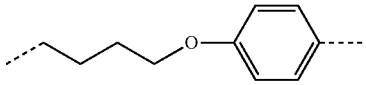
(S-k-7) 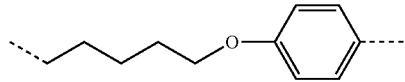
(S-k-8) 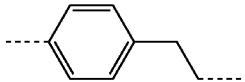

-continued
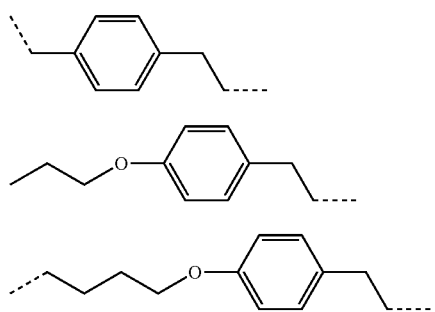
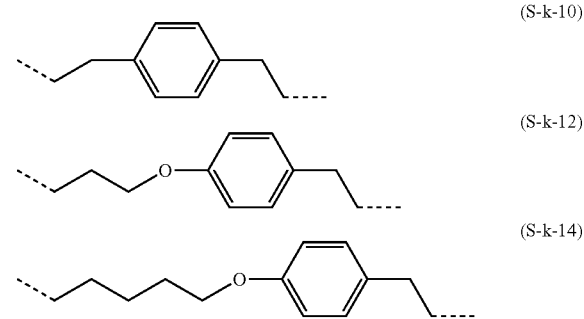
[Chem. 146]
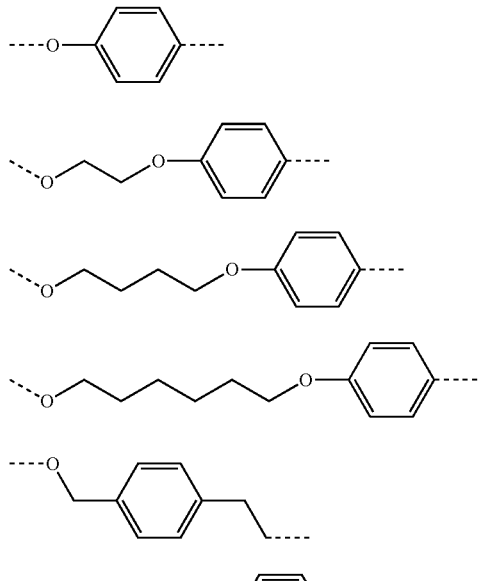
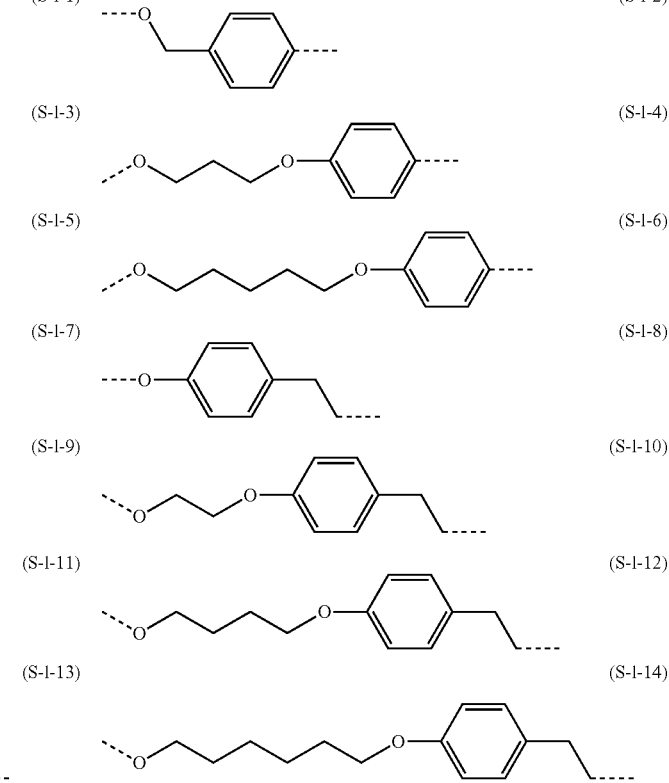
[Chem. 147]
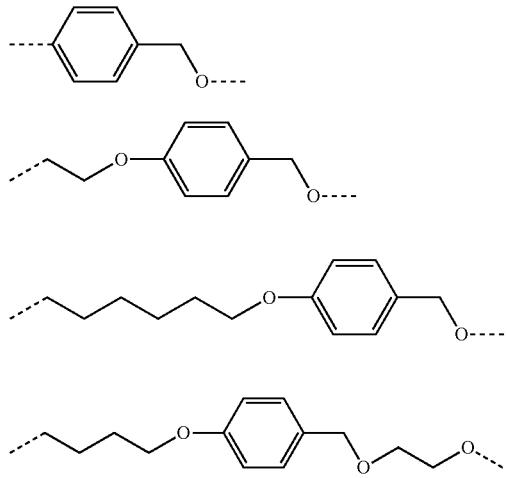
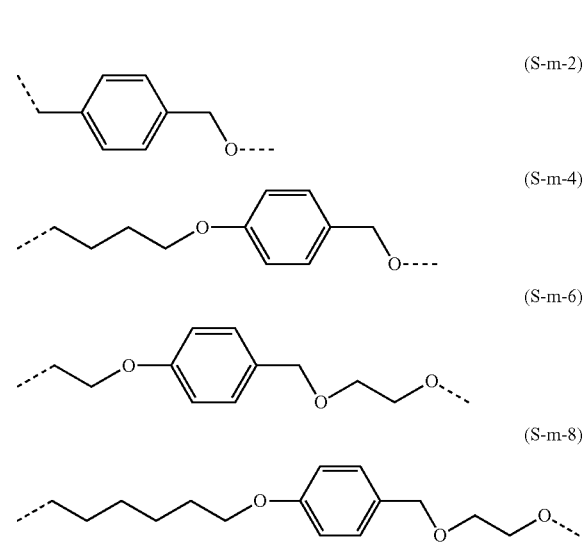

-continued
(S-m-9)
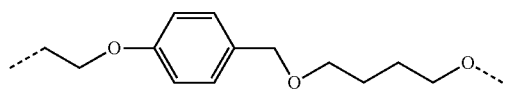
(S-m-10)
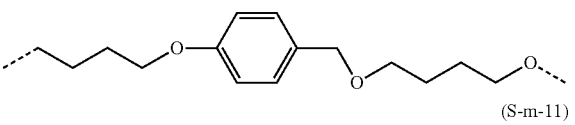
(S-m-11)
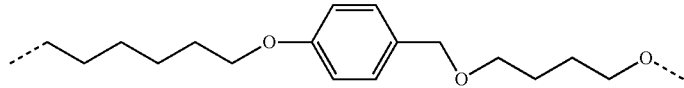
(S-m-12)
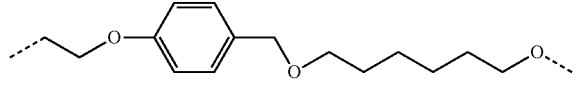
(S-m-13)
(S-m-14)
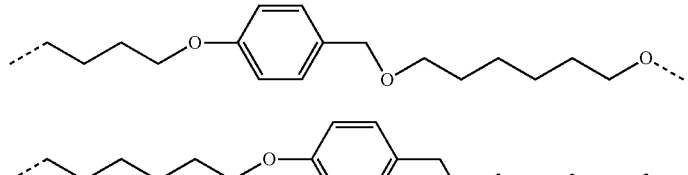
[Chem. 148]
(S-n-1)
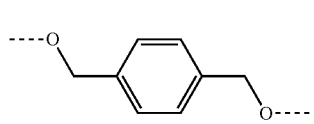
(S-n-2)
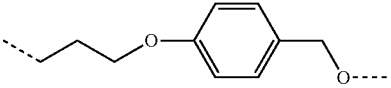
(S-n-3)
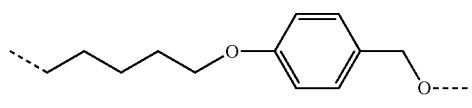
(S-n-4)
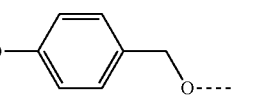
(S-n-5)
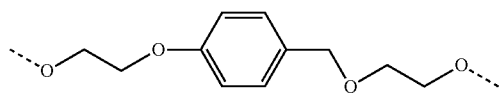
(S-n-6)
(S-n-7)
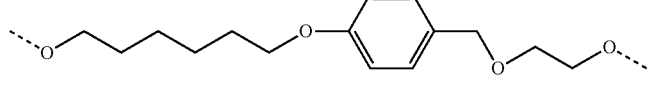
(S-n-8)
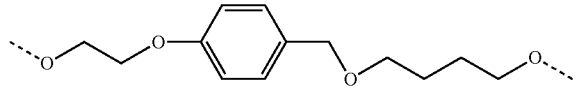
(S-n-9)
(S-n-10)
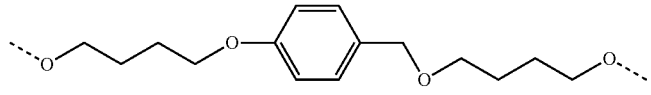
(S-n-11)
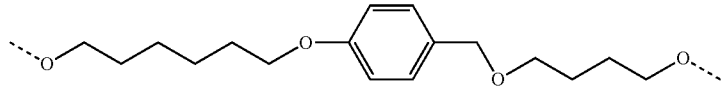
(S-n-12)
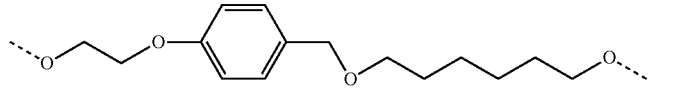

-continued
(S-n-13)
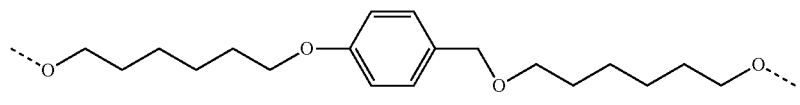
[Chem. 149]
(S-o-1) 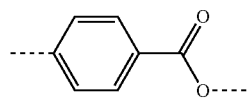  (S-o-2) 
(S-o-3) 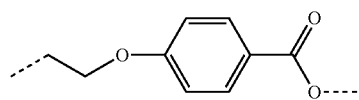  (S-o-4)
(S-o-5) 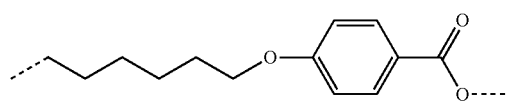  (S-o-6)
(S-o-7)   (S-o-8)
(S-o-9) 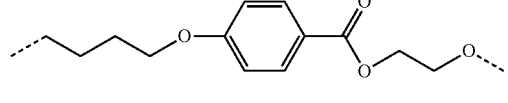  (S-o-10)
(S-o-11) 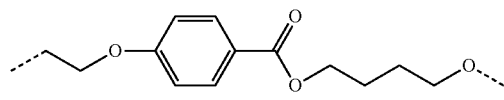
(S-o-12) 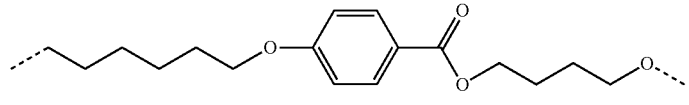
(S-o-13) 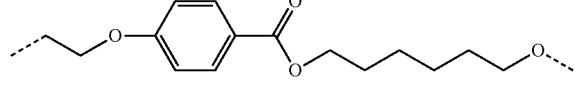
(S-o-14) 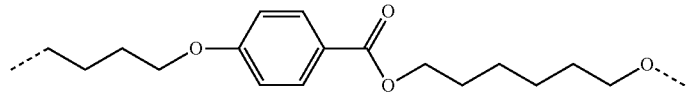
[Chem. 150]
(S-p-1) 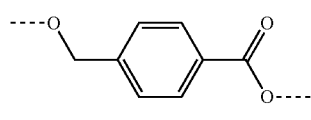  (S-p-2) 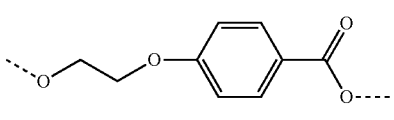
(S-p-3) 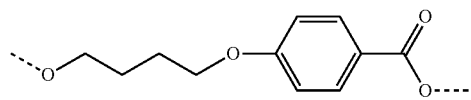  (S-p-4)
(S-p-5) 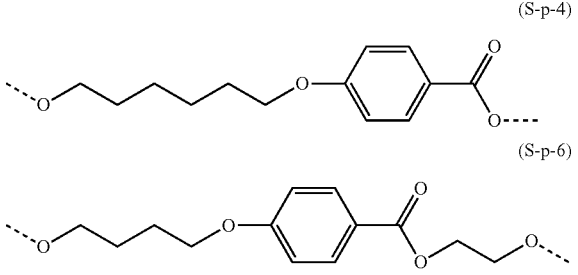  (S-p-6)

(S-p-7)
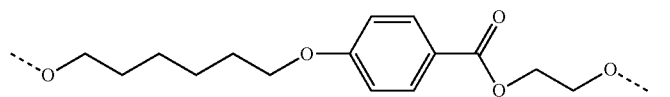
(S-p-8)
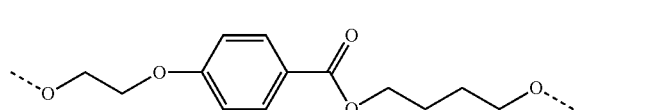
(S-p-9)
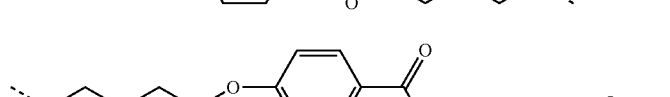
(S-p-10)
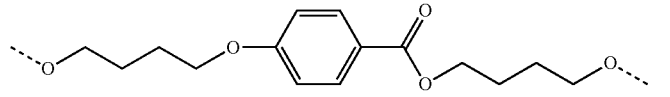
(S-p-11)
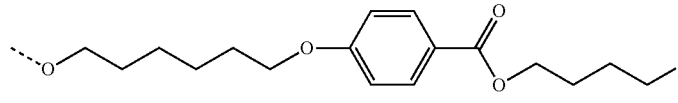
(S-p-12)
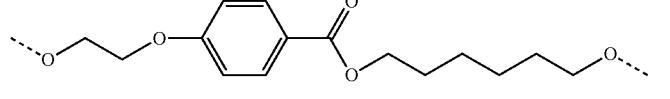
(S-p-13)
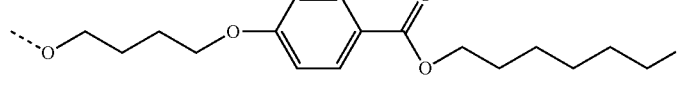
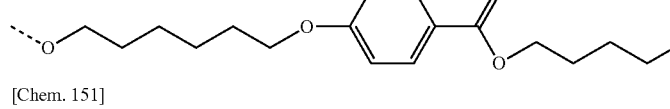
[Chem. 151]
(S-q-1)　　　　　　　　　　　　(S-q-2)
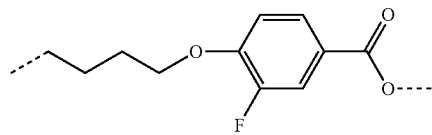 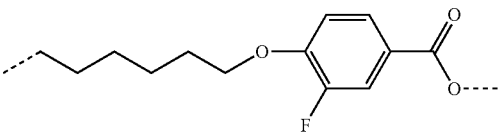
(S-q-3)　　　　　　　　　　　　(S-q-4)
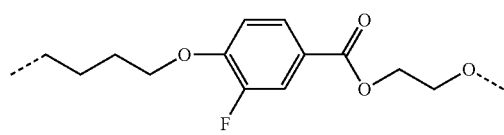 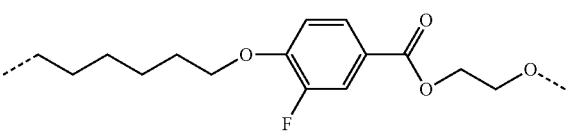
(S-q-5)
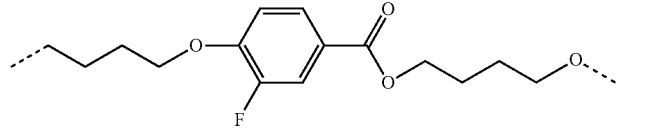
(S-q-6)
(S-q-7)
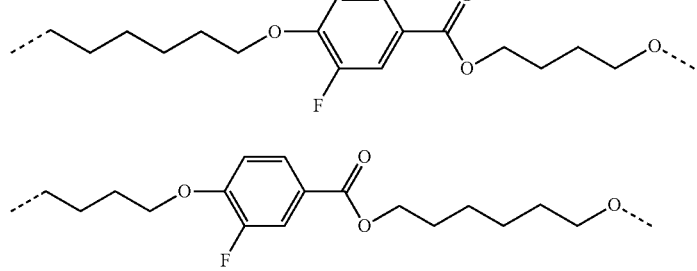

-continued
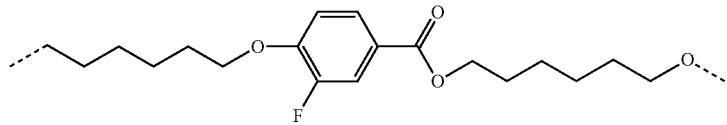
(S-q-8)
[Chem. 152]
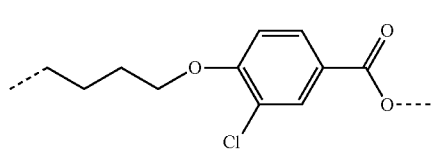 (S-r-1)  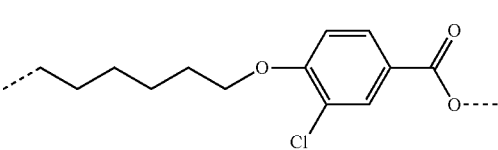 (S-r-2)
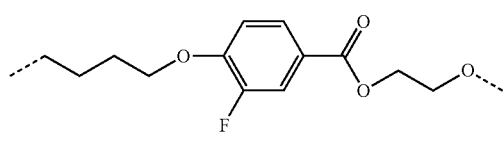 (S-r-3)  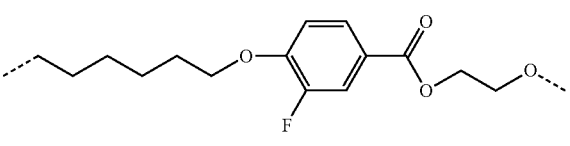 (S-r-4)
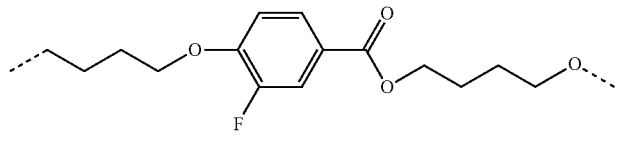 (S-r-5)
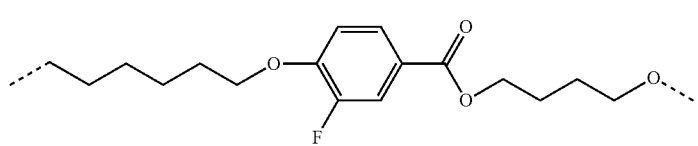 (S-r-6)
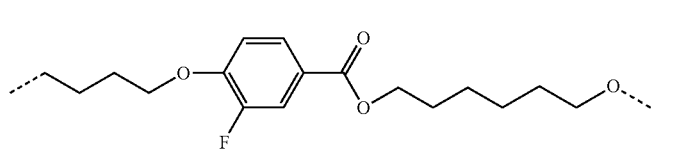 (S-r-7)
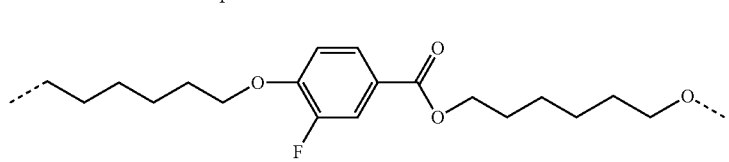 (S-r-8)
[Chem. 153]
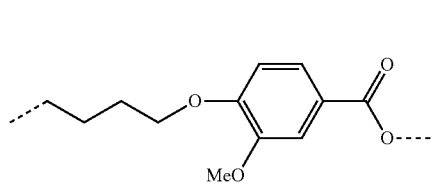 (S-s-1)  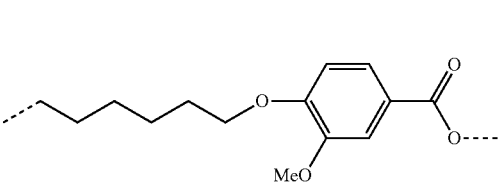 (S-s-2)
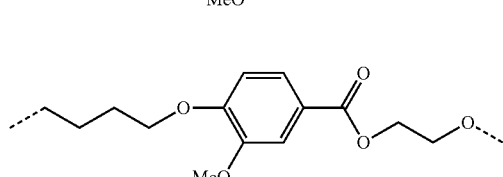 (S-s-3)  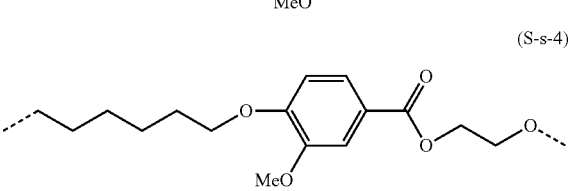 (S-s-4)
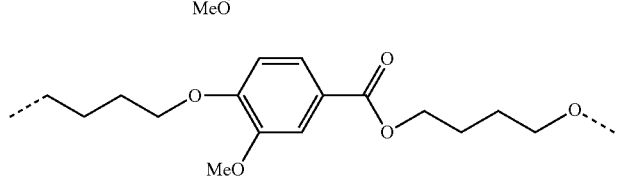 (S-s-5)

-continued
(S-s-6)
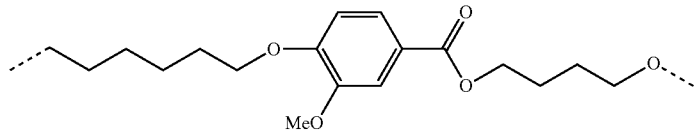
(S-s-7)
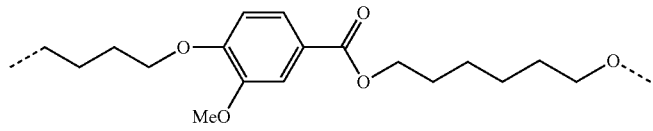
(S-s-8)
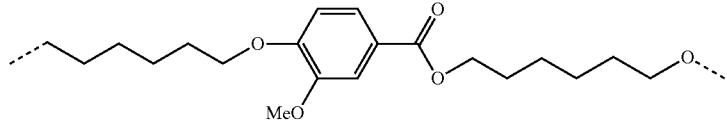
[Chem. 154]
(S-t-1)
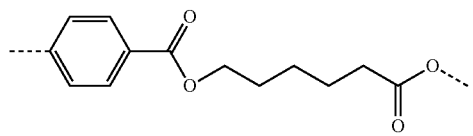
(S-t-2)
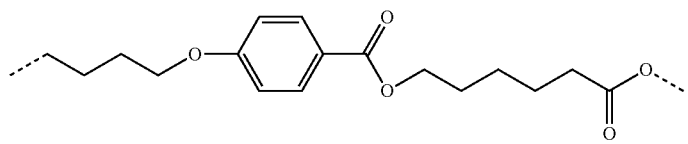
(S-t-3)
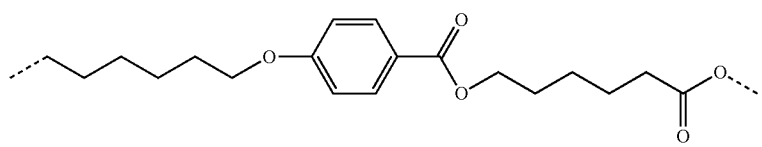
(S-t-4)
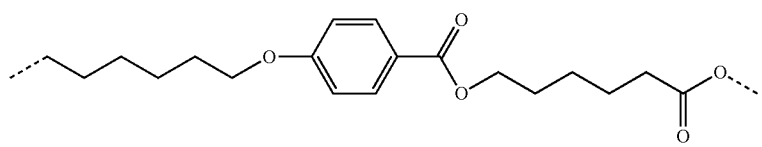
(S-t-5)
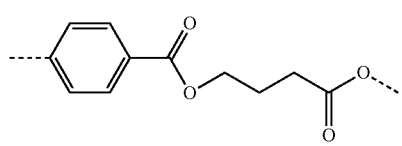
(S-t-6)
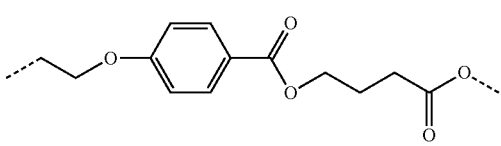
(S-t-7)
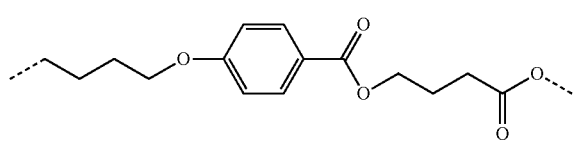
(S-t-8)
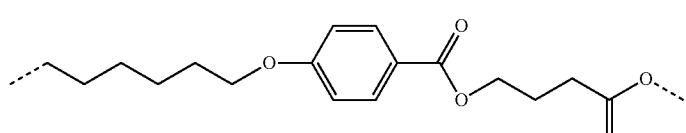
[Chem. 155]
(S-u-1)
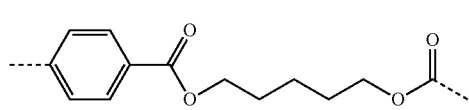
(S-u-2)
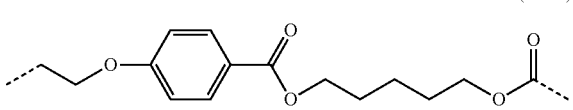

-continued
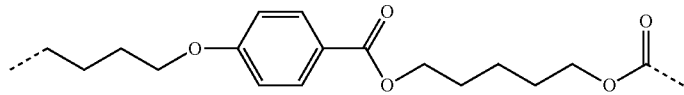
(S-u-3)
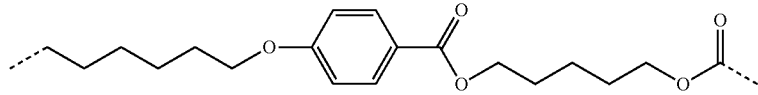
(S-u-4)
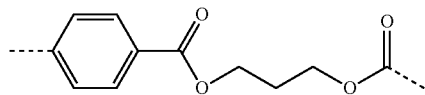
(S-u-5)
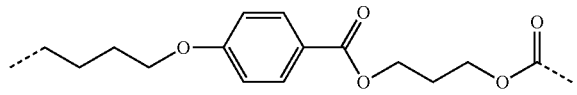
(S-u-6)
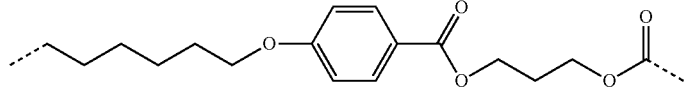
(S-u-7)
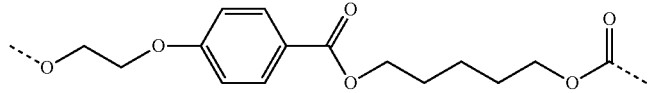
(S-u-8)
[Chem. 156]
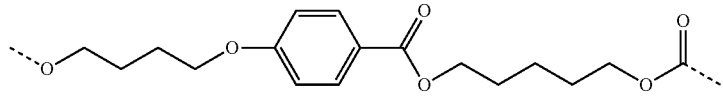
(S-v-1)
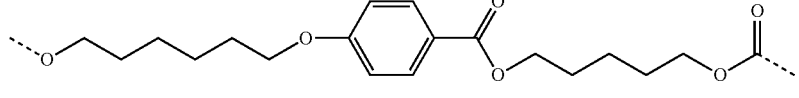
(S-v-2)
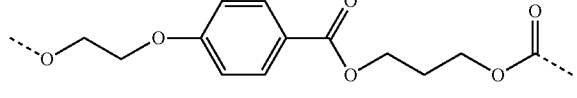
(S-v-3)
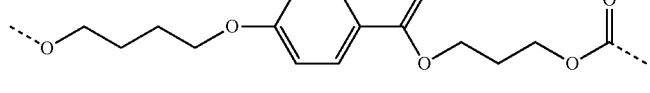
(S-v-4)
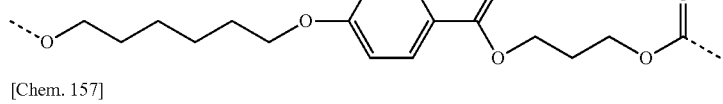
(S-v-5)
(S-v-6)
[Chem. 157]
(S-w-1)
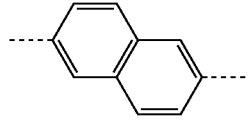
(S-w-2)
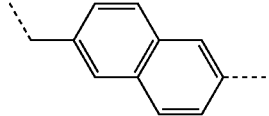
(S-w-3)
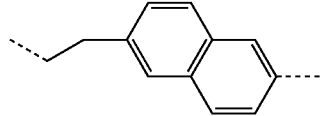
(S-w-4)
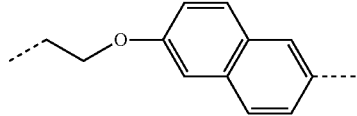

-continued
(S-w-5) 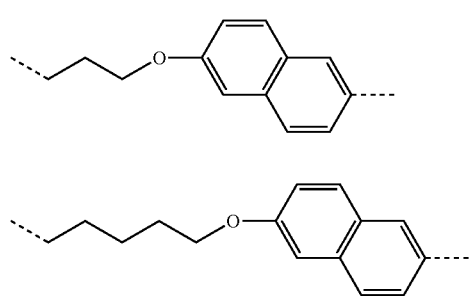 (S-w-6)
(S-w-7) (S-w-8)
[Chem. 158]
(S-x-1) 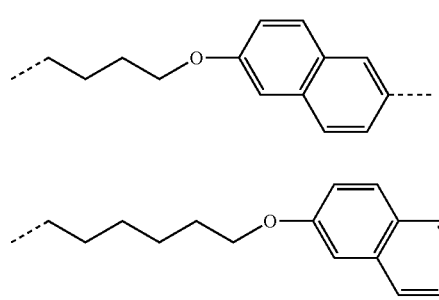 (S-x-2)
(S-x-3)
(S-x-4)
(S-x-5)
(S-x-6)
(S-x-7)
(S-x-8)
(S-x-9)
[Chem. 159]
(S-y-1) 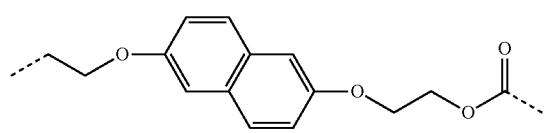 (S-y-2) 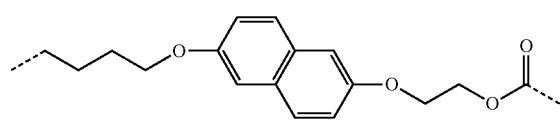

(S-y-3) 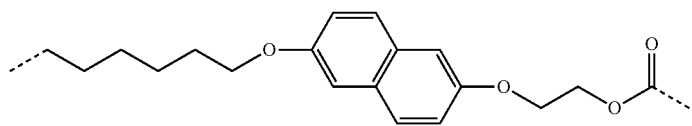
(S-y-4) 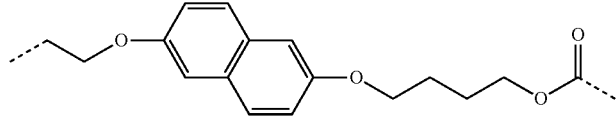
(S-y-5) 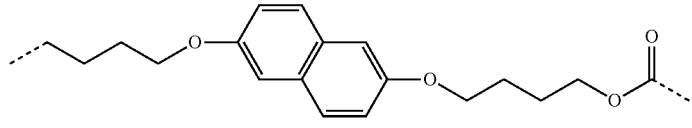
(S-y-6) 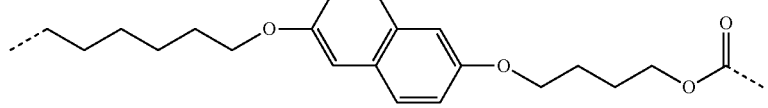
(S-y-7) 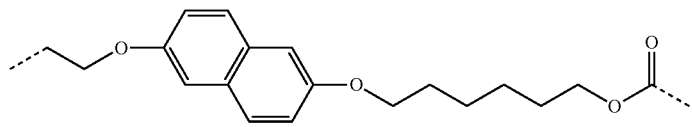
(S-y-8) 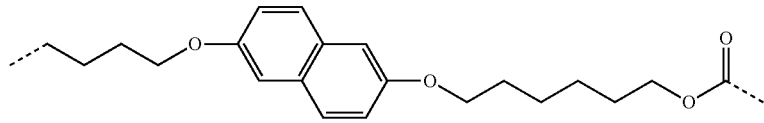
(S-y-9) 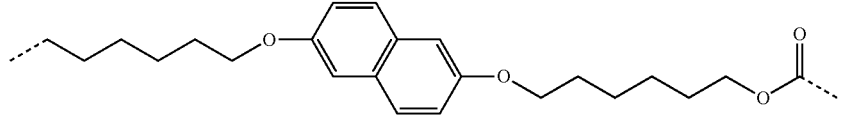
[Chem. 160]
(S-z-1) (S-z-2) 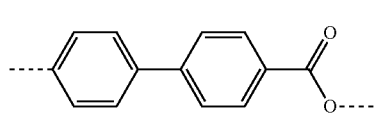
(S-z-3) (S-z-4) 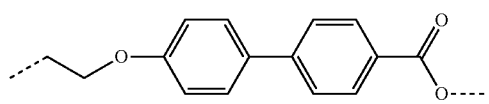
(S-z-5) 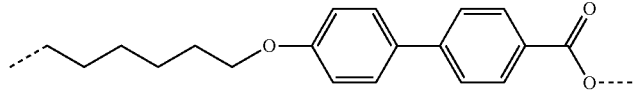
(S-z-6) (S-z-7) 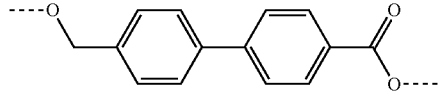
(S-z-8) 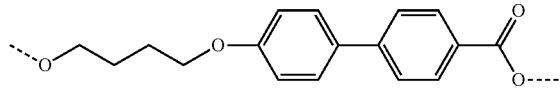

-continued
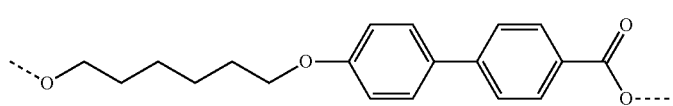
(S-z-9)
[Chem. 161]
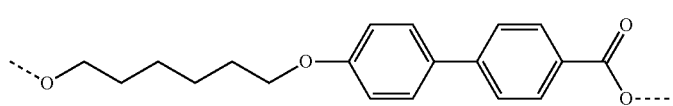
(S-aa-1)
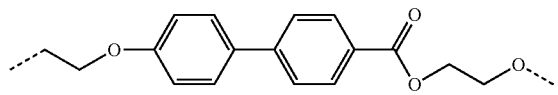
(S-aa-2)
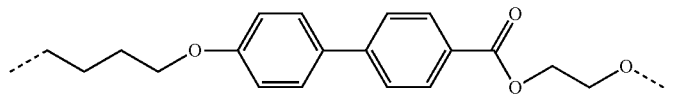
(S-aa-3)
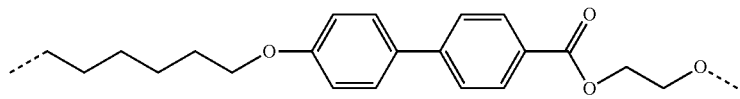
(S-aa-4)
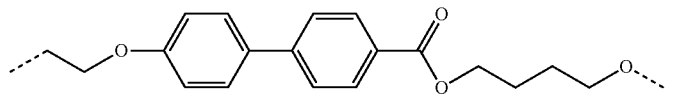
(S-aa-5)
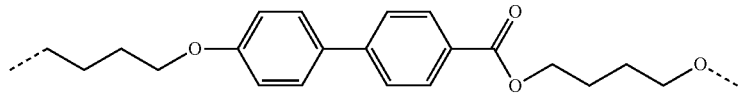
(S-aa-6)
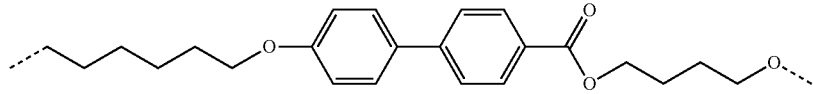
(S-aa-7)
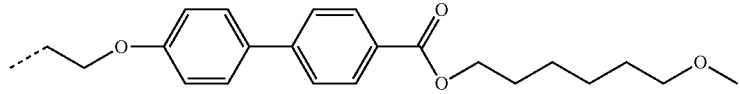
(S-aa-8)
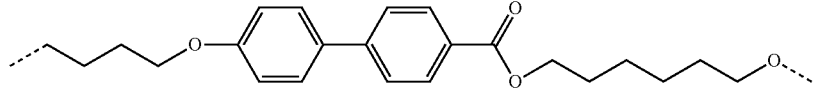
(S-aa-9)
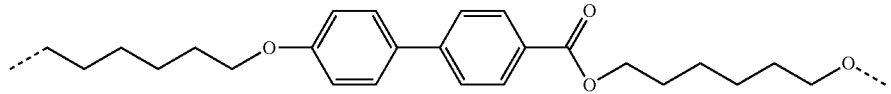
[Chem. 162]
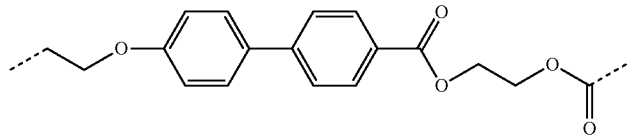
(S-ab-1)
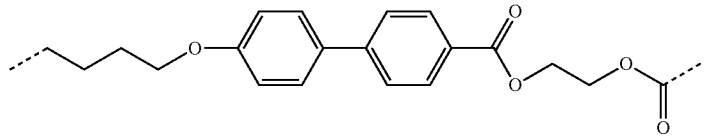
(S-ab-2)
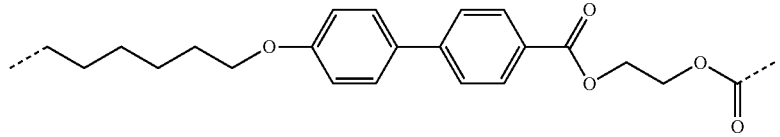
(S-ab-3)

-continued
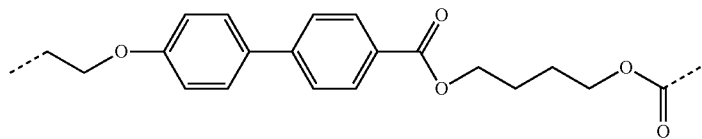 (S-ab-4)
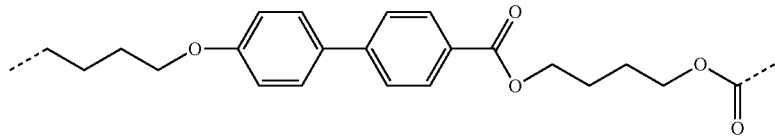 (S-ab-5)
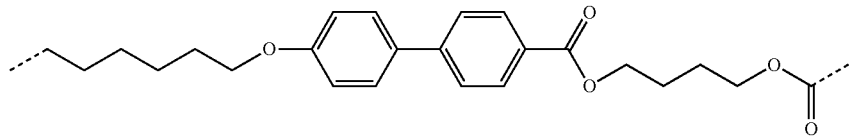 (S-ab-6)
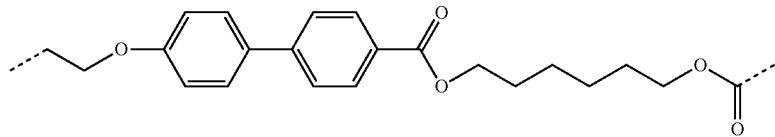 (S-ab-7)
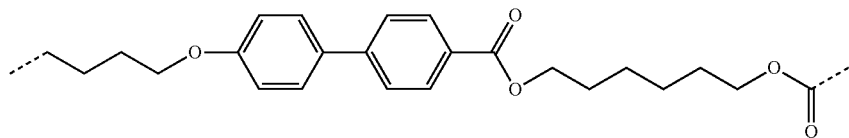 (S-ab-8)
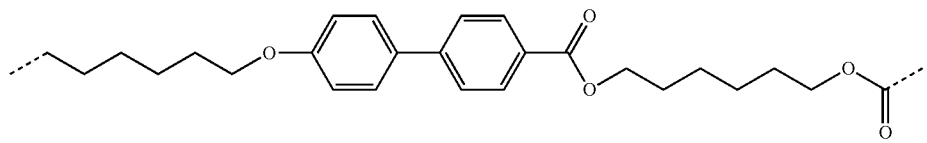 (S-ab-9)
[Chem. 163]
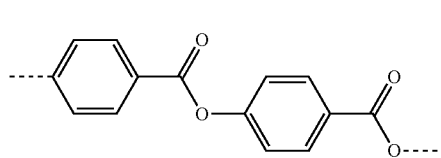
(S-ac-1) (S-ac-2)
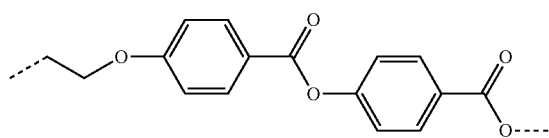 (S-ac-3)
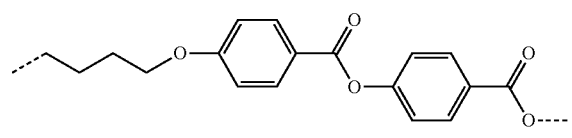 (S-ac-4)
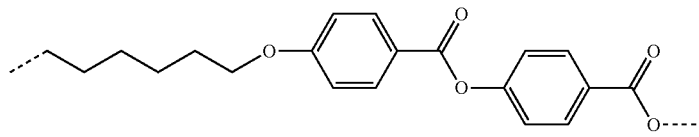 (S-ac-5)
[Chem. 164]
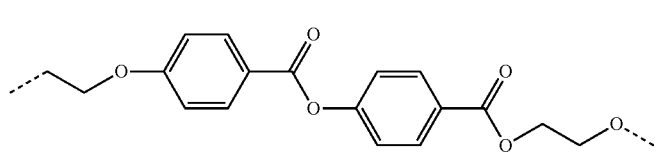 (S-ad-1)

-continued (S-ad-2)
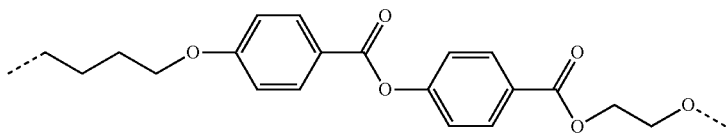

(S-ad-3)
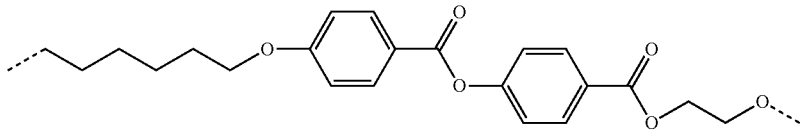

(S-ad-4)
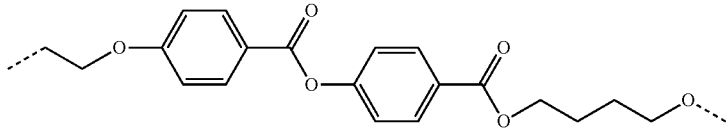

(S-ad-5)
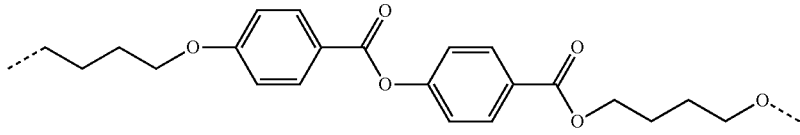

(S-ad-6)
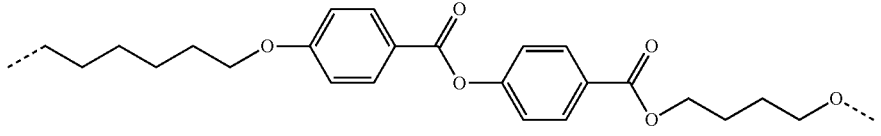

(S-ad-7)
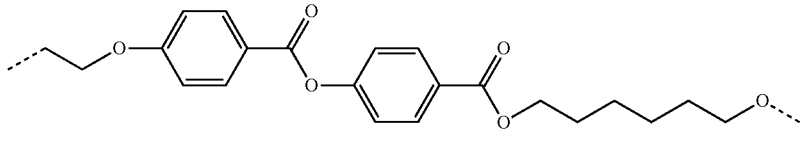

(S-ad-8)
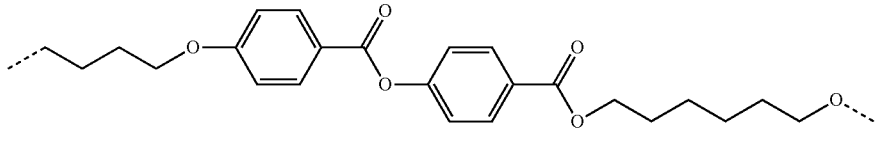

(S-ad-9)
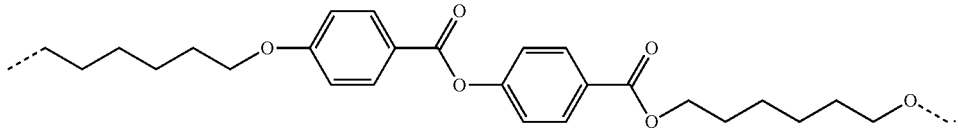

Among these, the compounds represented by the general formulae (S-a-6) to (S-a-16), the general formulae (S-b-3) to (S-b-10), the general formulae (S-c-3) to (S-c-10), the general formulae (S-d-3) to (S-d-12), the general formulae (S-k-4) to (S-k-7), the general formulae (S-l-13) to (S-l-17), the general formulae (S-o-3) to (S-o-14), the general formulae (S-p-2) to (S-p-13), the general formulae (S-s-1) to (S-s-8), the general formulae (S-t-1) to (S-t-8), the general formulae (S-y-1) to (S-y-9), and the general formulae (S-aa-1) to (S-aa-9) are more preferable.

Examples of the method of applying a solution of the cinnamic acid derivative, the composition, or the polymer of the present invention onto a substrate include spin coating, die coating, gravure coating, flexography, and inkjet printing methods. The concentration of the solid content in the solution used in the application is preferably 0.5 to 10% by weight, and is more preferably selected from this range by considering a method of applying the solution on the substrate, viscosity, volatility, or the like. Further, the applied surface is preferably heated after the application so as to remove the solvent. The drying conditions are preferably 50 to 300° C., and more preferably 80 to 200° C. for preferably 5 to 200 minutes, and more preferably 10 to 100 minutes.

As the light used for irradiation when subjecting a coating film composed of the polymer to curing, for example, ultraviolet rays or visible rays containing light having a wavelength of 150 nm to 800 nm may be used, and among these, ultraviolet rays having a wavelength of 270 nm to 450 nm are particularly preferable.

Examples of the light source include a xenon lamp, a high-pressure mercury lamp, an ultrahigh-pressure mercury lamp, and a metal halide lamp. Linear polarized light is obtained from these light sources through a polarizing filter and a polarizing prism. Further, the ultraviolet light and visible light obtained from such light sources may have a wavelength range for irradiation restricted by using an interference filter or a color filter. In addition, the irradiation energy is preferably 15 mJ/cm² to 500 mJ/cm², and more preferably 20 mJ/cm² to 300 mJ/cm². The luminous intensity is preferably 2 to 500 mW/cm², and more preferably 5 mJ/cm² to 300 mW/cm².

Fourth Embodiment

Next, a fourth embodiment of the present invention will be described while focusing on the difference from the first to third embodiments, and the description of the same contents will be omitted.

A compound represented by the general formula (I) is preferable:

[Chem. 165]

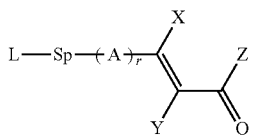
(I)

(wherein L represents a polymerizable group and Sp represents a spacer unit,

A represents a group selected from the group consisting of:
(a) a trans-1,4-cyclohexylene group (one methylene group or two or more non-adjacent methylene groups present in this group may be substituted with —O—, —NH—, or —S—),
(b) a 1,4-phenylene group (one or two or more —CH═'s present in this group may be substituted with —N═), and
(c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group,
in which the group (a), (b), or (c) may be each unsubstituted or may have one or more hydrogen atoms substituted with a fluorine atom, a chlorine atom, a cyano group, a methyl group, or a methoxy group,
r represents 0, 1, or 2, but in the case where r represents 2, a plurality of A's, may be the same as or different from each other, X and Y each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one $CH_2$ group or two or more non-adjacent $CH_2$ groups may be substituted with —O—, —CO—O—, —O—CO— and/or —CH═CH—, and Z is represented by the general formula (IIa) or (IIb):

[Chem. 166]

----O—R¹ (IIa)

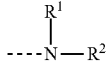 (IIb)

$R^1$ represents a linear or branched alkyl group having 1 to 30 carbon atoms (one or two or more —CH₂— groups in the alkyl group are each independently substituted with a cycloalkyl group having a ring member number of 3 to 8, and a hydrogen atom in the alkyl group may be substituted with an alkyl group having 1 to 20 carbon atoms, a cyano group, or a halogen atom), and $R^2$ represents a linear or branched alkyl group having 1 to 30 carbon atoms (one or two or more —CH₂— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom), and in the general formula (I), Sp is represented by the general formula (IVb):

[Chem. 167]

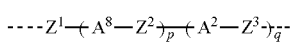
(IVb)

(wherein $Z^1$, $Z^2$, $Z^3$, $A^2$, p and q have the same definitions as in the general formula (IVa)), $A^8$ represents:

a trans-1,4-cyclohexylene group (one methylene group or two or more non-adjacent methylene groups present in this group may be substituted with —O—, —NH—, or —S—), and a 1,4-phenylene group (one or two —CH═'s present in this group may be substituted with —N═), and these may be each unsubstituted or one or more hydrogen atoms may be substituted with a fluorine atom, a chlorine atom, a cyano group, a methyl group, or a methoxy group), and r represents 0, 1, or 2).

The alkyl group having 1 to 30 carbon atoms, represented by $R^1$, is a linear or branched alkyl group, in which one —CH₂— group is preferably substituted with a cycloalkyl group having a ring member number of 3 to 8.

The alkyl group having 1 to 30 carbon atoms, represented by $R^2$, is preferably a linear or branched alkyl group or a cycloalkyl group having a ring member number of 3 to 8, which may have the alkyl group interposed therein as a linking group. In the general formula (IVb), $Z^1$, $Z^2$ and $Z^3$ are each independently preferably a single bond, —(CH₂)ᵤ— (wherein u represents 1 to 20, and one or more of the non-adjacent CH₂ groups may be independently substituted with —O—, —CO—O—, —O—CO—, —CH═CH—, or —C≡C—), —OCH₂—, —CH₂O—, —COO—, —OCO—, —CH═CH—, or —C≡C—.

In the general formula (IVb), q is preferably 0.
In the general formula (IVb), p is preferably 1.
In the general formula (IVb),
$A^8$ is preferably a trans-1,4-cyclohexylene group (one methylene group or two or more non-adjacent methylene groups present in this group may be substituted with —O—, —NH—, or —S—), and a 1,4-phenylene group (one or two —CH═'s present in this group may be substituted with —N═). In the general formula (IVb), $A^2$ is preferably any group of a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5- diyl group, or a 1,4-phenylene group. A hydrogen atom of these groups may be unsubstituted or one or more hydrogen atoms of these groups may be substituted with a fluorine atom, a chlorine atom, a methyl group, or a methoxy group.

EXAMPLES

The present invention will be described in further detail with reference to Examples below, but the present invention is not limited to Examples. The structure of a compound was identified with a nuclear magnetic resonance (NMR) spectrum, a mass spectrum (MS), or the like. Unless otherwise noted, "parts" and "%" are on a mass basis.

Synthesis of Cinnamic Acid Derivative

Example 1

Synthesis of Methyl=3-(4-(6-(6-(2-methylacryloyloxy)hexyloxy)naphthalene-2-carbonyloxy)phenylcarbonyloxy-3-methoxyphenyl)acrylate

[Chem. 168]

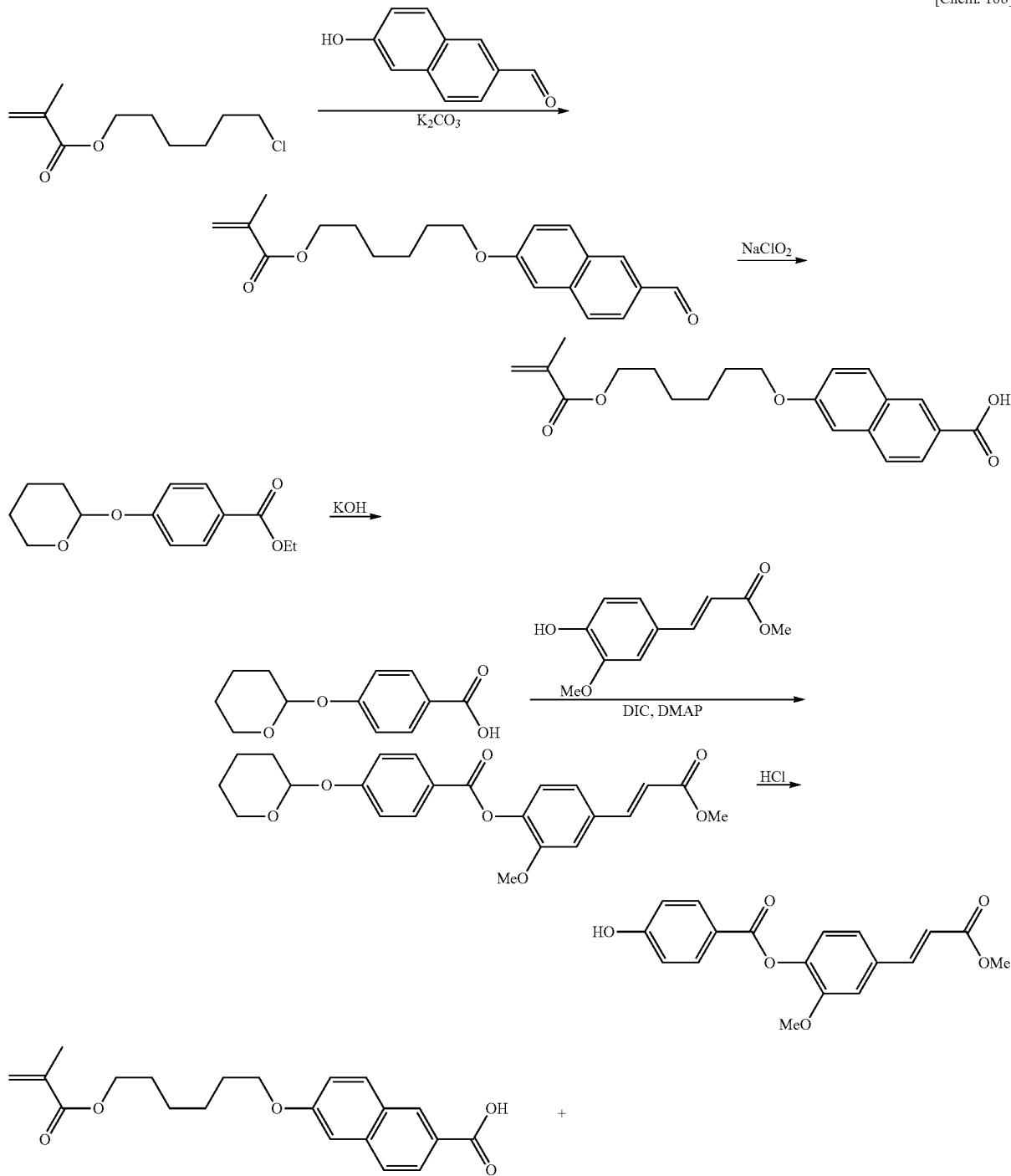

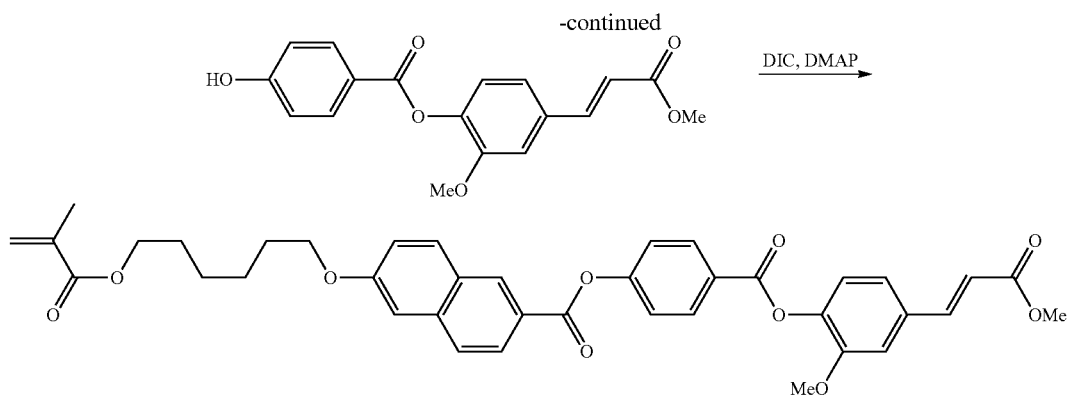

Synthesis of 6-(6-(2-Methylacryloxy)hexyloxy)-2-naphthoic acid

6-Chlorohexyl=2-methylacrylate (77.2 g), 6-hydroxy-2-naphthaldehyde (50.0 g), and potassium carbonate (60.0 g) were suspended in dimethyl formamide (150 ml), and the suspension was stirred at 95° C. for 8 hours. The suspension was cooled to 25° C. and 10% hydrochloric acid was added thereto. The mixture was extracted twice with toluene. The organic phase was combined, washed with saturated saline, and dried over anhydrous sodium sulfate. The solvent was evaporated under reduced pressure to obtain a brown liquid. The mixture was purified by column chromatography to obtain 6-(6-(2-methylacryloxy)hexyloxy)-2-naphthaldehyde (118.7 g) as a yellow liquid.

6-(6-(2-Methylacryloxy)hexyloxy)-2-naphthaldehyde (118.7 g), 2-methyl-2-butene (91.5 g), and sodium dihydrogen phosphate (67.9 g) were suspended in tert-butyl alcohol (750 ml) and water (204 ml), and a solution prepared by dissolving sodium chlorite (49.2 g) in water (172 ml) was added dropwise thereto at 25° C. The mixture was stirred at 25° C. for 8 hours. Thereafter, the mixture was stirred at 5° C. for 1 hour and the precipitated solid was collected by filtration. The solid was purified by reprecipitation to obtain 6-(6-(2-methylacryloxy)hexyloxy)-2-naphthoic acid (83.8 g) as a yellow powder.

$^1$H-NMR (400 MHz, CDCl$_3$) δ: 1.46-1.62 (m, 4H), 1.75 (dt, J=7.0 Hz, J=14.6 Hz, 2H), 1.89 (dt, J=6.9 Hz, J=14.6 Hz, 2H), 1.94 (s, 3H), 4.11 (t, J=6.5 Hz, 2H), 4.18 (t, J=6.6 Hz, 2H), 5.55 (s, 1H), 6.10 (s, 1H), 7.16 (bs, 1H), 7.22 (dd, J=2.4 Hz, J=8.8 Hz, 1H), 7.77 (d, J=8.8 Hz, 1H), 7.87 (d, J=9.0 Hz, 1H), 8.08 (dd, J=1.7 Hz, J=8.5 Hz, 1H), 8.63 (s, 1H).

Synthesis of Methyl=3-(4-(4-hydroxybenzoyloxy)-3-methoxyphenyl)acrylate

Ethyl=4-(3,4,5,6-tetrahydropyran-2-yloxy)benzoic acid (10.0 g) was dissolved in dimethoxyethane (60 ml), and a 5% aqueous potassium hydroxide solution (65.0 g) was added thereto at 25° C. The mixture was stirred at 60° C. for 2 hours, toluene was then added thereto to separate the organic phase and the aqueous phase. The aqueous phase was neutralized with a 1 M aqueous sodium hydrogen sulfate solution, and the precipitated solid was collected by filtration. The solid was dried under reduced pressure to obtain 4-(3,4,5,6-tetrahydropyran-2-yloxy)benzoic acid (8.88 g) as a colorless powder.

4-(3,4,5,6-Tetrahydropyran-2-yloxy)benzoic acid (7.33 g), methyl=4-hydroxy-3-methoxycinnamate (6.87 g), and 4-dimethyl aminopyridine (DMAP, 0.20 g) were suspended in dichloromethane (48 ml), and diisopropylcarbodiimide (DIC, 5.41 g) was added dropwise thereto at 25° C. After stirring at 25° C. for 2 hours, the solvent was evaporated under reduced pressure. Methanol (50 ml) was added thereto and the precipitated solid was collected by filtration. The residue was purified by column chromatography and reprecipitation to obtain methyl=3-(4-(4-(3,4,5,6-tetrahydropyran-2-yloxy)benzoyloxy)-3-methoxyphenyl)acrylate (13.8 g) as a colorless powder.

Methyl=3-(4-(4-(3,4,5,6-tetrahydropyran-2-yloxy)benzoyloxy)-3-methoxyphenyl)acrylate (6.9 g) was dissolved in dichloromethane (35 ml) and methanol (35 ml), and 30% hydrochloric acid (0.35 ml) was added thereto at 25° C. The mixture was stirred at 25° C. for 8 hours and neutralized by the addition of a 5% aqueous sodium hydrogen carbonate solution. The organic phase was collected by separation and the aqueous layer was extracted with dichloromethane.

The organic phase was combined, washed with saturated saline, and dried over anhydrous sodium sulfate. The solvent was evaporated under reduced pressure to obtain a pale brown solid. The solid was washed with hexane to obtain methyl=3-(4-(4-hydroxybenzoyloxy)-3-methoxyphenyl)acrylate (5.24 g) as a pale brown powder.

$^1$H-NMR (400 MHz, CDCl$_3$) δ: 3.82 (s, 3H), 3.84 (s, 3H), 5.60 (bs, 1H), 6.42 (d, J=16.1 Hz, 1H), 6.92 (d, J=8.5 Hz, 2H), 7.15 (d, J=12.0 Hz, 1H), 7.17 (s, 2H), 7.68 (d, J=15.9 Hz, 1H), 8.13 (d, J=8.5 Hz, 2H).

Synthesis of Methyl=3-(4-(6-(6-(2-methylacryloyloxy)hexyloxy)naphthalene-2-carbonyloxy)phenylcarbonyloxy-3-methoxyphenyl)acrylate Methyl=3-(4-(4-hydroxybenzoyloxy)-3-methoxyphenyl)acrylate (5.0 g), 6-(6-(2-methylacryloyloxy)hexyloxy)-2-naphthoic acid (5.43 g), and DMAP (0.092 g) were suspended in dichloromethane (50 ml), and DIC (2.49 g) was added dropwise thereto at 25° C. After stirring at 25° C. for 2 hours, the solvent was evaporated under reduced pressure. Methanol (50 ml) was added thereto and the precipitated solid was collected by filtration. The residue was purified by column chromatography and recrystallization to obtain methyl=3-(4-(6-(6-(2-methylacryloyloxy)hexyloxy)naphthalene-2-carbonyloxy)phenylcarbonyloxy-3-methoxyphenyl)acrylate as colorless powder (9.26 g).

Transition temperature Cr 141 Iso $^1$H-NMR (400 MHz, CDCl$_3$) δ: 1.46-1.64 (m, 4H), 1.75 (dt, J=7.0 Hz, J=14.4 Hz, 2H), 1.86-2.00 (m, 2H), 1.95 (s, 3H), 3.84 (s, 3H), 3.86 (s, 3H), 4.12 (t, J=6.4 Hz, 2H), 4.18 (t, J=6.5 Hz, 2H), 5.55 (t, J=1.5 Hz, 1H), 6.10 (s, 1H), 6.42

(d, J=16.1 Hz, 1H), 7.05-7.28 (m, 5H), 7.42 (d, J=8.3 Hz, 2H), 7.68 (d, J=16.1 Hz, 1H), 7.82 (d, J=8.8 Hz, 1H), 7.90 (d, J=9.0 Hz, 1H), 8.15 (dd, J=1.7 Hz, J=8.5 Hz, 1H), 8.32 (d, J=6.8 Hz, 2H), 8.72 (s, 1H).
The products obtained above may be sometimes referred to as CinNp-1 hereinafter.
In this manner, the following compounds CinNp-2 to CinNp-13 were synthesized.
[Chem. 169]
CinNp-2
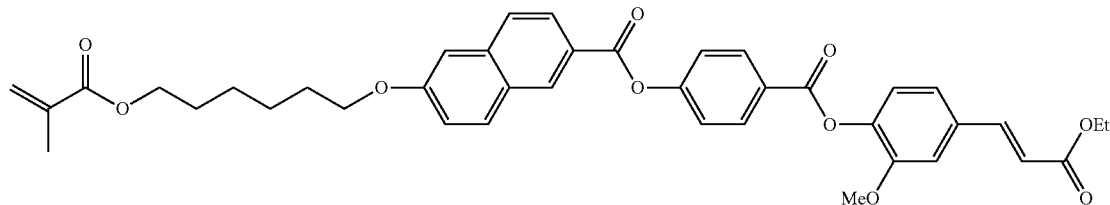
(Example 2)
CinNp-3
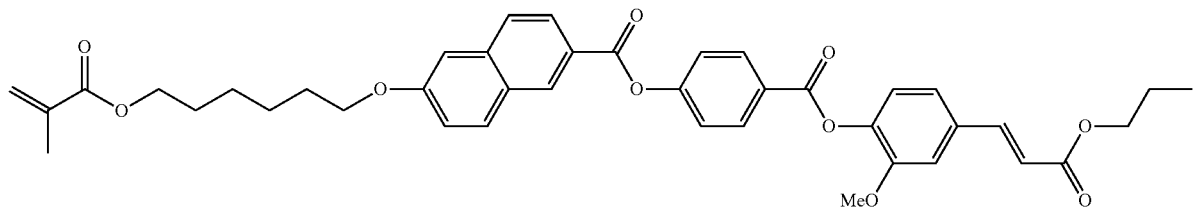
(Example 3)
[Chem. 170]
CinNp-4
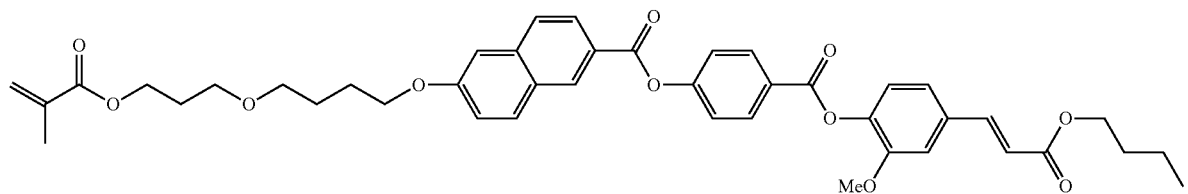
(Example 4)
CinNp-5
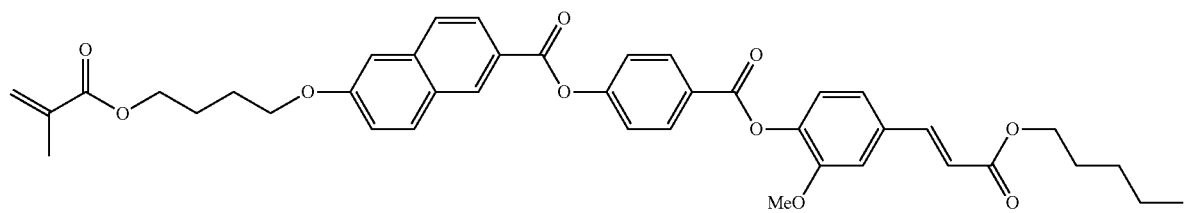
(Example 5)
[Chem. 171]
CinNp-6
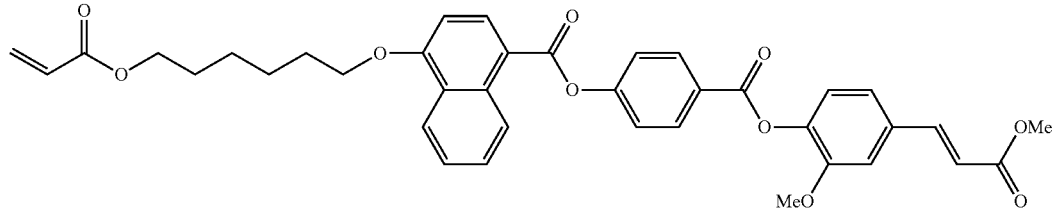
(Example 6)

-continued
CinNp-7
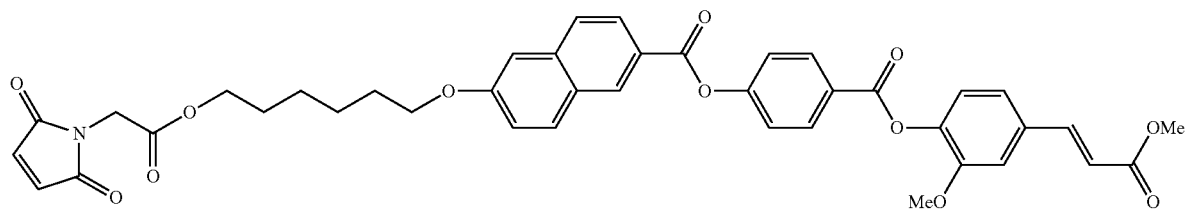
(Example 7)
[Chem. 172]
CinNp-8
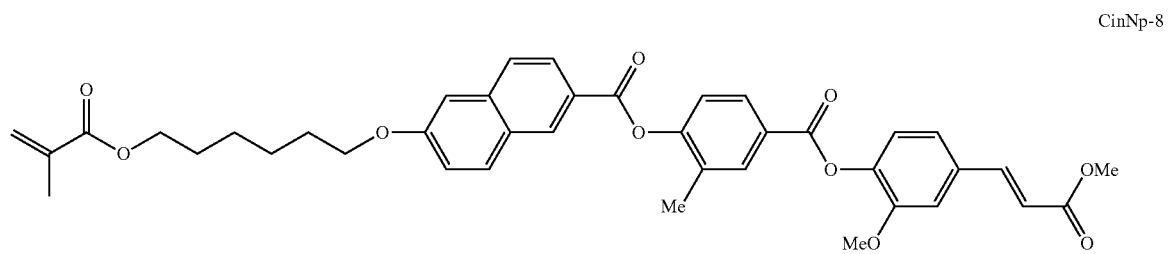
(Example 8)
CinNp-9
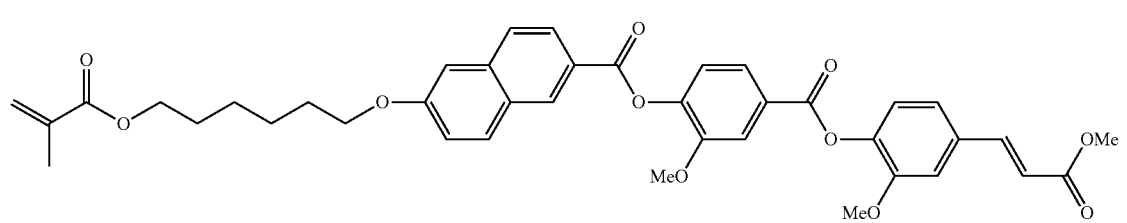
(Example 9)
[Chem. 173]
CinNp-10
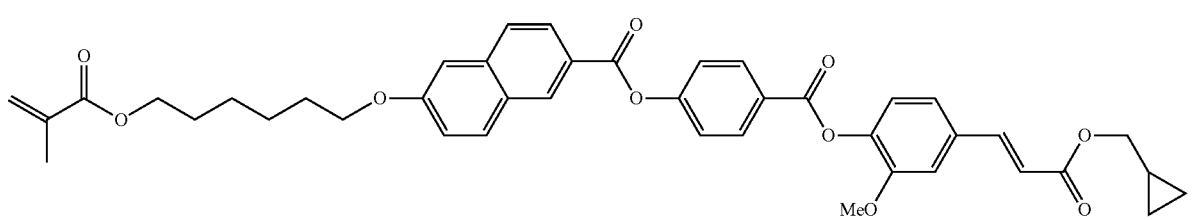
(Example 10)
CinNp-11
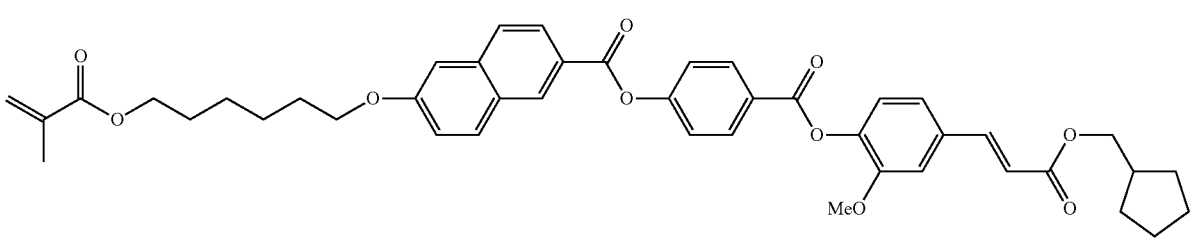
(Example 11)

CinNp-12

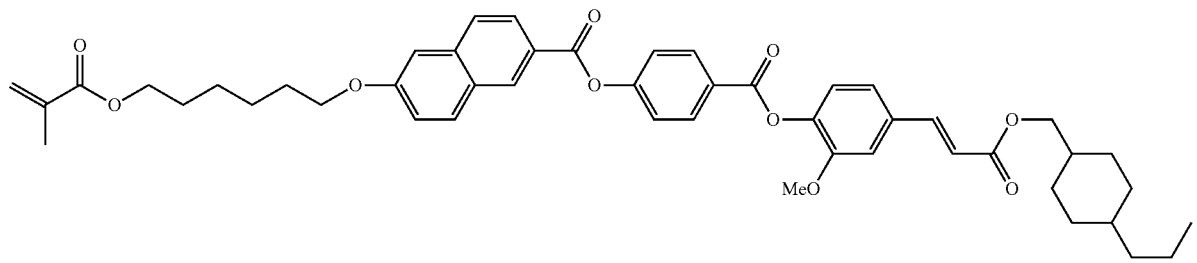

(Example 12)

CinNp-13

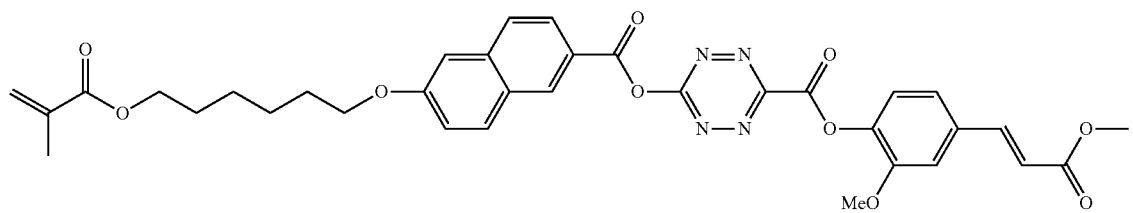

(Example 13)

Synthesis of Monomer for Copolymerization

[Chem. 174]

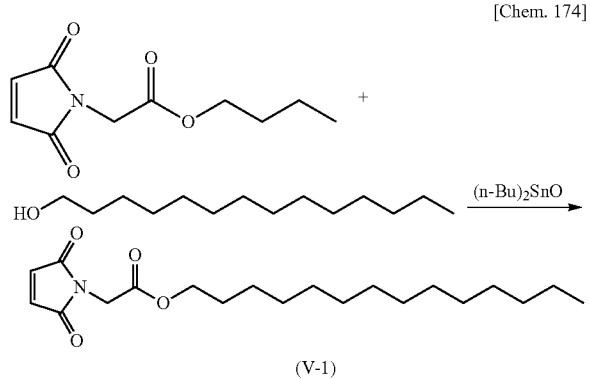

(V-1)

9.01 g of butyl maleimidoacetate, 0.33 g of dibutyltin (IV) oxide, and 9.14 g of tetradecanol were dissolved in 40 ml of toluene, followed by stirring for 15 hours while heating to reflux. The reaction solution was cooled to room temperature and 100 ml of toluene was added thereto. The mixture was subjected to liquid separation and washed with saturated sodium bicarbonate water and then with saturated saline. To this solution was added sodium sulfate, and the mixture was dried. Sodium sulfate was removed and the solvent was evaporated under reduced pressure to reduce the volume to about 50 ml, and 40 ml of hexane and 20 ml of dichloromethane were added thereto. The mixture was purified by column chromatography (alumina/silica gel, hexane/dichloromethane=2:1), the solvent was evaporated under reduced pressure, and the residue was reprecipitated with methanol to obtain (V-1) (7.95 g) as a white crystal.

$^1$H-NMR (400 MHz, CDCl$_3$) δ: 0.88 (t, J=6.8 Hz, 3H), 1.15-1.40 (m, 22H), 1.61-1.66 (tt, 2H), 4.14 (t, J=6.6 Hz, 2H), 4.15 (s, 2H), 6.79 (s, 2H) EI-MS: 351 [M$^+$]

[Chem. 175]

(V-2)

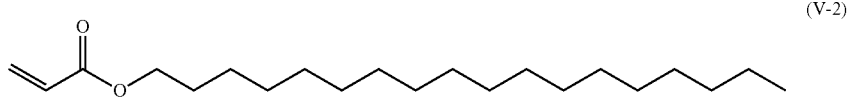

Stearyl acrylate (V-2) (manufactured by Tokyo Chemical Industry Co., Ltd.) was purchased and used.

[Chem. 176]

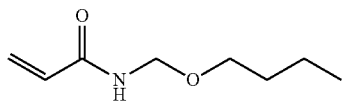

(V-3)

N-(Butoxymethyl)acrylamide (V-3) (manufactured by Tokyo Chemical Industry Co., Ltd.) was purchased and used.

[Chem. 177]

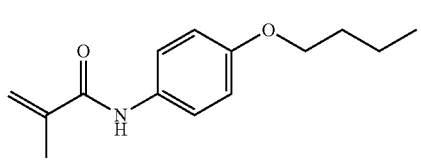

(V-4)

A compound (V-4) was synthesized according to the procedure described in a known document (Farmaco. Edizione Scientifica Vol. 22 (1967) 190, 590-598).

Preparation of Cinnamic Acid Polymer (NCE-1)

dropwise to 120 parts of ice-cooled methanol under stirring, and the precipitated solid was filtered. The obtained solid was dissolved in THF and then vacuum-dried to obtain a polymer (NCE-1).

Preparation of Cinnamic Acid Polymers (NCE-2) to (NCE-13)

In the same manner as for the cinnamic acid polymer (NCE-1), polymers (NCE-2) to (NCE-13) were obtained. The compositions of the respective polymers are as shown in Tables 1 and 2.

TABLE 1

| | Sample name | Blending amount (% by mole) | | | | | |
|---|---|---|---|---|---|---|---|
| | | CinNp-1 | CinNp-2 | CinNp-3 | CinNp-4 | CinNp-5 | CinNp-6 |
| Example 14 | NCE-1 | 100 | | | | | |
| Example 15 | NCE-2 | | 100 | | | | |
| Example 16 | NCE-3 | | | 100 | | | |
| Example 17 | NCE-4 | | | | 100 | | |
| Example 18 | NCE-5 | | | | | 100 | |
| Example 19 | NCE-6 | | | | | | 100 |

TABLE 2

| | Sample name | Blending amount (% by mole) | | | | | | |
|---|---|---|---|---|---|---|---|---|
| | | CinNp-7 | CinNp-8 | CinNp-9 | CinNp-10 | CinNp-11 | CinNp-12 | CinNp-13 |
| Example 20 | NCE-7 | 100 | | | | | | |
| Example 21 | NCE-8 | | 100 | | | | | |
| Example 22 | NCE-9 | | | 100 | | | | |
| Example 23 | NCE-10 | | | | 100 | | | |
| Example 24 | NCE-11 | | | | | 100 | | |
| Example 25 | NCE-12 | | | | | | 100 | |
| Example 27 | NCE-13 | | | | | | | 100 |

Preparation of Cinnamic Acid Polymer (NCE-1)

Example 14

1 part (10.0 mmol) of a compound represented by the formula (CinNp-1) was dissolved in 10 parts of ethyl methyl ketone to obtain a solution 1. To this solution 1 was added 0.01 parts of azobisisobutyronitrile (AIBN). The mixture was heated to reflux for 2 days under a nitrogen atmosphere to obtain a solution 2. Then, the solution 2 was added dropwise to 60 parts of methanol under stirring, and the precipitated solid was filtered. The obtained solid was dissolved in 5 parts of tetrahydrofuran (THF), the solution was added dropwise to 120 parts of ice-cooled hexane under stirring, and the precipitated solid was filtered. The obtained solid was dissolved in 5 parts of THF, the solution was added Preparation of Cinnamic Acid Polymer (NCEV-1)

Example 28

0.9 parts (9.0 mmol) of the compound represented by the formula (CinNp-1) and 0.1 parts (1.0 mmol) of a compound represented by the formula (V-1) were dissolved in 10 parts of ethyl methyl ketone to obtain a solution 3. To this solution 3 was added 0.01 parts of azobisisobutyronitrile (AIBN). The mixture was heated to reflux for 2 days under a nitrogen atmosphere to obtain a solution 4. Then, the solution 4 was added dropwise to 60 parts of methanol under stirring, and the precipitated solid was filtered. The obtained solid was dissolved in 5 parts of tetrahydrofuran (THF), the solution was added dropwise to 120 parts of ice-cooled hexane under stirring, and the precipitated solid was filtered. The obtained solid was dissolved in 5 parts of THF, the solution was added dropwise to 120 parts of ice-cooled methanol under stirring, and the precipitated solid was filtered. The obtained solid was dissolved in THF and then vacuum-dried to obtain a polymer (NCEV-1).

Preparation of Cinnamic Acid Polymers (NCEV-2) to (NCEV-50)

In the same manner as for the cinnamic acid polymer (NCEV-1), polymers (NCEV-2) to (NCEV-50) were obtained. The compositions of the respective polymers are as shown in Tables 3 and 4.

TABLE 3

| Example | Sample name | Blending amount (% by mole) | | | | | | | | | |
|---|---|---|---|---|---|---|---|---|---|---|---|
| | | CinNp-1 | CinNp-2 | CinNp-3 | CinNp-4 | CinNp-5 | CinNp-6 | V-1 | V-2 | V-3 | V-4 |
| 28 | NCEV-1 | 90 | | | | | | 10 | | | |
| 29 | NCEV-2 | 85 | | | | | | 15 | | | |
| 30 | NCEV-3 | 80 | | | | | | 20 | | | |
| 31 | NCEV-4 | 80 | | | | | | | 20 | | |
| 32 | NCEV-5 | 80 | | | | | | | | 20 | |
| 33 | NCEV-6 | 80 | | | | | | | | | 20 |
| 34 | NCEV-7 | | 80 | | | | | 20 | | | |
| 35 | NCEV-8 | | 80 | | | | | | 20 | | |
| 36 | NCEV-9 | | 80 | | | | | | | 20 | |
| 37 | NCEV-10 | | 80 | | | | | | | | 20 |
| 38 | NCEV-11 | | | 80 | | | | 20 | | | |
| 39 | NCEV-12 | | | 80 | | | | | 20 | | |
| 40 | NCEV-13 | | | 80 | | | | | | 20 | |
| 41 | NCEV-14 | | | 80 | | | | | | | 20 |
| 42 | NCEV-15 | | | | 80 | | | 20 | | | |
| 43 | NCEV-16 | | | | 80 | | | | 20 | | |
| 44 | NCEV-17 | | | | 80 | | | | | 20 | |
| 45 | NCEV-18 | | | | 80 | | | | | | 20 |
| 46 | NCEV-19 | | | | | 80 | | 20 | | | |
| 47 | NCEV-20 | | | | | 80 | | | 20 | | |
| 48 | NCEV-21 | | | | | 80 | | | | 20 | |
| 49 | NCEV-22 | | | | | 80 | | | | | 20 |
| 50 | NCEV-23 | | | | | | 80 | 20 | | | |
| 51 | NCEV-24 | | | | | | 80 | | 20 | | |
| 52 | NCEV-25 | | | | | | 80 | | | 20 | |
| 53 | NCEV-26 | | | | | | 80 | | | | 20 |

TABLE 4

| Example | Sample name | Blending amount (% by mole) | | | | | | | | | |
|---|---|---|---|---|---|---|---|---|---|---|---|
| | | CinNp-7 | CinNp-8 | CinNp-9 | CinNp-10 | CinNp-11 | CinNp-12 | CinNp-13 | V-1 | V-2 | V-3 | V-4 |
| 54 | NCEV-27 | 80 | | | | | | | 20 | | | |
| 55 | NCEV-28 | 80 | | | | | | | | 20 | | |
| 56 | NCEV-29 | 80 | | | | | | | | | 20 | |
| 57 | NCEV-30 | 80 | | | | | | | | | | 20 |
| 58 | NCEV-31 | | 80 | | | | | | 20 | | | |
| 59 | NCEV-32 | | 80 | | | | | | | 20 | | |
| 60 | NCEV-33 | | 80 | | | | | | | | 20 | |
| 61 | NCEV-34 | | 80 | | | | | | | | | 20 |
| 62 | NCEV-35 | | | 80 | | | | | 20 | | | |
| 63 | NCEV-36 | | | 80 | | | | | | 20 | | |
| 64 | NCEV-37 | | | 80 | | | | | | | 20 | |
| 65 | NCEV-38 | | | 80 | | | | | | | | 20 |
| 66 | NCEV-39 | | | | 80 | | | | 20 | | | |
| 67 | NCEV-40 | | | | 80 | | | | | 20 | | |
| 68 | NCEV-41 | | | | 80 | | | | | | 20 | |
| 69 | NCEV-42 | | | | 80 | | | | | | | 20 |
| 70 | NCEV-43 | | | | | 80 | | | 20 | | | |
| 71 | NCEV-44 | | | | | 80 | | | | 20 | | |
| 72 | NCEV-45 | | | | | 80 | | | | | 20 | |
| 73 | NCEV-46 | | | | | 80 | | | | | | 20 |
| 74 | NCEV-47 | | | | | | 80 | | 20 | | | |
| 75 | NCEV-48 | | | | | | 80 | | | 20 | | |
| 76 | NCEV-49 | | | | | | 80 | | | | 20 | |
| 77 | NCEV-50 | | | | | | 80 | | | | | 20 |
| 78 | NCEV-51 | | | | | | | 80 | 20 | | | |
| 79 | NCEV-52 | | | | | | | 80 | | 20 | | |

Preparation of Alignment Layer and Liquid Crystal Display Element

Example 80

The cinnamic acid polymer (NCE-1) was dissolved in cyclopentanone to 1.0% and the solution was stirred at room temperature for 10 minutes. Then, the solution was applied onto a glass plate as a base material, using a spin coater, and dried at 100° C. for 3 minutes. Then, the surface was visually observed and as a result, it was found that a polymer was uniformly applied on the glass plate to form a smooth film.

Next, the coated glass plate as a base material was irradiated with linear polarized and parallel light of visible ultraviolet light (wavelength: 313 nm, irradiation intensity: 8 mW/cm$^2$) using an ultrahigh-pressure mercury lamp via a wavelength cut filter, a band-pass filter, and a polarizing filter in a direction of 45 degrees with respect to the substrate. The irradiation dose was 100 mJ/cm$^2$. The thickness of the film was measured and found to be about 50 nm.

A liquid crystal cell was fabricated by using the coated glass plate prepared by the method above. The gap between the plates was set to 10 μm and the two glass plates were bonded in the anti-parallel direction. Next, a nematic liquid crystal mixture having a negative dielectric anisotropy with a composition described below was charged into the cell at a temperature just exceeding a transparent point (Tc=84.4° C.), and then cooled to room temperature. A polarizing plate was placed on the top and the bottom of the liquid crystal cell, and a back light was placed below. The light transmittance was changed by rotating the liquid crystal cell by 90 degrees and dark-light contrast was clearly observed and there was no abnormal domain and alignment unevenness, from which it was confirmed that the liquid crystals were normally aligned. The tilt angle of the liquid crystal in the cell was optically measured by a crystal rotation method, and the pretilt angle was found to be 1 degree. A voltage of 5 V was applied to this liquid crystal cell for an application time of 60 microseconds at a span of 167 milliseconds, and the voltage holding ratio after 167 milliseconds from the release of the voltage was measured by means of "VHR-AMP01" manufactured by TOYO Corporation at 23° C., and as a result, the voltage holding ratio (VHR) was found to be 99.3%.

[Chem. 178]

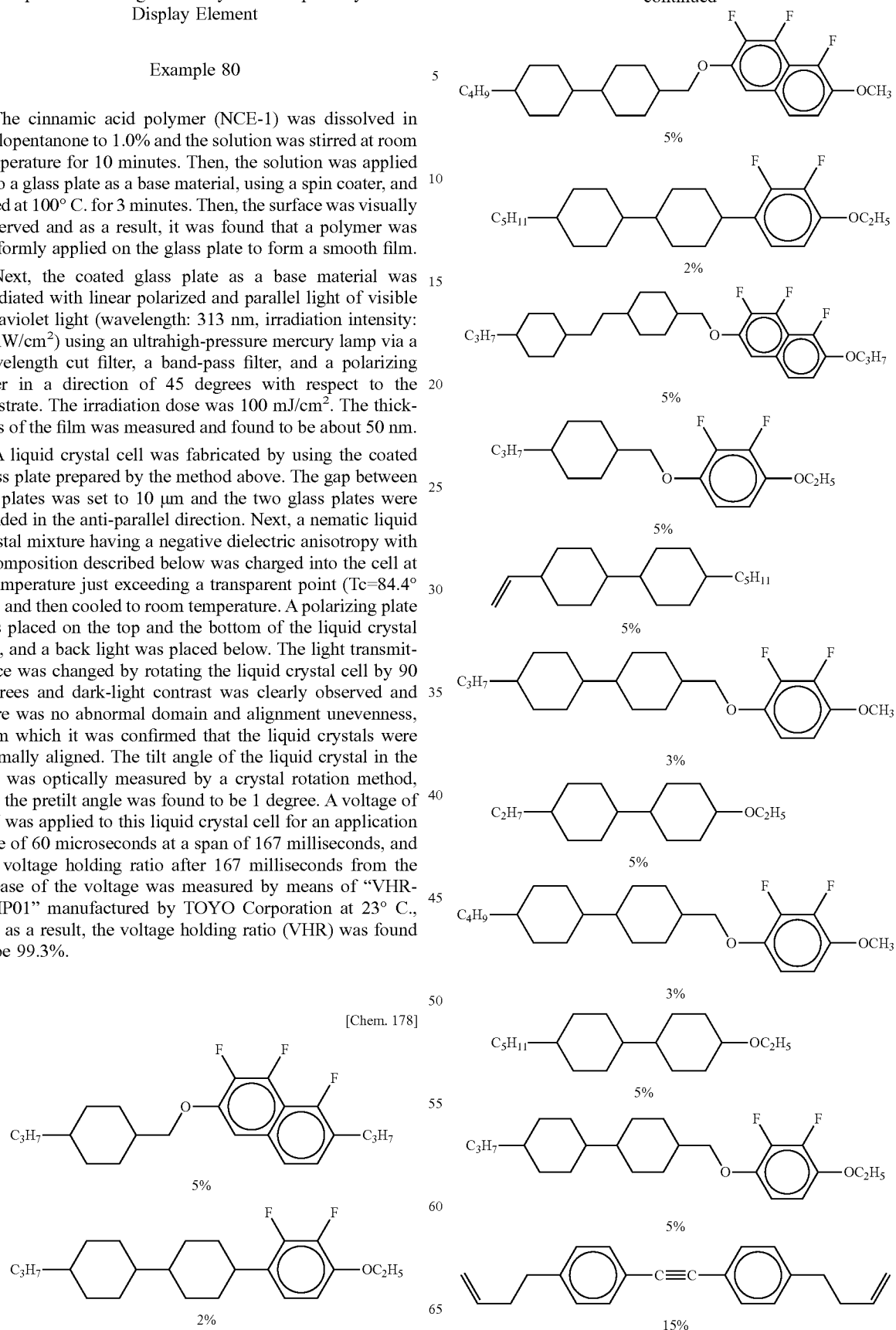

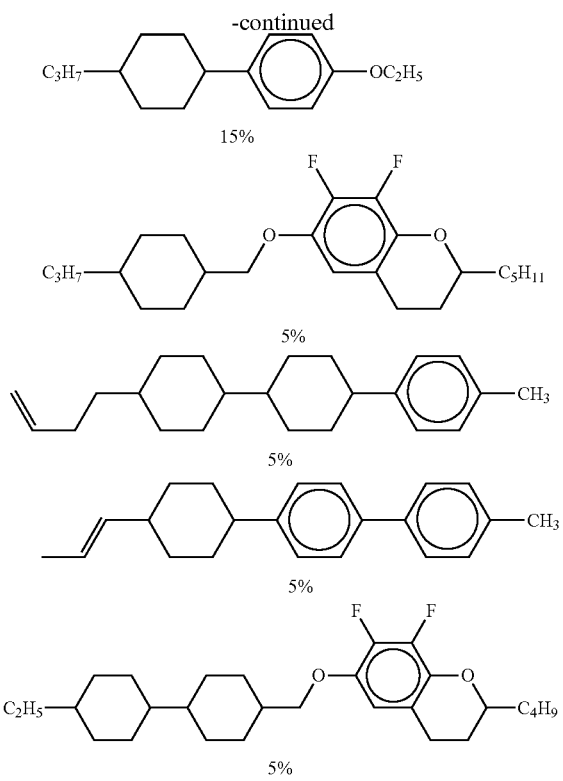

Hereinafter, in the same manner as the cinnamic acid polymer (NCE-1), for (NCE-2) to (NCE-12), and (NCEV-1) to (NCEV-50), alignment layers were fabricated and liquid crystal cells were fabricated. The measurement results of the irradiation doses of linear polarized light, liquid crystal alignment property, pretilt angle, VHR are shown in conjunction in Table 5. For the irradiation dose of linear polarized light, an irradiation dose of less than 120 mJ/cm² was denoted as O, an irradiation dose of 120 mJ/cm² or more and less than 300 mJ/cm² was denoted as Δ, and an irradiation dose of 300 mJ/cm² or more was denoted as X. For the liquid crystal alignment property, when the presence or absence of the abnormal domain and alignment unevenness of the liquid crystal cell was observed, a case where there was the abnormal domain and alignment unevenness at zero place was denoted as O, a case where there was the abnormal domain and alignment unevenness in two or less places was denoted as Δ, and a case where there was the abnormal domain and alignment unevenness in three or more places was denoted as X.

The pretilt angles were optically measured by a crystal rotation method, and a case where the pretilt angle was 80 degrees or more and less than 90 degrees was denoted as V, and a case where the pretilt angle was 0 degrees or more and less than 15 degrees was denoted as P. For VHR, a case where the VHR was 98% or more was denoted as O, a case where the VHR was 95% or more and less than 98% was denoted as Δ, and a case where the VHR was 95% or less was denoted as X.

TABLE 5

| | Sample name | Irradiation dose of linear polarized light | Liquid crystal alignment property | Pretilt angle | VHR |
|---|---|---|---|---|---|
| Example 80 | NCE-1 | O | O | P | O |
| Example 81 | NCE-2 | O | O | P | O |
| Example 82 | NCE-3 | O | O | P | O |
| Example 83 | NCE-4 | O | O | P | O |
| Example 84 | NCE-5 | O | O | P | O |
| Example 85 | NCE-6 | O | O | P | O |
| Example 86 | NCE-7 | O | O | P | O |
| Example 87 | NCE-8 | O | O | P | O |
| Example 88 | NCE-9 | O | O | P | O |
| Example 89 | NCE-10 | O | O | P | O |
| Example 90 | NCE-11 | O | O | P | O |
| Example 91 | NCE-12 | O | O | P | O |
| Example 92 | NCE-13 | O | O | P | O |

TABLE 6

| | Sample name | Irradiation dose of linear polarized light | Liquid crystal alignment property | Pretilt angle | VHR |
|---|---|---|---|---|---|
| Example 93 | NCEV-1 | O | O | V | O |
| Example 94 | NCEV-2 | O | O | V | O |
| Example 95 | NCEV-3 | O | O | V | O |
| Example 96 | NCEV-4 | O | O | V | O |
| Example 97 | NCEV-5 | O | O | P | O |
| Example 98 | NCEV-6 | O | O | P | O |
| Example 99 | NCEV-7 | O | O | V | O |
| Example 100 | NCEV-8 | O | O | V | O |
| Example 101 | NCEV-9 | O | O | P | O |
| Example 102 | NCEV-10 | O | O | P | O |
| Example 103 | NCEV-11 | O | O | V | O |
| Example 104 | NCEV-12 | O | O | V | O |
| Example 105 | NCEV-13 | O | O | P | O |
| Example 106 | NCEV-14 | O | O | P | O |
| Example 107 | NCEV-15 | O | O | V | O |
| Example 108 | NCEV-16 | O | O | V | O |
| Example 109 | NCEV-17 | O | O | P | O |
| Example 110 | NCEV-18 | O | O | P | O |
| Example 111 | NCEV-19 | O | O | V | O |
| Example 112 | NCEV-20 | O | O | V | O |
| Example 113 | NCEV-21 | O | O | P | O |
| Example 114 | NCEV-22 | O | O | P | O |
| Example 115 | NCEV-23 | O | O | V | O |
| Example 116 | NCEV-24 | O | O | V | O |
| Example 117 | NCEV-25 | O | O | P | O |
| Example 118 | NCEV-26 | O | O | P | O |

TABLE 7

| | Sample name | Irradiation dose of linear polarized light | Liquid crystal alignment property | Pretilt angle | VHR |
|---|---|---|---|---|---|
| Example 119 | NCEV-27 | O | O | V | O |
| Example 120 | NCEV-28 | O | O | V | O |
| Example 121 | NCEV-29 | O | O | P | O |
| Example 122 | NCEV-30 | O | O | P | O |
| Example 123 | NCEV-31 | O | O | V | O |
| Example 124 | NCEV-32 | O | O | V | O |
| Example 125 | NCEV-33 | O | O | P | O |
| Example 126 | NCEV-34 | O | O | P | O |
| Example 127 | NCEV-35 | O | O | V | O |
| Example 128 | NCEV-36 | O | O | V | O |
| Example 129 | NCEV-37 | O | O | P | O |
| Example 130 | NCEV-38 | O | O | P | O |
| Example 131 | NCEV-39 | O | O | V | O |
| Example 132 | NCEV-40 | O | O | V | O |
| Example 133 | NCEV-41 | O | O | P | O |
| Example 134 | NCEV-42 | O | O | P | O |
| Example 135 | NCEV-43 | O | O | V | O |

TABLE 7-continued

| Sample name | Irradiation dose of linear polarized light | Liquid crystal alignment property | Pretilt angle | VHR |
|---|---|---|---|---|
| Example 136 | NCEV-44 | ○ | ○ | V | ○ |
| Example 137 | NCEV-45 | ○ | ○ | P | ○ |
| Example 138 | NCEV-46 | ○ | ○ | P | ○ |
| Example 139 | NCEV-47 | ○ | ○ | V | ○ |
| Example 140 | NCEV-48 | ○ | ○ | V | ○ |
| Example 141 | NCEV-49 | ○ | ○ | P | ○ |
| Example 142 | NCEV-50 | ○ | ○ | P | ○ |
| Example 143 | NCEV-51 | ○ | ○ | V | ○ |
| Example 144 | NCEV-52 | ○ | ○ | P | ○ |

From the above results, it can be seen that an alignment layer, which allows a small irradiation dose of linear polarized light, and has a superior liquid crystal alignment property and a superior ability to control the pretilt, and exhibits a high voltage holding ratio, can be obtained, by the cinnamic acid polymerized product obtained by polymerizing the cinnamic acid derivatives of the present invention.

Comparative Example 1

For comparison, cinnamic acid derivatives (D-1) and (D-3) were synthesized, and thus, by the same method as in Example 14, cinnamic acid polymers (CE-1) to (CE-2) and (CEV-1) to (CEV-8) were prepared.

[Chem. 179]

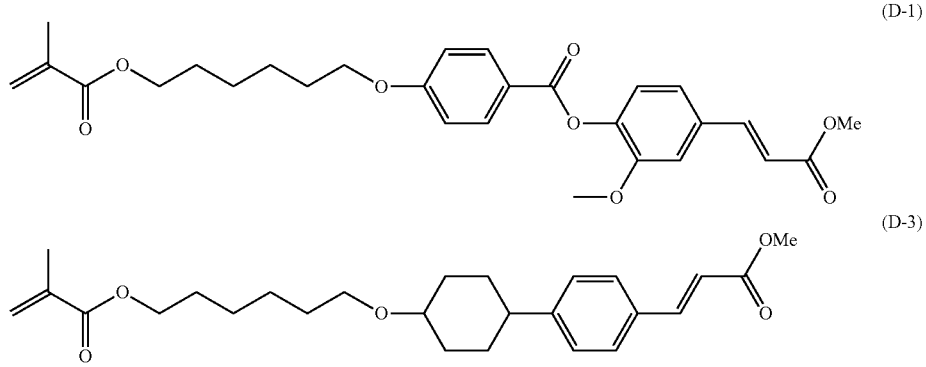

(D-1)

(D-3)

TABLE 8

| Sample name | Blending amount (% by mole) | | | | | |
|---|---|---|---|---|---|---|
| | D-1 | D-3 | V-1 | V-2 | V-3 | V-4 |
| Comparative Example 1 | CE-1 | 100 | | | | | |
| Comparative Example 2 | CE-2 | | 100 | | | | |
| Comparative Example 3 | CEV-1 | 80 | | 20 | | | |
| Comparative Example 4 | CEV-2 | 80 | | | 20 | | |
| Comparative Example 5 | CEV-3 | 80 | | | | 20 | |
| Comparative Example 6 | CEV-4 | 80 | | | | | 20 |
| Comparative Example 7 | CEV-5 | | 80 | 20 | | | |
| Comparative Example 8 | CEV-6 | | 80 | | 20 | | |
| Comparative Example 9 | CEV-7 | | 80 | | | 20 | |
| Comparative Example 10 | CEV-8 | | 80 | | | | 20 |

Furthermore, by the same method as in Example 80, an alignment layer was fabricated, and thus, various measurements were conducted and the results therefrom are shown in Table 9.

TABLE 9

| Sample name | Irradiation dose of linear polarized light | Liquid crystal alignment property | Pretilt angle | VHR |
|---|---|---|---|---|
| Comparative Example 11 | CE-1 | Δ | ○ | P | Δ |
| Comparative Example 12 | CE-2 | Δ | ○ | P | Δ |
| Comparative Example 13 | CEV-1 | Δ | Δ | V | ○ |
| Comparative Example 14 | CEV-2 | Δ | Δ | V | ○ |
| Comparative Example 15 | CEV-3 | Δ | ○ | P | Δ |
| Comparative Example 16 | CEV-4 | Δ | ○ | P | Δ |
| Comparative Example 17 | CEV-5 | Δ | Δ | V | ○ |
| Comparative Example 18 | CEV-6 | Δ | Δ | V | ○ |
| Comparative Example 19 | CEV-7 | Δ | ○ | P | Δ |
| Comparative Example 20 | CEV-8 | Δ | ○ | P | Δ |

Therefore, it can be seen that a liquid crystal alignment layer, and a display element using the liquid crystal alignment layer, each of which allows a small irradiation dose of linear polarized light during the production, and has the effects, such as having a superior ability to control the alignment of the liquid crystals and the pretilt angles, and exhibiting a high voltage holding ratio (VHR), can be obtained, by using the compound (cinnamic acid derivative) of the present invention and a polymer thereof.

Synthesis of Cinnamic Acid Derivative

Example 145

Next, 20.0 g of the obtained 4-(6-methacryloyloxy)benzaldehyde was suspended in 300 ml of acetonitrile, and 10 g of sodium dihydrogen phosphate dihydrate dissolved in 120 ml of water was added dropwise thereto. To this suspension was added 15 ml of 30% hydrogen peroxide, and then 13 g of sodium chlorite dissolved in 100 ml of water was added dropwise thereto, and the mixture was stirred at 45° C. for 3 hours. To the reaction solution was added dropwise 350 ml of water, and the mixture was stirred at 10° C. for 1 hour. The solid was separated by filtration, dissolved

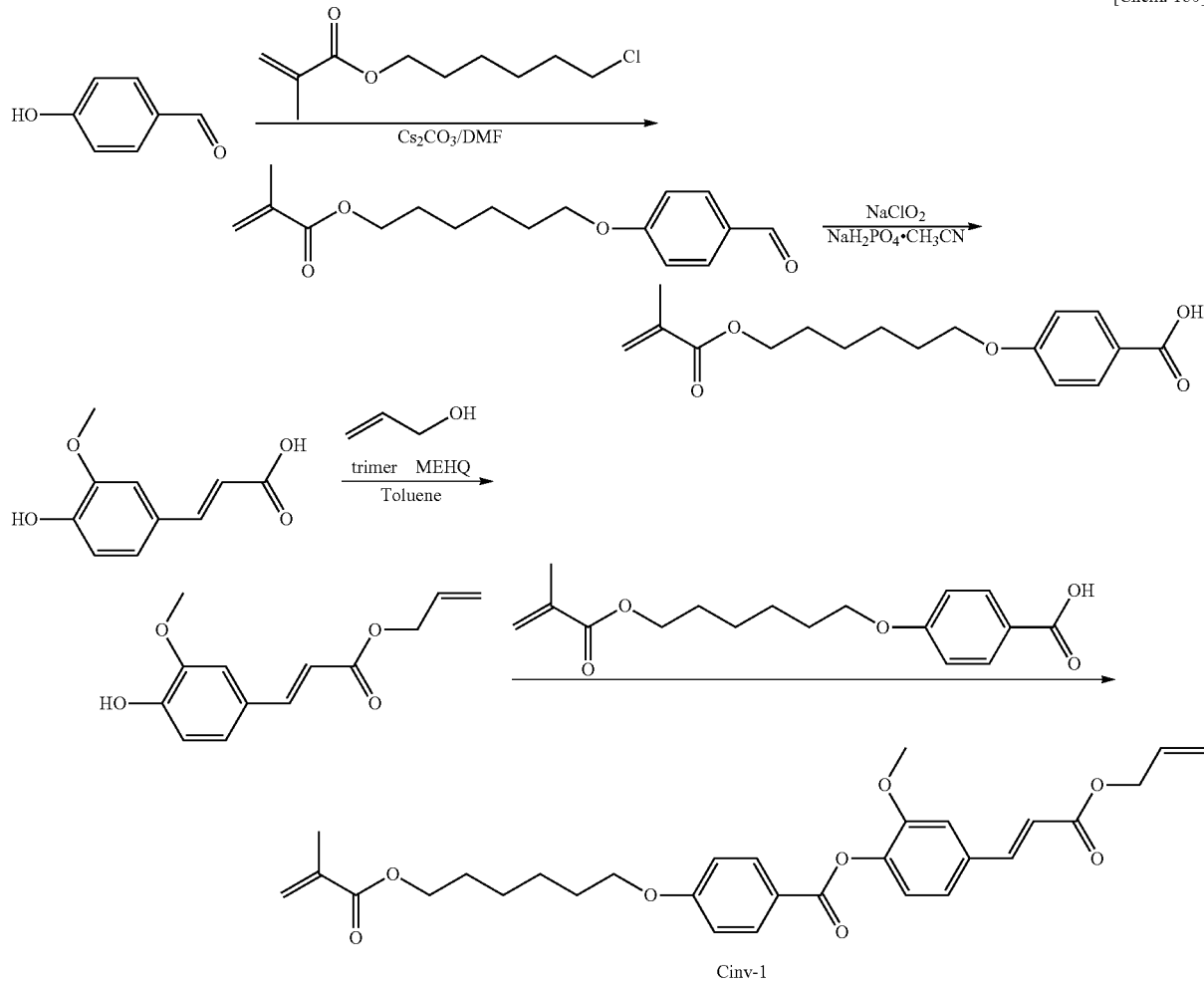

[Chem. 180]

11.5 g of 4-hydroxybenzaldehyde, 20.0 g of 6-chlorohexyl methacrylate, and 62 g of cesium carbonate were dissolved in 150 ml of dimethyl sulfoxide and the mixture was stirred at 60° C. for 3 hours. The reaction solution was cooled to room temperature, and 600 ml of water and 300 ml of dichloromethane were added thereto. The organic phase was separated and the aqueous layer was extracted twice with 150 ml of dichloromethane. The organic phase was combined, and washed with 10% hydrochloric acid, saturated sodium bicarbonate, and saturated saline, and then dried by the addition of sodium sulfate. Sodium sulfate was removed and the mixture was purified by column chromatography (alumina/silica gel, dichloromethane), and the solvent was evaporated under a reduced pressure to obtain 4-(6-methacryloyloxy)benzaldehyde (23 g) as a white solid.

in 120 ml of THF, washed with saturated saline, and then dried by the addition of sodium sulfate. Sodium sulfate was removed and the solvent was evaporated under reduced pressure. Then, 340 ml of ice-cooled hexane was added dropwise and the solid was separated by filtration to obtain 4-(6-methacryloyloxy)benzoic acid (22 g) as a white solid.

21.5 g of 4-hydroxy-3-methoxycinnamic acid, 80 g of 2-propen-1-ol, 0.5 g of propylphosphonic acid anhydride (trimer), and 0.03 g of p-methoxyphenol (MEHQ) were dissolved in 200 ml of toluene, and the mixture was heated at 135° C. for 24 hours. This reaction solution was cooled to room temperature and the toluene was evaporated. Then, the residue was purified by column chromatography (alumina/silica gel, dichloromethane) and the solvent was evaporated under reduced pressure to obtain 2-propenyl 4-hydroxy-3-methoxycinnamate (20.3 g) as a yellow liquid.

Next, 17 g of the obtained 2-propenyl 4-hydroxy-3-methoxycinnamate, 24.5 g of 4-(6-methacryloyloxy)benzoic acid, and 0.9 g of 4,4-dimethylaminopyridine were dissolved in 350 ml of dichloromethane, and the solution was cooled to 3° C. under a nitrogen atmosphere. 11 g of diisopropylcarbodiimide diluted with 30 ml of dichloromethane was added dropwise thereto, and the mixture was stirred at room temperature for 8 hours. The reaction solution was filtered and the solid was removed. Then, the residue was washed with 10% hydrochloric acid and saturated saline, and dried by the addition of sodium sulfate. Sodium sulfate was removed and the residue was purified by column chromatography (alumina/silica gel, hexane/dichloromethane). The solvent was evaporated under reduced pressure to obtain Cinv-1 (22 g) as a white solid.

$^1$H-NMR (400 MHz, CDCl$_3$) δ: 1.41-1.59 (m, 4H), 1.72 (tt, 2H), 1.84 (tt, 2H), 1.95 (s, 3H), 3.85 (s, 3H), 4.05 (t, J=6.4 Hz, 2H), 4.17 (t, J=6.4 Hz, 2H), 4.73 (d, J=5.6 Hz, 2H), 5.29 (d, J=10.4 Hz, 1H), 5.39 (d, J1=8.4 Hz, J2=1.0 Hz, 1H), 5.55 (s, 1H), 5.96-6.05 (m, 1H), 6.10 (s, 1H), 6.44 (d, J=16 Hz, 1H), 6.97 (d, J=8.8 Hz, 2H), 7.16 (s+d+d, 3H), 7.70 (d, J=16 Hz, 1H), 8.14 (d, J=8.8 Hz, 2H)

EI-MS: 522[M$^+$]

Example 146

21.5 g of 4-hydroxy-3-methoxycinnamic acid, 88 g of 2-buten-1-ol, 0.5 g of propylphosphonic acid anhydride (trimer), and 0.03 g of p-methoxyphenol (MEHQ) were dissolved in 200 ml of toluene, and the solution was heated to 135° C. for 24 hours. This reaction solution was cooled to room temperature and the toluene was evaporated. Then, the residue was purified by column chromatography (alumina/silica gel, dichloromethane), and the solvent was evaporated under reduced pressure to obtain 2-butenyl 4-hydroxy-3-methoxycinnamate (21.6 g) as a yellow liquid.

Next, 17.8 g of the obtained 2-butenyl 4-hydroxy-3-methoxycinnamate, 24.5 g of 4-(6-methacryloyloxy)benzoic acid, and 1.1 g of 4,4-dimethyl aminopyridine were dissolved in 350 ml of dichloromethane, and cooled to 3° C. under a nitrogen atmosphere. 11 g of diisopropylcarbodiimide diluted with 30 ml of dichloromethane was added dropwise thereto, and the mixture was stirred at room temperature for 8 hours. The reaction solution was filtered and the solid was removed. Then, the residue was washed with 10% hydrochloric acid and saturated saline, and dried by the addition of sodium sulfate. Sodium sulfate was removed and the residue was purified by column chromatography (alumina/silica gel, hexane/dichloromethane). The solvent was evaporated under reduced pressure to obtain Cinv-2 (26 g) as a white solid.

$^1$H-NMR (400 MHz, CDCl$_3$) δ: 1.41-1.59 (m, 4H), 1.67-1.79 (d+tt, 5H), 1.84 (tt, 2H), 1.95 (s, 3H), 3.84 (s, 3H), 4.05 (t, J=6.4 Hz, 2H), 4.17 (t, J=6.4 Hz, 2H), 4.65 (d, J=6.8 Hz, 2H), 5.56 (s, 1H), 5.62-5.71 (m, 1H), 5.79-5.88 (m, 1H), 6.10 (s, 1H), 6.42 (d, J=16 Hz, 1H), 6.97 (d, J=8.8 Hz, 2H), 7.16 (s+d+d, 3H), 7.70 (d, J=16 Hz, 1H), 8.15 (d, J=8.8 Hz, 2H)

EI-MS: 536[M$^+$]

In the same manner, the following compounds Cinv-3 to Cinv-12 were synthesized.

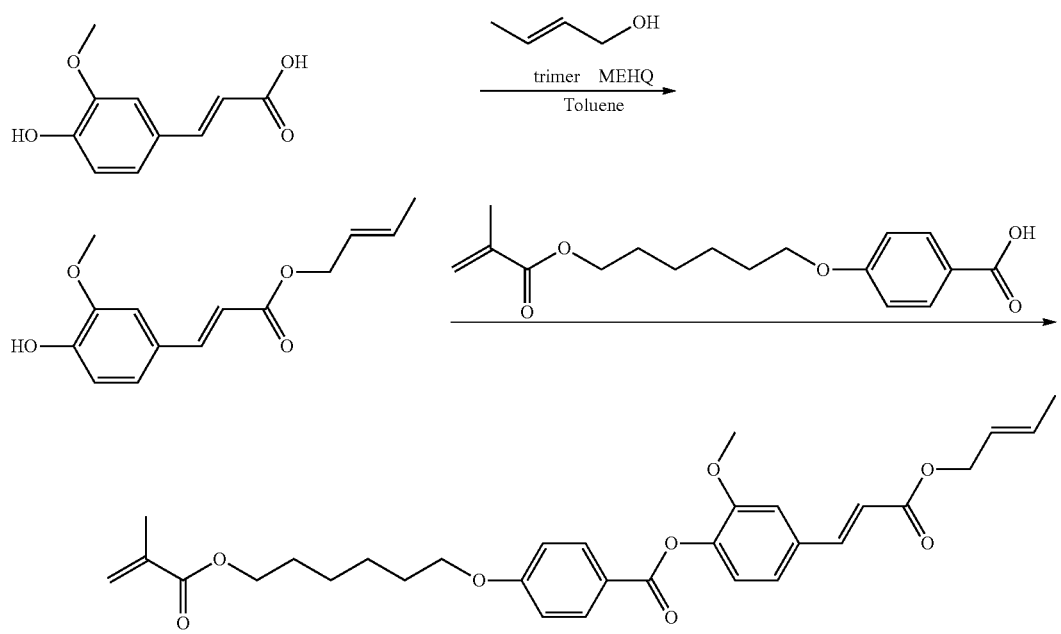

[Chem. 181]

Cinv-2

[Chem. 182]
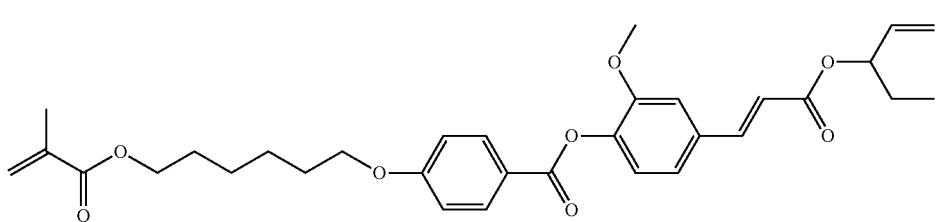
(Example 147) Cinv-3
[Chem. 183]
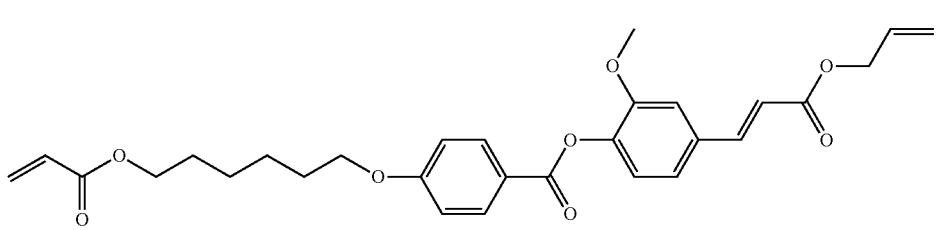
(Example 148) Cinv-4
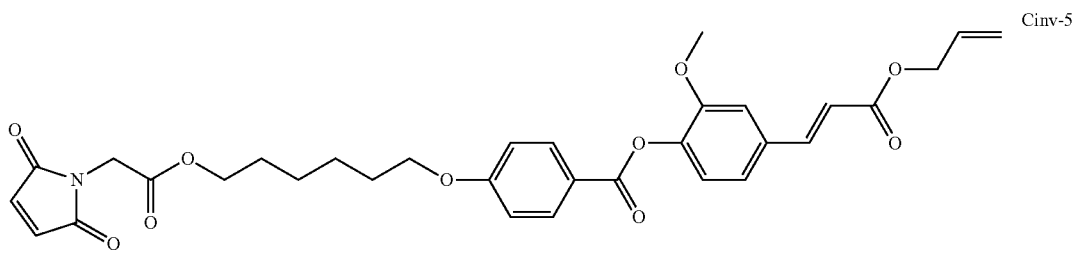
(Example 149) Cinv-5
[Chem. 184]
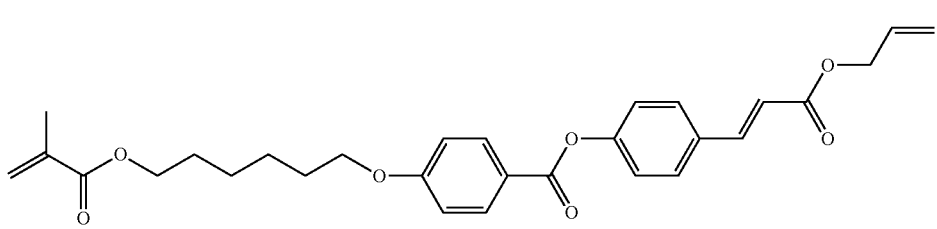
(Example 150) Cinv-6
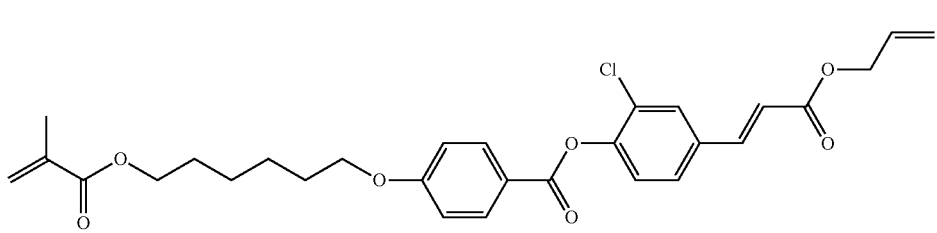
(Example 151) Cinv-7

-continued
[Chem. 185]
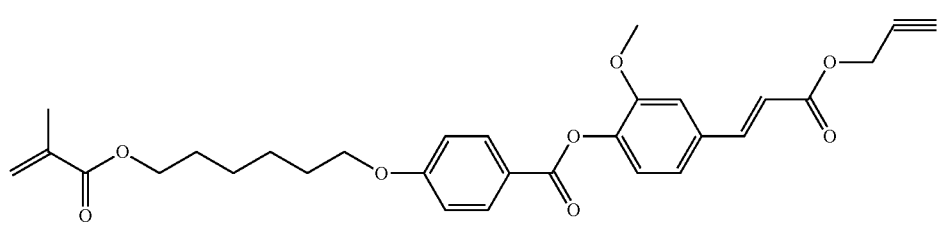
Cinv-8
(Example 152)
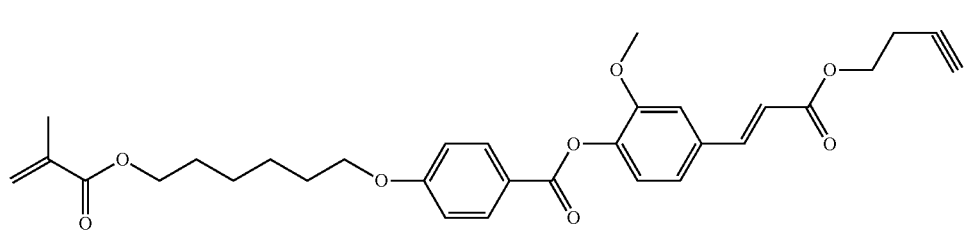
Cinv-9
(Example 153)
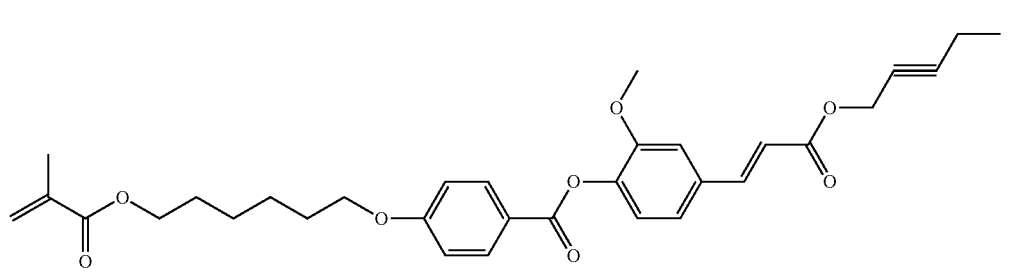
Cinv-10
(Example 154)
[Chem. 186]
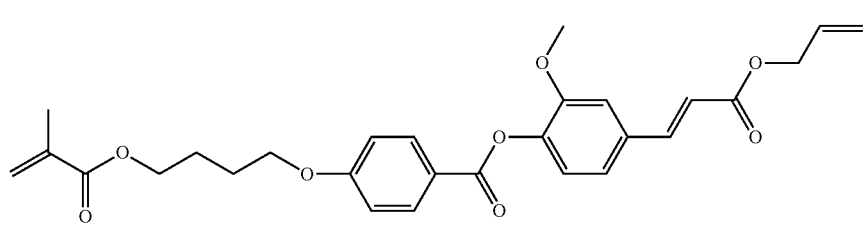
Cinv-11
(Example 155)
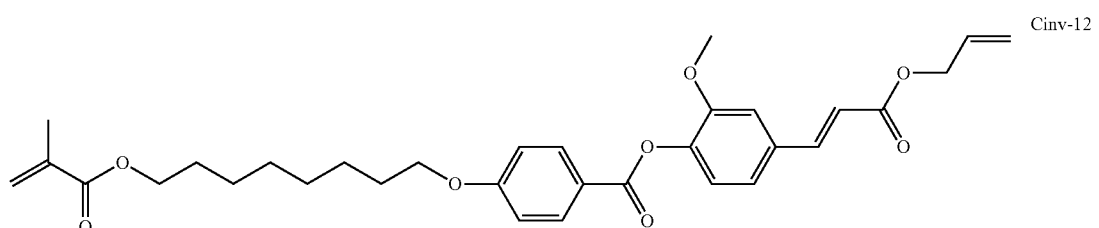
Cinv-12
(Example 156)

-continued

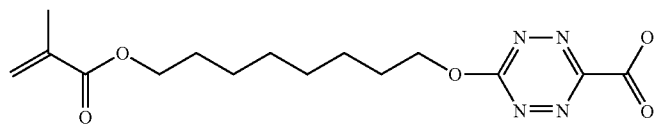

(Example 157)

Synthesis of Monomer for Copolymerization

[Chem. 187]

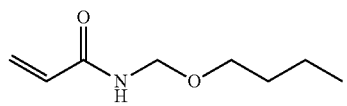

9.01 g of butyl maleimidoacetate, 0.33 g of dibutyltin (IV) oxide, and 9.14 g of tetradecanol were dissolved in 40 ml of toluene, followed by stirring for 15 hours while heating to reflux. The reaction solution was cooled to room temperature and 100 ml of toluene was added thereto. The mixture was subjected to liquid separation and washed with saturated sodium bicarbonate water and then with saturated saline. To this solution was added sodium sulfate, and the mixture was dried. Sodium sulfate was removed and the solvent was evaporated under reduced pressure to reduce the volume to about 50 ml, and 40 ml of hexane and 20 ml of dichloromethane were added thereto. The mixture was purified by column chromatography (alumina/silica gel, hexane/dichloromethane=2:1), the solvent was evaporated under reduced pressure, and the residue was reprecipitated with methanol to obtain (V-1) (7.95 g) as a white crystal.

$^1$H-NMR (400 MHz, CDCl$_3$) δ: 0.88 (t, J=6.8 Hz, 3H), 1.15-1.40 (m, 22H), 1.61-1.66 (tt, 2H), 4.14 (t, J=6.6 Hz, 2H), 4.15 (s, 2H), 6.79 (s, 2H)

EI-MS: 351[M$^+$]

[Chem. 188]

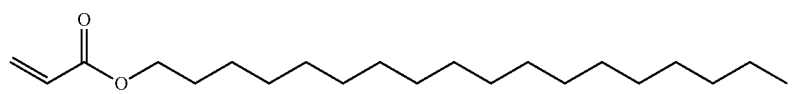

Stearyl acrylate (V-2) (manufactured by Tokyo Chemical Industry Co., Ltd.) was purchased and used.

[Chem. 189]

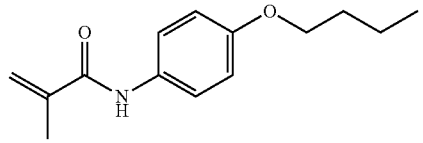

N-(Butoxymethyl)acrylamide (V-3) (manufactured by Tokyo Chemical Industry Co., Ltd.) was purchased and used.

[Chem. 190]

A compound (V-4) was synthesized according to the procedure described in a known document (Farmaco. Edizione Scientifica Vol. 22 (1967) 190, 590-598).

Preparation of Cinnamic Acid Polymer (CEv-1)

Example 158

1 part (10.0 mmol) of a compound represented by the formula (Cinv-1) was dissolved in 10 parts of ethyl methyl ketone to obtain a solution 1. To this solution 1 was added 0.01 parts of azobisisobutyronitrile (AIBN). The mixture was heated to reflux for 2 days under a nitrogen atmosphere to obtain a solution 2. Then, the solution 2 was added dropwise to 60 parts of methanol under stirring, and the precipitated solid was filtered. The obtained solid was dissolved in 5 parts of tetrahydrofuran (THF), the solution was added dropwise to 120 parts of ice-cooled hexane under stirring, and the precipitated solid was filtered. The obtained solid was dissolved in 5 parts of THF, the solution was added dropwise to 120 parts of ice-cooled methanol under stirring, and the precipitated solid was filtered. The obtained solid was dissolved in THF and then vacuum-dried to obtain a polymer (CEv-1).

Preparation of Cinnamic Acid Polymers (CEv-2) to (CEv-12)

In the same manner as for the cinnamic acid polymer (CEv-1), polymers (CEv-2) to (CEv-12) were obtained. The compositions of the respective polymers are as shown in Tables 1 and 2.

TABLE 10

| Sample name | Blending amount (% by mole) | | | | | |
|---|---|---|---|---|---|---|
| | Cinv-1 | Cinv-2 | Cinv-3 | Cinv-4 | Cinv-5 | Cinv-6 |
| Example 158 | CEv-1 | 100 | | | | | |
| Example 159 | CEv-2 | | 100 | | | | |
| Example 160 | CEv-3 | | | 100 | | | |
| Example 161 | CEv-4 | | | | 100 | | |
| Example 162 | CEv-5 | | | | | 100 | |
| Example 163 | CEv-6 | | | | | | 100 |

TABLE 11

| | Sample name | Blending amount (% by mole) | | | | | | |
|---|---|---|---|---|---|---|---|---|
| | | Cinv-7 | Cinv-8 | Cinv-9 | Cinv-10 | Cinv-11 | Cinv-12 | Cinv-13 |
| Example 164 | CEv-7 | 100 | | | | | | |
| Example 165 | CEv-8 | | 100 | | | | | |
| Example 166 | CEv-9 | | | 100 | | | | |
| Example 167 | CEv-10 | | | | 100 | | | |
| Example 168 | CEv-11 | | | | | 100 | | |
| Example 169 | CEv-12 | | | | | | 100 | |
| Example 170 | CEv-13 | | | | | | | 100 |

Preparation of Cinnamic Acid Polymer (CEvV-1)

Example 171

0.9 parts (9.0 mmol) of the compound represented by the formula (Cinv-1) and 0.1 parts (1.0 mmol) of a compound represented by the formula (V-1) were dissolved in 10 parts of ethyl methyl ketone to obtain a solution 3. To this solution 3 was added 0.01 parts of azobisisobutyronitrile (AIBN). The mixture was heated to reflux for 2 days under a nitrogen atmosphere to obtain a solution 4. Then, the solution 4 was added dropwise to 60 parts of methanol under stirring, and the precipitated solid was filtered. The obtained solid was dissolved in 5 parts of tetrahydrofuran (THF), the solution was added dropwise to 120 parts of ice-cooled hexane under stirring, and the precipitated solid was filtered. The obtained solid was dissolved in 5 parts of THF, the solution was added dropwise to 120 parts of ice-cooled methanol under stirring, and the precipitated solid was filtered. The obtained solid was dissolved in THF and then vacuum-dried to obtain a polymer (CEvV-1).

Preparation of Cinnamic Acid Polymers (CEvV-2) to (CEvV-50)

In the same manner as for the cinnamic acid polymer (CEvV-1), polymers (CEvV-2) to (CEvV-50) were obtained. The compositions of the respective polymers are as shown in Tables 3 and 4.

TABLE 12

| Example | Sample name | Blending amount (% by mole) | | | | | | | | | |
|---|---|---|---|---|---|---|---|---|---|---|---|
| | | Cinv-1 | Cinv-2 | Cinv-3 | Cinv-4 | Cinv-5 | Cinv-6 | V-1 | V-2 | V-3 | V-4 |
| 171 | CEvV-1 | 90 | | | | | | 10 | | | |
| 172 | CEvV-2 | 85 | | | | | | 15 | | | |
| 173 | CEvV-3 | 80 | | | | | | 20 | | | |
| 174 | CEvV-4 | 80 | | | | | | | 20 | | |
| 175 | CEvV-5 | 80 | | | | | | | | 20 | |
| 176 | CEvV-6 | 80 | | | | | | | | | 20 |
| 177 | CEvV-7 | | 80 | | | | | 20 | | | |
| 178 | CEvV-8 | | 80 | | | | | | 20 | | |
| 179 | CEvV-9 | | 80 | | | | | | | 20 | |
| 180 | CEvV-10 | | 80 | | | | | | | | 20 |
| 181 | CEvV-11 | | | 80 | | | | 20 | | | |
| 182 | CEvV-12 | | | 80 | | | | | 20 | | |
| 183 | CEvV-13 | | | 80 | | | | | | 20 | |
| 184 | CEvV-14 | | | 80 | | | | | | | 20 |
| 185 | CEvV-15 | | | | 80 | | | 20 | | | |
| 186 | CEvV-16 | | | | 80 | | | | 20 | | |
| 187 | CEvV-17 | | | | 80 | | | | | 20 | |
| 188 | CEvV-18 | | | | 80 | | | | | | 20 |
| 189 | CEvV-19 | | | | | 80 | | 20 | | | |
| 190 | CEvV-20 | | | | | 80 | | | 20 | | |
| 191 | CEvV-21 | | | | | 80 | | | | 20 | |
| 192 | CEvV-22 | | | | | 80 | | | | | 20 |
| 193 | CEvV-23 | | | | | | 80 | 20 | | | |
| 194 | CEvV-24 | | | | | | 80 | | 20 | | |
| 195 | CEvV-25 | | | | | | 80 | | | 20 | |
| 196 | CEvV-26 | | | | | | 80 | | | | 20 |

TABLE 13

| Example | Sample name | Cinv-7 | Cinv-8 | Cinv-9 | Cinv-10 | Cinv-11 | Cinv-12 | Cinv-13 | V-1 | V-2 | V-3 | V-4 |
|---|---|---|---|---|---|---|---|---|---|---|---|---|
| 197 | CEvV-27 | 80 | | | | | | | 20 | | | |
| 198 | CEvV-28 | 80 | | | | | | | | 20 | | |
| 199 | CEvV-29 | 80 | | | | | | | | | 20 | |
| 200 | CEvV-30 | 80 | | | | | | | | | | 20 |
| 201 | CEvV-31 | | 80 | | | | | | 20 | | | |
| 202 | CEvV-32 | | 80 | | | | | | | 20 | | |
| 203 | CEvV-33 | | 80 | | | | | | | | 20 | |
| 204 | CEvV-34 | | 80 | | | | | | | | | 20 |
| 205 | CEvV-35 | | | 80 | | | | | 20 | | | |
| 206 | CEvV-36 | | | 80 | | | | | | 20 | | |
| 207 | CEvV-37 | | | 80 | | | | | | | 20 | |
| 208 | CEvV-38 | | | 80 | | | | | | | | 20 |
| 209 | CEvV-39 | | | | 80 | | | | 20 | | | |
| 210 | CEvV-40 | | | | 80 | | | | | 20 | | |
| 211 | CEvV-41 | | | | 80 | | | | | | 20 | |
| 212 | CEvV-42 | | | | 80 | | | | | | | 20 |
| 213 | CEvV-43 | | | | | 80 | | | 20 | | | |
| 214 | CEvV-44 | | | | | 80 | | | | 20 | | |
| 215 | CEvV-45 | | | | | 80 | | | | | 20 | |
| 216 | CEvV-46 | | | | | 80 | | | | | | 20 |
| 217 | CEvV-47 | | | | | | 80 | | 20 | | | |
| 218 | CEvV-48 | | | | | | 80 | | | 20 | | |
| 219 | CEvV-49 | | | | | | 80 | | | | 20 | |
| 220 | CEvV-50 | | | | | | 80 | | | | | 20 |
| 221 | CEvV-51 | | | | | | | 80 | 20 | | | |
| 222 | CEvV-52 | | | | | | | 80 | | 20 | | |

Fabrication of Alignment Layer and Liquid Crystal Display Element

Example 223

The cinnamic acid polymer (CEv-1) was dissolved in cyclopentanone to 2.0% and the solution was stirred at room temperature for 10 minutes. Then, the solution was applied onto a glass plate as a base material at 2000 rpm for 30 seconds, using a spin coater, and dried at 100° C. for 3 minutes. Then, the surface was visually observed and as a result, it was found that a polymer was uniformly applied on the glass plate to form a smooth film.

Next, the coated glass plate as a base material was irradiated with linear polarized and parallel light of visible ultraviolet light (wavelength: 313 nm, irradiation intensity: 8 mW/cm$^2$) using an ultrahigh-pressure mercury lamp via a wavelength cut filter, a band-pass filter, and a polarizing filter in a direction of 45 degrees with respect to the substrate. The irradiation dose was 120 mJ/cm$^2$.

[Chem. 191]

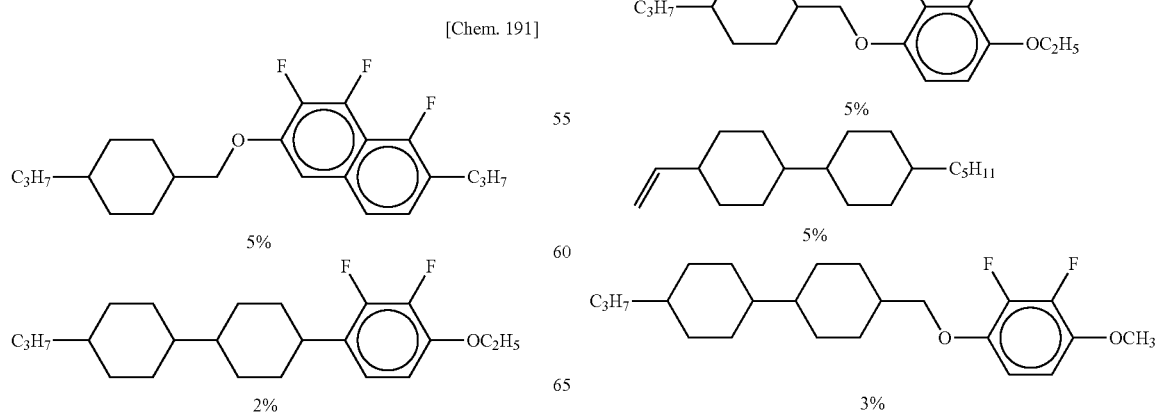

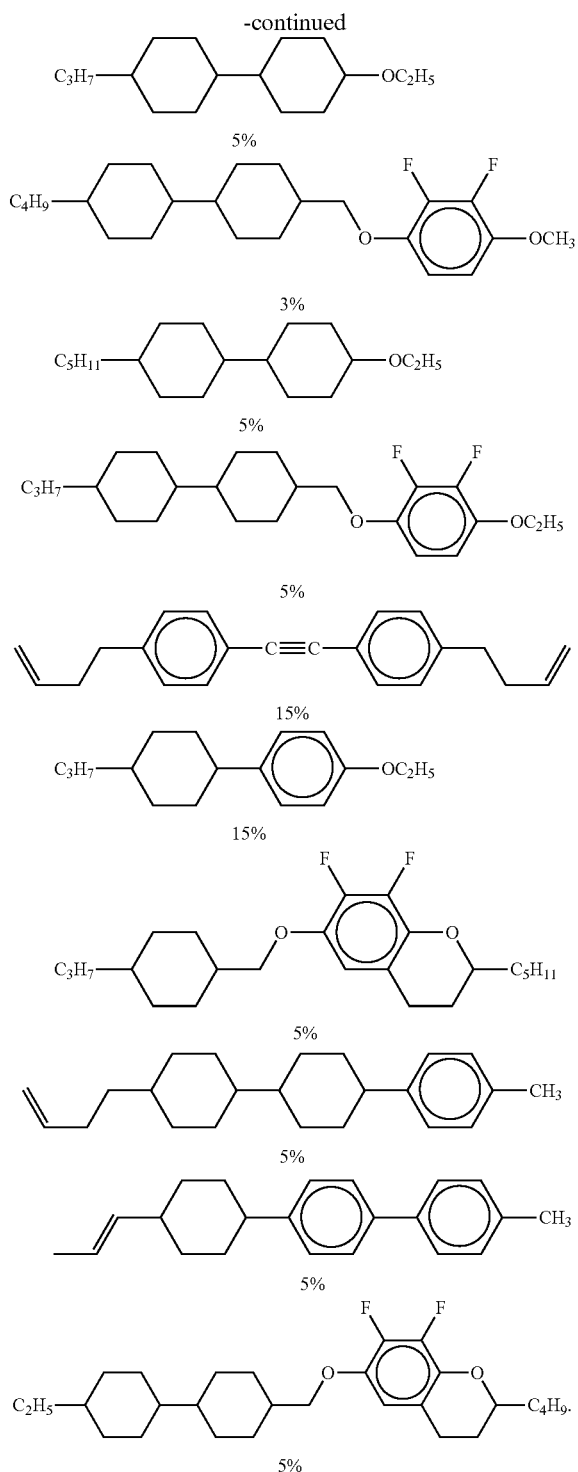

A liquid crystal cell was fabricated by using the coated glass plate prepared by the method above. The gap between the plates was set to 10 μm and the two glass plates were bonded in the anti-parallel direction. Next, a nematic liquid crystal mixture having a negative dielectric anisotropy with a composition described below was charged into the cell at a temperature just exceeding a transparent point (Tc=84.4° C.), and then cooled to room temperature. A polarizing plate was placed on the top and the bottom of the liquid crystal cell, and a back light was placed below. The light transmittance was changed by rotating the liquid crystal cell by 90 degrees and dark-light contrast was clearly observed and there was no abnormal domain and alignment unevenness, from which it was confirmed that the liquid crystals were normally aligned. The tilt angle of the liquid crystal in the cell was optically measured by a crystal rotation method, and the pretilt angle was found to be 1 degree. A voltage of 5 V was applied to this liquid crystal cell for an application time of 60 microseconds at a span of 167 milliseconds, and the voltage holding ratio after 167 milliseconds from the release of the voltage was measured by means of "VHR-AMP01" manufactured by TOYO Corporation at 23° C., and as a result, the voltage holding ratio (VHR) was found to be 99.3%.

Hereinafter, in the same manner as the cinnamic acid polymer (CEv-1), for (CEv-2) to (CEv-12), and (CEvV-1) to (CEvV-50), alignment layers were fabricated and liquid crystal cells were fabricated. The measurement results of the coatability, liquid crystal alignment property, pretilt angle, VHR are shown in conjunction in Table 5. For the coatability, when a film was formed by applying a polymer onto a glass plate and observed, a case where the polymer was uniformly applied to form a smooth film was denoted as O, a case where there was chipping and/or unevenness on the coated surface at one place was denoted as Δ, and a case where there was chipping and/or unevenness on the coated surface in two or more places was denoted as X. For the liquid crystal alignment property, when the presence or absence of the abnormal domain and alignment unevenness of the liquid crystal cell was observed, a case where there was the abnormal domain and alignment unevenness at zero place was denoted as O, a case where there was the abnormal domain and alignment unevenness in two or less places was denoted as Δ, and a case where there was the abnormal domain and alignment unevenness in three or more places was denoted as X. For the pretilt angles, the pretilt angles were optically measured by a crystal rotation method, and a case where the pretilt angle was 80 degrees or more and less than 90 degrees was denoted as V, and a case where the pretilt angle was 0 degrees or more and less than 15 degrees was denoted as P. For VHR, a case where the VHR was 98% or more was denoted as O, a case where the VHR was 95% or more and less than 98% was denoted as Δ, and a case where the VHR was 95% or less was denoted as X.

TABLE 14

| | Sample name | Coatability | Liquid crystal alignment property | Pretilt angle | VHR |
|---|---|---|---|---|---|
| Example 223 | CEv-1 | O | O | P | O |
| Example 224 | CEv-2 | O | O | P | O |
| Example 225 | CEv-3 | O | O | P | O |
| Example 226 | CEv-4 | O | O | P | O |
| Example 227 | CEv-5 | O | O | P | O |
| Example 228 | CEv-6 | O | O | P | O |
| Example 229 | CEv-7 | O | O | P | O |
| Example 230 | CEv-8 | O | O | P | O |
| Example 231 | CEv-9 | O | O | P | O |
| Example 232 | CEv-10 | O | O | P | O |
| Example 233 | CEv-11 | O | O | P | O |
| Example 234 | CEv-12 | O | O | P | O |
| Example 235 | CEv-13 | O | O | P | O |

TABLE 15

| Sample name | | Coatability | Liquid crystal alignment property | Pretilt angle | VHR |
|---|---|---|---|---|---|
| Example 236 | CEvV-1 | ○ | ○ | V | ○ |
| Example 237 | CEvV-2 | ○ | ○ | V | ○ |
| Example 238 | CEvV-3 | ○ | ○ | V | ○ |
| Example 239 | CEvV-4 | ○ | ○ | V | ○ |
| Example 240 | CEvV-5 | ○ | ○ | P | ○ |
| Example 241 | CEvV-6 | ○ | ○ | P | ○ |
| Example 242 | CEvV-7 | ○ | ○ | V | ○ |
| Example 243 | CEvV-8 | ○ | ○ | V | ○ |
| Example 244 | CEvV-9 | ○ | ○ | P | ○ |
| Example 245 | CEvV-10 | ○ | ○ | P | ○ |
| Example 246 | CEvV-11 | ○ | ○ | V | ○ |
| Example 247 | CEvV-12 | ○ | ○ | V | ○ |
| Example 248 | CEvV-13 | ○ | ○ | P | ○ |
| Example 249 | CEvV-14 | ○ | ○ | P | ○ |
| Example 250 | CEvV-15 | ○ | ○ | V | ○ |
| Example 251 | CEvV-16 | ○ | ○ | V | ○ |
| Example 252 | CEvV-17 | ○ | ○ | P | ○ |
| Example 253 | CEvV-18 | ○ | ○ | P | ○ |
| Example 254 | CEvV-19 | ○ | ○ | V | ○ |
| Example 255 | CEvV-20 | ○ | ○ | V | ○ |
| Example 256 | CEvV-21 | ○ | ○ | P | ○ |
| Example 257 | CEvV-22 | ○ | ○ | P | ○ |
| Example 258 | CEvV-23 | ○ | ○ | V | ○ |
| Example 259 | CEvV-24 | ○ | ○ | V | ○ |
| Example 260 | CEvV-25 | ○ | ○ | P | ○ |
| Example 261 | CEvV-26 | ○ | ○ | P | ○ |

TABLE 16

| Sample name | | Coatability | Liquid crystal alignment property | Pretilt angle | VHR |
|---|---|---|---|---|---|
| Example 262 | CEvV-27 | ○ | ○ | V | ○ |
| Example 263 | CEvV-28 | ○ | ○ | V | ○ |
| Example 264 | CEvV-29 | ○ | ○ | P | ○ |
| Example 265 | CEvV-30 | ○ | ○ | P | ○ |
| Example 266 | CEvV-31 | ○ | ○ | V | ○ |
| Example 267 | CEvV-32 | ○ | ○ | V | ○ |
| Example 268 | CEvV-33 | ○ | ○ | P | ○ |
| Example 269 | CEvV-34 | ○ | ○ | P | ○ |
| Example 270 | CEvV-35 | ○ | ○ | V | ○ |
| Example 271 | CEvV-36 | ○ | ○ | V | ○ |
| Example 272 | CEvV-37 | ○ | ○ | P | ○ |
| Example 273 | CEvV-38 | ○ | ○ | P | ○ |
| Example 274 | CEvV-39 | ○ | ○ | V | ○ |
| Example 275 | CEvV-40 | ○ | ○ | V | ○ |
| Example 276 | CEvV-41 | ○ | ○ | P | ○ |
| Example 277 | CEvV-42 | ○ | ○ | P | ○ |
| Example 278 | CEvV-43 | ○ | ○ | V | ○ |
| Example 279 | CEvV-44 | ○ | ○ | V | ○ |
| Example 280 | CEvV-45 | ○ | ○ | P | ○ |
| Example 281 | CEvV-46 | ○ | ○ | P | ○ |
| Example 282 | CEvV-47 | ○ | ○ | V | ○ |
| Example 283 | CEvV-48 | ○ | ○ | V | ○ |
| Example 284 | CEvV-49 | ○ | ○ | P | ○ |
| Example 285 | CEvV-50 | ○ | ○ | P | ○ |
| Example 286 | CEvV-51 | ○ | ○ | V | ○ |
| Example 287 | CEvV-52 | ○ | ○ | P | ○ |

From the above results, it can be seen that an alignment layer, which has good coatability, a superior liquid crystal alignment property, and a superior ability to control the pretilt, and exhibits a high voltage holding ratio, can be obtained, by the cinnamic acid polymerized product obtained by polymerizing the cinnamic acid derivatives of the present invention.

Comparative Example 21

For comparison, cinnamic acid derivatives (D-1) and (D-3) were synthesized, and thus, by the same method as in Example 158, cinnamic acid polymer (CE-1) to (CE-2) and (CEV-1) to (CEV-8) were prepared.

[Chem. 192]

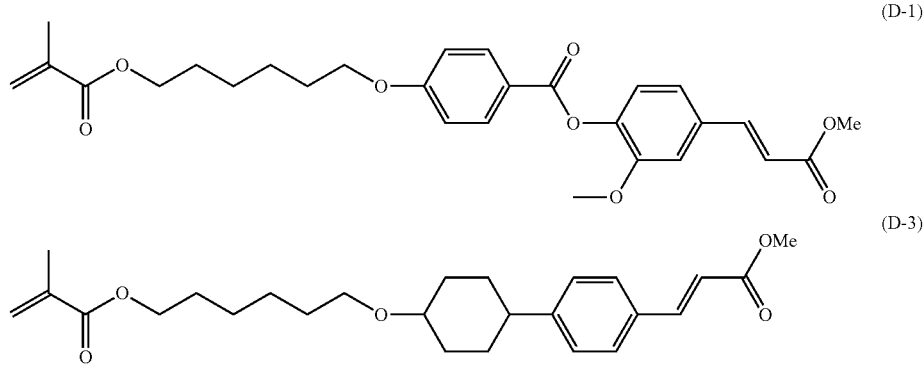

TABLE 17

| Sample name | Blending amount (% by mole) | | | | | |
|---|---|---|---|---|---|---|
| | | D-1 | D-3 | V-1 | V-2 | V-3 | V-4 |
| Comparative Example 21 | CE-1 | 100 | | | | | |
| Comparative Example 22 | CE-2 | | 100 | | | | |
| Comparative Example 23 | CEV-1 | 80 | | 20 | | | |
| Comparative Example 24 | CEV-2 | 80 | | | 20 | | |
| Comparative Example 25 | CEV-3 | 80 | | | | 20 | |

TABLE 17-continued

| Sample name | Blending amount (% by mole) | | | | | |
|---|---|---|---|---|---|---|
| | D-1 | D-3 | V-1 | V-2 | V-3 | V-4 |
| Comparative Example 26 | CEV-4 | 80 | | | | 20 |
| Comparative Example 27 | CEV-5 | | 80 | 20 | | |
| Comparative Example 28 | CEV-6 | | 80 | | 20 | |
| Comparative Example 29 | CEV-7 | | 80 | | | 20 |
| Comparative Example 30 | CEV-8 | | 80 | | | 20 |

Furthermore, by the same method as in Example 223, an alignment layer was fabricated, and thus, various measurements were conducted and the results therefrom are shown in Table 9.

TABLE 18

| Sample name | Coatability | Liquid crystal alignment property | Pretilt angle | VHR |
|---|---|---|---|---|
| Comparative Example 31 | CE-1 | Δ | ○ | P | Δ |
| Comparative Example 32 | CE-2 | Δ | ○ | P | Δ |
| Comparative Example 33 | CEV-1 | ○ | Δ | V | ○ |
| Comparative Example 34 | CEV-2 | ○ | Δ | V | ○ |
| Comparative Example 35 | CEV-3 | Δ | ○ | P | Δ |
| Comparative Example 36 | CEV-4 | Δ | ○ | P | Δ |
| Comparative Example 37 | CEV-5 | ○ | Δ | V | ○ |
| Comparative Example 38 | CEV-6 | ○ | Δ | V | ○ |
| Comparative Example 39 | CEV-7 | Δ | ○ | P | Δ |
| Comparative Example 40 | CEV-8 | Δ | ○ | P | Δ |

Therefore, it can be seen that according to the present invention, a display element using a liquid crystal alignment layer which has the effects such as having good coatability, and a superior ability to control the alignment of the liquid crystals and the pretilt angles, and exhibiting a high voltage holding ratio (VHR), and the composition is obtained.

Synthesis of Cinnamic Acid Derivative

Example 288

[Chem. 193]

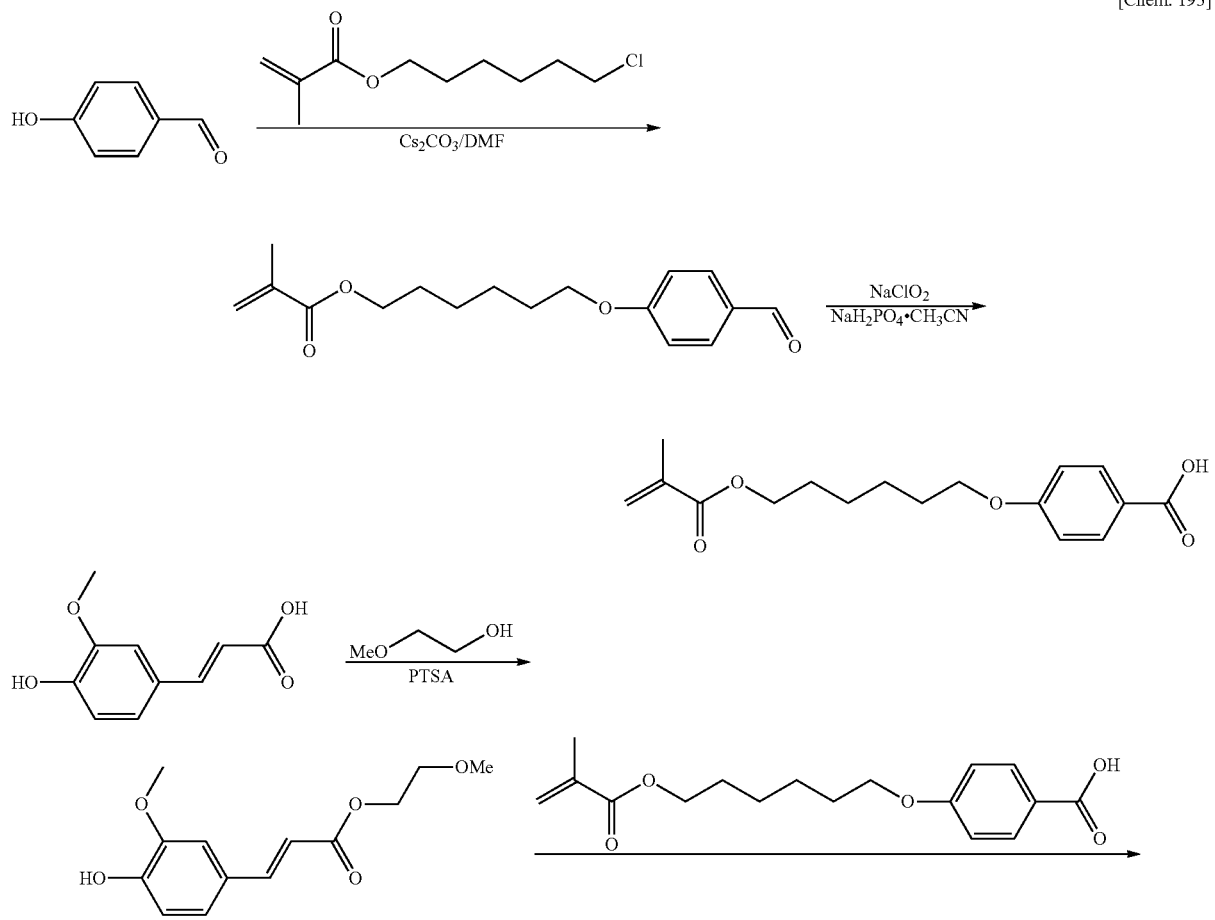

-continued

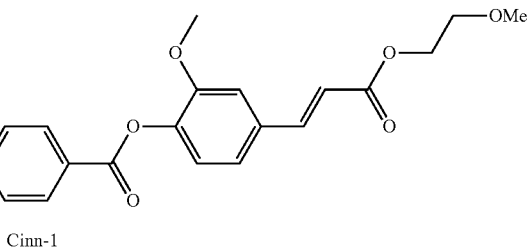

Cinn-1

11.5 g of 4-hydroxybenzaldehyde, 20.0 g of 6-chlorohexyl methacrylate, and 62 g of cesium carbonate were dissolved in 150 ml of dimethyl sulfoxide and the mixture was stirred at 60° C. for 3 hours. The reaction solution was cooled to room temperature, and 600 ml of water and 300 ml of dichloromethane were added thereto. The organic layer was separated and the aqueous layer was extracted twice with 150 ml of dichloromethane. The organic layer was combined, and washed with 10% hydrochloric acid, saturated sodium bicarbonate, and saturated saline, and then dried by the addition of sodium sulfate. Sodium sulfate was removed and the mixture was purified by column chromatography (alumina/silica gel, dichloromethane), and the solvent was evaporated under a reduced pressure to obtain 4-(6-methacryloyloxy)benzaldehyde (23 g) as a white solid.

Next, 20.0 g of the obtained 4-(6-methacryloyloxy)benzaldehyde was suspended in 300 ml of acetonitrile, and 10 g of sodium dihydrogen phosphate dihydrate dissolved in 120 ml of water was added dropwise thereto. To this suspension was added 15 ml of 30% hydrogen peroxide, and then 13 g of sodium chlorite dissolved in 100 ml of water was added dropwise thereto, and the mixture was stirred at 45° C. for 3 hours. To the reaction solution was added dropwise 350 ml of water, and the mixture was stirred at 10° C. for 1 hour. The solid was separated by filtration, dissolved in 120 ml of THF, washed with saturated saline, and then dried by the addition of sodium sulfate. Sodium sulfate was removed and the solvent was evaporated under reduced pressure. Then, 340 ml of ice-cooled hexane was added dropwise and the solid was separated by filtration to obtain 4-(6-methacryloyloxy)benzoic acid (22 g) as a white solid.

30 g of 4-hydroxy-3-methoxycinnamic acid, 20 g of 2-methoxyethanol, and 3 g of p-toluenesulfonic acid were dissolved in 200 ml of cyclohexane and 20 ml of diisopropyl ether, and heated to reflux for 6 hours while removing water produced. The residue was cooled to room temperature, 100 ml of ethyl acetate was added thereto, and the mixture was washed with saturated sodium bicarbonate, water, and saturated saline, and then dried by the addition of sodium sulfate. Sodium sulfate was removed and the solvent was evaporated under reduced pressure to obtain 2-methoxyethyl 4-hydroxy-3-methoxycinnamate (30 g) as a white solid.

Next, 15.1 g of the obtained 2-methoxyethyl 4-hydroxy-3-methoxycinnamate, 20.2 g of 4-(6-methacryloyloxy)benzoic acid, and 0.9 g of 4,4-dimethylaminopyridine were dissolved in 300 ml of dichloromethane, and the solution was cooled to 3° C. under a nitrogen atmosphere. 9.1 g of diisopropylcarbodiimide diluted with 100 ml of dichloromethane was added dropwise thereto, and the mixture was stirred at room temperature for 8 hours. The reaction solution was filtered and the solid was removed. Then, the residue was washed with 10% hydrochloric acid and saturated saline, and dried by the addition of sodium sulfate. Sodium sulfate was removed and the residue was purified by column chromatography (alumina/silica gel, heptane/dichloromethane/ethyl acetate). The solvent was evaporated under reduced pressure and the residue was recrystallized with methanol to obtain Cinn-1 (21.7 g) as a white solid.

$^1$H-NMR (400 MHz, CDCl$_3$) δ: 1.41-1.59 (m, 4H), 1.73 (tt, 2H), 1.84 (tt, 2H), 1.94 (s, 3H), 3.43 (s, 3H), 3.68 (t, J=4.6 Hz, 2H), 3.84 (s, 3H), 4.05 (t, J=6.4 Hz, 2H), 4.17 (t, J=6.4 Hz, 2H), 4.38 (t, J=4.6 Hz, 2H), 5.55 (s, 1H), 6.10 (s, 1H), 6.47 (d, J=15.8 Hz, 1H), 6.96 (d, J=8.8 Hz, 2H), 7.16 (s+d+d, 3H), 7.70 (d, J=15.8 Hz, 1H), 8.14 (d, J=8.8 Hz, 2H)

EI-MS: 540[M$^+$]

In the same manner, the following compounds Cinn-2 to Cinn-12 were synthesized.

[Chem. 194]

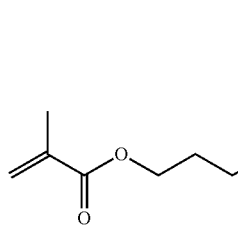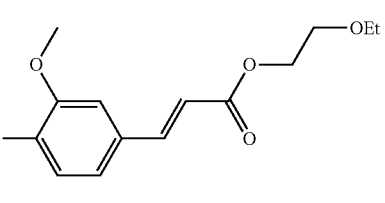

Cinn-2

(Example 289)

-continued
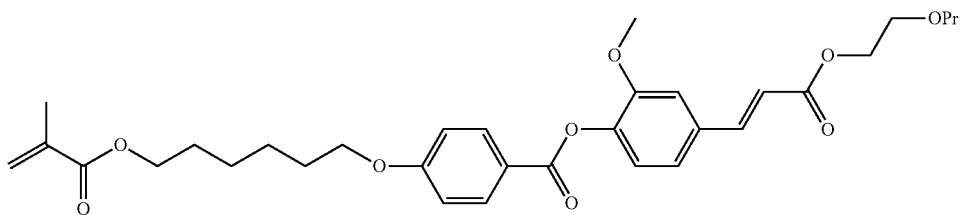
(Example 290) Cinn-3
[Chem. 195]
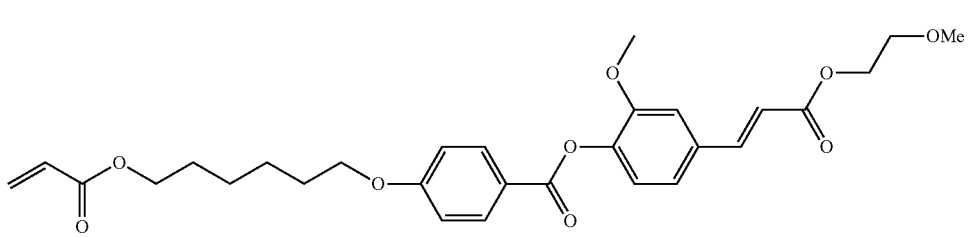
(Example 291) Cinn-4
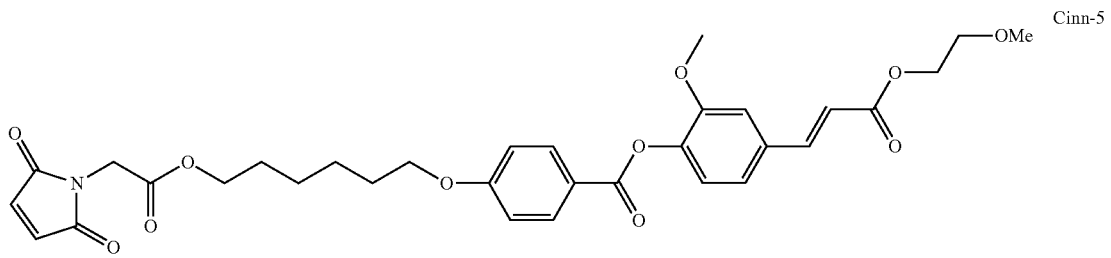
(Example 292) Cinn-5
[Chem. 196]
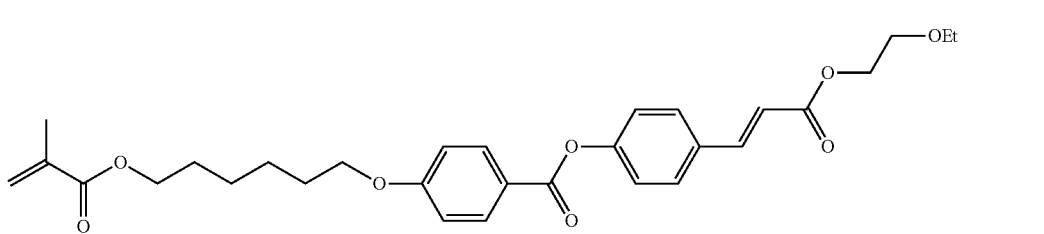
(Example 293) Cinn-6
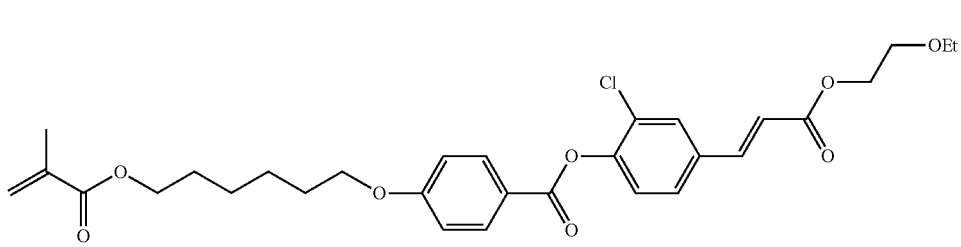
(Example 294) Cinn-7

-continued
[Chem. 197]
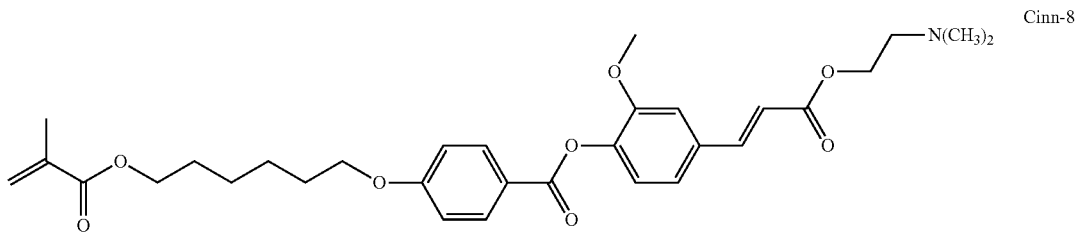
(Example 295) Cinn-8
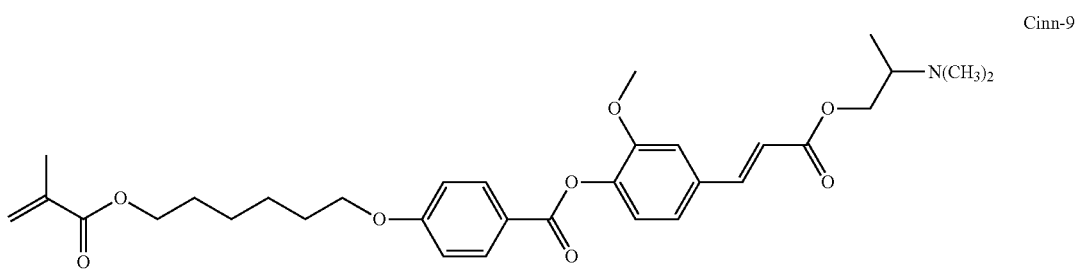
(Example 296) Cinn-9
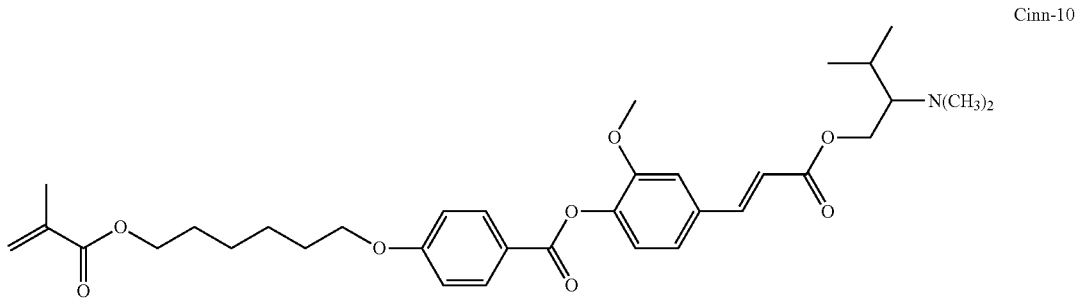
(Example 297) Cinn-10
[Chem. 198]
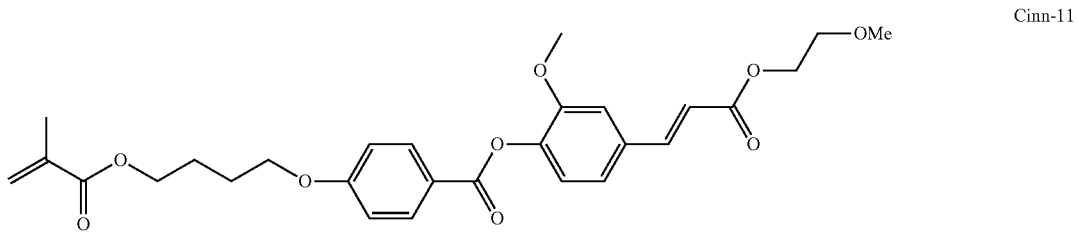
(Example 298) Cinn-11
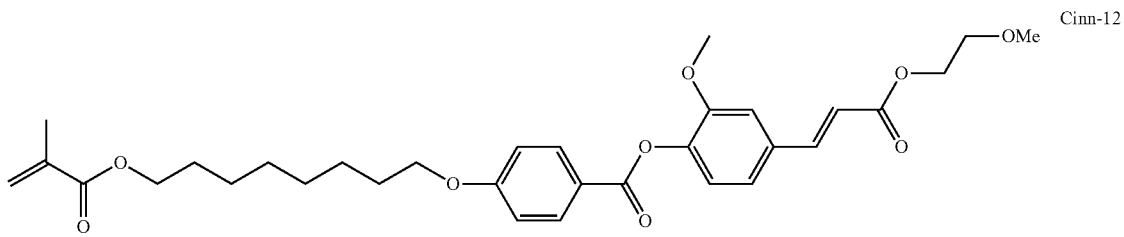
(Example 299) Cinn-12

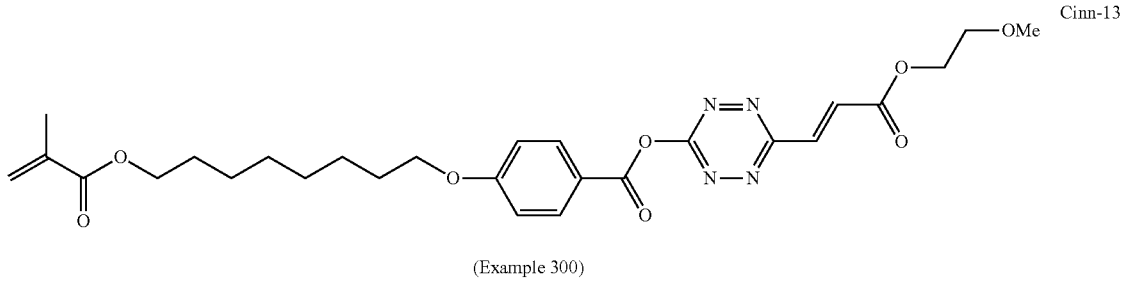

(Example 300)

Synthesis of Monomer for Copolymerization

[Chem. 199]

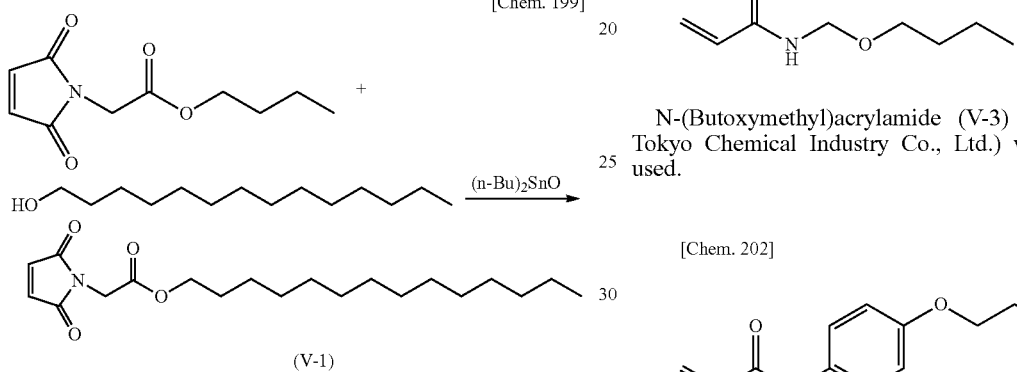

(V-1)

9.01 g of butyl maleimidoacetate, 0.33 g of dibutyltin (IV) oxide, and 9.14 g of tetradecanol were dissolved in 40 ml of toluene, followed by stirring for 15 hours while heating to reflux. The reaction solution was cooled to room temperature and 100 ml of toluene was added thereto. The mixture was subjected to liquid separation and washed with saturated sodium bicarbonate water and then with saturated saline. To this solution was added sodium sulfate, and the mixture was dried. Sodium sulfate was removed and the solvent was evaporated under reduced pressure to reduce the volume to about 50 ml, and 40 ml of hexane and 20 ml of dichloromethane were added thereto. The mixture was purified by column chromatography (alumina/silica gel, hexane/dichloromethane=2:1), the solvent was evaporated under reduced pressure, and the residue was reprecipitated with methanol to obtain (V-1) (7.95 g) as a white crystal.

$^1$H-NMR (400 MHz, CDCl$_3$) δ: 0.88 (t, J=6.8 Hz, 3H), 1.15-1.40 (m, 22H), 1.61-1.66 (tt, 2H), 4.14 (t, J=6.6 Hz, 2H), 4.15 (s, 2H), 6.79 (s, 2H)

EI-MS: 351[M$^+$]

[Chem. 200]

(V-2)

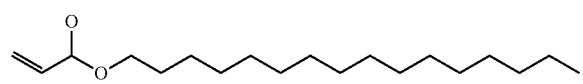

Stearyl acrylate (V-2) (manufactured by Tokyo Chemical Industry Co., Ltd.) was purchased and used.

[Chem. 201]

(V-3)

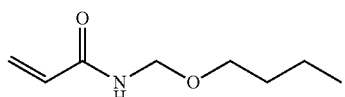

N-(Butoxymethyl)acrylamide (V-3) (manufactured by Tokyo Chemical Industry Co., Ltd.) was purchased and used.

[Chem. 202]

(V-4)

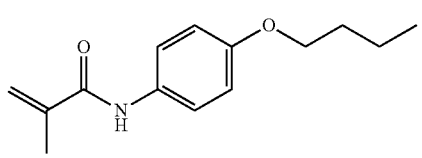

A compound (V-4) was synthesized according to the procedure described in a known document (Farmaco. Edizione Scientifica Vol. 22 (1967) 190, 590-598).

Preparation of Cinnamic Acid Polymer (CEE-1)

Example 301

1 part (10.0 mmol) of a compound represented by the formula (Cinn-1) was dissolved in 10 parts of ethyl methyl ketone to obtain a solution 1. To this solution 1 was added 0.01 parts of azobisisobutyronitrile (AIBN). The mixture was heated to reflux for 2 days under a nitrogen atmosphere to obtain a solution 2. Then, the solution 2 was added dropwise to 60 parts of methanol under stirring, and the precipitated solid was filtered. The obtained solid was dissolved in 5 parts of tetrahydrofuran (THF), the solution was added dropwise to 120 parts of ice-cooled hexane under stirring, and the precipitated solid was filtered. The obtained solid was dissolved in 5 parts of THF, the solution was added dropwise to 120 parts of ice-cooled methanol under stirring, and the precipitated solid was filtered. The obtained solid was dissolved in THF and then vacuum-dried to obtain a polymer (CEE-1).

Preparation of Cinnamic Acid Polymers (CEE-2) to (CEE-12)

In the same manner as for the cinnamic acid polymer (CEE-1), polymers (CEE-2) to (CEE-12) were obtained. The compositions of the respective polymers are as shown in Tables 1 and 2.

TABLE 19

| Sample name | Blending amount (% by mole) | | | | | |
|---|---|---|---|---|---|---|
| | Cinn-1 | Cinn-2 | Cinn-3 | Cinn-4 | Cinn-5 | Cinn-6 |
| Example 301 | CEE-1 | 100 | | | | | |
| Example 302 | CEE-2 | | 100 | | | | |
| Example 303 | CEE-3 | | | 100 | | | |
| Example 304 | CEE-4 | | | | 100 | | |
| Example 305 | CEE-5 | | | | | 100 | |
| Example 306 | CEE-6 | | | | | | 100 |

TABLE 20

| Sample name | Blending amount (% by mole) | | | | | | |
|---|---|---|---|---|---|---|---|
| | Cinn-7 | Cinn-8 | Cinn-9 | Cinn-10 | Cinn-11 | Cinn-12 | Cinn-13 |
| Example 307 | CEE-7 | 100 | | | | | | |
| Example 308 | CEE-8 | | 100 | | | | | |
| Example 309 | CEE-9 | | | 100 | | | | |
| Example 310 | CEE-10 | | | | 100 | | | |
| Example 311 | CEE-11 | | | | | 100 | | |
| Example 312 | CEE-12 | | | | | | 100 | |
| Example 313 | CEE-13 | | | | | | | 100 |

Preparation of Cinnamic Acid Polymer (CEEV-1)

Example 314

0.9 parts (9.0 mmol) of the compound represented by the formula (Cinn-1) and 0.1 parts (1.0 mmol) of a compound represented by the formula (V-1) were dissolved in 10 parts of ethyl methyl ketone to obtain a solution 3. To this solution 3 was added 0.01 parts of azobisisobutyronitrile (AIBN). The mixture was heated to reflux for 2 days under a nitrogen atmosphere to obtain a solution 4. Then, the solution 4 was added dropwise to 60 parts of methanol under stirring, and the precipitated solid was filtered. The obtained solid was dissolved in 5 parts of tetrahydrofuran (THF), the solution was added dropwise to 120 parts of ice-cooled hexane under stirring, and the precipitated solid was filtered. The obtained solid was dissolved in 5 parts of THF, the solution was added dropwise to 120 parts of ice-cooled methanol under stirring, and the precipitated solid was filtered. The obtained solid was dissolved in THF and then vacuum-dried to obtain a polymer (CEEV-1).

Preparation of Cinnamic Acid Polymers (CEEV-2) to (CEEV-50)

In the same manner as for the cinnamic acid polymer (CEEV-1), polymers (CEEV-2) to (CEEV-50) were obtained. The compositions of the respective polymers are as shown in Tables 3 and 4.

TABLE 21

| Example | Sample name | Blending amount (% by mole) | | | | | | | | | |
|---|---|---|---|---|---|---|---|---|---|---|---|
| | | Cinn-1 | Cinn-2 | Cinn-3 | Cinn-4 | Cinn-5 | Cinn-6 | V-1 | V-2 | V-3 | V-4 |
| 314 | CEEV-1 | 90 | | | | | | 10 | | | |
| 315 | CEEV-2 | 80 | | | | | | 20 | | | |
| 316 | CEEV-3 | 70 | | | | | | 30 | | | |
| 317 | CEEV-4 | 70 | | | | | | | 30 | | |
| 318 | CEEV-5 | 70 | | | | | | | | 30 | |
| 319 | CEEV-6 | 70 | | | | | | | | | 30 |
| 320 | CEEV-7 | | 70 | | | | | 30 | | | |
| 321 | CEEV-8 | | 70 | | | | | | 30 | | |
| 322 | CEEV-9 | | 70 | | | | | | | 30 | |
| 323 | CEEV-10 | | 70 | | | | | | | | 30 |
| 324 | CEEV-11 | | | 70 | | | | 30 | | | |
| 325 | CEEV-12 | | | 70 | | | | | 30 | | |
| 326 | CEEV-13 | | | 70 | | | | | | 30 | |
| 327 | CEEV-14 | | | 70 | | | | | | | 30 |
| 328 | CEEV-15 | | | | 70 | | | 30 | | | |
| 329 | CEEV-16 | | | | 70 | | | | 30 | | |
| 330 | CEEV-17 | | | | 70 | | | | | 30 | |
| 331 | CEEV-18 | | | | 70 | | | | | | 30 |
| 332 | CEEV-19 | | | | | 70 | | 30 | | | |
| 333 | CEEV-20 | | | | | 70 | | | 30 | | |
| 334 | CEEV-21 | | | | | 70 | | | | 30 | |
| 335 | CEEV-22 | | | | | 70 | | | | | 30 |
| 336 | CEEV-23 | | | | | | 70 | 30 | | | |
| 337 | CEEV-24 | | | | | | 70 | | 30 | | |
| 338 | CEEV-25 | | | | | | 70 | | | 30 | |
| 339 | CEEV-26 | | | | | | 70 | | | | 30 |

TABLE 22

| Example | Sample name | Blending amount (% by mole) | | | | | | | | | |
|---|---|---|---|---|---|---|---|---|---|---|---|
| | | Cinn-7 | Cinn-8 | Cinn-9 | Cinn-10 | Cinn-11 | Cinn-12 | Cinn-13 | V-1 | V-2 | V-3 | V-4 |
| 340 | CEEV-27 | 70 | | | | | | | 30 | | | |
| 341 | CEEV-28 | 70 | | | | | | | | 30 | | |
| 342 | CEEV-29 | 70 | | | | | | | | | 30 | |

TABLE 22-continued

| Example | Sample name | Blending amount (% by mole) | | | | | | | | | | |
|---|---|---|---|---|---|---|---|---|---|---|---|---|
| | | Cinn-7 | Cinn-8 | Cinn-9 | Cinn-10 | Cinn-11 | Cinn-12 | Cinn-13 | V-1 | V-2 | V-3 | V-4 |
| 343 | CEEV-30 | 70 | | | | | | | | | | 30 |
| 344 | CEEV-31 | | 70 | | | | | | 30 | | | |
| 345 | CEEV-32 | | 70 | | | | | | | 30 | | |
| 346 | CEEV-33 | | 70 | | | | | | | | 30 | |
| 347 | CEEV-34 | | 70 | | | | | | | | | 30 |
| 348 | CEEV-35 | | | 70 | | | | | 30 | | | |
| 349 | CEEV-36 | | | 70 | | | | | | 30 | | |
| 350 | CEEV-37 | | | 70 | | | | | | | 30 | |
| 351 | CEEV-38 | | | 70 | | | | | | | | 30 |
| 352 | CEEV-39 | | | | 70 | | | | 30 | | | |
| 353 | CEEV-40 | | | | 70 | | | | | 30 | | |
| 354 | CEEV-41 | | | | 70 | | | | | | 30 | |
| 355 | CEEV-42 | | | | 70 | | | | | | | 30 |
| 356 | CEEV-43 | | | | | 70 | | | 30 | | | |
| 358 | CEEV-44 | | | | | 70 | | | | 30 | | |
| 358 | CEEV-45 | | | | | 70 | | | | | 30 | |
| 359 | CEEV-46 | | | | | 70 | | | | | | 30 |
| 360 | CEEV-47 | | | | | | 70 | | 30 | | | |
| 361 | CEEV-48 | | | | | | 70 | | | 30 | | |
| 362 | CEEV-49 | | | | | | 70 | | | | 30 | |
| 363 | CEEV-50 | | | | | | 70 | | | | | 30 |
| 364 | CEEV-51 | | | | | | | 70 | 30 | | | |
| 365 | CEEV-52 | | | | | | | 70 | | 30 | | |

Fabrication of Alignment Layer and Liquid Crystal Display Element

Example 366

The cinnamic acid polymer (CEE-1) was dissolved in cyclopentanone to 0.5% and the solution was stirred at room temperature for 10 minutes. Then, the solution was applied onto a glass plate as a base material, using a spin coater, and dried at 100° C. for 30 minutes.

Next, the coated glass plate as a base material was irradiated with linear polarized and parallel light of visible ultraviolet light (wavelength: 313 nm, irradiation intensity: 10 mW/cm$^2$) using an ultrahigh-pressure mercury lamp via a wavelength cut filter, a band-pass filter, and a polarizing filter in a direction of 45 degrees with respect to the substrate. The irradiation dose was 100 mJ/cm$^2$.

A liquid crystal cell was fabricated by using the coated glass plate prepared by the method above. The gap between the plates was set to 10 μm and the two glass plates were bonded in the anti-parallel direction. Next, a nematic liquid crystal mixture having a negative dielectric anisotropy with a composition described below was charged into the cell at a temperature just exceeding a transparent point (Tc=84.4° C.), and then cooled to room temperature. A polarizing plate was placed on the top and the bottom of the liquid crystal cell, and a back light was placed below. The light transmittance was changed by rotating the liquid crystal cell by 90 degrees and dark-light contrast was clearly observed and there was no abnormal domain and alignment unevenness, from which it was confirmed that the liquid crystals were normally aligned. The tilt angle of the liquid crystal in the cell was optically measured by a crystal rotation method, and the pretilt angle was found to be 1 degree. A voltage of 5 V was applied to this liquid crystal cell for an application time of 60 microseconds at a span of 167 milliseconds, and the voltage holding ratio after 167 milliseconds from the release of the voltage was measured by means of "VHR-AMP01" manufactured by TOYO Corporation at 23° C., and as a result, the voltage holding ratio (VHR) was found to be 99.3%. A square wave of 60 Hz/±10 V having a voltage of DC 10 V superimposed therewith was applied to this liquid crystal cell at 60° C. for 60 minutes, and short-circuited for 1 second, and 10 minutes later, the residual voltage (RDC) in the liquid crystal cell was measured, and as a result, it was found to be 43 mV.

[Chem. 203]

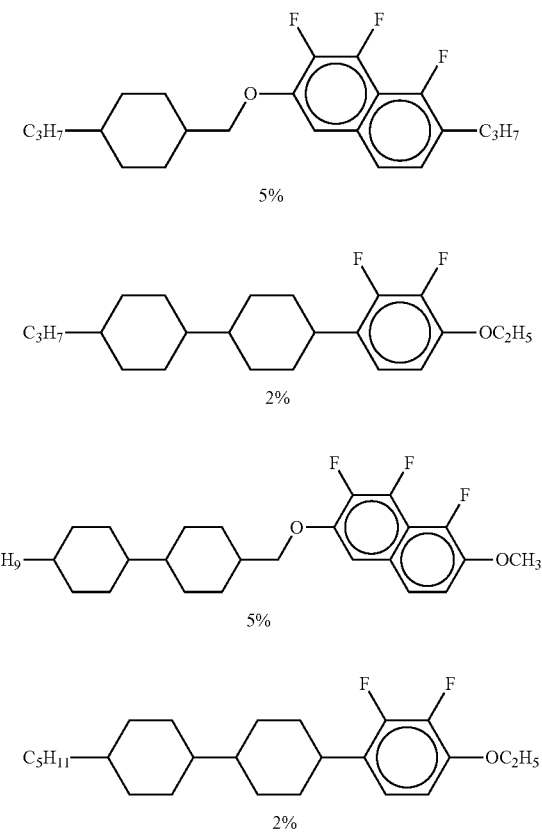

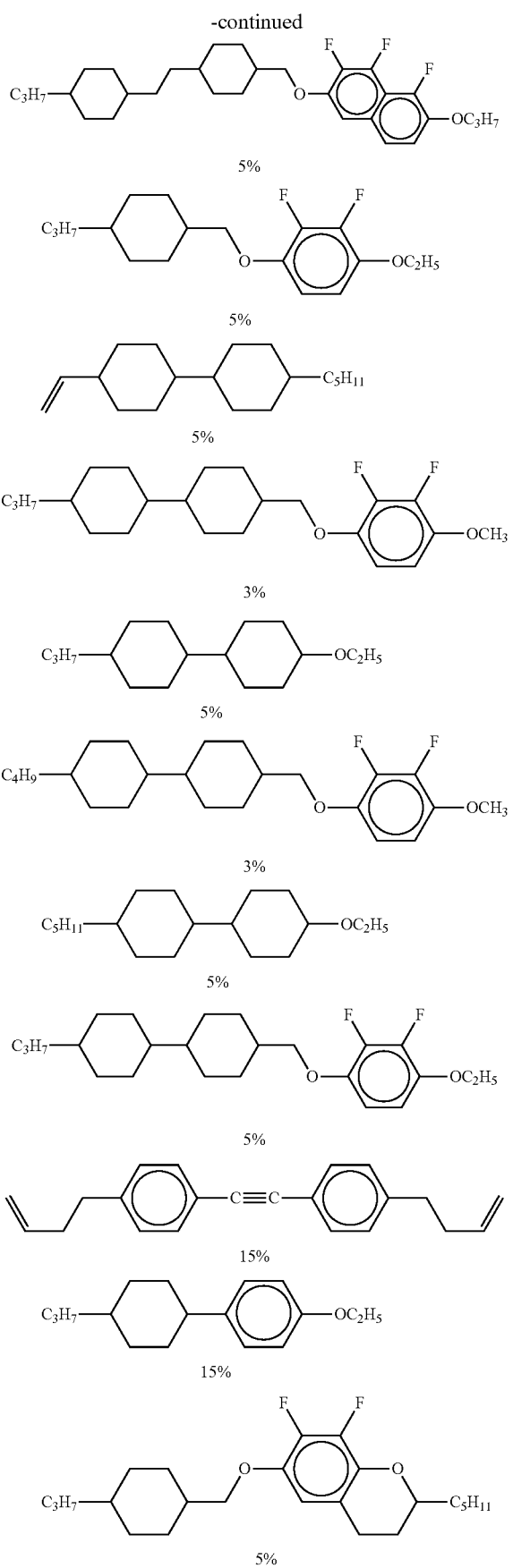
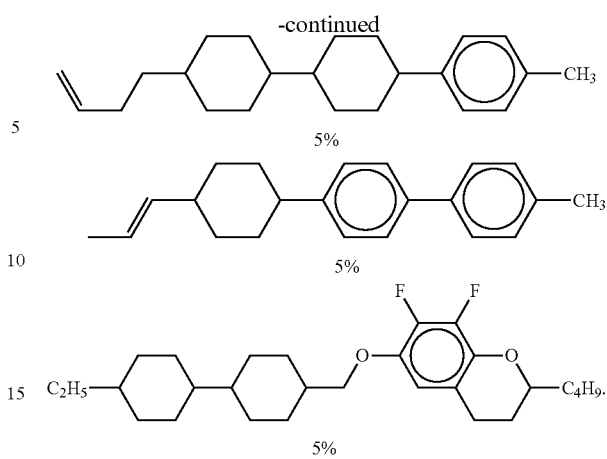

Hereinafter, in the same manner as the cinnamic acid polymer (CEE-1), for (CEE-2) to (CEE-12), and (CEEV-1) to (CEEV-50), alignment layers were fabricated and liquid crystal cells were fabricated. The measurement results of liquid crystal alignment property, pretilt angle, VHR, RDC are shown in conjunction in Table 5. For the liquid crystal alignment property, when the presence or absence of the abnormal domain and alignment unevenness of the liquid crystal cell was observed, a case where there was the abnormal domain and alignment unevenness at zero place was denoted as O, a case where there was the abnormal domain and alignment unevenness in two or less places was denoted as Δ, and a case where there was the abnormal domain and alignment unevenness in three or more places was denoted as X. For the pretilt angles, the pretilt angles were optically measured by a crystal rotation method, and a case where the pretilt angle was 80 degrees or more and less than 90 degrees was denoted as V, and a case where the pretilt angle was 0 degrees or more and less than 15 degrees was denoted as P. For VHR, a case where the VHR was 98% or more was denoted as O, a case where the VHR was 95% or more and less than 98% was denoted as Δ, and a case where the VHR was 95% or less was denoted as X. For RDC, a case where the RDC was less than 50 mV was denoted as O, a case where the RDC was 50 mV or more and 150 mV or less was denoted as Δ, and a case where the RDC was 150 mV or more was denoted as X. The RDC is indicative of afterimage characteristics (seizure), and thus, it can be said that when the value is approximately 150 mV or less, the afterimage characteristics are good, whereas when the value is approximately 50 mV or less, the afterimage characteristics are particularly excellent.

TABLE 23

| | Sample name | Liquid crystal alignment property | Pretilt angle | VHR | RDC |
|---|---|---|---|---|---|
| Example 366 | CEE-1 | O | P | O | O |
| Example 367 | CEE-2 | O | P | O | O |
| Example 368 | CEE-3 | O | P | O | O |
| Example 369 | CEE-4 | O | P | O | O |
| Example 370 | CEE-5 | O | P | O | O |
| Example 371 | CEE-6 | O | P | O | O |
| Example 372 | CEE-7 | O | P | O | O |
| Example 373 | CEE-8 | O | P | O | O |
| Example 374 | CEE-9 | O | P | O | O |
| Example 375 | CEE-10 | O | P | O | O |
| Example 376 | CEE-11 | O | P | O | O |

TABLE 23-continued

| Sample name | Liquid crystal alignment property | Pretilt angle | VHR | RDC |
|---|---|---|---|---|
| Example 377 CEE-12 | ○ | P | ○ | ○ |
| Example 378 CEE-13 | ○ | P | ○ | ○ |

TABLE 24

| Sample name | Liquid crystal alignment property | Pretilt angle | VHR | RDC |
|---|---|---|---|---|
| Example 379 CEEV-1 | ○ | V | ○ | ○ |
| Example 380 CEEV-2 | ○ | V | ○ | ○ |
| Example 381 CEEV-3 | ○ | V | ○ | ○ |
| Example 382 CEEV-4 | ○ | V | ○ | ○ |
| Example 383 CEEV-5 | ○ | P | ○ | ○ |
| Example 384 CEEV-6 | ○ | P | ○ | ○ |
| Example 385 CEEV-7 | ○ | V | ○ | ○ |
| Example 386 CEEV-8 | ○ | V | ○ | ○ |
| Example 387 CEEV-9 | ○ | P | ○ | ○ |
| Example 388 CEEV-10 | ○ | P | ○ | ○ |
| Example 389 CEEV-11 | ○ | V | ○ | ○ |
| Example 390 CEEV-12 | ○ | V | ○ | ○ |
| Example 391 CEEV-13 | ○ | P | ○ | ○ |
| Example 392 CEEV-14 | ○ | P | ○ | ○ |
| Example 393 CEEV-15 | ○ | V | ○ | ○ |
| Example 394 CEEV-16 | ○ | V | ○ | ○ |
| Example 395 CEEV-17 | ○ | P | ○ | ○ |
| Example 396 CEEV-18 | ○ | P | ○ | ○ |
| Example 397 CEEV-19 | ○ | V | ○ | ○ |
| Example 398 CEEV-20 | ○ | V | ○ | ○ |
| Example 399 CEEV-21 | ○ | P | ○ | ○ |
| Example 400 CEEV-22 | ○ | P | ○ | ○ |
| Example 401 CEEV-23 | ○ | V | ○ | ○ |
| Example 402 CEEV-24 | ○ | V | ○ | ○ |
| Example 403 CEEV-25 | ○ | P | ○ | ○ |
| Example 404 CEEV-26 | ○ | P | ○ | ○ |

TABLE 25

| Sample name | Liquid crystal alignment property | Pretilt angle | VHR | RDC |
|---|---|---|---|---|
| Example 405 CEEV-27 | ○ | V | ○ | ○ |
| Example 406 CEEV-28 | ○ | V | ○ | ○ |
| Example 407 CEEV-29 | ○ | P | ○ | ○ |
| Example 408 CEEV-30 | ○ | P | ○ | ○ |
| Example 409 CEEV-31 | ○ | V | ○ | ○ |
| Example 410 CEEV-32 | ○ | V | ○ | ○ |
| Example 411 CEEV-33 | ○ | P | ○ | ○ |
| Example 412 CEEV-34 | ○ | P | ○ | ○ |
| Example 413 CEEV-35 | ○ | V | ○ | ○ |
| Example 414 CEEV-36 | ○ | V | ○ | ○ |
| Example 415 CEEV-37 | ○ | P | ○ | ○ |
| Example 416 CEEV-38 | ○ | P | ○ | ○ |
| Example 417 CEEV-39 | ○ | V | ○ | ○ |
| Example 418 CEEV-40 | ○ | V | ○ | ○ |
| Example 419 CEEV-41 | ○ | P | ○ | ○ |
| Example 420 CEEV-42 | ○ | P | ○ | ○ |
| Example 421 CEEV-43 | ○ | V | ○ | ○ |
| Example 422 CEEV-44 | ○ | V | ○ | ○ |
| Example 423 CEEV-45 | ○ | P | ○ | ○ |
| Example 424 CEEV-46 | ○ | P | ○ | ○ |
| Example 425 CEEV-47 | ○ | V | ○ | ○ |
| Example 426 CEEV-48 | ○ | V | ○ | ○ |
| Example 427 CEEV-49 | ○ | P | ○ | ○ |
| Example 428 CEEV-50 | ○ | P | ○ | ○ |
| Example 429 CEEV-51 | ○ | V | ○ | ○ |
| Example 430 CEEV-52 | ○ | P | ○ | ○ |

From the above results, it can be seen that an alignment layer, which has a superior liquid crystal alignment property, and a superior ability to control the pretilt, and exhibits a high voltage holding ratio and a low residual voltage, can be obtained, by the cinnamic acid polymerized product obtained by polymerizing the cinnamic acid derivatives of the present invention.

Comparative Example 41

For comparison, cinnamic acid derivatives (D-1) and (D-3) were synthesized, and thus, by the same method as in Example 301, cinnamic acid polymers (CE-1) to (CE-2) and (CEV-1) to (CEV-8) were prepared.

[Chem. 204]

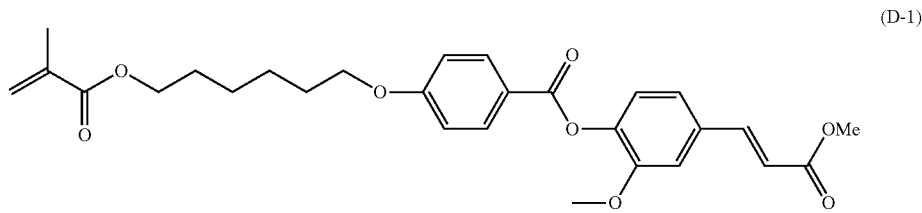

(D-1)

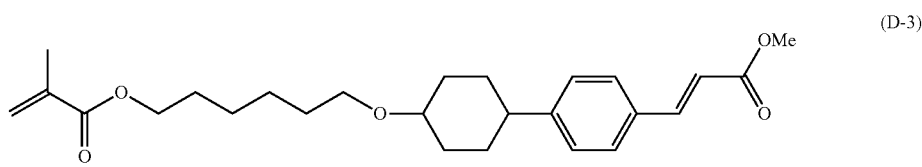

(D-3)

TABLE 26

| Sample name | \multicolumn{6}{c}{Blending amount (% by mole)} | | | | | |
|---|---|---|---|---|---|---|
| | D-1 | D-3 | V-1 | V-2 | V-3 | V-4 |
| Comparative Example 41 | CE-1 100 | | | | | |
| Comparative Example 42 | CE-2 | 100 | | | | |
| Comparative Example 43 | CEV-1 70 | | 30 | | | |
| Comparative Example 44 | CEV-2 70 | | | 30 | | |
| Comparative Example 45 | CEV-3 70 | | | | 30 | |
| Comparative Example 46 | CEV-4 70 | | | | | 30 |
| Comparative Example 47 | CEV-5 | 70 | 30 | | | |
| Comparative Example 48 | CEV-6 | 70 | | 30 | | |
| Comparative Example 49 | CEV-7 | 70 | | | 30 | |
| Comparative Example 50 | CEV-8 | 70 | | | | 30 |

Furthermore, by the same method as in Example 366, an alignment layer was fabricated, and thus, various measurements were conducted and the results therefrom are shown in Table 9.

TABLE 27

| | Sample name | Liquid crystal alignment property | Pretilt angle | VHR | RDC |
|---|---|---|---|---|---|
| Comparative Example 51 | CE-1 | ○ | P | Δ | Δ |
| Comparative Example 52 | CE-2 | ○ | P | Δ | Δ |
| Comparative Example 53 | CEV-1 | ○ | V | ○ | Δ |
| Comparative Example 54 | CEV-2 | ○ | V | ○ | Δ |
| Comparative Example 55 | CEV-3 | ○ | P | Δ | Δ |
| Comparative Example 56 | CEV-4 | ○ | P | Δ | Δ |
| Comparative Example 57 | CEV-5 | ○ | V | ○ | Δ |
| Comparative Example 58 | CEV-6 | ○ | V | ○ | Δ |
| Comparative Example 59 | CEV-7 | ○ | P | Δ | Δ |
| Comparative Example 60 | CEV-8 | ○ | P | Δ | Δ |

Therefore, it can be seen that according to the present invention, a display element using a liquid crystal alignment layer which has effects such as a superior ability to control the alignment of the liquid crystals and the pretilt angles, a high voltage holding ratio (VHR), and a low residual voltage, and in which it is difficult for seizure to occur, and the composition is obtained.

In the same manner as in Example 288, the following compounds CinCy-1 to CinCy-4 were synthesized.

[Chem. 205]

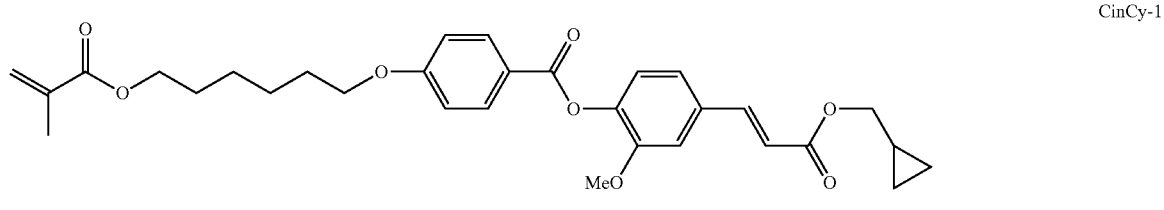

(Example 431) CinCy-1

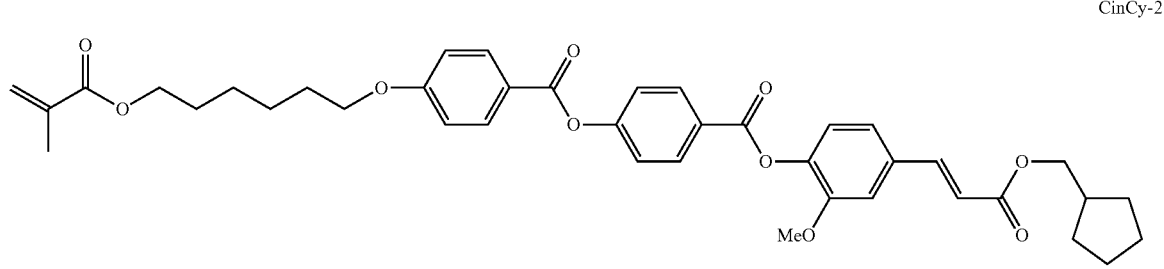

(Example 432) CinCy-2

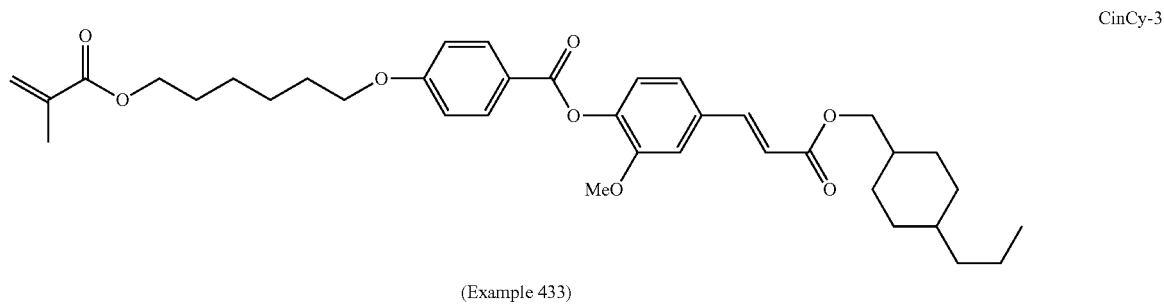

(Example 433) CinCy-3

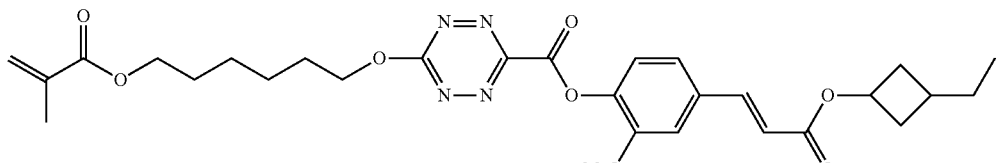

(Example 434)

Preparation of Cinnamic Acid Polymers (CEY-1) to (CEY-4)

In the same manner as for the cinnamic acid polymer (CEv-1), polymers (CEY-1) to (CEY-4) were obtained. The compositions of the respective polymers are as shown in Tables 28 and 29.

TABLE 28

| Sample | Blending amount (% by mole) | | | |
|---|---|---|---|---|
| name | CinCy-1 | CinCy-2 | CinCy-3 | CinCy-4 |
| Example 435 CEY-1 | 100 | | | |
| Example 436 CEY-2 | | 100 | | |
| Example 437 CEY-3 | | | 100 | |
| Example 438 CEY-4 | | | | 100 |

Preparation of Cinnamic Acid Polymers (CEYV-1) to (CEYV-18)

In the same manner as for the cinnamic acid polymer (CEvV-1), polymers (CEYV-1) to (CEYV-18) were obtained. The compositions of the respective polymers are as shown in Tables 30 and 31.

Hereinafter, in the same manner as the cinnamic acid polymer (CEv-1), for (CEY-1) to (CEY-4), and (CEYV-1) to (CEYV-18), alignment layers were fabricated and liquid crystal cells were fabricated. The measurement results of coatability, liquid crystal alignment property, pretilt angle, VHR are shown in conjunction in Tables 32 and 33. For the coatability, when a film was formed by applying a polymer onto a glass plate and observed, a case where the polymer was uniformly applied to form a smooth film was denoted as O, a case where there was chipping and/or unevenness on the coated surface at one place was denoted as Δ, and a case where there was chipping and/or unevenness on the coated surface in two or more places was denoted as X. For the liquid crystal alignment property, when the presence or absence of the abnormal domain and alignment unevenness of the liquid crystal cell was observed, a case where there was the abnormal domain and alignment unevenness at zero place was denoted as O, a case where there was the abnormal domain and alignment unevenness in two or less places was denoted as Δ, and a case where there was the abnormal domain and alignment unevenness in three or more places was denoted as X. For the pretilt angles, the pretilt angles were optically measured by a crystal rotation method, and a case where the pretilt angle was 80 degrees or more and less than 90 degrees was denoted as V, and a case where the

TABLE 29

| Example | Sample name | Blending amount (% by mole) | | | | | | | |
|---|---|---|---|---|---|---|---|---|---|
| | | CinCy-1 | CinCy-2 | CinCy-3 | CinCy-4 | V-1 | V-2 | V-3 | V-4 |
| 439 | CEYV-1 | 90 | | | | 10 | | | |
| 440 | CEYV-2 | 85 | | | | 15 | | | |
| 441 | CEYV-3 | 80 | | | | 20 | | | |
| 442 | CEYV-4 | 80 | | | | | 20 | | |
| 443 | CEYV-5 | 80 | | | | | | 20 | |
| 444 | CEYV-6 | 80 | | | | | | | 20 |
| 445 | CEYV-7 | | 80 | | | 20 | | | |
| 446 | CEYV-8 | | 80 | | | | 20 | | |
| 447 | CEYV-9 | | 80 | | | | | 20 | |
| 448 | CEYV-10 | | 80 | | | | | | 20 |
| 449 | CEYV-11 | | | 80 | | 20 | | | |
| 450 | CEYV-12 | | | 80 | | | 20 | | |
| 451 | CEYV-13 | | | 80 | | | | 20 | |
| 452 | CEYV-14 | | | 80 | | | | | 20 |
| 453 | CEYV-15 | | | | 80 | 20 | | | |
| 454 | CEYV-16 | | | | 80 | | 20 | | |
| 455 | CEYV-17 | | | | 80 | | | 20 | |
| 456 | CEYV-18 | | | | 80 | | | | 20 | pretilt angle was 0 degrees or more and less than 15 degrees was denoted as P. For VHR, a case where the VHR was 98% or more was denoted as O, a case where the VHR was 95% or more and less than 98% was denoted as Δ, and a case where the VHR was 95% or less was denoted as X.

TABLE 30

| Sample name | Coatability | Liquid crystal alignment property | Pretilt angle | VHR |
|---|---|---|---|---|
| Example 457 CEY-1 | ○ | ○ | P | ○ |
| Example 458 CEY-2 | ○ | ○ | P | ○ |
| Example 459 CEY-3 | ○ | ○ | P | ○ |
| Example 460 CEY-4 | ○ | ○ | P | ○ |

From the above results, it can be seen that an alignment layer, which has a superior liquid crystal alignment property and a superior ability to control the pretilt, and exhibits a high voltage holding ratio, is obtained, by the cinnamic acid polymerized product obtained by polymerizing the cinnamic acid derivatives of the present invention.

Comparative Example 61

For comparison, cinnamic acid derivatives (D-1) and (D-3) were synthesized, and thus, by the same method as in Example 301, cinnamic acid polymers (CE-1) to (CE-2) and (CEV-1) to (CEV-8) were prepared.

[Chem. 206]

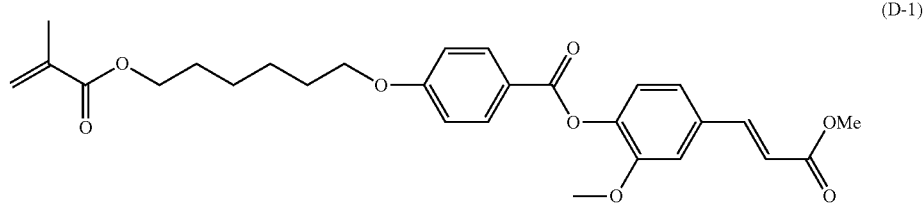

(D-1)

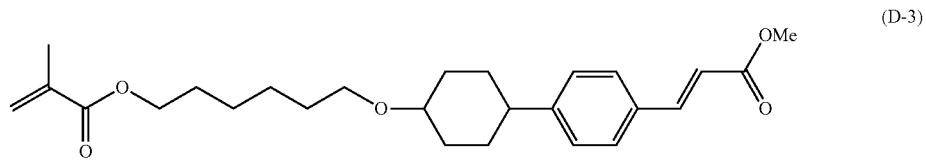

(D-3)

TABLE 31

| Sample name | Coatability | Liquid crystal alignment property | Pretilt angle | VHR |
|---|---|---|---|---|
| Example 461 CEYV-1 | ○ | ○ | V | ○ |
| Example 462 CEYV-2 | ○ | ○ | V | ○ |
| Example 463 CEYV-3 | ○ | ○ | V | ○ |
| Example 464 CEYV-4 | ○ | ○ | V | ○ |
| Example 465 CEYV-5 | ○ | ○ | P | ○ |
| Example 466 CEYV-6 | ○ | ○ | P | ○ |
| Example 467 CEYV-7 | ○ | ○ | V | ○ |
| Example 468 CEYV-8 | ○ | ○ | V | ○ |
| Example 469 CEYV-9 | ○ | ○ | P | ○ |
| Example 470 CEYV-10 | ○ | ○ | P | ○ |
| Example 471 CEYV-11 | ○ | ○ | V | ○ |
| Example 472 CEYV-12 | ○ | ○ | V | ○ |
| Example 473 CEYV-13 | ○ | ○ | P | ○ |
| Example 474 CEYV-14 | ○ | ○ | P | ○ |
| Example 475 CEYV-15 | ○ | ○ | V | ○ |
| Example 476 CEYV-16 | ○ | ○ | V | ○ |
| Example 477 CEYV-17 | ○ | ○ | P | ○ |
| Example 478 CEYV-18 | ○ | ○ | P | ○ |

TABLE 32

| Sample name | Blending amount (% by mole) | | | | | |
|---|---|---|---|---|---|---|
| | D-1 | D-3 | V-1 | V-2 | V-3 | V-4 |
| Comparative Example 61 CE-1 | 100 | | | | | |
| Comparative Example 62 CE-2 | | 100 | | | | |
| Comparative Example 63 CEV-1 | 80 | | 20 | | | |
| Comparative Example 64 CEV-2 | 80 | | | 20 | | |
| Comparative Example 65 CEV-3 | 80 | | | | 20 | |
| Comparative Example 66 CEV-4 | 80 | | | | | 20 |
| Comparative Example 67 CEV-5 | | 80 | 20 | | | |
| Comparative Example 68 CEV-6 | | 80 | | 20 | | |
| Comparative Example 69 CEV-7 | | 80 | | | 20 | |
| Comparative Example 70 CEV-8 | | 80 | | | | 20 |

Furthermore, by the same method as in Example 366, an alignment layer was fabricated, and thus, various measurements were conducted and the results therefrom are shown in Table 9.

TABLE 33

| Sample name | Coatability | Liquid crystal alignment property | Pretilt angle | VHR |
|---|---|---|---|---|
| Comparative Example 71 CE-1 | Δ | ○ | P | Δ |
| Comparative Example 72 CE-2 | Δ | ○ | P | Δ |
| Comparative Example 73 CEV-1 | ○ | Δ | V | ○ |
| Comparative Example 74 CEV-2 | ○ | Δ | V | ○ |
| Comparative Example 75 CEV-3 | Δ | ○ | P | Δ |
| Comparative Example 76 CEV-4 | Δ | ○ | P | Δ |
| Comparative Example 77 CEV-5 | ○ | Δ | V | ○ |
| Comparative Example 78 CEV-6 | ○ | Δ | V | ○ |
| Comparative Example 79 CEV-7 | Δ | ○ | P | Δ |
| Comparative Example 80 CEV-8 | Δ | ○ | P | Δ |

Therefore, it can be seen that according to the present invention, a display element using a liquid crystal alignment layer which has the effects such as having a superior ability to control the alignment of the liquid crystals and the pretilt angles, and exhibiting a high voltage holding ratio (VHR), and the composition is obtained.

INDUSTRIAL APPLICABILITY

A liquid crystal alignment layer which is efficiently provided with an alignment property at a low dose of irradiation of polarized light during the production, and has a superior ability to control the alignment of the liquid crystals and the pretilt angles, and a high voltage holding ratio (VHR); a polymer used for the liquid crystal alignment layer; a compound constituting the polymer; a liquid crystal display element using the liquid crystal alignment layer; and an optical anisotropic body using the polymer can be provided.

The invention claimed is:
1. A compound represented by the general formula (I):

[Chem. 1]

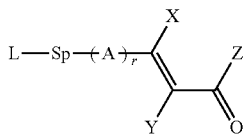

(wherein L represents a polymerizable group and Sp represents a spacer unit,
A represents a group selected from the group consisting of:
(a) a trans-1,4-cyclohexylene group (one methylene group or two or more non-adjacent methylene groups present in this group may be substituted with —O—, —NH—, or —S—),
(b) a 1,4-phenylene group (one or two or more —CH=’s present in this group may be substituted with —N=), and
(c) a 1,4-cyclohexenylene group, a 2,5-thiophenylene group, a 2,5-furanylene group, a 1,4-bicyclo(2.2.2) octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the groups (a), (b), and (c) have one or more hydrogen atoms substituted with a fluorine atom, a chlorine atom, a cyano group, a methyl group, or a methoxy group,
r represents 1 or 2, but in the case where r represents 2, a plurality of A's, may be the same as or different from each other,
X and Y each independently represent a hydrogen atom, a fluorine atom, a chlorine atom, a cyano group, or an alkyl group having 1 to 20 carbon atoms, but a hydrogen atom in the alkyl group may be substituted with a fluorine atom, and one $CH_2$ group or two or more non-adjacent $CH_2$ groups may be substituted with —O—, —CO—O—, —O—CO— and/or —CH=CH—, and
Z is represented by the general formula (IIa) or (IIb):

[Chem. 2]

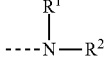

(wherein the broken line represents a bond to a carbon atom, to which Z is bonded,
$R^9$ represents a linear or branched alkyl group having 2 to 30 carbon atoms, in which one —$CH_2$— group or two or more non-adjacent —$CH_2$— groups in $R^9$ are substituted with —O—, —CO—, —CO—O—, —O—CO—, —CO—NH—, —NH—CO—, —$NCH_3$—, —CH=CH—, —CF=CF—, and/or —C≡C—, one or two or more —$CH_2$— groups in $R^9$ are independently substituted with a cycloalkyl group having a ring member number of 3 to 8, and/or a hydrogen atom in $R^9$ is substituted with a cyano group, or a halogen atom, and
$R^1$ and $R^2$ each independently represent a hydrogen atom or a linear or branched alkyl group having 1 to 30 carbon atoms in which one —$CH_2$— group or two or more non-adjacent —$CH_2$— groups in $R^1$ and $R^2$ may be substituted with —O—, —CO—, —CO—O—, —O—CO—, —CO—NH—, —NH—CO—, —$NCH_3$—, —CH=CH—, —CF=CF—, and/or —C≡C—, one or two or more —$CH_2$— groups in $R^1$ and $R^2$ may be each independently substituted with a cycloalkyl group having a ring member number of 3 to 8, and a hydrogen atom in $R^1$ and $R^2$ may be substituted with an alkyl group having 1 to 20 carbon atoms, a cyano group, or a halogen atom).

2. The compound according to claim 1, wherein in the general formula (IIa) or (IIb),
$R^1$ represents a linear or branched alkyl group having 1 to 30 carbon atoms (one —$CH_2$— group or two or more non-adjacent —$CH_2$— groups in the alkyl group are substituted with —O—, —CO—, —CO—O—, —O—CO—, —CO—NH—, —NH—CO—, or —$NCH_3$—, one or two or more —CH$_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), R$^9$ represents a linear or branched alkyl group having 2 to 30 carbon atoms (one —CH$_2$— group or two or more non-adjacent —CH$_2$— groups in the alkyl group are substituted with —O—, —CO—, —CO—O—, —O—CO—, —CO—NH—, —NH—CO—, or —NCH$_3$—, one or two or more —CH$_2$— groups in the alkyl group may be each independently substituted with a cycloalkyl group having a ring member number of 3 to 8, and a hydrogen atom in the alkyl group may be substituted with a cyano group, or a halogen atom), and R$^2$ represents a linear or branched alkyl group having 1 to 30 carbon atoms (one or two or more —CH$_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom).

3. The compound according to claim 1, wherein in the general formula (IIa) or (IIb), each of R$^1$ and R$^9$ is represented by the general formula (IIc):

[Chem. 3]

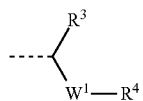

(IIc)

(wherein the broken line represents a bond to an oxygen atom or a nitrogen atom, W$^1$ represents a methylene group (a hydrogen atom in the methylene group may be unsubstituted or substituted with an alkyl group having 1 to 5 carbon atoms), —CO—O—, or —CO—NH—, R$^3$ represents a hydrogen atom or an alkyl group having 1 to 5 carbon atoms, and R$^4$ represents a linear or branched alkyl group having 1 to 20 carbon atoms (one —CH$_2$— group or two or more non-adjacent —CH$_2$— groups in the alkyl group are substituted with —O—, —CO—, —CO—O—, —O—CO—, —CO—NH—, —NH—CO—, or —NCH$_3$—, one or two or more —CH$_2$— groups in the alkyl group may be each independently substituted with a cycloalkyl group having a ring member number of 3 to 8, and a hydrogen atom in the alkyl group may be unsubstituted or substituted with a fluorine atom or a chlorine atom).

4. The compound according to claim 1, wherein in the general formula (IIa) or (IIb), R$^1$ represents a linear or branched alkyl group having 1 to 30 carbon atoms (one —CH$_2$— group or two or more non-adjacent —CH$_2$— groups in the alkyl group are substituted with —CH=CH—, —CF=CF—, and/or —C≡C—, and one or two or more —CH$_2$— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom), R$^9$ represents a linear or branched alkyl group having 2 to 30 carbon atoms (one —CH$_2$— group or two or more non-adjacent —CH$_2$— groups in the alkyl group are substituted with —CH=CH—, —CF=CF—, and/or —C≡C—, and one or two or more —CH$_2$— groups in the alkyl group may be each independently substituted with a cycloalkyl group having a ring member number of 3 to 8, and a hydrogen atom in the alkyl group may be substituted with a cyano group, or a halogen atom), and R$^2$ represents a linear or branched alkyl group having 1 to 30 carbon atoms (one or two or more —CH$_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom).

5. The compound according to claim 1, wherein in the general formula (IIa) or (IIb), each of R$^1$ and R$^9$ is represented by the general formulae (IId) or (IIf):

[Chem. 4]

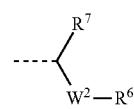

(IId)

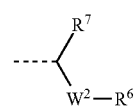

(IIe)

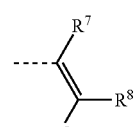

(IIf)

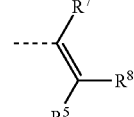

(IIg)

(wherein the broken line represents a bond to an oxygen atom or a nitrogen atom, W$^2$ represents a single bond, —CH$_2$—, —CO—O—, or —CO—NH—, R$^7$ represents a hydrogen atom or an alkyl group having 1 to 5 carbon atoms, R$^8$ represents a hydrogen atom, or a linear or branched alkyl group having 1 to 20 carbon atoms (one or two or more —CH$_2$— groups in the alkyl group may be each independently substituted with a cycloalkyl group having a ring member number of 3 to 8, and a hydrogen atom in the alkyl group may be unsubstituted or substituted with a fluorine atom or a chlorine atom), R$^5$ represents an alkyl group having 1 to 20 carbon atoms, in which a hydrogen atom in the alkyl group may be substituted with a fluorine atom, and R$^6$ represents an alkyl group having 1 to 20 carbon atoms (one —CH$_2$— group or two or more non-adjacent —CH₂— groups in the alkyl group are substituted with —CH═CH—, —CF═CF—, and/or —C≡C—, and one or two or more —CH₂— groups in the alkyl group may be each independently substituted with a cycloalkyl group having a ring member number of 3 to 8, and a hydrogen atom in the alkyl group may be substituted with a fluorine atom or a chlorine atom)).

6. The compound according to claim 1, wherein in the general formula (I), Sp is represented by the following general formula (IVa):

[Chem. 5]

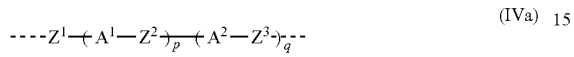
(IVa)

(wherein the left broken line represents a bond to L, and the right broken line represents a bond to A or a bond to a carbon atom, to which X is bonded, $Z^1$, $Z^2$ and $Z^3$ each independently represent a single bond, —(CH₂)$_u$— (wherein u represents 1 to 20), —OCH₂—, —CH₂O—, —COO—, —OCO—, —CH═CH—, —CF═CF—, —CF₂O—, —OCF₂—, —CF₂CF₂—, or —C≡C—, but one or more of the non-adjacent CH₂ groups in these substituents may be independently substituted with —O—, —CO—, —CO—O—, —O—CO—, —Si(CH₃)₂—O—Si(CH₃)₂—, —NR—, —NR—CO—, —CO—NR—, —NR—CO—O—, —O—CO—NR—, —NR—CO—NR—, —CH═CH—, —C≡C—, or —O—CO—O— (wherein R's independently represent hydrogen or an alkyl group having 1 to 5 carbon atoms), $A^1$ and $A^2$ each independently represent a group selected from the group consisting of:
(a) a trans-1,4-cyclohexylene group (one methylene group or two or more non-adjacent methylene groups present in this group may be substituted with —O—, —NH—, or —S—),
(b) a 1,4-phenylene group (one or two or more —CH═'s present in this group may be substituted with —N═), and
(c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group,
in which the group (a), (b), or (c) may be each unsubstituted or may have one or more hydrogen atoms substituted with a fluorine atom, a chlorine atom, a cyano group, a methyl group, or a methoxy group, and p and q each independently represent 0 or 1).

7. The compound according to claim 1, wherein in the general formula (IIa) or (IIb),
$R^1$ represents a linear or branched alkyl group having 1 to 30 carbon atoms (one or two or more —CH₂— groups in the alkyl group may be each independently substituted with a cycloalkyl group having a ring member number of 3 to 8, and a hydrogen atom in the alkyl group may be substituted with an alkyl group having 1 to 20 carbon atoms, a cyano group, or a halogen atom),
$R^9$ represents a linear or branched alkyl group having 2 to 30 carbon atoms (one or two or more —CH₂— groups in the alkyl group may be each independently substituted with a cycloalkyl group having a ring member number of 3 to 8, and a hydrogen atom in the alkyl group may be substituted with a cyano group, or a halogen atom), and
$R^2$ represents a linear or branched alkyl group having 1 to 30 carbon atoms (one or two or more —CH₂— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom), and
in the general formula (I), Sp is represented by the general formula (IVc):

[Chem. 6]

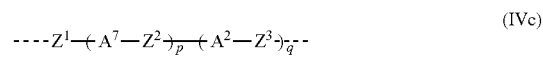
(IVc)

(wherein $Z^1$, $Z^2$ and $Z^3$ each independently represent a single bond, —(CH₂)$_u$— (wherein u represents 1 to 20), —OCH₂—, —CH₂O—, —COO—, —OCO—, —CH═CH—, —CF═CF—, —CF₂O—, —OCF₂—, —CF₂CF₂—, or —C≡C—, but one or more of the non-adjacent CH₂ groups in these substituents may be independently substituted with —O—, —CO—, —CO—O—, —O—CO—, —Si(CH₃)₂—O—Si(CH₃)₂—, —NR—, —NR—CO—, —CO—NR—, —NR—CO—O—, —O—CO—NR—, —NR—CO—NR—, —CH═CH—, —C≡C—, or —O—CO—O— (wherein R's independently represent hydrogen or an alkyl group having 1 to 5 carbon atoms), wherein $A^2$ represents a group selected from the group consisting of:
(a) a trans-1,4-cyclohexylene group (one methylene group or two or more non-adjacent methylene groups present in this group may be substituted with —O—, —NH—, or —S—),
(b) a 1,4-phenylene group (one or two or more —CH═'s present in this group may be substituted with —N═), and
(c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group,
in which the group (a), (b), or (c) may be each unsubstituted or may have one or more hydrogen atoms substituted with a fluorine atom, a chlorine atom, a cyano group, a methyl group, or a methoxy group, wherein $A^7$ represents a group selected from the group consisting of:
a 1,4-phenylene group (three or more —CH═'s present in this group are substituted with —N═), a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, and these may be each unsubstituted or have one or more hydrogen atoms substituted with a fluorine atom, a chlorine atom, a cyano group, a methyl group, or a methoxy group, and p represents 1 and q represents 1 or 2, but, in the case where q represents 2, a plurality of $A^2$ and $Z^3$ are present, and they may be the same as or different from each other).

8. The compound according to claim 1, wherein in the general formula (IIa) or (IIb), $R^1$ represents a linear or branched alkyl group having 1 to 30 carbon atoms (one or two or more —$CH_2$— groups in the alkyl group are each independently substituted with a cycloalkyl group having a ring member number of 3 to 8, and a hydrogen atom in the alkyl group may be substituted with an alkyl group having 1 to 20 carbon atoms, a cyano group, or a halogen atom), $R^9$ represents a linear or branched alkyl group having 2 to 30 carbon atoms (one or two or more —$CH_2$— groups in the alkyl group are each independently substituted with a cycloalkyl group having a ring member number of 3 to 8, and a hydrogen atom in the alkyl group may be substituted with a cyano group, or a halogen atom), and $R^2$ represents a linear or branched alkyl group having 1 to 30 carbon atoms (one or two or more —$CH_2$— groups in the alkyl group may be each independently substituted with a cycloalkyl group having a ring member number of 3 to 8, and a hydrogen atom in the alkyl group may be unsubstituted or may be substituted with an alkyl group having 1 to 20 carbon atoms, a cyano group, or a halogen atom), and in the general formula (I), Sp is represented by the general formula (IVb):

[Chem. 7]

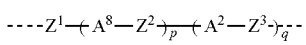

(IVb)

(wherein $Z^1$, $Z^2$ and $Z^3$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, but one or more of the non-adjacent $CH_2$ groups in these substituents may be independently substituted with —O—, —CO—, —CO—O—, —O—CO—, —$Si(CH_3)_2$—O—Si$(CH_3)_2$—, —NR—, —NR—CO—, —CO—NR—, —NR—CO—O—, —O—CO—NR—, —NR—CO—NR—, —CH=CH—, —C≡C—, or —O—CO—O— (wherein R's independently represent hydrogen or an alkyl group having 1 to 5 carbon atoms), wherein $A^2$ represents a group selected from the group consisting of:

(a) a trans-1,4-cyclohexylene group (one methylene group or two or more non-adjacent methylene groups present in this group may be substituted with —O—, —NH—, or —S—), (b) a 1,4-phenylene group (one or two or more —CH='s present in this group may be substituted with —N=), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, p and q each independently represent 0 or 1, wherein $A^8$ represents:

a trans-1,4-cyclohexylene group (one methylene group or two or more non-adjacent methylene groups present in this group may be substituted with —O—, —NH—, or —S—), and a 1,4-phenylene group (one or two —CH='s present in this group may be substituted with —N=), and these may be each unsubstituted or have one or more hydrogen atoms substituted with a fluorine atom, a chlorine atom, a cyano group, a methyl group, or a methoxy group).

9. The compound according to claim 1, wherein in the general formula (I), L represents any substituent selected from the group consisting of the general formulae (III-1) to (III-17):

[Chem. 8]

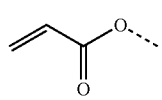

(III-1)

[Chem. 45]

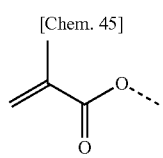

(III-2)

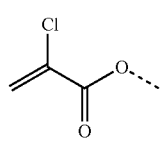

(III-3)

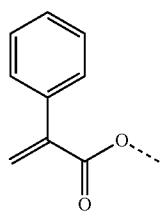

(III-4)

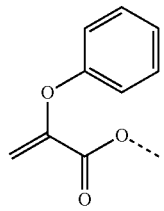

(III-5)

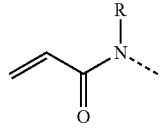

(III-6)

-continued

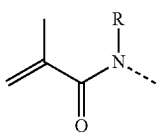 (III-7)

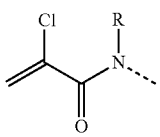 (III-8)

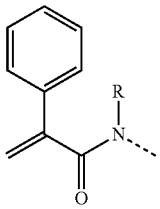 (III-9)

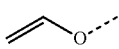 (III-10)

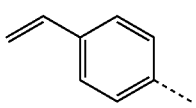 (III-11)

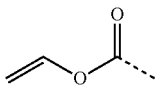 (III-12)

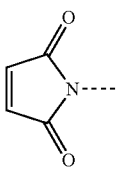 (III-13)

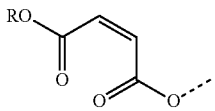 (III-14)

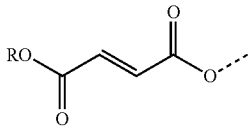 (III-15)

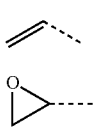 (III-16)

(III-17)

(wherein the broken line represents a bond to Sp and R's independently represent hydrogen or an alkyl group having 1 to 5 carbon atoms).

10. The compound according to claim 1, wherein in the general formula (I), X and Y each represent a hydrogen atom.

11. The compound according to claim 6, wherein in the general formulae (IVa), $A^2$ represents any group of a trans-1,4-cyclohexylene group, a 2,6-naphthylene group, a pyridine-2,5-diyl group, a pyrimidine-2,5-diyl group, or a 1,4-phenylene group, one or more hydrogen atoms in any group of these groups may be substituted with a fluorine atom, a chlorine atom, a methyl group, or a methoxy group, $Z^3$ represents any one of a single bond, —(CH$_2$)$_u$— (wherein u represents 1 to 20), —OCH$_2$—, —CH$_2$O—, —COO—, —OCO—, —CH=CH—, or —C≡C—, one or more of the non-adjacent CH$_2$ groups in any one of these groups may be independently substituted with —O—, —CO—, —CO—O—, —O—CO—, —CH=CH—, or —C≡C—, and q represents 1.

12. The compound according to claim 9, wherein in the general formula (I), L is represented by the general formula (III-1), (III-2), (III-6), (III-7), or (III-13).

13. The compound according to claim 1, wherein in the general formula (I), A represents a 1,4-phenylene group having one or more hydrogen atoms which may be substituted with a fluorine atom, a chlorine atom, a methyl group, or a methoxy group.

14. The compound according to claim 6, wherein in the general formulae (IVa), $A^2$ represents a 1,4-phenylene group having one or more hydrogen atoms which may be substituted with a fluorine atom, a chlorine atom, a methyl group, or a methoxy group.

15. The compound according to claim 9, wherein in the general formula (I), L is represented by the general formula (III-1) or (III-2).

16. The compound according to claim 7, wherein in the general formula (IVc), $A^7$ represents a 2,6-naphthylene group and one or more hydrogen atoms in the 2,6-naphthylene group may be substituted with a fluorine atom, a chlorine atom, a methyl group, or a methoxy group.

17. A polymer constituted with a cured product of a composition containing a compound according to claim 1, wherein the cured product has a structural unit represented by the general formula (PI):

[Chem. 9]

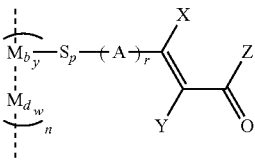 (PI)

(wherein Sp, A, X, Y, Z and r have the same definitions as in the general formula (I), $M_b$ and $M_d$ each represent a monomer unit of the polymer, y and w each represent a molar fraction of the copolymer, each satisfying 0<y≤1 and 0≤w<1, n represents 4 to 100,000, the order in which $M_b$ and $M_d$ are arranged may be the same as or different from that shown in the formula, and the monomer units of $M_b$ and $M_d$ may be each independently constituted with one or two or more different units).

18. The polymer according to claim 17, wherein in the general formula (PI), $M_b$ represents any one or more selected from the group consisting of the general formulae (QIII-A-1) to (QIII-A-17):

[Chem. 10]

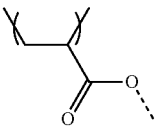 (QIII-A-1)

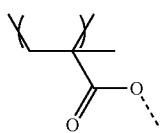 (QIII-A-2)

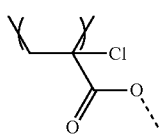 (QIII-A-3)

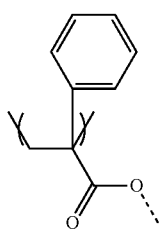 (QIII-A-4)

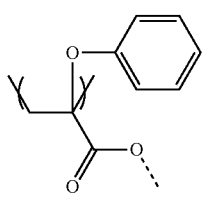 (QIII-A-5)

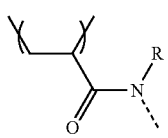 (QIII-A-6)

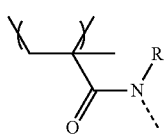 (QIII-A-7)

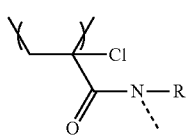 (QIII-A-8)

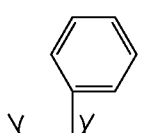 (QIII-A-9)

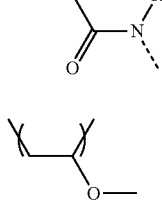 (QIII-A-10)

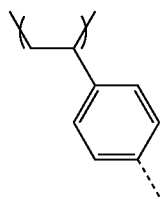 (QIII-A-11)

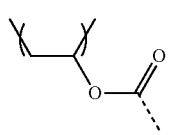 (QIII-A-12)

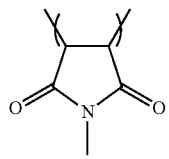 (QIII-A-13)

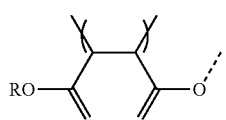 (QIII-A-14)

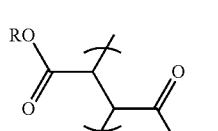 (QIII-A-15)

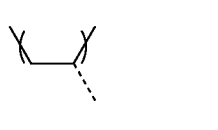 (QIII-A-16)

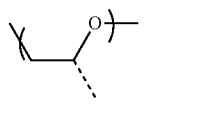 (QIII-A-17)

(wherein the broken line represents a bond to Sp, R's independently represent hydrogen or an alkyl group having 1 to 5 carbon atoms, and any hydrogen atom in each of the structures may be substituted with a fluorine atom, a chlorine atom, a methyl group, or a methoxy group).

19. The polymer according to claim 17, wherein in the general formula (PI), $M_d$ represents any one or more selected from the group consisting of the general formulae (QIII-1) to (QIII-17):

[Chem. 11]

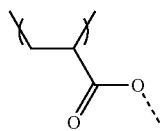 (QIII-1)

-continued

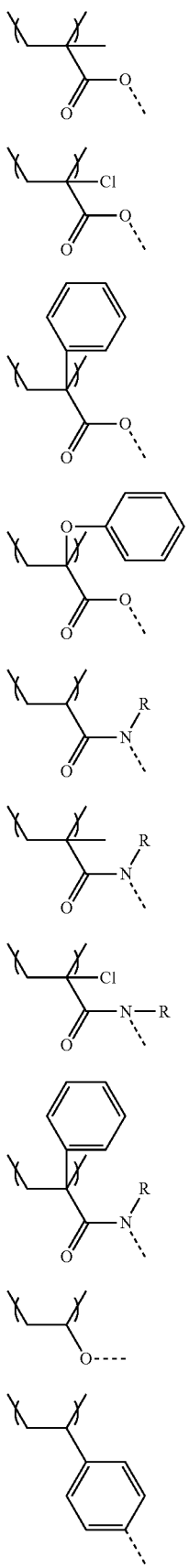

(QIII-2)
(QIII-3)
(QIII-4)
(QIII-5)
(QIII-6)
(QIII-7)
(QIII-8)
(QIII-9)
(QIII-10)
(QIII-11)

-continued (QIII-12)
(QIII-13)
(QIII-14)
(QIII-15)
(QIII-16)
(QIII-17)

(wherein the broken line represents a bond to a hydrogen atom or a monovalent organic group, R's independently represent hydrogen or an alkyl group having 1 to 5 carbon atoms, and any hydrogen atom in each of the structures may be substituted with a fluorine atom, a chlorine atom, a methyl group, or a methoxy group).

20. The polymer according to claim 19, wherein in the general formulae (QIII-1) to (QIII-17), the monovalent organic group is represented by the general formula (QIV):

[Chem. 12]

$$—S_a—V_a \quad\quad\quad (QIV)$$

(wherein the broken line represents a bond to $M_d$, $S_a$ represents a structure represented by the general formula (IVa), and $V_a$ is represented by the following general formula (VI):

[Chem. 5]

$$----Z^1\!\!-\!\!(\!A^1\!\!-\!\!Z^2\!)_{\overline{p}}\!(\!A^2\!\!-\!\!Z^3\!)_{\overline{q}}\!----  \quad\quad (IVa)$$

(wherein the left broken line represents a bond to L, and the right broken line represents a bond to A or a bond to a carbon atom, to which X is bonded, $Z^1$, $Z^2$ and $Z^3$ each independently represent a single bond, —$(CH_2)_u$— (wherein u represents 1 to 20), —$OCH_2$—, —$CH_2O$—, —COO—, —OCO—, —CH=CH—, —CF=CF—, —$CF_2O$—, —$OCF_2$—, —$CF_2CF_2$—, or —C≡C—, but one or more of the non-adjacent $CH_2$ groups in these substituents may be independently substituted with —O—, —CO—, —CO—O—, —O—CO—, —Si(CH₃)₂—O—Si(CH₃)₂—, —NR—, —NR—CO—, —CO—NR—, —NR—CO—O—, —O—CO—NR—, —NR—CO—NR—, —CH═CH—, —C≡C—, or —O—CO—O— (wherein R's independently represent hydrogen or an alkyl group having 1 to 5 carbon atoms), A¹ and A² each independently represent a group selected from the group consisting of:

(a) a trans-1,4-cyclohexylene group (one methylene group or two or more non-adjacent methylene groups present in this group may be substituted with —O—, —NH—, or —S—), (b) a 1,4-phenylene group (one or two or more —CH═'s present in this group may be substituted with —N═), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, and p and q each independently represent 0 or 1)

[Chem. 13]

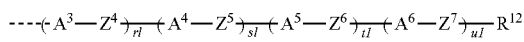

(VI)

(wherein the broken line represents a bond to $S_a$;

$Z^4$, $Z^5$, $Z^6$ and $Z^7$ each independently represent a single bond, —(CH₂)ᵤ— (wherein u represents 1 to 20), —OCH₂—, —CH₂O—, —COO—, —OCO—, —CH═CH—, —CF═CF—, —CF₂O—, —OCF₂—, —CF₂CF₂— or —C≡C—, but one or more of the non-adjacent CH₂ groups in these substituents may be independently substituted with —O—, —CO—, —CO—O—, —O—CO—, —Si(CH₃)₂—O—Si(CH₃)₂—, —NR—, —NR—CO—, —CO—NR—, —NR—CO—O—, —O—CO—NR—, —NR—CO—NR—, —CH═CH—, —C≡C—, or —O—CO—O— (wherein R's independently represent hydrogen or an alkyl group having 1 to 5 carbon atoms), A³, A⁴, A⁵ and A⁶ each independently represent a group selected from the group consisting of:

(a) a trans-1,4-cyclohexylene group (one methylene group or two or more non-adjacent methylene groups present in this group may be substituted with —O—, —NH—, or —S—), (b) a 1,4-phenylene group (one or two or more —CH═'s present in this group may be substituted with —N═), and (c) a 1,4-cyclohexenylene group, a 2,5-thiophenylene group, a 2,5-furanylene group, a 1,4-bicyclo(2.2.2)octylene group, a naphthalene-1,4-diyl group, a naphthalene-2,6-diyl group, a decahydronaphthalene-2,6-diyl group, and a 1,2,3,4-tetrahydronaphthalene-2,6-diyl group, in which the group (a), (b), or (c) may be each unsubstituted or may have one or more hydrogen atoms substituted with a fluorine atom, a chlorine atom, a cyano group, a methyl group, or a methoxy group, r1, s1, t1, and u1 each independently represent 0 or 1, and $R^{12}$ represents hydrogen, fluorine, chlorine, a cyano group, or an alkyl group having 1 to 20 carbon atoms, a hydrogen atom in the alkyl group may be substituted with a fluorine atom, and one CH₂ group or two or more non-adjacent CH₂ groups may be substituted with —O—, —CO—O—, —O—CO— and/or —CH═CH—)).

21. A liquid crystal alignment layer for a vertical alignment mode liquid crystal display element, comprising the polymer according to claim 17.

22. A vertical alignment mode liquid crystal display element comprising the liquid crystal alignment layer according to claim 21.

23. A liquid crystal alignment layer for a horizontal alignment mode liquid crystal display element, comprising the polymer according to claim 17.

24. A horizontal alignment mode liquid crystal display element comprising the liquid crystal alignment layer according to claim 23.

25. An optical anisotropic body, comprising the polymer according to claim 17, and
a polymer of a polymerizable liquid crystal composition, wherein polymerizable liquid crystal molecules in the polymerizable liquid crystal composition are aligned.

26. The compound according to claim 1, wherein Z is represented by the general formula (IIa), and $R^9$ is selected from the group consisting of —CH₂—CH═CH—CH₃, —C₂H₄—C≡CH, —CH₂—C≡C—C₂H₅, —C₂H₄—O—CH₃, —C₂H₄—O—C₂H₅, —C₂H₄—O—C₃H₇, —C₂H₄—N(CH₃)₂, —CH₂—CH(CH₃)—N(CH₃)₂, —CH₂—CH(CH(CH₃)₂)—N(CH₃)₂,

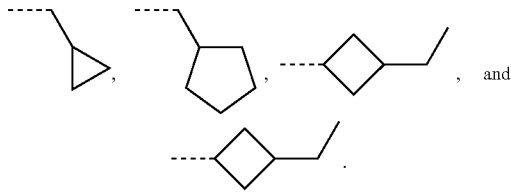

* * * * *